United States Patent
Rau et al.

(10) Patent No.: US 11,559,482 B2
(45) Date of Patent: Jan. 24, 2023

(54) BIODEGRADABLE POLYETHYLENE GLYCOL BASED WATER-INSOLUBLE HYDROGELS

(75) Inventors: Harald Rau, Heidelberg (DE); Ulrich Hersel, Heidelberg (DE); Mathias Krusch, Hirschhorn (DE); Dirk Vetter, Heidelberg (DE); Tobias Voigt, Heidelberg (DE)

(73) Assignee: Ascendis Pharma A/S, Hellerup (DE)

( * ) Notice: Subject to any disclaimer, the term of this patent is extended or adjusted under 35 U.S.C. 154(b) by 251 days.

(21) Appl. No.: 13/387,971

(22) PCT Filed: Jul. 30, 2010

(86) PCT No.: PCT/EP2010/061155
§ 371 (c)(1),
(2), (4) Date: Mar. 6, 2012

(87) PCT Pub. No.: WO2011/012715
PCT Pub. Date: Feb. 3, 2011

(65) Prior Publication Data
US 2012/0156259 A1    Jun. 21, 2012

(30) Foreign Application Priority Data

Jul. 31, 2009    (EP) .................................... 09167026
Oct. 6, 2009     (EP) .................................... 09172339

(51) Int. Cl.
*A61K 47/10* (2017.01)
*C08J 3/075* (2006.01)
(Continued)

(52) U.S. Cl.
CPC ............ *A61K 9/0024* (2013.01); *A61K 47/10* (2013.01); *A61K 47/60* (2017.08); *A61K 47/6903* (2017.08); *C08J 3/075* (2013.01)

(58) Field of Classification Search
CPC ...... A61K 47/60; A61K 47/6903; C08J 3/075
See application file for complete search history.

(56) References Cited

U.S. PATENT DOCUMENTS 7,585,831 B2    9/2009  Shechter et al.
7,776,240 B2 *  8/2010  Chu .................... A61K 9/0024
                                                                    264/4.1
(Continued)

FOREIGN PATENT DOCUMENTS

EA        011351 B1      5/2004
EP        0627911        12/1994
(Continued)

OTHER PUBLICATIONS

Wathier et al., dendritic macromers as in situ polymerizing biomaterials for securing, J. Am. Chem. Soc., 2004, vol. 126, pp. 12744-12746.*
(Continued)

*Primary Examiner* — Kortney L. Klinkel
(74) *Attorney, Agent, or Firm* — Haug Partners LLP

(57) ABSTRACT

The present invention relates to biodegradable polyethylene glycol based water-insoluble hydrogels comprising backbone moieties which are interconnected by hydrolytically degradable bonds, the backbone moieties further comprising reactive functional groups, wherein the water-insoluble hydrogel is further characterized in that the ratio between the time period for the complete degradation of the hydrogel by hydrolysis of the degradable bonds into water-soluble degradation products comprising one or more backbone moieties and the time period for the release of the first 10 mol-% of water-soluble degradation products comprising one or more backbone moieties based on the total amount of backbone moieties in the hydrogel is greater than 1 and equal to or less than 2. The invention further relates to conjugates of such hydrogels with ligands or ligating
(Continued)

groups, prodrugs and pharmaceutical compositions as well as their use in a medicament.

10 Claims, 15 Drawing Sheets

(51) Int. Cl.
*A61K 47/60* (2017.01)
*A61K 47/69* (2017.01)
*A61K 9/00* (2006.01)

(56) References Cited

U.S. PATENT DOCUMENTS

| | | | |
|---|---|---|---|
| 2003/0023023 | A1 | 1/2003 | Harris et al. |
| 2005/0009988 | A1 | 1/2005 | Harris et al. |
| 2005/0260259 | A1* | 11/2005 | Bolotin ............... A61K 9/0019 424/450 |
| 2008/0187568 | A1 | 8/2008 | Sawhney |
| 2008/0220047 | A1* | 9/2008 | Sawhney et al. ............ 424/426 |
| 2008/0293827 | A1 | 11/2008 | Lee et al. |
| 2012/0253071 | A1* | 10/2012 | Rau et al. ..................... 564/153 |
| 2013/0189328 | A1* | 7/2013 | Cleemann et al. .......... 424/400 |

FOREIGN PATENT DOCUMENTS

| | | | |
|---|---|---|---|
| EP | 08150973.9 | | 2/2008 |
| EP | 2 397 164 | | 12/2011 |
| JP | 2008-212683 | | 9/2008 |
| WO | WO 1993/17669 | | 9/1993 |
| WO | WO 1999/14259 | | 3/1999 |
| WO | WO 1999/25354 | | 5/1999 |
| WO | WO 2001/047562 | | 7/2001 |
| WO | WO 02/089789 | | 11/2002 |
| WO | WO-2005-00360 | | 1/2005 |
| WO | WO 2005/099768 | | 10/2005 |
| WO | WO 2006/003014 | | 1/2006 |
| WO | WO 2006/136586 | | 12/2006 |
| WO | WO 2007/082088 | | 7/2007 |
| WO | WO 2008/034122 | | 3/2008 |
| WO | WO 2008038038 | * | 4/2008 ............. C08G 73/02 |
| WO | WO 2008/066787 | | 6/2008 |
| WO | WO 2008/125655 | | 10/2008 |
| WO | WO 2009/095479 | | 8/2009 |
| WO | WO 2009/134336 | | 11/2009 |

OTHER PUBLICATIONS

Malkoch et al., recent advances n crosslinked dendritic networks, Applied Polymer Science, 2013, 39876, pp. 1-13.*
Haag et al. Dendritic polyglycerols for biomedical applications, Advanced matterials, 2010, No. 22, pp. 190-218.*
Fox et al. (soluble polymer carrier for the treatment of cancer: the important of molecular architecture, Accounts of Chemical Research, vol. 42, p. 1141-1151, published online in Jun. 2009).*
Schwall et al., Micro- and Nanoscale hydrogel systems for drug delivery and tissue engineering, Material, 2009, vol. 2, p. 579, 3rd para., p. 599, p. 600; published online on May 13, 2009.*
Oh et al. The development of microgel/nanogel for drug delivery application, Prog. Polym. Sci. 2008, vol. 33, Abstract, Introduction, p. 454.*
Vier et al., Hydrogels formed by endlinking PEG to dendrimer crosslink agents, Polymer Preprints, 2000, vol. 41, pp. 728-729.*
Fife et al., Mechanism of thiazolidine hydrolysis. Ring opening and hydrolysis of 1,3-thiazolidine derivatives of p-(dimethylamino)cinnamaldehyde. J Am Chem Soc., 1991, vol. 113, pp. 3071-3079.*
Rozenberg, Kinetics, thermodynamics and mechanism of reactions of epoxy oligomers with amines. In: Dusek K. (eds) Epoxy Resins and Composites II. Advances in Polymer Science, vol. 75. Springer, Berlin, Heidelberg, 1986, p. 143 (Year: 1986).*
Agilent monograph, Polymer molecular weight distribution and definition of MW average, 2011, pp. 1-2 (Year: 2011).*
Ellman et al., "A New and Rapid Colorimetric Determinaion of Acetylcholinesterase Activity", Biochemical Pharmacology, 1961, pp. 88-95, vol. 7, Pergamon Press Ltd., Great Briain.
Jenkem Technology USA Product List, Apr. 2009.
English et al., "Orally Effective Acid Prodrugs of the β-Lactamase Inhibitor Sulbactam", J. Med. Chem., 1990, pp. 344-347, vol. 33, American Chemical Society, U.S.
Physicians' Desk Reference 57th Edition, 2003, pp. 2768-2772.
Testa et al., Hydrolysis in Drug and Prodrug Metabolism, Wiley-VCH, 2003.
Eng et al., "Isolation and Characterization of Exendin-4, an Exendin-3 Analogue, from *Heloderma suspectum* Venom", J. of Bio. Chem., 1992, pp. 7402-7405, vol. 267, No. 11, American Society for Biochemistry and Molecular Biology. Rockville, MD.
Zhao et al., "Novel Degradable Poly(ethylene glycol) Hydrogels for Controlled Release of Protein" J. of Pharm. Sciences, 1998, pp. 1450-1458, vol. 87, No. 11, ACS Publications, Washington, D.C.
Gude, M. et al., "An accurate method for the quantitation of Fmoc-derivatized solid phase", Letters in Peptide Science, 2002, vol. 9, 203-206, Kluwer Academic Publishers, Netherlands.

* cited by examiner

BIODEGRADABLE POLYETHYLENE GLYCOL BASED WATER-INSOLUBLE HYDROGELS

The present invention relates to biodegradable polyethylene glycol based water-insoluble hydrogels. The invention further relates to conjugates of such biodegradable hydrogels with affinity ligands or chelating groups or ion exchange groups, carrier-linked prodrugs in which the biodegradable hydrogel of the present invention is the carrier and pharmaceutical compositions thereof as well as their use in a medicament.

Poly(ethylene glycol) (PEG)-based hydrogels are of interest for pharmaceutical applications such as wound closure, tissue engineering and drug delivery. PEG-based hydrogels are three-dimensional crosslinked molecular networks that can take up a large amount of water. PEG-based hydrogels typically contain a high proportion of poly(ethylene glycol) chains. PEG based hydrogels are known in the art.

A hydrogel based on PEG in the substantial absence of non-PEG polymers is described WO-A 99/14259. Here, degradable PEG based hydrogels are described which show controlled half-life.

Biodegradable PEG-based hydrogels are advantageous for many in vivo applications. In particular for safety reasons, it is strongly preferred to engineer biodegradability into the PEG hydrogel if it is intended for use in humans. Biodegradability may be introduced into a hydrogel by ester bonds that undergo spontaneous or enzymatic hydrolysis in the aqueous in vivo environment.

Different types of reactions may be employed for performing the actual polymerization step, and the choice of polymerization chemistry determines the structure of the macromer starting materials. For instance, radical polymerization has been used widely in PEG-based resin manufacture and for the creation of biocompatible hydrogels (see e.g. EP-A 0627911). Also addition reactions have been applied in the polymerization of hydrogels from PEG-based macromers (WO-A 2008/125655).

Alternatively, condensation- or ligation-type reactions for hydrogel polymerization relying on ester, carbamate, carbonate or imine formation have been described. These linkages may be used to engineer degradability into the hydrogel by means of labile aromatic carbamates (WO-A 01/47562) or carbonates (US-A 2003/0023023), esters or imines (WO-A 99/14259).

In contrast to the formation of hydrolytically labile bonds during the polymerization step, biodegradability can be engineered into PEG-based hydrogels by the presence of hydrolytically labile ester bonds in one of the macromer starting materials. If such ester-containing macromers are used, an efficient reaction to be used for hydrogel formation is amide bond formation. In this way, the hydrogel is generated by condensation reactions between activated carboxyl and amine functionalities resulting in a three dimensional network formed by hydrolytically stable amide bonds. Biodegradation may then proceed through hydrolysis of the ester groups provided by at least one of the starting materials now incorporated into the hydrogel network.

Biodegradable PEG-based hydrogels generated through amide bond formation may be prepared from two different macromer starting materials, a macromer providing more than 2 amino functionalities suitable as backbone reagent, and a different macromer usually named crosslinker reagent, providing at least two activated carboxyl functionalities. Biodegradable ester bonds may be incorporated into one of the macromers like the crosslinker reagent. In such a system, hydrogel degradation kinetics may be recorded by plotting the release of the non-degradable macromer moiety from the hydrogel over time. It is understood that released non-degradable macromer will be conjugated through amide bonds to groups remaining from the ester-hydrolysis induced degradation of the degradable, ester-containing macromer.

Zhao and Harris et al., J. Pharmaceutical Sciences 87 (1998) 1450-1458, describe the degradation kinetics of PEG-based hydrogels. Ester-containing, amine-reactive PEG derivates were employed as one macromer, and branched PEG amines or proteins were employed as second non-degradable macromer to form the hydrogel. FIG. 3 of the Zhao and Harris paper details the release of fluorescently-labeled bovine serum albumin macromer from degradable PEG-based hydrogels. In that study, labeled bovine serum albumin was used as precursor together with 4-arm PEG tetraamine, or 8-arm PEG octaamine, or human serum albumin. Degradation profiles are recorded in buffer (at pH 7, at 37° C.) over time and characterized by a "burst" at a late stage of degradation. During this burst phase, 40% up to 60% of the non-degradable macromer were released within a very short period of time, i.e. within a few hours, whereas the previous lag phase of hydrogel degradation continued for 100 up to 400 hours. In this investigation the focus was put on engineering the hydrogel in such a way, that the "undesirable late burst" could be avoided. The authors succeeded in their effort by shortening the gelation time during hydrogel formation and achieved an almost zero order release profile of the non-degradable macromer.

However such a degradation profile for a hydrogel is disadvantageous in the field of prodrug delivery since there is a prolonged time of hydrogel fragmentation during release of a drug by a prodrug based on such hydrogels.

Therefore one object of the present invention is to provide hydrogels which show a more convenient degradation profile than those degradable hydrogels described in the art.

This object is achieved by a biodegradable polyethylene glycol based water-insoluble hydrogel comprising backbone moieties which are interconnected by hydrolytically degradable bonds, the backbone moieties further comprising reactive functional groups, wherein the water-insoluble hydrogel is further characterized in that the ratio between the time period for the complete degradation of the hydrogel by hydrolysis of the degradable bonds into water-soluble degradation products comprising one or more backbone moieties and the time period for the release of the first 10 mol-% of water-soluble degradation products comprising one or more backbone moieties based on the total amount of backbone moieties in the hydrogel is greater than 1 and equal to or less than 2, preferably greater than 1 or equal to or less than 1.5.

It was found that particularly in the field of drug delivery it is desirable for the polymeric carrier material not to be present much longer than is required for the release of the amount of drug necessary to achieve the intended therapeutic effect. For instance if PEG hydrogels are employed as polymeric carriers for carrier-linked prodrugs, it is desirable to deplete the hydrogel of its drug load before disintegration of the hydrogel material takes place. Consequently it will be highly advantageous to employ hydrogels exhibiting a highly pronounced burst effect during hydrogel degradation in that these hydrogels show the abovementioned degradation profile in that the time period for the complete degradation of the hydrogel by hydrolysis of the degradable bonds into water-soluble degradation products comprising one or more backbone moieties is at most 2-fold or less than the time period for the release of the first 10 mol-% of reactive functional groups based on the total amount of reactive functional groups in the hydrogel.

It was now surprisingly discovered, that reactive biodegradable PEG hydrogels can be engineered in such a way that the release of backbone moieties carrying functional groups (90% or more) occurs within a very short time frame compared to the preceding lag phase during which the first 10% of backbone moieties are released.

The term "hydrogel" refers to a three-dimensional, hydrophilic or amphiphilic polymeric network capable of taking up large quantities of water. Such network may be composed of homopolymers or copolymers, and is insoluble due to the presence of covalent chemical or physical (ionic, hydrophobic interactions, entanglements) crosslinks. The crosslinks provide the network structure and physical integrity. Hydrogels exhibit a thermodynamic compatibility with water which allows them to swell in aqueous media. The chains of the network are connected in such a fashion that pores exist and that a substantial fraction of these pores are of dimensions between 1 nm and 1000 nm.

The terms "hydrolytically degradable", "biodegradable" or "hydrolytically cleavable", "cleavable", "auto-cleavable", or "self-cleavage", "self-cleavable", "reversible", "transient" or "temporary" refers within the context of the present invention to bonds and linkages which are non-enzymatically hydrolytically degradable or cleavable under physiological conditions (aqueous buffer at pH 7.4, 37° C.) with half-lives ranging from one hour to three months, including, but are not limited to, aconityls, acetals, amides, carboxylic anhydrides, esters, imines, hydrazones, maleamic acid amides, ortho esters, phosphamides, phosphoesters, phosphosilyl esters, silyl esters, sulfonic esters, aromatic carbamates, combinations thereof, and the like.

If present in a hydrogel according to the invention as degradable interconnected functional group, preferred biodegradable linkages are carboxylic esters, carbonates, phosphoesters and sulfonic acid esters and most preferred are carboxylic esters or carbonates.

It is understood that for in vitro studies accelerated conditions like, for example, pH 9, 37° C., aqueous buffer, may be used for practical purposes. By running two side-by-sides studies in which only the pH varies (pH 7.4 or pH 9, respectively), a factor can be calculated which can be used in future experiments run at pH 9 to calculate the equivalent reaction kinetics of an experiment performed at pH 7.4.

Permanent linkages are non-enzymatically hydrolytically degradable under physiological conditions (aqueous buffer at pH 7.4, 37° C.) with half-lives of six months or longer, such as, for example, amides.

The term "reagent" refers to an intermediate or starting reagent used in the assembly process leading to biodegradable hydrogels, conjugates, and prodrugs of the present invention.

The term "chemical functional group" refers to carboxylic acid and activated derivatives, amino, maleimide, thiol and derivatives, sulfonic acid and derivatives, carbonate and derivatives, carbamate and derivatives, hydroxyl, aldehyde, ketone, hydrazine, isocyanate, isothiocyanate, phosphoric acid and derivatives, phosphonic acid and derivatives, haloacetyl, alkyl halides, acryloyl and other alpha-beta unsaturated michael acceptors, arylating agents like aryl fluorides, hydroxylamine, disulfides like pyridyl disulfide, vinyl sulfone, vinyl ketone, diazoalkanes, diazoacetyl compounds, oxirane, and aziridine.

If a chemical functional group is coupled to another chemical functional group, the resulting chemical structure is referred to as "linkage". For example, the reaction of an amine group with a carboxyl group results in an amide linkage.

"Reactive functional groups" are chemical functional groups of the backbone moiety, which are connected to the hyperbranched moiety.

"Functional group" is the collective term used for "reactive functional group", "degradable interconnected functional group", or "conjugate functional group".

A "degradable interconnected functional group" is a linkage comprising a biodegradable bond which on one side is connected to a spacer moiety connected to a backbone moiety and on the other side is connected to the crosslinking moiety. The terms "degradable interconnected functional group", "biodegradable interconnected functional group", "interconnected biodegradable functional group" and "interconnected functional group" are used synonymously.

A "conjugate functional group" comprises an affinity ligand or chelating group or ion exchange group and a permanent linkage connecting the affinity ligand or chelating group to the hyperbranched moiety of the backbone moiety.

The terms "blocking group" or "capping group" are used synonymously and refer to moieties which are irreversibly (especially permanent) connected to reactive functional groups to render them incapable of reacting with for example chemical functional groups.

The terms "protecting group" or "protective group" refers to a moiety which is reversibly connected to reactive functional groups to render them incapable of reacting with for example other chemical functional groups.

The term "interconnectable functional group" refers to chemical functional groups, which participate in a radical polymerization reaction and are part of the crosslinker reagent or the backbone reagent.

The term "polymerizable functional group" refers to chemical functional groups, which participate in a ligation-type polymerization reaction and are part of the crosslinker reagent and the backbone reagent.

A backbone moiety may comprise a spacer moiety which at one end is connected to the backbone moiety and on the other side to the crosslinking moiety.

The term "derivatives" refers to chemical functional groups suitably substituted with protecting and/or activation groups or to activated forms of a corresponding chemical functional group which are known to the person skilled in the art. For example, activated forms of carboxyl groups include but are not limited to active esters, such as succinimidyl ester, benzotriazyl ester, nitrophenyl ester, pentafluorophenyl ester, azabenzotriazyl ester, acyl halogenides, mixed or symmetrical anhydrides, acyl imidazole.

The term "non-enzymatically cleavable linker" refers to linkers that are hydrolytically degradable under physiological conditions without enzymatic activity.

"Non-biologically active linker" means a linker which does not show the pharmacological effects of the drug (D-H) derived from the biologically active moiety.

The terms "spacer", "spacer group", "spacer molecule", and "spacer moiety" are used interchangeably and refer to any moiety suitable for connecting two moieties, such as $C_{1-50}$ alkyl, $C_{2-50}$ alkenyl or $C_{2-50}$ alkinyl, which fragment is optionally interrupted by one or more groups selected from —NH—, —N($C_{1-4}$ alkyl)-, —O—, —S—, —C(O)—, —C(O)NH—, —C(O)N($C_{1-4}$ alkyl)-, —O—C(O)—, —S(O)—, —S(O)$_2$—, 4 to 7 membered heterocyclyl, phenyl or naphthyl.

The terms "terminal", "terminus" or "distal end" refer to the position of a functional group or linkage within a molecule or moiety, whereby such functional group may be a chemical functional group and the linkage may be a degradable or permanent linkage, characterized by being located adjacent to or within a linkage between two moieties or at the end of an oligomeric or polymeric chain.

The terms "drug", "drug moiety", "biologically active molecule", "biologically active moiety", "biologically active agent", and the like are used synonymously and mean any substance which can affect any physical or biochemical properties of a biological organism, including but not limited to viruses, bacteria, fungi, plants, animals, and humans. In particular, as used herein, biologically active molecules include any substance intended for diagnosis, cure, mitigation, treatment, or prevention of disease in humans or other animals, or to otherwise enhance physical or mental well-being of humans or animals. Examples of biologically active molecules include, but are not limited to, peptides, proteins, enzymes, small molecule drugs (e.g., nonpeptidic drugs), dyes, lipids, nucleosides, oligonucleotides, polynucleotides, nucleic acids, cells, viruses, liposomes, microparticles and micelles. Classes of biologically active agents that are suitable for use with the invention include, but are not limited to, antibiotics, fungicides, anti-viral agents, anti-inflammatory agents, anti-tumor agents, cardiovascular agents, anti-anxiety agents, hormones, growth factors, steroidal agents, and the like.

The phrases "in bound form" or "moiety" refer to substructures which are part of a larger molecule. The phrase "in bound form" is used to simplify reference to moieties by naming or listing reagents, starting materials or hypothetical starting materials well known in the art, and whereby "in bound form" means that for example one or more hydrogen radicals (—H), or one or more activating or protecting groups present in the reagents or starting materials are not present in the moiety.

It is understood that all reagents and moieties comprising polymeric moieties refer to macromolecular entities known to exhibit variabilities with respect to molecular weight, chain lengths or degree of polymerization, or the number of functional groups. Structures shown for backbone reagents, backbone moieties, crosslinker reagents, and crosslinker moieties are thus only representative examples.

The term "water-soluble" refers to degradation products of the biodegradable hydrogel of the invention separated from water-insoluble degradation products by filtration.

A reagent or moiety may be linear or branched. If the reagent or moiety has two terminal groups, it is referred to as a linear reagent or moiety. If the reagent or moiety has more than two terminal groups, it is considered to be a branched or multi-functional reagent or moiety.

Starting Materials

Biodegradable hydrogels of the present invention may either be polymerized through radical polymerization, ionic polymerization or ligation reactions.

In case the biodegradable hydrogel of the present invention is processed through radical or ionic polymerization, the at least two starting materials for the biodegradable hydrogel of the present invention are crosslinking macromonomers or crosslinking monomers—which are referred to as crosslinker reagents—and a multi-functional macromonomer, which is referred to as backbone reagent. The crosslinker reagent carries at least two interconnectable functional groups and the backbone reagent carries at least one interconnectable functional group and at least one chemical functional group which is not intended to participate in the polymerization step. Additional diluent monomers may or may not be present.

Useful interconnectable functional groups include but are not limited to radically polymerizable groups like vinyl, vinyl-benzene, acrylate, acrylamide, methacylate, methacrylamide and ionically polymerizable groups like oxetane, aziridine, and oxirane.

In an alternative method of preparation, the biodegradable hydrogel according to the invention is generated through chemical ligation reactions. In such reactions, the starting material is at least one macromolecular starting material with complementary functionalities which undergo a reaction such as a condensation or addition reaction. In one alternative, only one macromolecular starting material is used, which is a heteromultifunctional backbone reagent, comprising a number of polymerizable functional groups.

Alternatively, in the case if two or more macromolecular starting materials one of these starting materials is a crosslinker reagent with at least two identical polymerizable functional groups and the other starting material is a homomultifunctional or heteromultifunctional backbone reagent, also comprising a number of polymerizable functional groups.

Suitable polymerizable functional groups present on the crosslinker reagent include primary and secondary amino, carboxylic acid and derivatives, maleimide, thiol, hydroxyl and other alpha,beta unsaturated Michael acceptors such as vinylsulfone groups, preferably terminal primary or secondary amino, carboxylic acid and derivatives, maleimide, thiol, hydroxyl and other alpha,beta unsaturated Michael acceptors such as vinylsulfone groups. Suitable polymerizable functional groups present in the backbone reagent include but are not limited to primary and secondary amino, carboxylic acid and derivatives, maleimide, thiol, hydroxyl and other alpha,beta unsaturated Michael acceptors like vinylsulfone groups.

Preferentially, a backbone moiety is characterized by having a branching core, from which at least three PEG-based polymeric chains extend. Accordingly, in a preferred aspect of the present invention the backbone reagent comprises a branching core, from which at least three PEG-based polymeric chains extend. Such branching cores may comprise in bound form poly- or oligoalcohols, preferably pentaerythritol, tripentaerythritol, hexaglycerine, sucrose, sorbitol, fructose, mannitol, glucose, cellulose, amyloses, starches, hydroxyalkyl starches, polyvinylalcohols, dextranes, hyualuronans, or branching cores may comprise in bound form poly- or oligoamines such as ornithine, diaminobutyric acid, trilysine, tetralysine, pentalysine, hexylysine, heptalysine, octalysine, nonalysine, decalysine, undecalysine, dodecalysine, tridecalysine, tetradecalysine, pentadecalysine or oligolysines, polyethyleneimines, polyvinylamines.

Preferably, the branching core extends three to sixteen PEG-based polymeric chains, more preferably four to eight. Preferred branching cores may comprise pentaerythritol, trilysine, tetralysine, pentalysine, hexylysine, heptalysine or oligolysine, low-molecular weight PEI, hexaglycerine, tripentaerythritol in bound form. Preferably, the branching core extends three to sixteen PEG-based polymeric chains, more preferably four to eight. Preferably, a PEG-based polymeric chain is a suitably substituted poly(ethylene glycol) derivative.

The term "poly(ethylene glycol) based polymeric chain" or "PEG based chain" refers to an oligo- or polymeric molecular chain.

Preferably, such poly(ethylene glycol) based polymeric chain is connected to a branching core, it is a linear poly(ethylene glycol) chain, of which one terminus is connected to the branching core and the other to a hyperbranched dendritic moiety. It is understood that a PEG-based chain may be terminated or interrupted by alkyl or aryl groups optionally substituted with heteroatoms and chemical functional groups.

If the term "poly(ethylene glycol) based polymeric chain" is used in reference to a crosslinker reagent, it refers to a crosslinker moiety or chain comprising at least 20 weight % ethylene glycol moieties.

Preferred structures comprising PEG-based polymeric chains extending from a branching core suitable for backbone reagents are multi-arm PEG derivatives as, for instance, detailed in the products list of JenKem Technology, USA (accessed by download from www.jenkemusa.com on Jul. 28, 2009), 4ARM-PEG Derivatives (pentaerythritol core), 8ARM-PEG Derivatives (hexaglycerin core) and 8ARM-PEG Derivatives (tripentaerythritol core). Most preferred are 4arm PEG Amine (pentaerythritol core) and 4arm PEG Carboxyl (pentaerythritol core), 8arm PEG Amine (hexaglycerin core), 8arm PEG Carboxyl (hexaglycerin core), 8arm PEG Amine (tripentaerythritol core) and 8arm PEG Carboxyl (tripentaerythritol core). Preferred molecular weights for such multi-arm PEG-derivatives in a backbone reagent are 1 kDa to 20 kDa, more preferably 1 kDa to 15 kDa and even more preferably 1 kDa to 10 kDa. It is understood that the terminal amine groups are further conjugated to provide interconnected and reactive functional groups of a backbone moiety.

The terms "branching core" and "core" are used interchangeably.

The hyperbranched dendritic moiety provides polymerizable functional groups. Preferably, each dendritic moiety has a molecular weight in the range of from 0.4 kDa to 4 kDa, more preferably 0.4 kDa to 2 kDa. Preferably, each dendritic moiety has at least 3 branchings and at least 4 polymerizable functional groups, and at most 63 branchings and 64 polymerizable functional groups, preferred at least 7 branchings and at least 8 polymerizable functional groups and at most 31 branchings and 32 polymerizable functional groups.

Examples for such dendritic moieties are trilysine, tetralysine, pentalysine, hexylysine, heptalysine, octalysine, nonalysine, decalysine, undecalysine, dodecalysine, tridecalysine, tetradecalysine, pentadecalysine, hexadecalysine, heptadecalysine, octadecalysine, nonadecalysine, ornithine, and diaminobutyric acid. Examples for such preferred dendritic moieties are trilysine, tetralysine, pentalysine, hexylysine, heptalysine, most preferred trilysine, pentalysine or heptalysine in bound form.

The crosslinker reagent may be a linear or branched molecule and preferably is a linear molecule. If the crosslinker reagent has two polymerizable functional groups, it is referred to as a "linear crosslinker reagent"; if the crosslinker reagent has more than two polymerizable functional groups it is considered to be a "branched crosslinker reagent".

A crosslinker reagent is terminated by two polymerizable functional groups and may comprise no biodegradable group or may comprise at least one biodegradable bond. Preferably, the crosslinker reagent comprises at least one biodegradable bond.

In one embodiment, a crosslinker reagent consists of a polymer. Preferably, crosslinker reagents have a molecular weight in the range of from 60 Da to 5 kDa, more preferably, from 0.5 kDa to 4 kDa, even more preferably from 1 kDa to 4 kDa, even more preferably from 1 kDa to 3 kDa.

In addition to oligomeric or polymeric crosslinking reagents, low-molecular weight crosslinking reagents may be used, especially when hydrophilic high-molecular weight backbone moieties are used for the biodegradable hydrogel formation.

In one embodiment, crosslinker reagent comprises monomers connected by biodegradable bonds, i.e. the crosslinker reagent is formed from monomers connected by biodegradable bonds. Such polymeric crosslinker reagents may contain up to 100 biodegradable bonds or more, depending on the molecular weight of the crosslinker reagent and the molecular weight of the monomer units. Examples for such crosslinker reagents may comprise poly(lactic acid) or poly(glycolic acid) based polymers.

Preferably, the crosslinker reagents are PEG based, preferably represented by only one PEG based molecular chain. Preferably, the poly(ethylene glycol) based crosslinker reagents are hydrocarbon chains comprising connected ethylene glycol units, wherein the poly(ethylene glycol) based crosslinker reagents comprise at least each methylene glycol units, and wherein m is an integer in the range of from 3 to 100, preferably from 10 to 70. Preferably, the poly(ethylene glycol) based crosslinker reagents have a molecular weight in the range of from 0.5 kDa to 5 kDa.

An example of a simplified backbone reagent is shown in FIG. 1 to illustrate the terminology used. From a central branching core (C) extend four PEG-based polymeric chains (thin black line), at which ends hyperbranched dendritic moieties ("Hyp"; ovals) are attached. The hyperbranched dendritic moieties carry polymerizable functional groups (small white circles), of which only a selection is shown, i.e. a hyperbranched dendritic moiety comprises more reactive functional groups than those shown in FIG. 1.

FIG. 2 shows four exemplary crosslinker reagents. In addition to their polymerizable functional groups (small white circles), crosslinking reagents may comprises one or more biodegradable linkages (white arrows) which comprise a biodegradable bond.

Crosslinker reagent 2A comprises no biodegradable bond. If such crosslinker reagents are used for biodegradable hydrogel synthesis, biodegradable linkages are formed through the reaction of a polymerizable functional group of the crosslinker reagent with a polymerizable functional group of the backbone reagent.

Crosslinker reagent 2B comprises one biodegradable linkage, crosslinker reagent 2C comprises two biodegradable linkages and crosslinker reagent 2D comprises four biodegradable linkages.

The moiety between the polymerizable group and the first biodegradable bond is referred to as a spacer and is indicated in the different crosslinker moieties by asterisks, where applicable.

Reactive Biodegradable Hydrogel

The reactive biodegradable hydrogel of the present invention is a multi-functionalized material, meaning that it comprises reactive functional groups and interconnected functional groups in a three-dimensional crosslinked matrix swellable in water.

The reactive biodegradable hydrogel is composed of backbone moieties interconnected by hydrolytically degradable bonds and the backbone moieties may be linked together through crosslinker moieties.

In one embodiment, the backbone moieties of the reactive biodegradable hydrogel may be linked together directly, i.e. without crosslinker moieties. The hyperbranched dendritic moieties of two backbone moieties of such reactive biodegradable hydrogel may either be directly linked through an interconnected functional group that connects the two hyperbranched dendritic moieties. Alternatively, two hyperbranched dendritic moieties of two different backbone moieties may be interconnected through two spacer moieties separated by an interconnected functional moiety.

Preferably, the reactive biodegradable hydrogel is composed of backbone moieties interconnected by hydrolytically degradable bonds and the backbone moieties are linked together through crosslinker moieties.

The term biodegradable or hydrolytically degradable bond describes linkages that are non-enzymatically hydrolytically degradable under physiological conditions (aqueous buffer at pH 7.4, 37° C.) with half-lives ranging from one hour to three months, include, but are not limited to, aconityls, acetals, carboxylic anhydrides, esters, imines, hydrazones, maleamic acid amides, ortho esters, phosphamides, phosphoesters, phosphosilyl esters, silyl esters, sulfonic esters, aromatic carbamates, combinations thereof, and the like. Preferred biodegradable linkages are esters, carbonates, phosphoesters and sulfonic acid esters and most preferred are esters or carbonates.

In reactive biodegradable hydrogels of the present invention, the hydrolysis rate of the biodegradable bonds between backbone moieties and crosslinker moieties is influenced or determined by the number and type of connected atoms in the spacer moieties between the hyperbranched moiety and interconnected functional groups. For instance by selecting from succinic, adipic or glutaric acid for crosslinker PEG ester formation it is possible to vary the degradation half-lives of the reactive biodegradable hydrogel.

Each crosslinker moiety is terminated by at least two of the hydrolytically degradable bonds. In addition to the terminating biodegradable bonds, the crosslinker moieties may contain further biodegradable bonds. Thus, each terminus of the crosslinker moiety linked to a backbone moiety comprises a hydrolytically degradable bond, and additional biodegradable bonds may optionally be present in the crosslinker moiety.

The reactive biodegradable hydrogel may contain one or more different types of crosslinker moieties, preferably one. The crosslinker moiety may be a linear or branched molecule and preferably is a linear molecule. In a preferred embodiment of the invention, the crosslinker moiety is connected to backbone moieties by at least two biodegradable bonds.

Preferably, crosslinker moieties have a molecular weight in the range of from 60 Da to 5 kDa, more preferably, from 0.5 kDa to 4 kDa, even more preferably from 1 kDa to 4 kDa, even more preferably from 1 kDa to 3 kDa. In one embodiment, a crosslinker moiety consists of a polymer.

Alternatively, low-molecular weight crosslinker moieties may be used, especially when hydrophilic high-molecular weight backbone moieties are used for the reactive biodegradable hydrogel formation.

In one embodiment, monomers constituting the polymeric crosslinker moieties are connected by biodegradable bonds. Such polymeric crosslinker moieties may contain up to 100 biodegradable bonds or more, depending on the molecular weight of the crosslinker moiety and the molecular weight of the monomer units. Examples for such crosslinker moieties are or poly(glycolic acid) based polymers. It is understood that such poly(lactic acid) or poly(glycolic acid) chain may be terminated or interrupted by alkyl or aryl groups and that they may optionally be substituted with heteroatoms and chemical functional groups.

Preferably, the crosslinker moieties are PEG based, preferably represented by only one PEG based molecular chain. Preferably, the poly(ethylene glycol) based crosslinker moieties are hydrocarbon chains comprising ethylene glycol units, optionally comprising further chemical functional groups, wherein the poly(ethylene glycol) based crosslinker moieties comprise at least each methylene glycol units, wherein m is an integer in the range of from 3 to 100, preferably from 10 to 70. Preferably, the poly(ethylene glycol) based crosslinker moieties have a molecular weight in the range of from 0.5 kDa to 5 kDa.

If used in reference to a crosslinker moiety or a PEG-based polymeric chain connected to a branching core, the term "PEG-based" refers to a crosslinker moiety or PEG-based polymeric chain comprising at least 20 weight % ethylene glycol moieties.

It is understood that a PEG-based polymeric chain may be terminated or interrupted by alkyl or aryl groups optionally substituted with heteroatoms and chemical functional groups.

In a preferred embodiment of the present invention the crosslinker moiety consists of PEG, which is symmetrically connected through ester bonds to two alpha, omega-aliphatic dicarboxylic spacers provided by backbone moieties connected to the hyperbranched dendritic moiety through permanent amide bonds.

The dicarboxylic acids of the spacer moieties consist of 3 to 12 carbon atoms, most preferably between 5 and 8 carbon atoms and may be substituted at one or more carbon atom. Preferred substituents are alkyl groups, hydroxyl groups or amido groups or substituted amino groups. One or more of the aliphatic dicarboxylic acid's methylene groups may optionally be substituted by O or NH or alkyl-substituted N. Preferred alkyl is linear or branched alkyl with 1 to 6 carbon atoms.

Preferentially, a backbone moiety is characterized by having a branching core, from which at least three PEG-based polymeric chains extend. Accordingly, in a preferred aspect of the present invention the backbone moiety comprises a branching core, from which at least three PEG-based polymeric chains extend. Such branching cores may comprise in bound form poly- or oligoalcohols, preferably pentaerythritol, tripentaerythritol, hexaglycerine, sucrose, sorbitol, fructose, mannitol, glucose, cellulose, amyloses, starches, hydroxyalkyl starches, polyvinylalcohols, dextranes, hyualuronans, or branching cores may comprise in bound form poly- or oligoamines such as trilysine, tetralysine, pentalysine, hexylysine, hepta lysine, octalysine, nonalysine, decalysine, undecalysine, dedecalysine, tridecalysine, tetradecalysine, pentadecalysine or oligolysines, polyethyleneimines, polyvinylamines.

Preferably, the branching core extends three to sixteen PEG-based polymeric chains, more preferably four to eight. Preferred branching cores may comprise pentaerythritol, ornithine, diaminobuyric acid, trilysine, tetralysine, pentalysine, hexylysine, heptalysine or oligolysine, low-molecular weight PEI, hexaglycerine, tripentaerythritol in bound form. Preferably, the branching core extends three to sixteen PEG-based polymeric chains, more preferably four to eight. Preferably, a PEG-based polymeric chain is a suitably substituted poly(ethylene glycol) derivative.

Preferably, such PEG-based polymeric chain connected to a branching core is a linear poly(ethylene glycol) chain, of which one terminus is connected to the branching core and the other to a hyperbranched dendritic moiety. It is understood that a PEG-based chain may be terminated or interrupted by alkyl or aryl groups optionally substituted with heteroatoms and chemical functional groups.

Preferred structures comprising PEG-based polymeric chains extending from a branching core suitable for backbone moieties are multi-arm PEG derivatives as, for instance, detailed in the products list of JenKem Technology, USA (accessed by download from www.jenkemusa.com on Jul. 28, 2009), 4ARM-PEG Derivatives (pentaerythritol core), 8ARM-PEG Derivatives (hexaglycerin core) and 8ARM-PEG Derivatives (tripentaerythritol core). Most preferred are 4arm PEG Amine (pentaerythritol core) and 4arm PEG Carboxyl (pentaerythritol core), 8arm PEG Amine (hexaglycerin core), 8arm PEG Carboxyl (hexaglycerin core), 8arm PEG Amine (tripentaerythritol core) and 8arm PEG Carboxyl (tripentaerythritol core). Preferred molecular weights for such multi-arm PEG-derivatives in a backbone reagent are 1 kDa to 20 kDa, more preferably 1 kDa to 15 kDa and even more preferably 1 kDa to 10 kDa. It is understood that the terminal amine groups of the above mentioned multi-arm molecules are present in bound form in the backbone moiety to provide further interconnected functional groups and reactive functional groups of a backbone moiety.

Such additional functional groups may be provided by dendritic moieties. Preferably, each dendritic moiety has a molecular weight in the range of from 0.4 kDa to 4 kDa, more preferably 0.4 kDa to 2 kDa. Preferably, each dendritic moiety has at least 3 branchings and at least 4 reactive functional groups, and at most 63 branchings and 64 reactive functional groups, preferred at least 7 branchings and at least 8 reactive functional groups and at most 31 branchings and 32 reactive functional groups.

Examples for such dendritic moieties comprise trilysine, tetralysine, pentalysine, hexylysine, heptalysine, octalysine, nonalysine, decalysine, undecalysine, dodecalysine, tridecalysine, tetradecalysine, pentadecalysine, hexadecalysine, heptadecalysine, octadecalysine, nonadecalysine in bound form. Examples for such preferred dendritic moieties comprise trilysine, tetralysine, pentalysine, hexylysine, heptalysine, most preferred trilysine, pentalysine or heptalysine in bound form.

It is preferred that the sum of interconnected functional groups and reactive functional groups of a backbone moiety is equally divided by the number of PEG-based polymeric chains extending from the branching core. For instance, if there are 32 interconnected functional groups and reactive functional groups, eight groups may be provided by each of the four PEG-based polymeric chains extending from the core, preferably by means of dendritic moieties attached to the terminus of each PEG-based polymeric chain. Alternatively, four groups may be provided by each of eight PEG-based polymeric chains extending from the core or two groups by each of sixteen PEG-based polymeric chains.

If the number of PEG-based polymeric chains extending from the branching core does not allow for an equal distribution, it is preferred that the deviation from the mean number of the sum of interconnected functional groups and reactive functional groups per PEG-based polymeric chain is kept to a minimum.

The reactive functional groups may serve as attachment points for direct or indirect linkage of an affinity ligand, chelating group, ion exchange group, a drug, prodrug, carrier-linked prodrug, blocking group, capping group, or the like.

Ideally, the reactive functional groups are dispersed homogeneously throughout the reactive biodegradable, and may or may not be present on the surface of the reactive biodegradable hydrogel. Non-limiting examples of such reactive functional groups include but are not limited to the following chemical functional groups connected to the hyperbranched dendritic moiety: carboxylic acid and activated derivatives, amino, maleimide, thiol and derivatives, sulfonic acid and derivatives, carbonate and derivatives, carbamate and derivatives, hydroxyl, aldehyde, ketone, hydrazine, isocyanate, isothiocyanate, phosphoric acid and derivatives, phosphonic acid and derivatives, haloacetyl, alkyl halides, acryloyl and other alpha-beta unsaturated michael acceptors, arylating agents like aryl fluorides, hydroxylamine, disulfides like pyridyl disulfide, vinyl sulfone, vinyl ketone, diazoalkanes, diazoacetyl compounds, oxirane, and aziridine. Preferred reactive functional groups include thiol, maleimide, amino, carboxylic acid and derivatives, carbonate and derivatives, carbamate and derivatives, aldehyde, and haloacetyl. Preferably, the reactive functional groups are primary amino groups or carboxylic acids, most preferred primary amino groups.

Such reactive functional groups are characterized by being chemoselectively addressable in the presence of other functional groups and further characterized in that the concentration of reactive functional groups in such reactive biodegradable hydrogels is almost constant during the first half of the time required for complete degradation of the reactive biodegradable hydrogel.

To be "almost constant" the weight concentration of said reactive functional groups does not fall below 90% of the original concentration within the first half of the time required for complete degradation of the reactive biodegradable hydrogel.

Reactive functional groups may be capped with suitable protecting reagents.

Most preferably, the reactive biodegradable hydrogel of the present invention is characterized in that the backbone moiety has a quarternary carbon of formula $C(A\text{-Hyp})_4$, wherein each A is independently a poly(ethylene glycol) based polymeric chain terminally attached to the quarternary carbon by a permanent covalent bond and the distal end of the PEG-based polymeric chain is covalently bound to a dendritic moiety Hyp, each dendritic moiety Hyp having at least four functional groups representing the interconnected and reactive functional groups.

Preferably, each A is independently selected from the formula $—(CH2)_{n1}(OCH2CH2)nX—$, wherein n1 is 1 or 2; n is an integer in the range of from 5 to 50; and X is a chemical functional group covalently linking A and Hyp.

Preferably, A and Hyp are covalently linked by an amide linkage.

Preferably, the dendritic moiety Hyp is a hyperbranched polypeptide. Preferably, the hyperbranched polypeptide is comprised of lysines in bound form. Preferably, each dendritic moiety Hyp has a molecular weight in the range of from 0.4 kDa to 4 kDa. It is understood that a backbone moiety $C(A\text{-Hyp})_4$ can consist of the same or different dendritic moieties Hyp and that each Hyp can be chosen independently. Each moiety Hyp consists of between 5 and 32 lysines, preferably of at least 7 lysines, i.e. each moiety Hyp is comprised of between 5 and 32 lysines in bound form, preferably of at least 7 lysines in bound form. Most preferably Hyp is comprised of heptalysinyl.

Preferably, there is a permanent amide bond between the hyperbranched dendritic moiety and the spacer moiety.

Preferably, $C(A\text{-Hyp})_4$ has a molecular weight in the range of from 1 kDa to 20 kDa, more preferably 1 kDa to 15 kDa and even more preferably 1 kDa to 10 kDa.

In a reactive biodegradable hydrogel according to the invention, a backbone moiety is characterized by a number of functional groups, consisting of interconnected biodegradable groups and reactive functional groups. Preferably, the sum of interconnected biodegradable groups and reactive functional groups is equal to or greater than 16, preferably 16-128, preferred 20-100, also preferred 20-40, more preferred 24-80, also more preferred 28-32 even more preferred 30-60; most preferred 30-32. It is understood that in addition to the interconnected functional groups and the reactive functional groups also protective groups may be present.

FIG. 3 gives a schematic overview of the different ways in which two backbone moieties may be interconnected in a reactive biodegradable hydrogel of the present invention. A hyperbranched dendritic moiety ("Hyp", oval) comprises a number of reactive functional groups (black dots) and a permanent linkage (white diamond). It is understood that each hyperbranched moiety comprises more reactive functional groups and permanent linkages than shown in FIG. 3 and that FIG. 3 is used for illustrative purposes only.

Spacer moieties are indicated with asterisks, interconnected functional groups are shown as white arrows. Dashed lines indicate the attachment to a larger moiety which is not shown.

FIG. 3a illustrates a section of a reactive biodegradable hydrogel in which individual backbone moieties are directly interconnected through an interconnected functional group comprising a biodegradable bond.

In FIG. 3b the hyperbranched dendritic moieties of two different backbone moieties are interconnected through two interconnected functional groups separated through a spacer moiety.

In FIG. 3c the hyperbranched dendritic moieties of two different backbone moieties are interconnected through two spacer moieties and one interconnected functional group.

FIGS. 3d and 3e show a section of a reactive biodegradable hydrogel in which two hyperbranched dendritic moieties are interconnected through crosslinker moieties, which are marked with "#". The crosslinker moieties may or may not comprise at least one interconnected functional group (see FIGS. 3d and 3e, respectively).

Thin black lines indicate PEG-based polymeric chains extending from a branching core (not shown).

Modified Reactive Biodegradable Hydrogel

Another aspect of the present invention is a conjugate comprising a modified reactive biodegradable hydrogel of the present invention, characterized by being composed of backbone moieties interconnected by hydrolytically degradable bonds and additionally carrying permanent linkages to spacer molecules, blocking groups, protecting groups, or multi-functional moieties.

The reactive functional groups of the backbone moieties of reactive biodegradable hydrogels serve as attachment points for spacer molecules, blocking groups, protecting groups, or multi-functional moieties.

Protecting groups are known in the art and are used for the reversible protection of chemical functional groups during synthesis processes. A suitable protecting group for amine functionalities is the fmoc group.

It is understood that only one type of protecting group or that two or more different protecting groups may be used, such as to provide for orthogonal protection, i.e. the different protecting groups may be removed under different conditions.

A modified reactive biodegradable hydrogel according to the invention may be functionalized with a spacer carrying the same reactive functional group. For instance, amino groups may be introduced into the modified reactive biodegradable hydrogel by coupling a heterobifunctional spacer, such as suitably activated COOH-(EG)$_6$-NH-fmoc (EG=ethylene glycol), and removing the fmoc-protecting group. Such reactive biodegradable hydrogel can be further connected to a spacer carrying a different functional group, such as a maleimide group. An accordingly modified reactive biodegradable hydrogel may be further conjugated to drug-linker reagents, which carry a reactive thiol group on the linker moiety.

In such modified reactive biodegradable hydrogel, all remaining reactive functional groups may be capped with suitable blocking reagents.

In an alternative embodiment of this invention, multi-functional moieties are coupled to the reactive functional groups of the polymerized reactive biodegradable hydrogel to increase the number of reactive functional groups which allows for instance increasing the drug load of the biodegradable hydrogel according to the invention. Such multi-functional moieties may be comprised of lysine, dilysine, trilysine, tetralysine, pentalysine, hexylysine, heptalysine, or oligolysine, low-molecular weight PEI in bound form. Preferably, the multi-functional moiety is comprised of lysines in bound form. Optionally, such multi-functional moiety may be protected with protecting groups.

In such modified reactive biodegradable hydrogel, all remaining reactive functional groups may be capped with suitable blocking reagents.

FIG. 4 shows a schematic drawing of a section of a modified reactive biodegradable hydrogel. A hyperbranched moiety (oval, "Hyp") comprises a number of reactive functional groups modified with spacer molecules or blocking groups (black dots with half-moon shaped structures). The thin black line indicates a PEG-based polymeric chain extending from a branching core (not shown), the thick black line indicates a spacer moiety, which is attached to the hyperbranched moiety though a permanent bond (white diamond). White arrows indicate interconnected functional groups.

Dashed lines indicate the attachment to a larger moiety, which was not fully drawn for simplicity.

Biodegradable Hydrogels Comprising Conjugate Functional Groups

Another aspect of the present invention is a conjugate comprising a biodegradable hydrogel of the present invention, characterized by being composed of backbone moieties interconnected by hydrolytically degradable bonds and additionally carrying permanent linkages to conjugate functional groups, comprising for example ligands or chelating groups or ion exchange groups. Accordingly, a biodegradable hydrogel comprising conjugate functional groups of the present invention comprises backbone moieties interconnected by hydrolytically degradable bonds and additionally carrying permanent linkages to conjugate functional groups, comprising for example ligands or chelating groups or ion exchange groups.

The reactive functional groups of the backbone moieties of reactive biodegradable hydrogels and modified reactive biodegradable hydrogels serve as attachment points for direct or indirect linkage of affinity ligands or chelating groups or ion exchange groups or a combination thereof. Ideally, the ligands or chelating groups or ion exchange groups are dispersed homogeneously throughout the hydrogel according to the invention, and may or may not be present on the surface of the hydrogel according to the invention.

Remaining reactive functional groups which are not connected to affinity ligand- or chelating- or ion exchange-groups, may be capped with suitable blocking reagents.

Such affinity ligands or chelating groups or ion exchange groups are characterized in that the concentration of affinity ligands or chelating groups or ion exchange groups in such hydrogels according to the invention is almost constant during the first half of the time required for complete degradation of the hydrogel according to the invention.

To be "almost constant" the weight concentration of said affinity ligands or chelating groups or ion exchange groups does not fall below 90% of the original concentration within the first half of the time required for complete degradation of the hydrogel according to the invention.

In a hydrogel carrying affinity ligands or chelating groups or ion exchange groups according to the invention, a backbone moiety is characterized by a number of functional groups, consisting of interconnected functional groups and conjugate functional groups comprising affinity ligands or chelating groups or ion exchange groups. Preferably, the sum of interconnected functional groups and conjugate functional groups carrying affinity ligands or chelating groups or ion exchange groups is 16-128, preferred 20-100, more preferred 24-80 and most preferred 30-60. It is understood that in addition to the interconnected functional groups and the reactive functional groups also blocking groups may be present.

Preferably, the sum of interconnected functional groups and conjugate functional groups carrying affinity ligands or chelating groups or ion exchange groups of a backbone moiety is equally divided by the number of PEG-based polymeric chains extending from the branching core. For instance, if there are 32 interconnected functional groups and conjugate functional groups carrying affinity ligands or chelating groups or ion exchange groups, eight groups may be provided by each of the four PEG-based polymeric chains extending from the core, preferably by means of dendritic moieties attached to the terminus of each PEG-based polymeric chain. Alternatively, four groups may be provided by each of eight PEG-based polymeric chains extending from the core or two groups by each of sixteen PEG-based polymeric chains. If the number of PEG-based polymeric chains extending from the branching core does not allow for an equal distribution, it is preferred that the deviation from the mean number of the sum of interconnected functional groups and conjugate functional groups carrying affinity ligands or chelating groups or ion exchange groups per PEG-based polymeric chain is kept to a minimum.

Also preferably, the sum of interconnected biodegradable functional groups and permanent linkages to conjugate functional groups carrying ligands or chelating groups or ion exchange groups, or optionally spacer molecules, or blocking groups is equal to or greater than 16, preferred 20-40, more preferred 28-32 and most preferred 30-32.

In the simplest case, a hydrogel carrying ion exchange groups is identical with a reactive biodegradable hydrogel.

Suitable ligands present in bound form in a biodegradable hydrogels comprising conjugate functional groups of the invention are e.g. affinity ligands like biotin. Further ligands are for example affinity ligands like: 4-Aminobenzamidine, 3-(2'-Aminobenzhydryloxy)tropane, ε-Aminocaproyl-p-chlorobenzylamide, 1-Amino-4-[3-(4,6-dichlorotriazin-2-ylamino)-4-sulfophenylamino]anthraquinone-2-sulfonic acid, 2-(2'-Amino-4'-methylphenylthio)-N,N-dimethylbenzylamine dihydrochloride, Angiopoietin-1, aptamers, arotinoid acid, avidin, biotin, calmodulin, cocaethylene, cytosporone B, N,N-Dihexyl-2-(4-fluorophenyl)indole-3-acetamide, N,N-Dipropyl-2-(4-chlorophenyl)-6,8-dichloroimidazo[1,2-a]pyridine-3-acetamide, 5-Fluoro-2'-deoxyuridine 5'-(p-aminophenyl)monophosphate, S-Hexyl-L-glutathione, (S,S)-4-Phenyl-α-(4-phenyloxazolidin-2-ylidene)-2-oxazoline-2-acetonitrile, Pro-Leu-Gly hydroxamate, 2-(4-(2-(trifluoromethyl)phenyl)piperidine-1-carboxamido)benzoic acid, Trimethyl(m-aminophenyl)ammonium chloride, Urocortin III, cofactors like adenosin triphosphate, s-adenosyl methionine, ascorbic acid, cobalamine, coenzyme A, coenzyme B, coenzyme M, coenzyme Q, coenzyme F420, cytidine triphosphate, flavin mononucleotide, flavin adenine dinucleotide, glutathion, heme, lipoamide, menaquinone, methanofuran, methylcobalamine, molybdopterin, NAD+, NADP+, nucleotide sugars, 3'-phosphoadenosine-5'-phosphosulfate, pyridoxal phosphate, polyhistidines, pyrroloquinoline quinone, riboflavin, streptavidin, tetrahydrobiopterin, tetrahydromethanopterin, tetrahydrofolic acid, biotin carboxyl carrier protein (BCCP), chitin binding protein, FK506 binding proteins (FKBP), FLAG tag, green fluorescent protein, glutathion-S-transferase, hemagglutinin (HA), maltose binding protein, myc tag, NusA, protein C epitope, S-tag, strep-tag, thioredoxins, triazines—preferably 2,4,6-trisubstituted triazines—, affinity scaffold proteins such as antibody fragments Suitable chelating groups present in bound form in a biodegradable hydrogel comprising conjugate functional groups of the invention are e.g. ionic groups capable of interacting with a substrate like in the form of an ion exchange material. Other examples of chelating groups are complexing, groups. Different types of chelating groups are for example 2,2'-bipyridyl, 1,2-bis(2-aminophenoxy)ethane-N,N,N',N'-tetraacetic acid, deferoxamine mesylate, deferriferrichrome, diethylenetriamine, 2,3-dimercapto-1-propanol, dimercaptosuccinic acid, dimethylglyoxine, 2,2'-dipyridyl, Ethylene diamine, ethylenediaminetetra(methylenephosphonic acid), 1,2-Bis(2-amino-5-bromophenoxy)ethane-N,N,N',N'-tetraacetic acid, 8-hydroxychinoline, iminodiacetate, iminodi(methylphosphonic acid), L-mimosine, nitrilotriacetate, oxalate, 1,10-phenantroline, phytic acid, tartrate, 1,4,7,10-tetraazacyclododecane-1,4,7,10-tetraacetate, N,N,N',N'-tetrakis(2-pyridylmethyl)ethylenediamine, triaminotriethylamine, iminodiacetic acid, thiourea, 2-picolylamine.

Ion-exchange groups present in bound form in a biodegradable hydrogel comprising conjugate functional groups of the invention are chemical functional groups commonly used attached to ion exchange resins, such as strongly acidic groups, for instance sulfonic acid groups, e.g. propylsulfonic acid; strongly basic groups, such as quaternary amino groups, for example trimethylammonium groups, e.g. propyltrimethylammonium chloride; weakly acidic groups, e.g. alkyl carboxylic acid groups; or weakly basic groups, such as primary, secondary, and/or ternary alkyl amino groups.

FIG. 5 shows a schematic drawing of a relevant section of a hydrogel comprising conjugate functional groups. A hyperbranched moiety (oval, "Hyp") comprises a number of permanent bonds (white diamonds) to either conjugates such as affinity ligands or chelating groups (black ovals) or a spacer moiety (thick black line). Asterisks indicate the spacer moiety; #indicate crosslinker moieties; dashed lines indicate the attachment to a larger moiety which is not shown. Thin black line indicates a PEG-based polymeric chain extending from a branching core (not shown).

Hydrogel Prodrugs

Another aspect of the present invention is a carrier-linked prodrug comprising a biodegradable hydrogel of the present invention as carrier, wherein a number of permanent linkages of the backbone moieties exist with a transient prodrug linker to which a biologically active moiety is covalently attached.

A "prodrug" is any compound that undergoes biotransformation before exhibiting its pharmacological effects. Prodrugs can thus be viewed as drugs containing specialized non-toxic protective groups used in a transient manner to alter or to eliminate undesirable properties in the parent molecule. This clearly also includes the enhancement of desirable properties in the drug and the suppression of undesirable properties.

The terms "carrier-linked prodrug", "carrier prodrug" refer to a prodrug that contains a temporary linkage of a given active substance with a transient carrier group that produces improved physicochemical or pharmacokinetic properties and that can be easily removed in vivo, usually by a hydrolytic cleavage.

The reactive functional groups of a reactive biodegradable hydrogel or modified reactive biodegradable hydrogel serve as attachment points for direct linkage through the before mentioned permanent linkages of a drug, drug-linker conjugate, prodrug, carrier-linked prodrug or the like. Ideally, the hydrogel-connected drug-linker conjugates are dispersed homogeneously throughout the hydrogel, and may or may not be present on the surface of the hydrogel according to the invention.

Remaining reactive functional groups which are not connected to a transient prodrug linker or to a spacer connected to a transient prodrug linker may be capped with suitable blocking reagents.

Preferably, the covalent attachment formed between the reactive functional groups provided by the backbone moieties and the prodrug linker are permanent bonds. Suitable functional groups for attachment of the prodrug linker to the hydrogel according to the invention include but are not limited to carboxylic acid and derivatives, carbonate and derivatives, hydroxyl, hydrazine, hydroxylamine, maleamic acid and derivatives, ketone, amino, aldehyde, thiol and disulfide.

In a hydrogel carrying drug-linker conjugates according to the invention, a backbone moiety is characterized by a number of hydrogel-connected drug-linker conjugates; functional groups, comprising biodegradable interconnected functional groups; and optionally capping groups. Preferably, the sum of biodegradable interconnected functional groups, drug-linker conjugates and capping groups is 16-128, preferred 20-100, more preferred 24-80 and most preferred 30-60.

Preferably, the sum of interconnected functional groups, hydrogel-connected drug-linker conjugates and capping groups of a backbone moiety is equally divided by the number of PEG-based polymeric chains extending from the branching core. For instance, if there are 32 interconnected functional groups, hydrogel-connected drug-linker conjugates and capping groups, eight groups may be provided by each of the four PEG-based polymeric chains extending from the core, preferably by means of dendritic moieties attached to the terminus of each PEG-based polymeric chain. Alternatively, four functional groups may be provided by each of eight PEG-based polymeric chains extending from the core or two groups by each of sixteen PEG-based polymeric chains. If the number of PEG-based polymeric chains extending from the branching core does not allow for an equal distribution, it is preferred that the deviation from the mean number of the sum of interconnected functional groups, hydrogel-connected drug-linker conjugates and capping groups per PEG-based polymeric chain is kept to a minimum.

In such carrier-linked prodrugs according to the invention, it is desirable that almost all drug release (>90%) has occurred before a significant amount of release of the backbone moieties (<10%) has taken place. This can be achieved by adjusting the carrier-linked prodrug's half-life versus the hydrogel degradation kinetics.

It is preferred for the linking agent to form a reversible linkage to the biologically active moiety, preferably in such a fashion that after cleavage of the linker, the biologically active moiety is released in an unmodified form. A variety of different linking agents or linking groups that may be applied for this purpose are described by B. Testa et al. (B. Testa, J. Mayer, Hydrolysis in Drug and Prodrug Metabolism, Wiley-VCH, 2003).

"Linker", "linking group", "linker structure" or "linking agent" refers to the moiety which on its one end is attached to the drug moiety through a reversible linkage and at another end is attached through a permanent bond to either a spacer molecule permanently attached to a hyperbranched dendritic moiety or is directly attached through a permanent bond to a hyperbranched dendritic moiety.

It is also preferred that the majority of the linker structure remains attached to the hydrogel according to the invention after cleavage of the biodegradable linkage with the biologically active moiety. If the linker is a cascade prodrug linker, it is preferred for the activating group to remain stably bound to the hydrogel according to the invention.

Preferably, the transient prodrug linker is attached to the biologically active moiety by an auto-cleavable functional group. Preferably, the linker has self-cleavable properties and as a consequence the hydrogel-linker-drug is a carrier-linked prodrug, capable of releasing drug from the conjugate and in such a way that the release is predominantly dependent upon the self-cleavage of the linker.

The terms "auto-cleavable" or "hydrolytically degradable" are used synonymously.

Preferably, the linkage between prodrug-linker and bioactive moiety is hydrolytically degradable under physiological conditions (aqueous buffer at pH 7.4, 37° C.) with half-lives ranging from one hour to three months, include, but are not limited to, aconityls, acetals, amides, carboxlic anhydrides, esters, imines, hydrazones, maleamic acid amides, ortho esters, phosphamides, phosphoesters, phosphosilyl esters, silyl esters, sulfonic esters, aromatic carbamates, combinations thereof, and the like. Preferred biodegradable linkages between prodrug linker and biologically active moieties not intended for transient linkage via a primary or aromatic amino group are esters, carbonates, phosphoesters and sulfonic acid esters and most preferred are esters or carbonates. Preferred biodegradable linkages between prodrug linker and biologically active moieties intended for transient linkage via a primary or aromatic amino group are amides or carbamates.

An "auto-cleavable functional group" comprises a hydrolytically degradable bond.

If the auto-cleavable linkage is formed together with a primary or aromatic amino group of the biologically active moiety, a carbamate or amide group is preferred.

After loading the drug-linker conjugate to the maleimido group-containing hydrogel according to the invention, all remaining functional groups are capped with suitable capping reagents to prevent undesired side-reactions.

FIG. 6 shows a schematic drawing of a relevant section of a hydrogel according to the invention comprising permanent linkages of the backbone moieties with a transient prodrug linker to which a biologically active moiety is covalently attached. A hyperbranched moiety (oval, "Hyp") comprises permanent bonds (white diamonds) to either the transient prodrug linker (black arrow) or a spacer moiety (thick black line). The thin black line indicates a PEG-based polymeric chain extending from a branching core (not shown). Dashed lines indicate the attachment to a larger moiety, which was not fully drawn.

FIG. 6a shows the direct linkage of a transient prodrug linker to the hyperbranched moiety, whereas FIG. 6b shows an indirect linkage of the transient prodrug linker to the hyperbranched moiety. In FIG. 6b the transient prodrug linker is coupled to the hyperbranched moiety through a spacer moiety (thick grey line), which is coupled to the transient prodrug linker through a permanent bond (white diamond). In each case, the drug moiety (large white circle) is coupled to the transient prodrug linker through a biodegradable linkage (white arrow).

Degradants—Water-Soluble Degradation Products

The degradation of the hydrogel according to the invention is a multi-step reaction where a multitude of degradable bonds is cleaved resulting in degradation products which may be water-soluble or water-insoluble. However water-insoluble degradation products may further comprise degradable bonds so that they can be cleaved in that water-soluble degradation products are obtained. These water-soluble degradation products may comprise one or more backbone moieties. It is understood that released backbone moieties may, for instance, be permanently conjugated to spacer or blocking or linker groups or affinity groups and/or prodrug linker degradation products and that also water-soluble degradation products may comprise degradable bonds.

The structures of the branching core, PEG-based polymeric chains, hyperbranched dendritic moieties and moieties attached to the hyperbranched dendritic moieties can be inferred from the corresponding descriptions provided in the sections covering the different hydrogels of the present invention. It is understood that the structure of a degradant depends on the type of hydrogel according to the invention undergoing degradation.

The total amount of backbone moieties can be measured in solution after complete degradation of the hydrogel according to the invention, and during degradation, fractions of soluble backbone degradation products can be separated from the insoluble hydrogel according to the invention and can be quantified without interference from other soluble degradation products released from the hydrogel according to the invention. A hydrogel object may be separated from excess water of buffer of physiological osmolality by sedimentation or centrifugation. Centrifugation may be performed in such way that the supernatant provides for at least 10% of the volume of the swollen hydrogel according to the invention. Soluble hydrogel degradation products remain in the aqueous supernatant after such sedimentation or centrifugation step.

Preferably, water-soluble degradation products may be separated from water-insoluble degradation products by filtration through 0.45 μm filters, after which the water-soluble degradation products can be found in the flow-through. Water-soluble degradation products may also be separated from water-insoluble degradation products by a combination of a centrifugation and a filtration step.

Water-soluble degradation products comprising one or more backbone moieties are detectable by subjecting aliquots of such supernatant to suitable separation and/or analytical methods. For instance the backbone moieties may carry groups that exhibit UV absorption at wavelengths where other degradation products do not exhibit UV absorption. Such selectively UV-absorbing groups may be structural components of the backbone moiety such as amide bonds or may be introduced into the backbone by attachment to its reactive functional groups by means of aromatic ring systems such as indoyl groups.

FIG. 7 shows a schematic drawing of different degradation products. The exemplary degradation product of FIG. 7a results from the degradation of a biodegradable hydrogel carrying conjugate functional groups. From a central branching core (C) extend four PEG-based polymeric chains (thin black lines), at which ends hyperbranched dendritic moieties ("Hyp"; ovals) are attached. Said hyperbranched dendritic moieties contain a number of permanent linkages (white diamonds) to either spacer moieties (asterisk) or to conjugates such as affinity ligands or chelating groups (black ovals). Dashed lines indicate the attachment to a larger moiety which is not shown.

The exemplary degradation product of FIG. 7b results from the degradation of a hydrogel carrying prodrugs. From a central branching core (C) extend four PEG-based polymeric chains (thin black lines), at which ends hyperbranched dendritic moieties ("Hyp"; ovals) are attached. Said hyperbranched dendritic moieties contain a number of permanent linkages to either spacer moieties (asterisk) or to spacer moieties (white rectangle) which are connected to transient prodrug linkers (black arrow). It is understood that said spacer moiety is optional and depends on hydrogel product. Dashed lines indicate the attachment to a larger moiety which is not shown.

It is understood that the hyperbranched dendritic moieties of the degradation products comprise more permanent linkages to spacer moieties, conjugates or transient prodrug linkers than shown in FIGS. 7a and 7b.

conjugate functional group; white diamond: permanent bonds; asterisk: spacer moiety connected to a backbone moiety and on the other side connected to a crosslinking moiety; #: crosslinker moiety; thin black line: PEG-based polymeric chain; dashed lines indicate the attachment to a larger moiety which is not shown.

Figure 6:
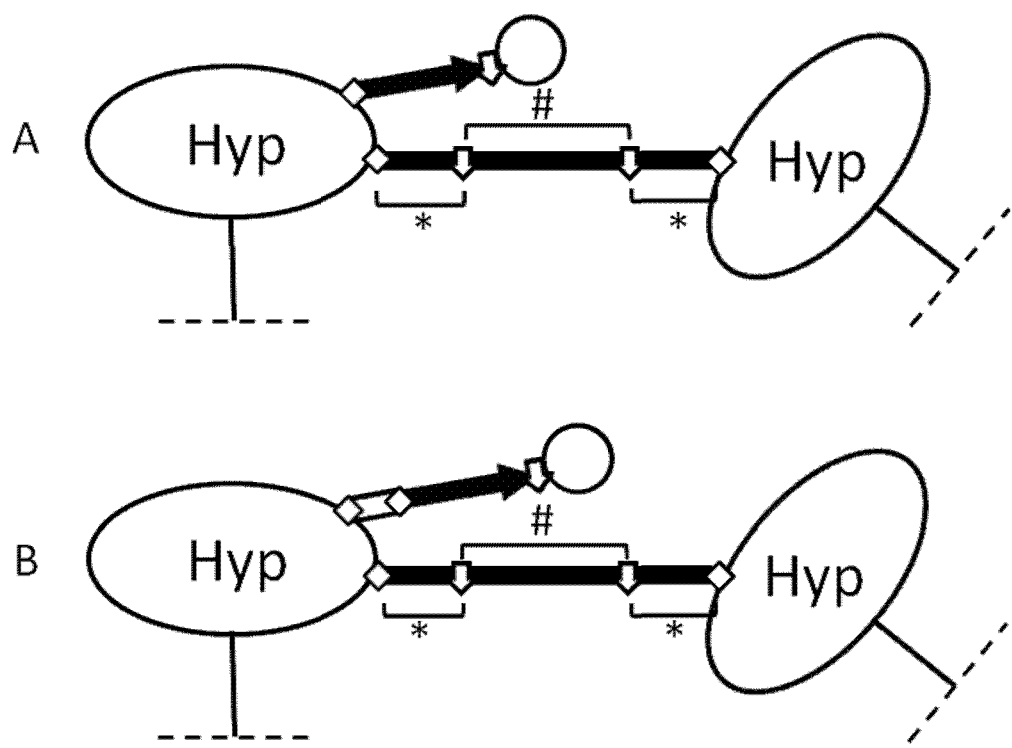

FIG. 6 shows a schematic drawing of a hydrogel comprising permanent linkages to transient prodrug linkers, either directly (FIG. 6a) or indirectly through a spacer moiety (FIG. 6b). "Hyp"/oval: hyperbranched dendritic moiety; white diamond: permanent bond; asterisk: spacer moiety connected to a backbone moiety and on the other side connected to a crosslinking moiety; white rectangle: spacer; white arrow: interconnected functional group; black arrow: linker; large white circle: drug; #: crosslinker moiety; dashed lines indicate the attachment to a larger moiety which is not shown.

Figure 7:
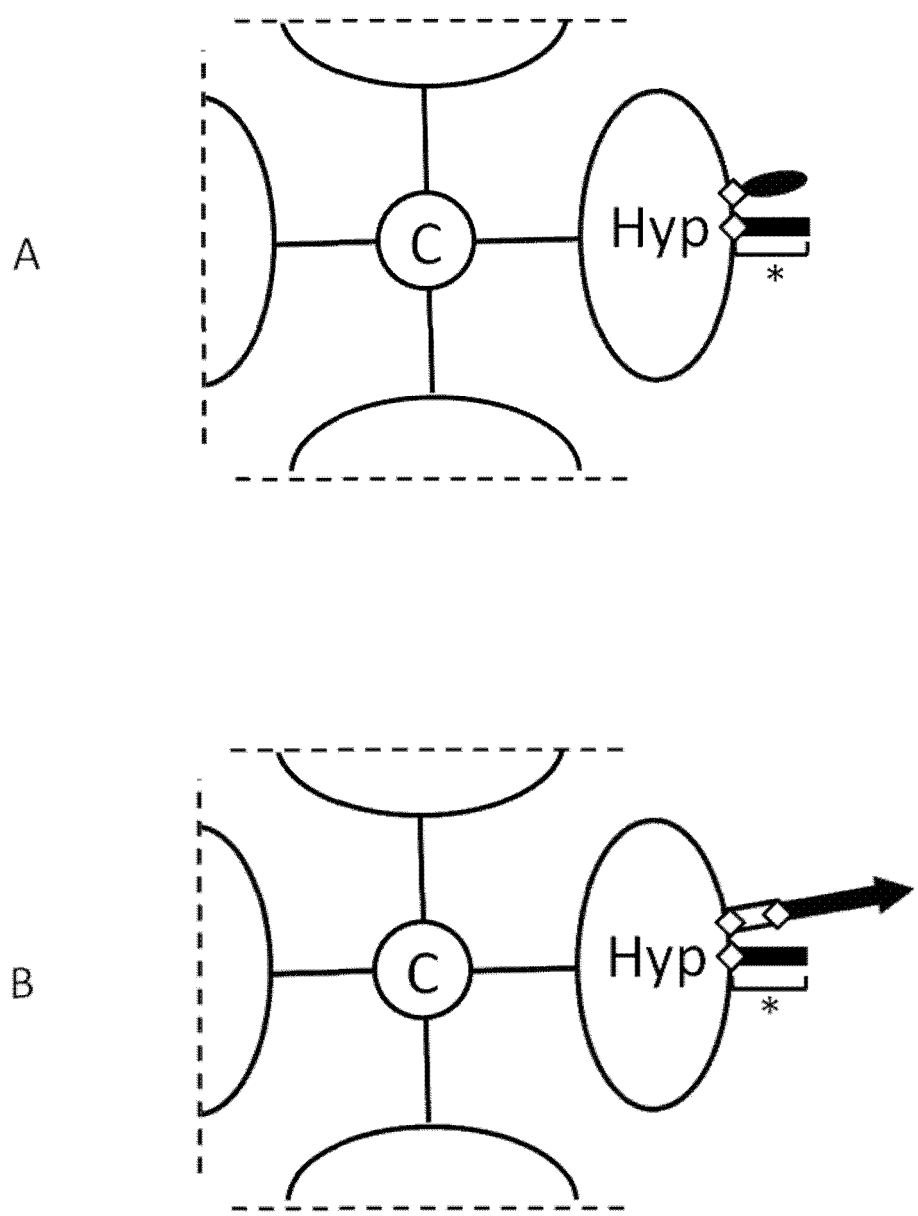

FIG. 7 shows schematic drawings of degradation products, either from the degradation of a biodegradable hydrogel comprising conjugate functional groups (FIG. 7a) or from the degradation of a hydrogel prodrug (FIG. 7b). (C): branching core; thin black line: PEG-based polymeric chain; "Hyp"/oval: hyperbranched dendritic moiety; white diamond: permanent bond; asterisk: spacer moiety connected to a backbone moiety and on the other side connected to a crosslinking moiety; black oval; conjugate functional group; whited rectangle: spacer; black arrow: linker; dashed lines indicate the attachment to a larger moiety which is not shown.

Figure 8:
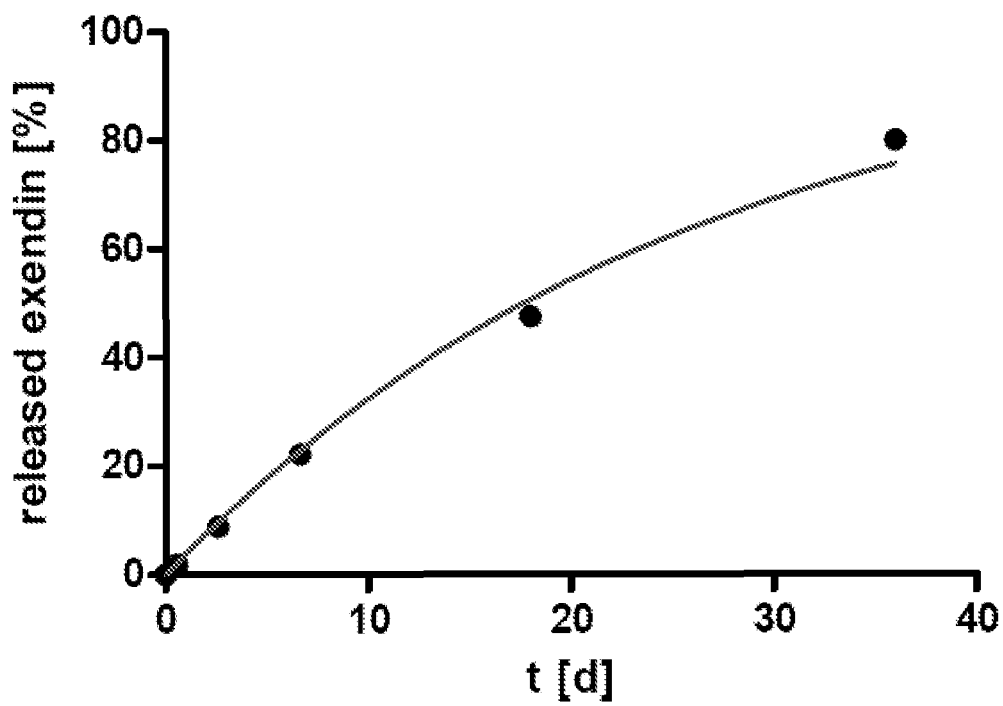

FIG. 8 shows the in vitro release kinetics of compound 9 at pH 7.4 and 37° C.

Figure 9:
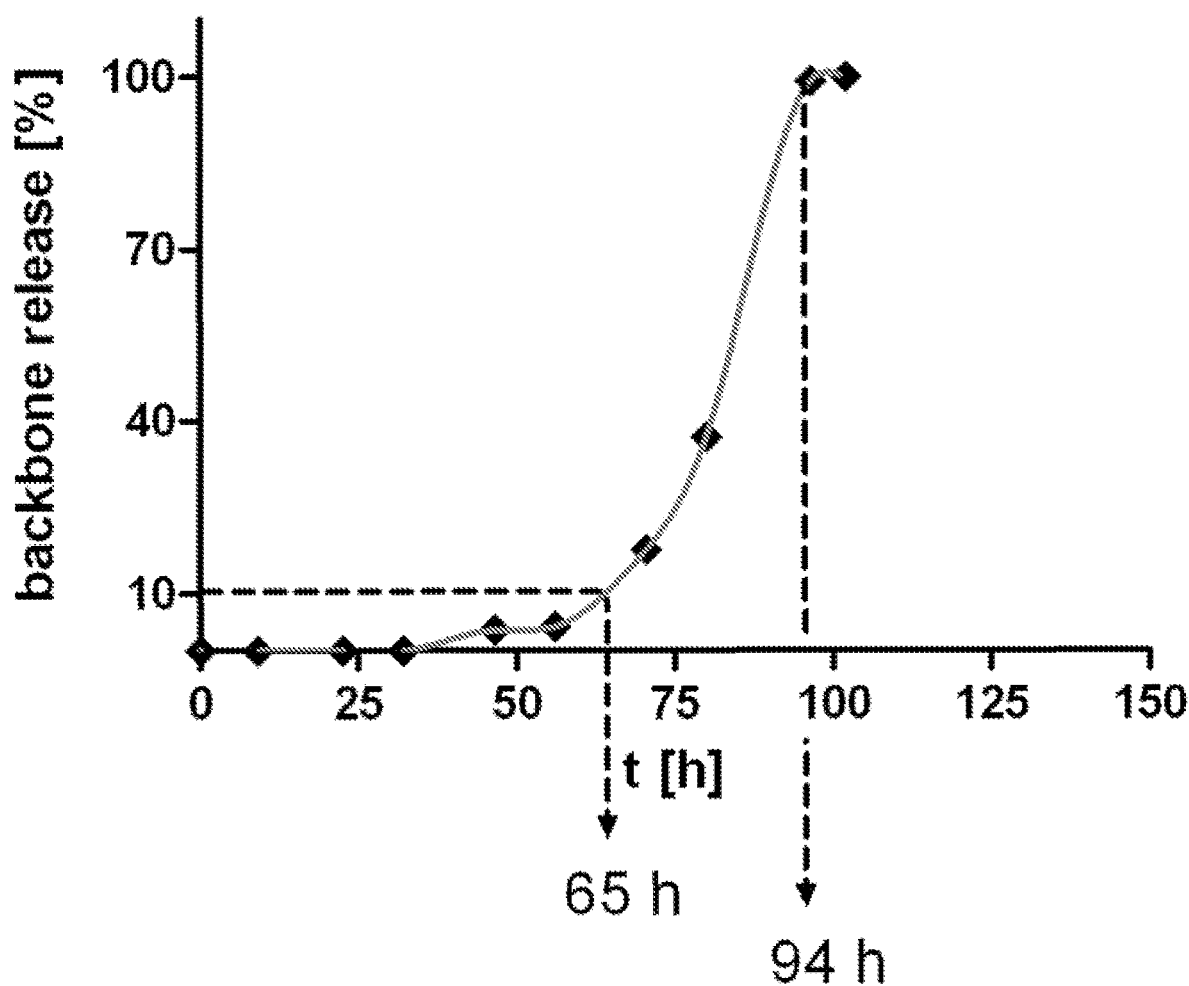

FIG. 9 shows an in vitro degradation of compound 15 at pH 9 and 37° C.

Figure 10:
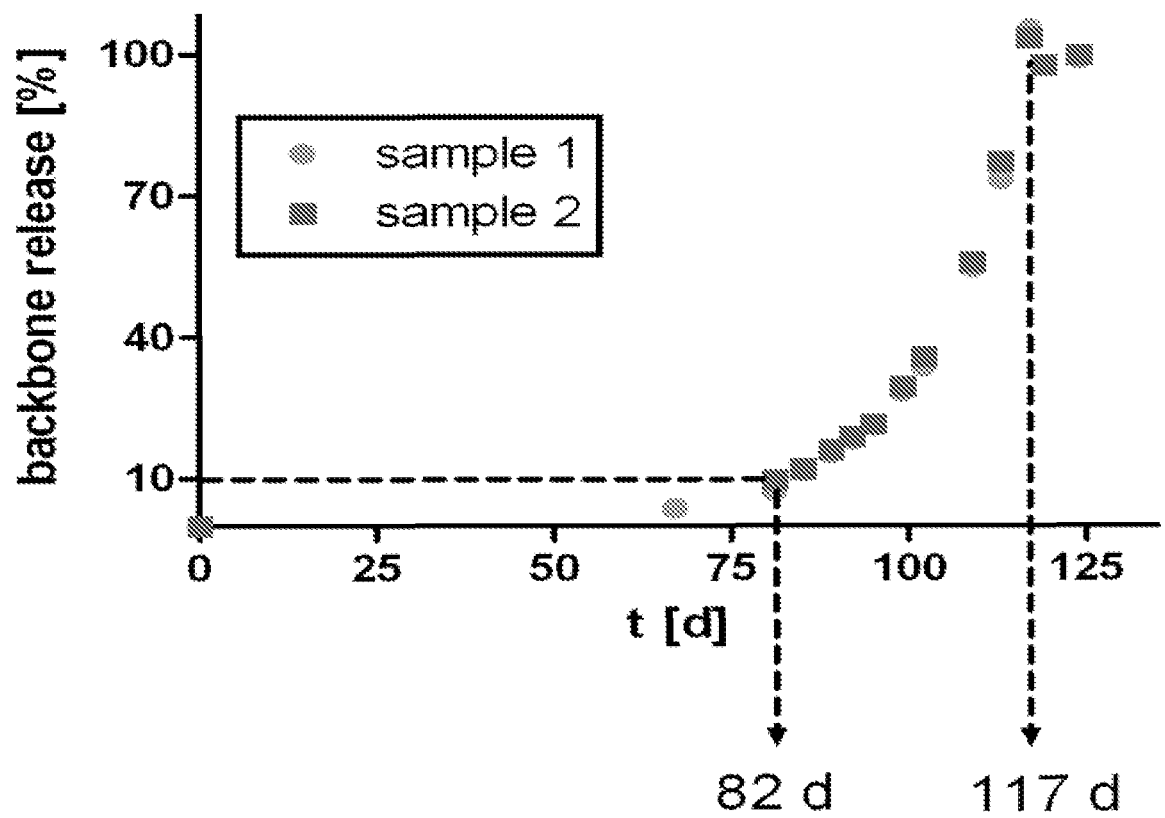

FIG. 10 shows an in vitro degradation of compound 15 (in duplicates) at pH 7.4 and 37° C.

Figure 11:
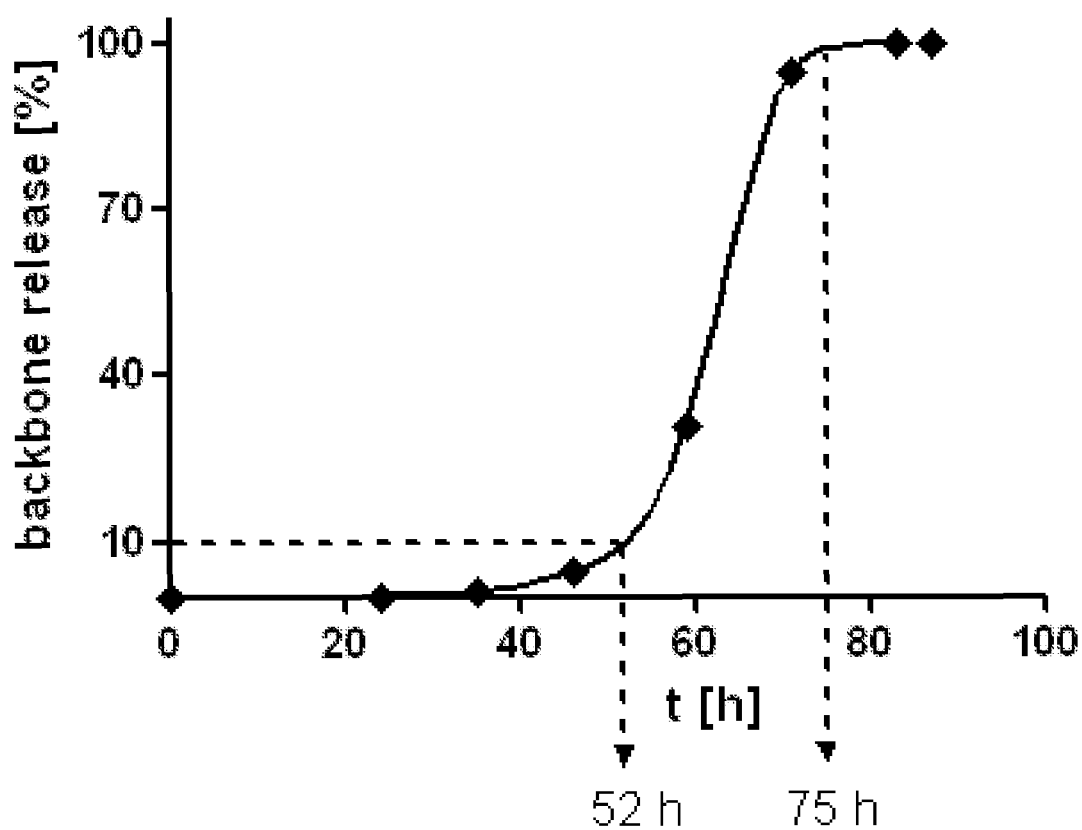

FIG. 11 shows an in vitro degradation of compound 5 at pH 9 and 37° C.

Figure 12:
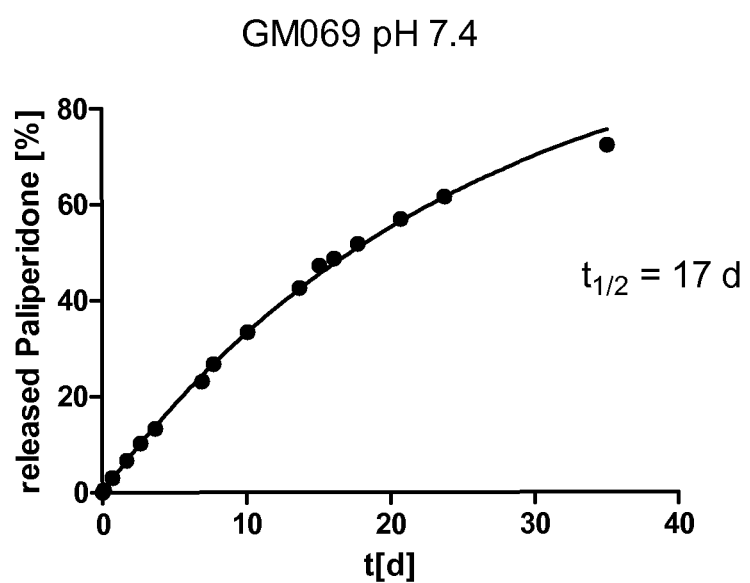

FIG. 12 shows an in vitro degradation of compound 19a at pH 9 and 37° C.

Figure 13:
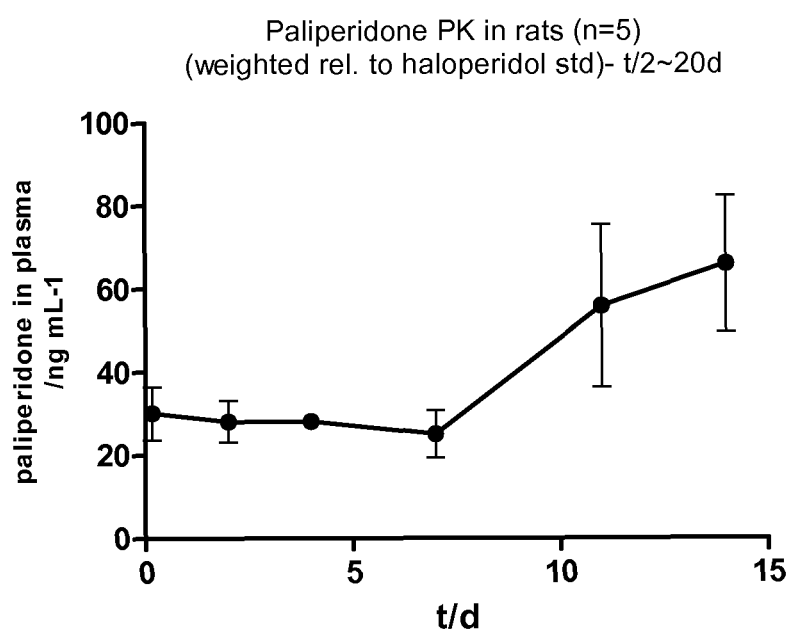

FIG. 13 shows the pharmacokinetics of compound 19c in rat.

Figure 14:
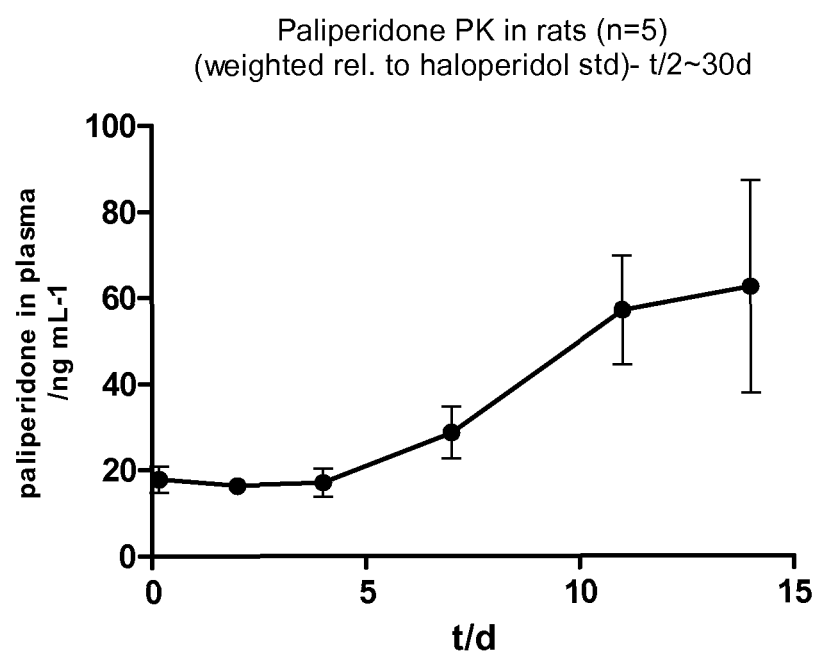

FIG. 14 shows the pharmacokinetics of compound 19e in rat.

Figure 15:
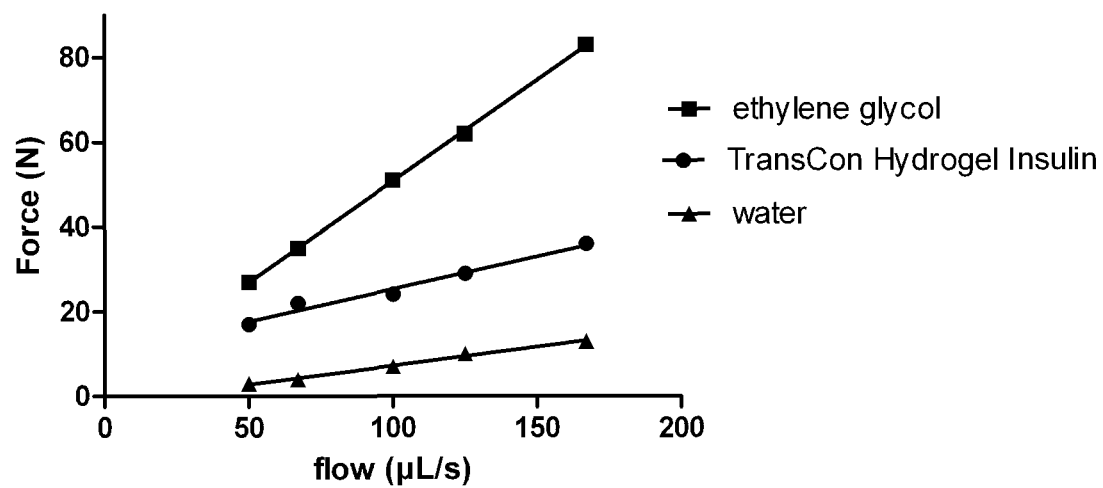

FIG. 15 shows a graph plotting force versus flow using a 30 G needle. Data points: black squares=ethylene glycol; black triangles=water; black dots=hydrogel insulin prodrug.

The present invention provides biodegradable poly(ethylene glycol) (PEG) based water-insoluble hydrogels. The term "PEG based" or "PEG-based" as understood herein means that the mass proportion of PEG chains in the hydrogel according to the invention is at least 10% by weight, preferably at least 25%, based on the total weight of the hydrogel according to the invention. The remainder can be made up of other polymers. The term "polymer" describes a molecule comprised of repeating structural units connected by chemical bonds in a linear, circular, branched, crosslinked or dendrimeric way or a combination thereof, which can be of synthetic or biological origin or a combination of both. Examples include, but are not limited, to poly(acrylic acids), poly(acrylates), poly(acrylamides), poly(alkyloxy)polymers, poly(amides), poly(amidoamines), poly(amino acids), poly(anhydrides), poly(aspartamide), poly(butyric acid), poly(caprolacton), poly(carbonates), poly(cyanoacrylates), poly(dimethylacrylamide), poly(esters), poly(ethylene), poly(ethylene glycol), poly(ethylene oxide), poly(ethyloxazoline), poly(glycolic acid), poly(hydroxyethyl acrylate), poly(hydroxyethyloxazoline), poly(hydroxypropylmethacrylamide), poly(hydroxypropyl methacrylate), poly(hydroxypropyloxazoline), poly(iminocarbonates), poly(N-isopropylacrylamide), polylactic acid), poly(lactic-co-glycolic acid), poly(methacrylamide), poly(methacrylates), poly(methyloxazoline), poly(propylene fumarate), poly(organophosphazenes), poly(ortho esters), poly(oxazolines), poly(propylene glycol), poly(siloxanes), poly(urethanes), poly(vinylalcohols), poly(vinylamines), poly(vinylmethylether), poly(vinylpyrrolidone), silicones, ribonucleic acids, desoxynucleic acid, albumins, antibodies and fragments thereof, blood plasma protein, collagens, elastin, fascin, fibrin, keratins, polyaspartate, polyglutamate, prolamins, transferrins, cytochromes, flavoprotein, glycoproteins, hemoproteins, lipoproteins, metalloproteins, phytochromes, phosphoproteins, opsins, agar, agarose, alginate, arabinans, arabinogalactans, carrageenan, cellulose, carbomethyl cellulose, hydroxypropyl methylcellulose and other carbohydrate-based polymers, chitosan, dextran, dextrin, gelatin, hyaluronic acid and derivatives, mannan, pectins, rhamnogalacturonans, starch, hydroxyalkyl starch, xylan, and copolymers and functionalized derivatives thereof.

If a polymer is present as a promoiety in a prodrug, it may be referred to by the term "carrier".

Moreover the term "water-insoluble" refers to a swellable three-dimensionally crosslinked molecular network forming the hydrogel according to the invention. The hydrogel according to the invention if suspended in a large surplus of water or aqueous buffer of physiological osmolality may take up a substantial amount of water, e.g. up to 10-fold on a weight per weight basis, and is therefore swellable but after removing excess water still retains the physical stability of a gel and a shape. Such shape may be of any geometry and it is understood that such an individual hydrogel object according to the invention is to be considered as a single molecule consisting of components wherein each component is connected to each other component through chemical bonds.

Starting Materials

Biodegradable hydrogels of the present invention may either be polymerized through radical polymerization, ionic polymerization or ligation reactions.

In case the biodegradable hydrogel of the present invention is processed through radical or ionic polymerization, the at least two starting materials for the biodegradable hydrogel of the present invention are crosslinking macromonomers or crosslinking monomers—which are referred to as crosslinker reagents—and a multi-functional macromonomer, which is referred to as backbone reagent. The crosslinker reagent carries at least two interconnectable functional groups and the backbone reagent carries at least one interconnectable functional group and at least one chemical functional group which is not intended to participate in the polymerization step. Additional diluent monomers may or may not be present.

Useful interconnectable functional groups include but are not limited to radically polymerizable groups like vinyl, vinyl-benzene, acrylate, acrylamide, methacylate, methacrylamide and ionically polymerizable groups like oxetane, aziridine, and oxirane.

In an alternative method of preparation, the biodegradable hydrogel according to the invention is generated through chemical ligation reactions. In such reactions, the starting material is at least one macromolecular starting material with complementary functionalities which undergo a reaction such as a condensation or addition reaction. In one alternative, only one macromolecular starting material is used, which is a heteromultifunctional backbone reagent, comprising a number of polymerizable functional groups.

Alternatively, in the case if two or more macromolecular starting materials one of these starting materials is a cross-linker reagent with at least two identical polymerizable functional groups and the other starting material is a homo-multifunctional or heteromultifunctional backbone reagent, also comprising a number of polymerizable functional groups.

Suitable polymerizable functional groups present on the crosslinker reagent include primary and secondary amino, carboxylic acid and derivatives, maleimide, thiol, hydroxyl and other alpha,beta unsaturated Michael acceptors such as vinylsulfone groups, preferably terminal primary or secondary amino, carboxylic acid and derivatives, maleimide, thiol, hydroxyl and other alpha,beta unsaturated Michael acceptors such as vinylsulfone groups. Suitable polymerizable functional groups present in the backbone reagent include but are not limited to primary and secondary amino, carboxylic acid and derivatives, maleimide, thiol, hydroxyl and other alpha,beta unsaturated Michael acceptors like vinylsulfone groups.

Preferentially, a backbone reagent is characterized by having a branching core, from which at least three PEG-based polymeric chains extend. Accordingly, in a preferred aspect of the present invention the backbone reagent comprises a branching core, from which at least three PEG-based polymeric chains extend. Such branching cores may be comprised of poly- or oligoalcohols in bound form, preferably pentaerythritol, tripentaerythritol, hexaglycerine, sucrose, sorbitol, fructose, mannitol, glucose, cellulose, amyloses, starches, hydroxyalkyl starches, polyvinylalcohols, dextranes, hyualuronans, or branching cores may be comprised of poly- or oligoamines such as ornithines, diaminobutyric acid, trilysine, tetralysine, pentalysine, hexylysine, heptalysine, octalysine, nonalysine, decalysine, undecalysine, dedecalysine, tridecalysine, tetradecalysine, pentadecalysine or oligolysines, polyethyleneimines, polyvinylamines in bound form.

Preferably, the branching core extends three to sixteen PEG-based polymeric chains, more preferably four to eight. Preferred branching cores may be comprised of pentaerythritol, trilysine, tetralysine, pentalysine, hexylysine, heptalysine or oligolysine, low-molecular weight PEI, hexaglycerine, tripentaerythritol in bound form. Preferably, the branching core extends three to sixteen PEG-based polymeric chains, more preferably four to eight. Preferably, a PEG-based polymeric chain is a suitably substituted poly(ethylene glycol) derivative.

Preferably, such PEG-based polymeric chain connected to a branching core is a linear poly(ethylene glycol) chain, of which one end is connected to the branching core and the other to a hyperbranched dendritic moiety. It is understood that a polymeric PEG-based chain may be terminated or interrupted by alkyl or aryl groups optionally substituted with heteroatoms and chemical functional groups.

If used in reference to a crosslinker reagent or a PEG-based polymeric chain connected to a branching core, the term "PEG-based" refers to a crosslinker moiety or PEG-based polymeric chain comprising at least 20 weight % ethylene glycol moieties.

Preferred structures comprising PEG-based polymeric chains extending from a branching core suitable for backbone reagents are multi-arm PEG derivatives as, for instance, detailed in the products list of JenKem Technology, USA (accessed by download from www.jenkemusa.com on Jul. 28, 2009), 4ARM-PEG Derivatives (pentaerythritol core), 8ARM-PEG Derivatives (hexaglycerin core) and 8ARM-PEG Derivatives (tripentaerythritol core). Most preferred are 4arm PEG Amine (pentaerythritol core) and 4arm PEG Carboxyl (pentaerythritol core), 8arm PEG Amine (hexaglycerin core), 8arm PEG Carboxyl (hexaglycerin core), 8arm PEG Amine (tripentaerythritol core) and 8arm PEG Carboxyl (tripentaerythritol core). Preferred molecular weights for such multi-arm PEG-derivatives in a backbone reagent are 1 kDa to 20 kDa, more preferably 1 kDa to 15 kDa and even more preferably 1 kDa to 10 kDa. It is understood that the terminal amine groups are further conjugated to provide interconnected and reactive functional groups of a backbone moiety.

The terms "branching core" and "core" are used interchangeably.

The hyperbranched dendritic moiety provides polymerizable functional groups. Preferably, each dendritic moiety has a molecular weight in the range of from 0.4 kDa to 4 kDa, more preferably 0.4 kDa to 2 kDa. Preferably, each dendritic moiety has at least 3 branchings and at least 4 polymerizable functional groups, and at most 63 branchings and 64 polymerizable functional groups, preferred at least 7 branchings and at least 8 polymerizable functional groups and at most 31 branchings and 32 polymerizable functional groups.

Examples for such dendritic moieties are trilysine, tetralysine, pentalysine, hexylysine, heptalysine, octalysine, nonalysine, decalysine, undecalysine, dodecalysine, tridecalysine, tetradecalysine, pentadecalysine, hexadecalysine, heptadecalysine, octadecalysine, nonadecalysine, ornithine, and diaminobutyric acid. Examples for such preferred dendritic moieties are trilysine, tetralysine, pentalysine, hexylysine, heptalysine, most preferred trilysine, pentalysine or heptalysine, ornithine, diaminobutyric acid in bound form.

The crosslinker reagent may be a linear or branched molecule and preferably is a linear molecule. If the crosslinker reagent has two polymerizable functional groups, it is referred to as a "linear crosslinker reagent", if the crosslinker reagent has more than two polymerizable functional groups it is considered to be a "branched crosslinker reagent".

A crosslinker reagent is terminated by two polymerizable functional groups and may comprise no biodegradable group or may comprise at least one biodegradable bond. Preferably, the crosslinker reagent comprises at least one biodegradable bond.

In one embodiment, a crosslinker reagent consists of a polymer. Preferably, crosslinker reagents have a molecular weight in the range of from 60 Da to 5 kDa, more preferably, from 0.5 kDa to 4 kDa, even more preferably from 1 kDa to 4 kDa, even more preferably from 1 kDa to 3 kDa.

In addition to oligomeric or polymeric crosslinking reagents, low-molecular weight crosslinking reagents may be used, especially when hydrophilic high-molecular weight backbone moieties are used for the formation of biodegradable hydrogels according to the invention.

In one embodiment, crosslinker reagent comprises monomers connected by biodegradable bonds. Such polymeric crosslinker reagents may contain up to 100 biodegradable bonds or more, depending on the molecular weight of the crosslinker reagent and the molecular weight of the monomer units. Examples for such crosslinker reagents may comprise poly(lactic acid) or poly(glycolic acid) based polymers.

Preferably, the crosslinker reagents are PEG based, preferably represented by only one PEG based molecular chain. Preferably, the poly(ethylene glycol) based crosslinker reagents are hydrocarbon chains comprising ethylene glycol units, wherein the poly(ethylene glycol) based crosslinker reagents comprise at least each methylene glycol units, and wherein m is an integer in the range of from 3 to 100, preferably from 10 to 70. Preferably, the poly(ethylene glycol) based crosslinker reagents have a molecular weight in the range of from 0.5 kDa to 5 kDa.

Figure 1:
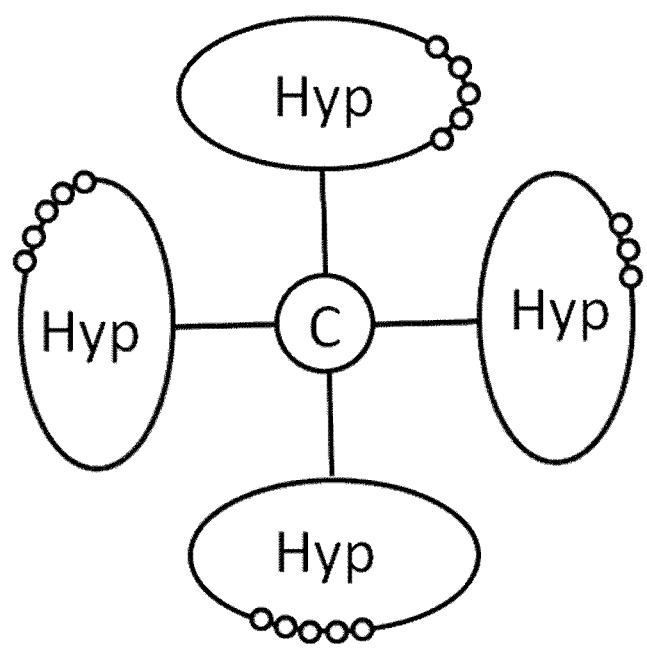
FIG. 1 shows an exemplary backbone reagent. (C): branching core; thin black line: PEG-based polymeric chain; "Hyp"/oval: hyperbranched dendritic moiety; small white circle: polymerizable functional groups; dashed lines indicate the attachment to a larger moiety which is not shown.

An example of a simplified backbone reagent is shown in FIG. 1 to illustrate the terminology used. From a central branching core (C) extend four PEG-based polymeric chains (thin black line), at which ends hyperbranched dendritic moieties ("Hyp"; ovals) are attached. The hyperbranched dendritic moieties carry polymerizable functional groups (small white circles), of which only a selection is shown, i.e. a hyperbranched dendritic moiety comprises more reactive functional groups than those shown in FIG. 1.

Figure 2:
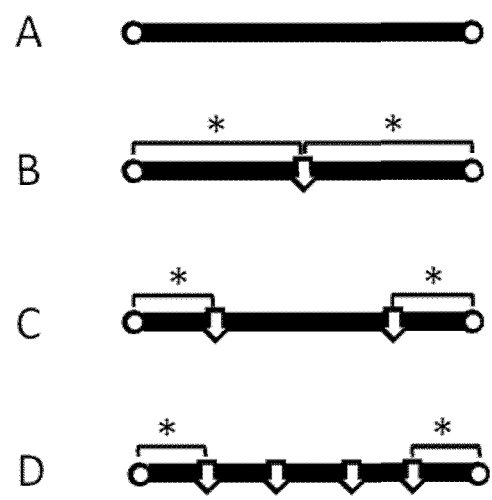
FIG. 2 shows exemplary crosslinker reagents. Small white circle: polymerizable functional group; white arrow: biodegradable linkage; asterisk: spacer moiety connected to a backbone moiety and on the other side connected to a crosslinking moiety.

FIG. 2 shows four exemplary crosslinker reagents. In addition to their polymerizable functional groups (small white circles), crosslinking reagents may comprises one or more biodegradable linkages (white arrows) which comprise a biodegradable bond.

Crosslinker reagent 2A comprises no biodegradable bond. If such crosslinker reagents are used for hydrogel synthesis according to the invention, biodegradable linkages are formed through the reaction of a polymerizable functional group of the crosslinker reagent with a polymerizable functional group of the backbone reagent.

Crosslinker reagent 2B comprises one biodegradable linkage, crosslinker reagent 2C comprises two biodegradable linkages and crosslinker reagent 2D comprises four biodegradable linkages.

The moiety between the polymerizable group and the first biodegradable bond is referred to as spacer moiety connected to a backbone moiety and on the other side connected to a crosslinking moiety and is indicated in the different crosslinker moieties by asterisks, where applicable.

Reactive Biodegradable Hydrogel

In one embodiment, the hydrogel according to the invention is a multi-functionalized material, i.e. a biodegradable hydrogel comprising reactive functional groups and interconnected functional groups in a three-dimensional cross-linked matrix swellable in water. Such hydrogel is also referred to as reactive biodegradable hydrogel. The reactive functional groups serve as attachment points for direct or indirect linkage of an affinity ligand, chelating group, ion exchange group, a drug, prodrug, carrier-linked prodrug, blocking group, capping group or the like.

Ideally, the reactive functional groups are dispersed homogeneously throughout the hydrogel according to the invention, and may or may not be present on the surface of the reactive biodegradable hydrogel. Non-limiting examples of such reactive functional groups include but are not limited to the following chemical functional groups connected to the hyperbranched dendritic moiety: carboxylic acid and activated derivatives, amino, maleimide, thiol and derivatives, sulfonic acid and derivatives, carbonate and derivatives, carbamate and derivatives, hydroxyl, aldehyde, ketone, hydrazine, isocyanate, isothiocyanate, phosphoric acid and derivatives, phosphonic acid and derivatives, haloacetyl, alkyl halides, acryloyl and other alpha-beta unsaturated michael acceptors, arylating agents like aryl fluorides, hydroxylamine, disulfides like pyridyl disulfide, vinyl sulfone, vinyl ketone, diazoalkanes, diazoacetyl compounds, oxirane, and aziridine. Preferred reactive functional groups include thiol, maleimide, amino, carboxylic acid and derivatives, carbonate and derivatives, carbamate and derivatives, aldehyde, and haloacetyl. Preferably, the reactive functional groups are primary amino groups or carboxylic acids, most preferred primary amino groups.

Such reactive functional groups are characterized by being chemoselectively addressable in the presence of other functional groups and further characterized in that the concentration of reactive functional groups in such reactive biodegradable hydrogels is almost constant during the first half of the time required for complete degradation of the hydrogel according to the invention.

To be "almost constant" the weight concentration of said reactive functional groups does not fall below 90% of the original concentration within the first half of the time required for complete degradation of the reactive biodegradable hydrogel.

Reactive functional groups may be capped with suitable protecting reagents.

According to this invention, the hydrogel is composed of backbone moieties interconnected by hydrolytically degradable bonds and the backbone moieties may be linked together through crosslinker moieties.

Preferably, the backbone moiety has a molecular weight in the range of from 1 kDa to 20 kDa, more preferably from 1 kDa to 15 kDa and even more preferably from 1 kDa to 10 kDa. The backbone moieties are preferably also PEG-based comprising one or more PEG chains.

It is understood that a polymeric PEG-based chain may be terminated or interrupted by alkyl or aryl groups optionally substituted with heteroatoms and chemical functional groups.

In a reactive biodegradable hydrogel according to the invention, a backbone moiety is characterized by a number of functional groups, consisting of interconnected biodegradable functional groups and reactive functional groups. Preferably, the sum of interconnected biodegradable functional groups and reactive functional groups is equal to or greater than 16, preferably 16-128, preferred 20-100, also preferred 20-40, more preferred 24-80, also more preferred 28-32 even more preferred 30-60; most preferred 30-32. It is understood that in addition to the interconnected functional groups and the reactive functional groups also protective groups may be present.

Preferentially, a backbone moiety is characterized by having a branching core, from which at least three PEG-based polymeric chains extend. Accordingly, in a preferred aspect of the present invention the backbone reagent comprises a branching core, from which at least three PEG-based polymeric chains extend. Such branching cores may be comprised of poly- or oligoalcohols in bound form, preferably pentaerythritol, tripentaerythritol, hexaglycerine, sucrose, sorbitol, fructose, mannitol, glucose, cellulose, amyloses, starches, hydroxyalkyl starches, polyvinylalcohols, dextranes, hyualuronans, or branching cores may be comprised of poly- or oligoamines such as ornithine, diaminobutyric acid, trilysine, tetralysine, pentalysine, hexylysine, heptalysine, octalysine, nonalysine, decalysine, undecalysine, dodecalysine, tridecalysine, tetradecalysine, pentadecalysine or oligolysines, polyethyleneimines, polyvinylamines in bound form.

Preferably, the branching core extends three to sixteen PEG-based polymeric chains, more preferably four to eight. Preferred branching cores may be comprised of pentaerythritol, ornithine, diaminobutyric acid, trilysine, tetra lysine, pentalysine, hexylysine, heptalysine or oligolysine, low-molecular weight PEI, hexaglycerine, tripentaerythritol in bound form. Preferably, the branching core extends three to sixteen PEG-based polymeric chains, more preferably four to eight. Preferably, a PEG-based polymeric chain is a linear poly(ethylene glycol) chain, of which one end is connected to the branching core and the other to a hyperbranched dendritic moiety. It is understood that a polymeric PEG-based chain may be terminated or interrupted by alkyl or aryl groups optionally substituted with heteroatoms and chemical functional groups.

Preferably, a PEG-based polymeric chain is a suitably substituted polyethylene glycol derivative (PEG based).

Preferred structures for corresponding PEG-based polymeric chains extending from a branching core contained in a backbone moiety are multi-arm PEG derivatives as, for instance, detailed in the products list of JenKem Technology, USA (accessed by download from www.jenkemusa.com on Jul. 28, 2009), 4ARM-PEG Derivatives (pentaerythritol core), 8ARM-PEG Derivatives (hexaglycerin core) and 8ARM-PEG Derivatives (tripentaerythritol core). Most preferred are 4arm PEG Amine (pentaerythritol core) and 4arm PEG Carboxyl (pentaerythritol core), 8arm PEG Amine (hexaglycerin core), 8arm PEG Carboxyl (hexaglycerin core), 8arm PEG Amine (tripentaerythritol core) and 8arm PEG Carboxyl (tripentaerythritol core). Preferred molecular weights for such multi-arm PEG-derivatives in a backbone moiety are 1 kDa to 20 kDa, more preferably 1 kDa to 15 kDa and even more preferably 1 kDa to 10 kDa. It is understood that the terminal amine groups are further conjugated to provide interconnected and reactive functional groups of a backbone moiety.

It is preferred that the sum of interconnected functional groups and reactive functional groups of a backbone moiety is equally divided by the number of PEG-based polymeric chains extending from the branching core. If the number of PEG-based polymeric chains extending from the branching core does not allow for an equal distribution, it is preferred that the deviation from the mean number of the sum of interconnected and reactive functional groups per PEG-based polymeric chain is kept to a minimum.

More preferably, the sum of interconnected and reactive functional groups of a backbone moiety is equally divided by the number of PEG-based polymeric chains extending from the branching core. For instance, if there are 32 interconnected functional groups and reactive functional groups, eight groups may be provided by each of the four PEG-based polymeric chains extending from the core, preferably by means of dendritic moieties attached to the terminus of each PEG-based polymeric chain. Alternatively, four groups may be provided by each of eight PEG-based polymeric chains extending from the core or two groups by each of sixteen PEG-based polymeric chains.

Such additional functional groups may be provided by dendritic moieties. Preferably, each dendritic moiety has a molecular weight in the range of from 0.4 kDa to 4 kDa, more preferably 0.4 kDa to 2 kDa. Preferably, each dendritic moiety has at least 3 branchings and at least 4 reactive functional groups, and at most 63 branchings and 64 reactive functional groups, preferred at least 7 branchings and at least 8 reactive functional groups and at most 31 branchings and 32 reactive functional groups.

Examples for such dendritic moieties are comprised of trilysine, tetralysine, pentalysine, hexylysine, heptalysine, octalysine, nonalysine, decalysine, undecalysine, dodecalysine, tridecalysine, tetradecalysine, pentadecalysine, hexadecalysine, heptadecalysine, octadecalysine, nonadecalysine in bound form. Examples for such preferred dendritic moieties are comprised of trilysine, tetralysine, pentalysine, hexylysine, heptalysine in bound form, most preferred trilysine, pentalysine or heptalysine, ornithine, diaminobutyric acid in bound form.

Most preferably, the reactive biodegradable hydrogel of the present invention is characterized in that the backbone moiety has a quarternary carbon of formula $C(A\text{-}Hyp)_4$, wherein each A is independently a poly(ethylene glycol) based polymeric chain terminally attached to the quarternary carbon by a permanent covalent bond and the distal end of the PEG-based polymeric chain is covalently bound to a dendritic moiety Hyp, each dendritic moiety Hyp having at least four functional groups representing the interconnected functional groups and reactive functional groups.

Preferably, each A is independently selected from the formula $-(CH_2)_{n1}(OCH_2CH_2)_n X-$, wherein n1 is 1 or 2; n is an integer in the range of from 5 to 50; and X is a chemical functional group covalently linking A and Hyp.

Preferably, A and Hyp are covalently linked by an amide linkage.

Preferably, the dendritic moiety Hyp is a hyperbranched polypeptide. Preferably, the hyperbranched polypeptide comprises lysine in bound form. Preferably, each dendritic moiety Hyp has a molecular weight in the range of from 0.4 kDa to 4 kDa. It is understood that a backbone moiety $C(A\text{-}Hyp)_4$ can consist of the same or different dendritic moieties Hyp and that each Hyp can be chosen independently. Each moiety Hyp consists of between 5 and 32 lysines, preferably of at least 7 lysines, i.e. each moiety Hyp is comprised of between 5 and 32 lysines in bound form, preferably of at least 7 lysines in bound form. Most preferably Hyp is comprised of heptalysinyl.

The reaction of polymerizable functional groups a backbone reagent, more specifically of Hyp with the polymerizable functional groups of polyethyleneglycol based crosslinker reagents results in a permanent amide bond.

Preferably, $C(A\text{-}Hyp)_4$ has a molecular weight in the range of from 1 kDa to 20 kDa, more preferably 1 kDa to 15 kDa and even more preferably 1 kDa to 10 kDa.

One preferred backbone moiety is shown below, dashed lines indicate interconnecting biodegradable linkages to crosslinker moieties and n is an integer of from 5 to 50:

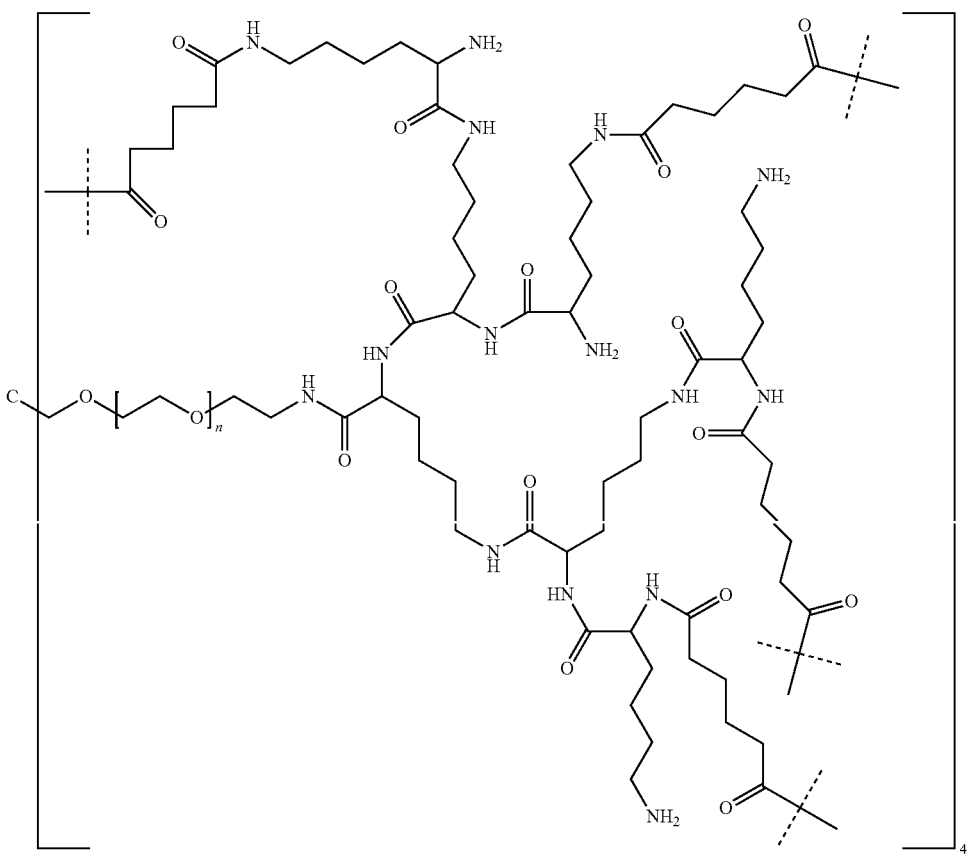

Biodegradability of the hydrogels according to the present invention is achieved by introduction of hydrolytically degradable bonds.

The terms "hydrolytically degradable", "biodegradable" or "hydrolytically cleavable", "auto-cleavable", or "self-cleavage", "self-cleavable", "transient" or "temporary" refers within the context of the present invention to bonds and linkages which are non-enzymatically hydrolytically degradable or cleavable under physiological conditions (aqueous buffer at pH 7.4, 37° C.) with half-lives ranging from one hour to three months, including, but are not limited to, aconityls, acetals, amides, carboxylic anhydrides, esters, imines, hydrazones, maleamic acid amides, ortho esters, phosphamides, phosphoesters, phosphosilyl esters, silyl esters, sulfonic esters, aromatic carbamates, combinations thereof, and the like.

If present in a hydrogel according to the invention as degradable interconnected functional group, preferred biodegradable linkages are esters, carbonates, phosphoesters and sulfonic acid esters and most preferred are esters or carbonates.

Permanent linkages are non-enzymatically hydrolytically degradable under physiological conditions (aqueous buffer at pH 7.4, 37° C.) with half-lives of six months or longer, such as, for example, amides.

To introduce the hydrolytically cleavable bonds, the backbone moieties can be directly linked to each other by means of biodegradable bonds.

In one embodiment, the backbone moieties of the reactive biodegradable hydrogel may be linked together directly, i.e. without crosslinker moieties. The hyperbranched dendritic moieties of two backbone moieties of such reactive biodegradable hydrogel may either be directly linked through an interconnected functional group that connects the two hyperbranched dendritic moieties. Alternatively, two hyperbranched dendritic moieties of two different backbone moieties may be interconnected through two spacer moieties connected to a backbone moiety and on the other side connected to a crosslinking moiety separated by interconnected functional groups.

Alternatively, backbone moieties may be linked together through crosslinker moieties, each crosslinker moiety is terminated by at least two of the hydrolytically degradable bonds. In addition to the terminating degradable bonds, the crosslinker moieties may contain further biodegradable bonds. Thus, each end of the crosslinker moiety linked to a backbone moiety comprises a hydrolytically degradable bond, and additional biodegradable bonds may optionally be present in the crosslinker moiety.

Preferably, the reactive biodegradable hydrogel is composed of backbone moieties interconnected by hydrolytically degradable bonds and the backbone moieties are linked together through crosslinker moieties.

The reactive biodegradable hydrogel may contain one or more different types of crosslinker moieties, preferably one. The crosslinker moiety may be a linear or branched molecule and preferably is a linear molecule. In a preferred embodiment of the invention, the crosslinker moiety is connected to backbone moieties by at least two biodegradable bonds.

The term biodegradable bond describes linkages that are non-enzymatically hydrolytically degradable under physiological conditions (aqueous buffer at pH 7.4, 37° C.) with half-lives ranging from one hour to three months, include, but are not limited to, aconityls, acetals, carboxylic anhydrides, esters, imines, hydrazones, maleamic acid amides, ortho esters, phosphamides, phosphoesters, phosphosilyl esters, silyl esters, sulfonic esters, aromatic carbamates, combinations thereof, and the like. Preferred biodegradable linkages are esters, carbonates, phosphoesters and sulfonic acid esters and most preferred are esters or carbonates.

Preferably, crosslinker moieties have a molecular weight in the range of from 60 Da to 5 kDa, more preferably, from 0.5 kDa to 4 kDa, even more preferably from 1 kDa to 4 kDa, even more preferably from 1 kDa to 3 kDa. In one embodiment, a crosslinker moiety consists of a polymer.

In addition to oligomeric or polymeric crosslinking moieties, low-molecular weight crosslinking moieties may be used, especially when hydrophilic high-molecular weight backbone moieties are used for the formation of a biodegradable hydrogel according to the invention.

Preferably, the poly(ethylene glycol) based crosslinker moieties are hydrocarbon chains comprising ethylene glycol units, optionally comprising further chemical functional groups, wherein the poly(ethylene glycol) based crosslinker moieties comprise at least each methylene glycol units, wherein m is an integer in the range of from 3 to 100, preferably from 10 to 70. Preferably, the poly(ethylene glycol) based crosslinker moieties have a molecular weight in the range of from 0.5 kDa to 5 kDa.

If used in reference to a crosslinker moiety or a PEG-based polymeric chain connected to a branching core, the term "PEG-based" refers to a crosslinker moiety or PEG-based polymeric chain comprising at least 20 weight % ethylene glycol moieties.

In one embodiment, monomers constituting the polymeric crosslinker moieties are connected by biodegradable bonds. Such polymeric crosslinker moieties may contain up to 100 biodegradable bonds or more, depending on the molecular weight of the crosslinker moiety and the molecular weight of the monomer units. Examples for such crosslinker moieties are poly(lactic acid) or poly(glycolic acid) based polymers. It is understood that such poly(lactic acid) or poly(glycolic acid) chain may be terminated or interrupted by alkyl or aryl groups and that they may optionally be substituted with heteroatoms and chemical functional groups.

Preferably, the crosslinker moieties are PEG based, preferably represented by only one PEG based molecular chain. Preferably, the poly(ethylene glycol) based crosslinker moieties are hydrocarbon chains comprising ethylene glycol units, optionally comprising further chemical functional groups, wherein the poly(ethylene glycol) based crosslinker moieties comprise at least each methylene glycol units, wherein m is an integer in the range of from 3 to 100, preferably from 10 to 70. Preferably, the poly(ethylene glycol) based crosslinker moieties have a molecular weight in the range of from 0.5 kDa to 5 kDa.

In a preferred embodiment of the present invention the crosslinker moiety consists of PEG, which is symmetrically connected through ester bonds to two alpha, omega-aliphatic dicarboxylic spacers provided by backbone moieties connected to the hyperbranched dendritic moiety through permanent amide bonds.

The dicarboxylic acids of the spacer moieties connected to a backbone moiety and on the other side is connected to a crosslinking moiety consist of 3 to 12 carbon atoms, most preferably between 5 and 8 carbon atoms and may be substituted at one or more carbon atom. Preferred substituents are alkyl groups, hydroxyl groups or amido groups or substituted amino groups. One or more of the aliphatic dicarboxylic acid's methylene groups may optionally be substituted by O or NH or alkyl-substituted N. Preferred alkyl is linear or branched alkyl with 1 to 6 carbon atoms.

Preferably, there is a permanent amide bond between the hyperbranched dendritic moiety and the spacer moiety connected to a backbone moiety and on the other side is connected to a crosslinking moiety.

One preferred crosslinker moiety is shown below; dashed lines indicate interconnecting biodegradable linkages to backbone moieties:

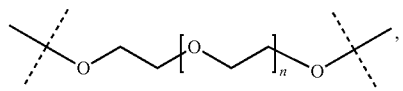

wherein n is an integer of from 5 to 50.

In reactive biodegradable hydrogels, the hydrolysis rate of the biodegradable bonds between backbone moieties and crosslinker moieties is influenced or determined by the number and type of connected atoms adjacent to the PEG-ester carboxy group. For instance, by selecting from succinic, adipic or glutaric acid for PEG ester formation it is possible to vary the degradation half-lives of the biodegradable hydrogel according to the invention.

In a reactive biodegradable hydrogel the presence of reactive functional groups can be quantified according to methods well known in the art, e.g. for solid phase peptide synthesis. Such presence of reactive functional groups in a water-insoluble hydrogel can be quantified as loading in mol of functional group per gram of reactive biodegradable hydrogel.

Amino group content of hydrogel can be determined by conjugation of a fmoc-amino acid to the free amino groups on the hydrogel and subsequent fmoc-determination as described by Gude, M., J. Ryf, et al. (2002) *Letters in Peptide Science* 9(4): 203-206.

For determination of maleimide content, an aliquot of hydrogel beads can be lyophilized and weighed out. Another aliquot of hydrogel can be reacted with excess mercaptoethanol (in 50 mM sodium phosphate buffer, 30 min at RT), and mercaptoethanol consumption can be detected by Ellman test (Ellman, G. L. et al., *Biochem. Pharmacol.,* 1961, 7, 88-95).

Preferably, in a reactive biodegradable hydrogel the loading is between 0.02 to 2 mmol/g, more preferably, 0.05 to mol/g reactive biodegradable hydrogel.

Figure 3:
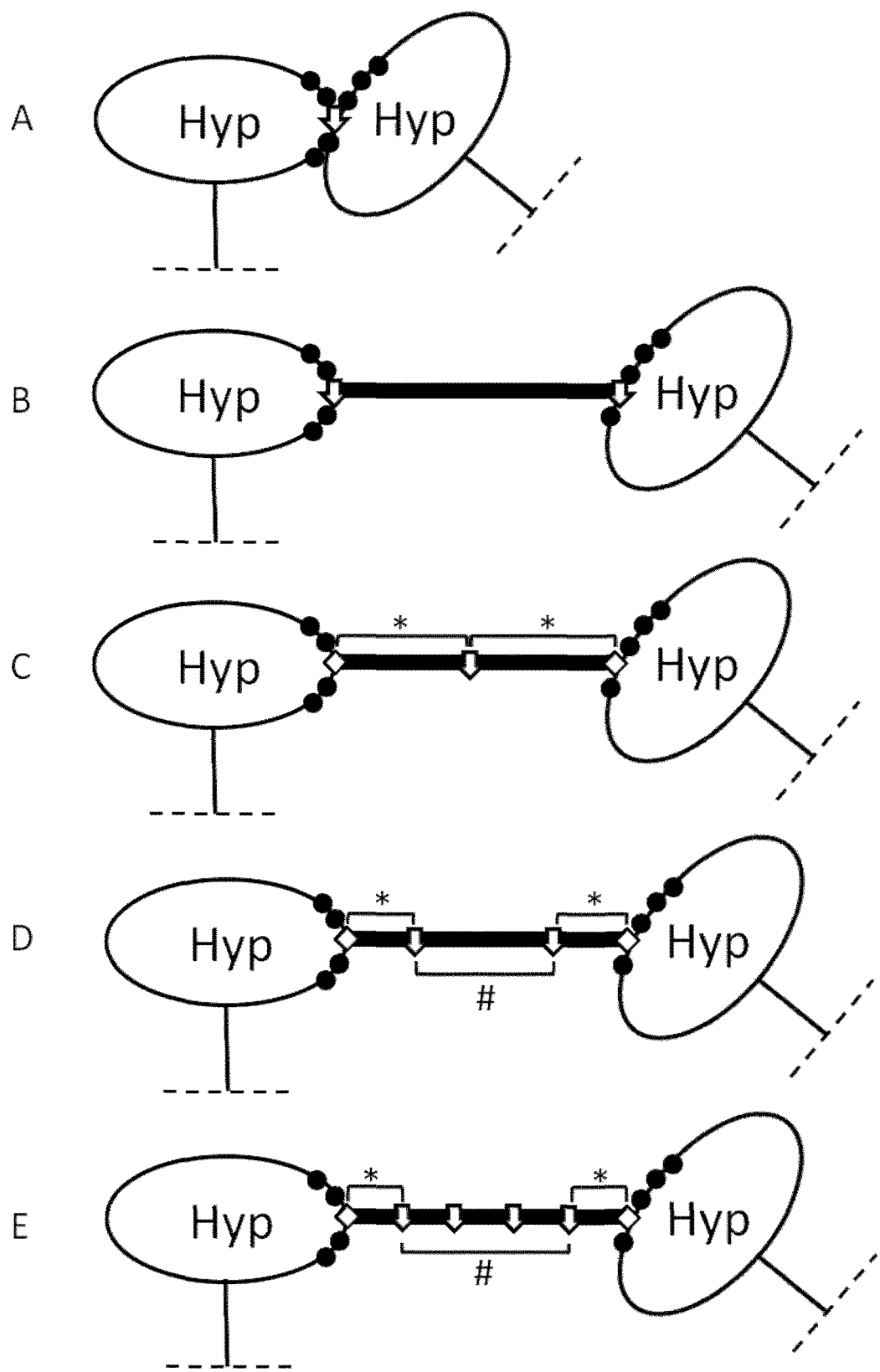
FIG. 3 shows a schematic overview of different ways in which two backbone moieties may be interconnected in a reactive biodegradable hydrogel. "Hyp"/oval: hyperbranched dendritic moiety; black dot: reactive functional group; white diamond: permanent linkage; asterisk: spacer moiety connected to a backbone moiety and on the other side connected to a crosslinking moiety; white arrows: interconnected functional groups; #: crosslinker moiety; thin black line: PEG-based polymeric chain; dashed lines indicate the attachment to a larger moiety which is not shown.

FIG. 3 gives a schematic overview of the different ways in which two backbone moieties may be interconnected in a reactive biodegradable hydrogel of the present invention. A hyperbranched dendritic moiety ("Hyp", oval) comprises a number of reactive functional groups (black dots) and a permanent linkage (white diamond). It is understood that each hyperbranched moiety comprises more reactive functional groups and permanent linkages than shown in FIG. 3 and that FIG. 3 is used for illustrative purposes only.

Spacer moieties connected to a backbone moiety and on the other side connected to a crosslinking moiety are indicated with asterisks, interconnected functional groups are shown as white arrows. Dashed lines indicate the attachment to a larger moiety which is not shown.

FIG. 3*a* illustrates a section of a reactive biodegradable hydrogel in which individual backbone moieties are directly interconnected through an interconnected functional group comprising a biodegradable bond.

In FIG. 3b the hyperbranched dendritic moieties of two different backbone moieties are interconnected through two interconnected functional groups separated through a spacer moiety.

In FIG. 3c the hyperbranched dendritic moieties of two different backbone moieties are interconnected through two spacer moieties connected to a backbone moiety and on the other side connected to a crosslinking moiety and one interconnected functional group.

FIGS. 3d and 3e show a section of a reactive biodegradable hydrogel in which two hyperbranched dendritic moieties are interconnected through crosslinker moieties, which are marked with "#". The crosslinker moieties may or may not comprise at least one interconnected functional group (see FIGS. 3d and 3e, respectively).

Thin black lines indicate PEG-based polymeric chains extending from a branching core (not shown).

Modified Reactive Biodegradable Hydrogel

Another aspect of the present invention is a conjugate comprising a hydrogel of the present invention, characterized by being composed of backbone moieties interconnected by hydrolytically degradable bonds and additionally carrying permanent linkages to spacer molecules, blocking groups, protecting groups, or multi-functional moieties.

The reactive functional groups of the backbone moieties of reactive biodegradable hydrogels serve as attachment points for spacer molecules, blocking groups, protecting groups, or multi-functional moieties.

Protecting groups are known in the art and are used for the reversible protection of chemical functional groups during synthesis processes. A suitable protecting group for amine functionalities is the fmoc group.

It is understood that only one protecting group or that two or more different protecting groups may be used, such as to provide for orthogonal protection, i.e. the different protecting groups may be removed under different conditions.

A modified reactive biodegradable hydrogel according to the invention may be functionalized with a spacer carrying the same reactive functional group. For instance, amino groups may be introduced into the modified reactive biodegradable hydrogel by coupling a heterobifunctional spacer, such as suitably activated $COOH\text{-}(EG)_6\text{-}NH\text{-}fmoc$ (EG=ethylene glycol), and removing the fmoc-protecting group. Such reactive biodegradable hydrogel can be further connected to a spacer carrying a different functional group, such as a maleimide group. An accordingly modified reactive biodegradable hydrogel may be further conjugated to drug-linker reagents, which carry a reactive thiol group on the linker moiety.

In such modified reactive biodegradable hydrogel, all remaining reactive functional groups may be capped with suitable blocking reagents.

In an alternative embodiment of this invention, multi-functional moieties are coupled to the reactive functional groups of the polymerized reactive biodegradable hydrogel to increase the number of reactive functional groups which allows for instance increasing the drug load of the biodegradable hydrogel according to the invention. Such multi-functional moieties may be comprised of lysine, dilysine, trilysine, tetralysine, pentalysine, hexylysine, heptalysine, or oligolysine, low-molecular weight PEI in bound form. Preferably, the multi-functional moiety comprises lysine in bound form. Optionally, such multi-functional moiety may be protected with protecting groups.

In such modified reactive biodegradable hydrogel, all remaining reactive functional groups may be capped with suitable blocking reagents.

Figure 4:
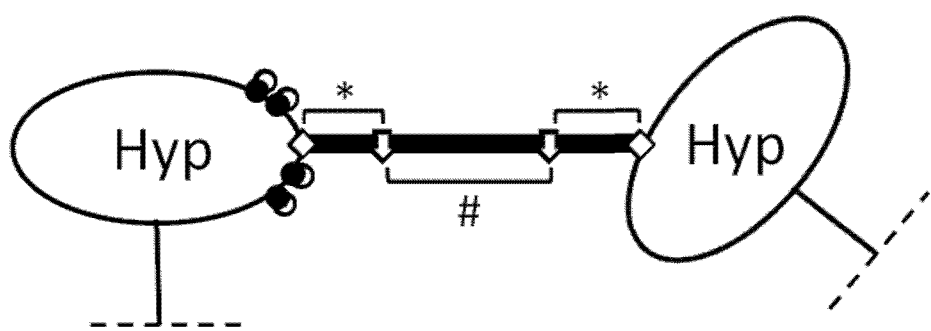
FIG. 4 shows a schematic drawing of a modified reactive biodegradable hydrogel. "Hyp"/oval: hyperbranched dendritic moiety; black dot with half-moon shaped structure: reactive functional groups modified with spacer molecules, blocking groups or protecting groups; white arrow: interconnected functional group; thin black line: PEG-based polymeric chain; white arrow: interconnected functional group; asterisk: spacer moiety connected to a backbone moiety and on the other side connected to a crosslinking moiety; #: crosslinker moiety; dashed lines indicate the attachment to a larger moiety which is not shown.

FIG. 4 shows a schematic drawing of a section of a modified reactive biodegradable hydrogel. A hyperbranched moiety (oval, "Hyp") comprises a number of reactive functional groups modified with spacer molecules or blocking groups (black dots with half-moon shaped structures). The thin black line indicates a PEG-based polymeric chain extending from a branching core (not shown), the thick black line indicates part of the spacer moieties connected to a backbone moiety and on the other side connected to a crosslinking moiety, which is attached to the hyperbranched moiety though a permanent bond (white diamond). White arrows indicate interconnected functional groups.

Dashed lines indicate the attachment to a larger moiety, which was not fully drawn for simplicity.

Biodegradable Hydrogels Comprising Conjugate Functional Groups

Another aspect of the present invention is a conjugate comprising a biodegradable hydrogel of the present invention, characterized by being composed of backbone moieties interconnected by hydrolytically degradable bonds and additionally carrying permanent linkages to conjugate functional groups comprising for example ligands or chelating groups or ion exchange groups. Accordingly, a biodegradable hydrogel comprising conjugate functional groups of the present invention comprises backbone moieties interconnected by hydrolytically degradable bonds and additionally carrying permanent linkages to conjugate functional groups, comprising for example ligands or chelating groups or ion exchange groups.

The reactive functional groups of the backbone moieties of reactive biodegradable hydrogels and modified reactive biodegradable hydrogels serve as attachment points for direct or indirect linkage of an affinity ligand or chelating group or ion exchange group or a combination thereof. Ideally, the ligands or chelating groups or ion exchange groups are dispersed homogeneously throughout the hydrogel according to the invention, and may or may not be present on the surface of the hydrogel according to the invention.

Remaining reactive functional groups which are not connected to affinity ligand- or chelating- or ion exchange-groups, may be capped with suitable blocking reagents.

Such affinity ligands or chelating groups or ion exchange groups are characterized in that the concentration of affinity ligands or chelating groups or ion exchange groups in such hydrogels according to the invention is almost constant during the first half of the time required for complete degradation of the hydrogel.

To be "almost constant" the weight concentration of said affinity ligands or chelating groups or ion exchange groups does not fall below 90% of the original concentration within the first half of the time required for complete degradation of the hydrogel according to the invention.

According to this invention, the biodegradable hydrogel comprising conjugate functional groups is composed of backbone moieties interconnected by hydrolytically degradable bonds.

In a hydrogel carrying affinity ligands or chelating groups or ion exchange groups according to the invention, a backbone moiety is characterized by a number of functional groups, consisting of interconnected biodegradable functional groups and conjugate functional groups comprising affinity ligands or chelating groups or ion exchange groups. Preferably, the sum of interconnected biodegradable functional groups and conjugate functional groups carrying affinity ligands or chelating groups or ion exchange groups is 16-128, preferred 20-100, more preferred 24-80 and most preferred 30-60. It is understood that in addition to the interconnected functional groups and the reactive functional groups also blocking groups may be present.

Preferably, the sum of interconnected functional groups and conjugate functional groups carrying affinity ligands or chelating groups or ion exchange groups of a backbone moiety is equally divided by the number of PEG-based polymeric chains extending from the branching core. For instance, if there are 32 interconnected functional groups and conjugate functional groups carrying affinity ligands or chelating groups or ion exchange groups, eight groups may be provided by each of the four PEG-based polymeric chains extending from the core, preferably by means of dendritic moieties attached to the terminus of each PEG-based polymeric chain. Alternatively, four groups may be provided by each of eight PEG-based polymeric chains extending from the core or two groups by each of sixteen PEG-based polymeric chains. If the number of PEG-based polymeric chains extending from the branching core does not allow for an equal distribution, it is preferred that the deviation from the mean number of the sum of interconnected functional group and conjugate functional groups carrying affinity ligands or chelating groups or ion exchange groups per PEG-based polymeric chain is kept to a minimum.

Also preferably, the sum of interconnected biodegradable functional groups and permanent linkages to conjugate functional groups carrying ligands or chelating groups or ion exchange groups, or optionally spacer molecules, or blocking groups is equal to or greater than 16, preferred 20-40, more preferred 28-32 and most preferred 30-32.

In the simplest case, a hydrogel carrying ion exchange groups is identical with a reactive biodegradable hydrogel.

Preferably, each dendritic moiety of a backbone moiety of a biodegradable hydrogel comprising conjugate functional groups has at least 3 branchings and at least 4 biodegradable and/or permanent linkages, more preferably 5 branchings and 6 biodegradable and/or permanent linkages, most preferably 7 branchings and 8 biodegradable and/or permanent linkages or optionally 15 branchings and 16 biodegradable and/or permanent linkages.

Suitable ligands present in bound form in a biodegradable hydrogels comprising conjugate functional groups of the invention are e.g. affinity ligands like biotin. Further ligands are for example affinity ligands like: 4-Aminobenzamidine, 3-(2'-Aminobenzhydryloxy)tropane, ε-Aminocaproyl-p-chlorobenzylamide, 1-Amino-4-[3-(4,6-dichlorotriazin-2-ylamino)-4-sulfophenylamino]anthraquinone-2-sulfonic acid, 2-(2'-Amino-4'-methylphenylthio)-N,N-dimethylbenzylamine dihydrochloride, Angiopoietin-1, aptamers, arotinoid acid, avidin, biotin, calmodulin, cocaethylene, cytosporone B, N,N-Dihexyl-2-(4-fluorophenyl)indole-3-acetamide, N,N-Dipropyl-2-(4-chlorophenyl)-6,8-dichloroimidazo[1,2-a]pyridine-3-acetamide, 5-Fluoro-2'-deoxyuridine 5'-(p-aminophenyl)monophosphate, S-Hexyl-L-glutathione, (S,S)-4-Phenyl-α-(4-phenyloxazolidin-2-ylidene)-2-oxazoline-2-acetonitrile, Pro-Leu-Gly hydroxamate, 2-(4-(2-(trifluoromethyl)phenyl)piperidine-1-carboxamido)benzoic acid, Trimethyl(m-aminophenyl)ammonium chloride, Urocortin III, cofactors like adenosin triphosphate, s-adenosyl methionine, ascorbic acid, cobalamine, coenzyme A, coenzyme B, coenzyme M, coenzyme Q, coenzyme F420, cytidine triphosphate, flavin mononucleotide, flavin adenine dinucleotide, glutathion, heme, lipoamide, menaquinone, methanofuran, methylcobalamine, molybdopterin, NAD+, NADP+, nucleotide sugars, 3'-phosphoadenosine-5'-phosphosulfate, pyridoxal phosphate, polyhistidines, pyrroloquinoline quinone, riboflavin, streptavidin, tetrahydrobiopterin, tetrahydromethanopterin, tetrahydrofolic acid, biotin carboxyl carrier protein (BCCP), chitin binding protein, FK506 binding proteins (FKBP), FLAG tag, green fluorescent protein, glutathion-S-transferase, hemagglutinin (HA), maltose binding protein, myc tag, NusA, protein C epitope, S-tag, strep-tag, thioredoxins, triazines—preferably 2,4,6-trisubstituted triazines—, affinity scaffold proteins such as antibody fragments.

Suitable chelating groups present in bound form in a biodegradable hydrogels comprising conjugate functional groups of the invention are e.g. ionic groups capable of interacting with a substrate like in the form of an ion exchange material. Other examples of chelating groups are complexing, groups. Different types of chelating groups are for example:

2,2'-bipyridyl, 1,2-bis(2-aminophenoxy)ethane-N,N,N', N'-tetraacetic acid, deferoxamine mesylate, deferriferrichrome, diethylenetriamine, 2,3-dimercapto-1-propanol, dimercaptosuccinic acid, dimethylglyoxine, 2,2'-dipyridyl, Ethylene diamine, ethylenediaminetetra(methylenephosphonic acid), 1,2-Bis(2-amino-5-bromophenoxy)ethane-N, N,N',N'-tetraacetic acid, 8-hydroxychinoline, iminodiacetate, iminodi(methylphosphonic acid), L-mimosine, nitrilotriacetate, oxalate, 1,10-phenantroline, phytic acid, tartrate, 1,4,7,10-tetraazacyclododecane-1,4,7,10-tetraacetate, N,N,N',N'-tetrakis(2-pyridylmethyl)ethylenediamine, triaminotriethylamine, iminodiacetic acid, thiourea, 2-picolylamine.

Ion-exchange groups present in bound form in a biodegradable hydrogels comprising conjugate functional groups of the invention are chemical functional groups commonly used attached to ion exchange resins, such as strongly acidic groups, for instance sulfonic acid groups, e.g. propylsulfonic acid; strongly basic groups, such as quaternary amino groups, for example trimethylammonium groups, e.g. propyltrimethylammonium chloride; weakly acidic groups, e.g. alkyl carboxylic acid groups; or weakly basic groups, such as primary, secondary, and/or ternary alkyl amino groups.

Figure 5:
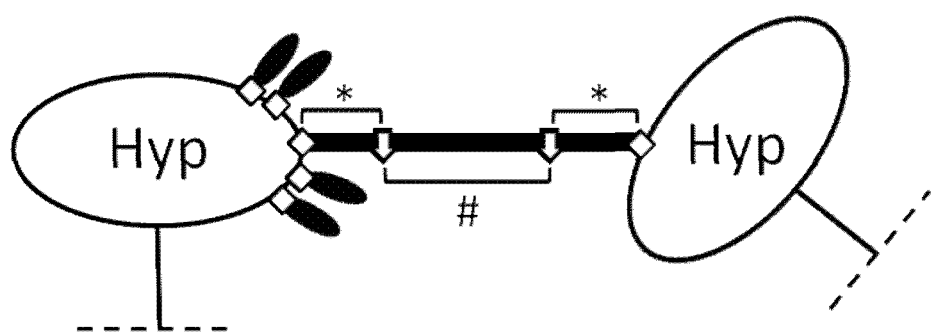
FIG. 5 shows a schematic drawing of a hydrogel according to the invention comprising conjugate functional groups. "Hyp"/oval: hyperbranched dendritic moiety; black oval.

FIG. 5 shows a schematic drawing of a relevant section of a hydrogel comprising conjugate functional groups. A hyperbranched moiety (oval, "Hyp") comprises a number of permanent bonds (white diamonds) to either conjugates such as affinity ligands or chelating groups (black ovals) or a spacer moiety connected to a backbone moiety and on the other side connected to a crosslinking moiety (thick black line). Asterisks indicate spacer moieties connected to a backbone moiety and on the other side connected to a crosslinking moiety; #indicate crosslinker moieties; dashed lines indicate the attachment to a larger moiety which is not shown. Thin black line indicates a PEG-based polymeric chain extending from a branching core (not shown).

Hydrogel Prodrugs

Another aspect of the present invention is a carrier-linked prodrug comprising a biodegradable hydrogel of the present invention as carrier, wherein a number of permanent linkages of the backbone moieties exist with a transient prodrug linker to which a biologically active moiety is covalently attached.

A "prodrug" is any compound that undergoes biotransformation before exhibiting its pharmacological effects. Prodrugs can thus be viewed as drugs containing specialized non-toxic protective groups used in a transient manner to alter or to eliminate undesirable properties in the parent molecule. This clearly also includes the enhancement of desirable properties in the drug and the suppression of undesirable properties.

The terms "carrier-linked prodrug", "carrier prodrug" refer to a prodrug that contains a temporary linkage of a given biologically active substance with a transient carrier group that produces improved physicochemical or pharmacokinetic properties and that can be easily removed in vivo, usually by a hydrolytic cleavage.

The reactive functional groups of a reactive biodegradable hydrogel or modified reactive biodegradable hydrogel serve as attachment points for direct linkage through the before mentioned permanent linkages of a drug, drug-linker conjugate, prodrug, carrier-linked prodrug or the like. Ideally, the hydrogel-connected drug-linker conjugates are dispersed homogeneously throughout the hydrogel according to the invention, and may or may not be present on the surface of the hydrogel according to the invention.

Remaining reactive functional groups which are not connected to a transient prodrug linker or to a spacer connected to a transient prodrug linker may be capped with suitable blocking reagents.

Preferably, the covalent attachment formed between the reactive functional groups provided by the backbone moieties and the prodrug linker are permanent bonds. Suitable functional groups for attachment of the prodrug linker to the hydrogel according to the invention include but are not limited to carboxylic acid and derivatives, carbonate and derivatives, hydroxyl, hydrazine, hydroxylamine, maleamic acid and derivatives, ketone, amino, aldehyde, thiol and disulfide. After loading the drug-linker conjugate to the maleimido group-containing hydrogel, all remaining functional groups are capped with suitable capping reagents to prevent undesired side-reactions.

According to this invention, the biodegradable hydrogel according to the invention is composed of backbone moieties interconnected by hydrolytically degradable bonds.

In a hydrogel carrying drug-linker conjugates according to the invention, a backbone moiety is characterized by a number of functional groups, comprising interconnected biodegradable functional groups and hydrogel-connected drug-linker conjugates, and optionally capping groups. This means that a backbone moiety is characterized by a number of hydrogel-connected drug-linker conjugates; functional groups, comprising biodegradable interconnected functional groups; and optionally capping groups. Preferably, the sum of interconnected biodegradable functional groups and drug-linker conjugates and capping groups is 16-128, preferred 20-100, more preferred 24-80 and most preferred 30-60.

Preferably, the sum of interconnected functional groups and hydrogel-connected drug-linker conjugates and capping groups of a backbone moiety is equally divided by the number of PEG-based polymeric chains extending from the branching core. For instance, if there are 32 interconnected functional groups and hydrogel-connected drug-linker conjugates and capping groups, eight groups may be provided by each of the four PEG-based polymeric chains extending from the core, preferably by means of dendritic moieties attached to the terminus of each PEG-based polymeric chain. Alternatively, four groups may be provided by each of eight PEG-based polymeric chains extending from the core or two groups by each of sixteen PEG-based polymeric chains. If the number of PEG-based polymeric chains extending from the branching core does not allow for an equal distribution, it is preferred that the deviation from the mean number of the sum of interconnected functional groups and hydrogel-connected drug-linker conjugates and capping groups per PEG-based polymeric chain is kept to a minimum.

In such carrier-linked prodrugs according to the invention, it is desirable that almost all drug release (>90%) has occurred before a significant amount of release of the backbone moieties (<10%) has taken place. This can be achieved by adjusting the carrier-linked prodrug's half-life versus the degradation kinetics of the hydrogel according to the invention.

"Linker", "linking group", "linker structure" or "linking agent" refers to the moiety which on its one end is attached to the drug moiety through a reversible linkage and at another end is attached through a permanent bond to either a spacer molecule permanently attached to a hyperbranched dendritic moiety or is directly attached through a permanent bond to a hyperbranched dendritic moiety.

It is preferred for the linking agent to form a reversible linkage to the biologically active moiety, preferably in such a fashion that after cleavage of the linker, the biologically active moiety is released in an unmodified form. A variety of different linking agents or linking groups that may be applied for this purpose are described by B. Testa et al. (B. Testa, J. Mayer, Hydrolysis in Drug and Prodrug Metabolism, Wiley-VCH, 2003).

It is also preferred that the majority of the linker structure remains attached to the hydrogel according to the invention after cleavage of the biodegradable linkage with the biologically active moiety. If the linker is a cascade prodrug linker, it is preferred for the activating group to remain permanently bound to the hydrogel according to the invention.

Preferably, the transient prodrug linker is attached to the biologically active moiety by an auto-cleavable functional group. Preferably, the linker has self-cleavable properties and as a consequence the hydrogel-linker-drug is a carrier-linked prodrug, capable of releasing drug from the conjugate and in such a way that the release is predominantly dependent upon the self-cleavage of the linker.

The terms "auto-cleavable" or "hydrolytically degradable" are used synonymously.

An "auto-cleavable functional group" comprises a hydrolytically degradable bond.

If the auto-cleavable linkage is formed together with a primary or aromatic amino group of the biologically active moiety, a carbamate or amide group is preferred.

Examples of such biologically active compounds or drugs are selected from the group consisting of central nervous system-active agents, anti-infective, anti-allergic, immunomodulating, anti-obesity, anticoagulants, antidiabetic, antineoplastic, antibacterial, anti-fungal, analgesic, contraceptive, anti-inflammatory, steroidal, vasodilating, vasoconstricting, and cardiovascular agents. Examples include but are not limited to ACTH, adenosine deaminase, agalsidase, albumin, alfa-1 antitrypsin (AAT), alfa-1 proteinase inhibitor (API), alglucosidase, alteplase, anistreplase, ancrod serine protease, antibodies (monoclonal or polyclonal and fragments or fusions), antithrombin antitrypsins, aprotinin, asparaginases, biphalin, bone-morphogenic proteins, calcitonin (salmon), collagenase, DNase, endorphins, enfuvirtide, enkephalins, erythropoietins, factor VIIa, factor VIII, factor VIIIa, factor IX, fibrinolysin, fusion proteins, follicle-stimulating hormones, granulocyte colony stimulating factor (G-CSF), galactosidase, glucagon, glucagon-like peptides like GLP-1, glucocerebrosidase, granulocyte macrophage colony stimulating factor (GM-CSF), chorionic gonadotropin (hCG), hemoglobins, hepatitis B vaccines, hirudin, hyaluronidases, idurnonidase, immune globulins, influenza vaccines, interleukines (1 alfa, 1 beta, 2, 3, 4, 6, 10, 11, 12), IL-1 receptor antagonist (rhIL-1ra), insulins, interferons (alfa 2a, alfa 2b, alfa 2c, beta 1a, beta 1b, gamma 1a, gamma 1b), keratinocyte growth factor (KGF), lactase, leuprolide, levothyroxine, luteinizing hormone, lyme vaccine, natriuretic peptide, pancrelipase, papain, parathyroid hormone, PDGF, pepsin, phospholipase-activating protein (PLAP), platelet activating factor alcetylhydrolase (PAF-AH), prolactin, protein C, octreotide, secretin, sermorelin, superoxide dismutase (SOD), somatropins (growth hormone), somatostatin, streptokinase, sucrase, tetanus toxin fragment, tilactase, thrombins, thymosin, thyroid stimulating hormone, thyrothropin, transforming growth factors, tumor necrosis factor (TNF), TNF receptor-IgG Fc, tissue plasminogen activator (tPA), transferrin, TSH, urate oxidase, urokinase, vaccines, plant proteins such as lectins and ricins, acarbose, acivicin, alaproclate, alendronate, amantadine, ambrisentan, amikacin, amineptine, aminoglutethimide, amisulpride, amlodipine, amotosalen, amoxapine, amoxicillin, amphetamine, amphotericin B, ampicillin, amprenavir, aminone, anagrelid, anileridine, antibiotics, apraclonidine, apramycin, arsen(III)-oxide, articaine, atenolol, atomoxetine, avizafone, baclofen, benazepril, benserazide, benzocaine, betaine anhydricum, betaxolol, bleomycin, bosentan, bromfenac, brofaromine, busulfan, calcitonin, carvedilol, cathine, cathinone, carbutamid, cefalexine, celexoxib, ciprofloxacin, cladribin, clinafloxacin, clofarabin, dasatinib, deferoxamine, delavirdine, desipramine, daunorubicin, dexmethylphenidate, dexmethylphenidate, diaphenylsulfon, dizocilpine, dopamin, dobutamin, dorzolamide, doxorubicin, duloxetine, eflornithine, enalapril, epinephrine, epirubicin, ergoline, ertapenem, esmolol, enoxacin, ethambutol, fenfluramine, fenoldopam, fenoterol, fingolimod, flecamide, fluvoxamine, folic acid, fosamprenavir, frovatriptan, furosemide, fluoexetine, gabapentin, gatifloxacin, gemiflocacin, gentamicin, grepafloxacin, hexylcaine, hydralazine, hydrochlorothiazide, icofungipen, idarubicin, imiquimod, inversine, isoproterenol, isradipine, kanamycin A, ketamin, labetalol, lamivudine, levobunolol, levodopa, levothyroxine, lisinopril, lomefloxacin, loracarbef, maprotiline, mefloquine, melphalan, memantine, meropenem, mesalazine, mescaline, methyldopa, methylenedioxymethamphetamine, metoprolol, milnacipran, mitoxantron, moxifloxacin, norepinephrine, norfloxacin, nortriptyline, neomycin B, nystatin, oseltamivir, pamidronic acid, paroxetine, pazufloxacin, pemetrexed, perindopril, phenmetrazine, phenelzine, pregabalin, procaine, pseudoephedrine, protriptyline, reboxetine, ritodrine, sabarubicin, salbutamol, serotonin, sertraline, sitagliptin, sotalol, spectinomycin, sulfadiazin, sulfamerazin, sertraline, sprectinomycin, sulfalen, sulfamethoxazol, tacrine, tamsulosin, terbutaline, timolol, tirofiban, tobramycin, tocamide, tosufloxacin, trandolapril, tranexamic acid, tranylcypromine, trimerexate, trovafloxacin, valaciclovir, valganciclovir, vancomycin, viomycin, viloxazine, vitamines, and zalcitabine.

Preferably, the linkage between prodrug-linker and bioactive moiety is hydrolytically degradable under physiological conditions (aqueous buffer at pH 7.4, 37° C.) with half-lives ranging from one hour to three months, include, but are not limited to, aconityls, acetals, amides, carboxlic anhydrides, esters, imines, hydrazones, maleamic acid amides, ortho esters, phosphamides, phosphoesters, phosphosilyl esters, silyl esters, sulfonic esters, aromatic carbamates, combinations thereof, and the like. Preferred biodegradable linkages are esters, carbonates, phosphoesters and sulfonic acid esters and most preferred are esters or carbonates for biologically active moieties or drugs not transiently linked via a primary or aromatic amino group.

If the auto-cleavable linkage is formed together with a primary or aromatic amino group of the biologically active moiety, a carbamate or amide group is preferred.

A preferred transient prodrug is described in WO-A 2005/099768 and thus is selected from the general formula (I) and (II):

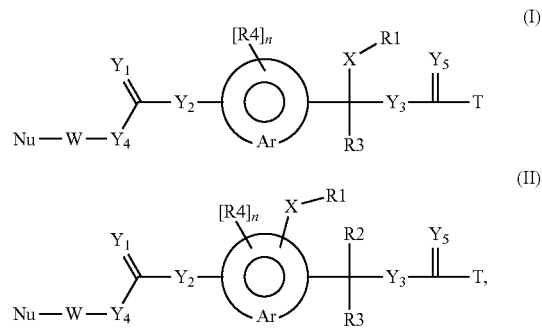

wherein X, $Y_1$, $Y_2$, $Y_3$, $Y_4$, $Y_5$, R1, R2, R3, R4, Nu, W, n, and T of formula (I) and (II) have the following meaning:

T represents an amine-comprising biologically active moiety which is attached to the rest of the structures shown in formula (I) and (II) by forming a —O—(C=O)—N—; —O—(C=S)—N—; —S—(C=O)—N—; or —S—(C=S)—N— linkage;

X represents a spacer moiety;

$Y_1$ and $Y_2$ each independently represent O, S or NR6;

$Y_3$ represents O or S;

$Y_4$ is O, NR6, or —C(R7)(R8)-;

$Y_5$ is O or S;

$Y_4$ represents O, NR6 or —C(R7)(R8);

R3 represents a moiety selected from the group consisting of hydrogen, substituted or unsubstituted linear, branched or cyclical alkyl or heteroalkyl groups, aryls, substituted aryls, substituted or unsubstituted heteroaryls, cyano groups, nitro groups, halogens, carboxy groups, carboxyalkyl groups, alkylcarbonyl groups or carboxamidoalkyl groups;

R4 represents a moiety selected from the group consisting of hydrogen, substituted or unsubstituted linear, branched or cyclical alkyls or heteroalkyls, aryls, substituted aryls, substituted or unsubstituted heteroaryl, substituted or unsubstituted linear, branched or cyclical alkoxys, substituted or unsubstituted linear, branched or cyclical heteroalkyloxys, aryloxys or heteroaryloxys, cyano groups and halogens;

R7 and R8 are each independently selected from the group consisting of hydrogen, substituted or unsubstituted linear, branched or cyclical alkyls or heteroalkyls, aryls, substituted aryls, substituted or unsubstituted heteroaryls, carboxyalkyl groups, alkylcarbonyl groups, carboxamidoalkyl groups, cyano groups, and halogens;

R6 represents a group selected from hydrogen, substituted or unsubstituted linear, branched or cyclical alkyls or heteroalkyls, aryls, substituted aryls and substituted or unsubstituted heteroaryls;

R1 represents the biodegradable hydrogel of the present invention;

W represents a group selected from substituted or unsubstituted linear, branched or cyclical alkyls, aryls, substituted aryls, substituted or unsubstituted linear, branched or cyclical heteroalkyls, substituted or unsubstituted heteroaryls;

Nu represents a nucleophile;

n represents zero or a positive integer; and

Ar represents a multi-substituted aromatic hydrocarbon or multi-substituted aromatic heterocycle.

Another preferred prodrug of the present invention is described in WO-A 2006/136586. Accordingly, the following structures selected from the general formula of (III), (IV) and (V) are preferred:

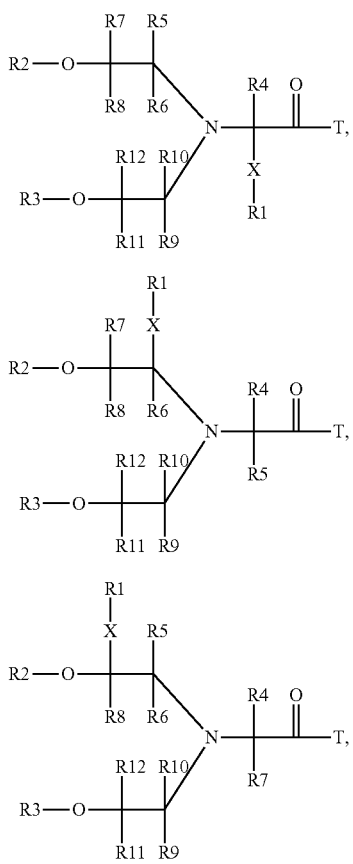

wherein R1, R2, R3, R4, R5, R6, R7, R8, R9, R10, R11, R12, X, and T auf formula (III), (IV) and (V) have the following meaning:

T is the biologically active moiety;

X is a spacer moiety such as R13-Y1;

Y1 is O, S, NR6, succinimide, maleimide, unsaturated carbon-carbon bonds or any heteratom containing a free electron pair or is absent;

R13 is selected from substituted or non-substituted linear, branched or cyclical alkyl or heteroalkyl, aryls, substituted aryls, substituted or non-substituted heteroaryls;

R2 and R3 are selected independently from hydrogen, acyl groups, or protecting groups for hydroxyl groups;

R4 to R12 are selected independently from hydrogen, substituted or non-substituted linear, branched or cyclical alkyl or heteroalkyl, aryls, substituted aryls, substituted or non-substituted heteroaryls, cyano, nitro, halogen, carboxy, carboxamide;

R1 is the biodegradable hydrogel of the present invention.

In yet another preferred embodiment, a preferred structure for a prodrug of the present invention is given by a prodrug conjugate D-L, wherein -D is the biologically active moiety; and -L is a non-biologically active linker moiety $-L^1$ represented by formula (VI),

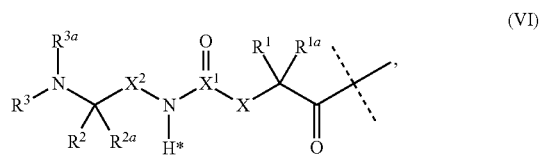

wherein the dashed line indicates the attachment to a primary or secondary amino group of an amine-containing biologically active moiety D by forming an amide bond; and wherein X, $X^1$, $X^2$, $R^1$, $R^{1a}$, $R^2$, $R^{2a}$, $R^3$, and $R^{3a}$ of formula (VI) have the following meaning:

X is $C(R^4R^{4a})$; $N(R^4)$; O; $C(R^4R^{4a})$—$C(R^5R^{5a})$; $C(R^5R^{5a})$—$C(R^4R^{4a})$; $C(R^4R^{4a})$—$N(R^6)$; $N(R^6)$—$C(R^4R^{4a})$; $C(R^4R^{4a})$—O; or O—$C(R^4R^{4a})$;

$X^1$ is C; or S(O);

$X^2$ is $C(R^7, R^{7a})$; or $C(R^7, R^{7a})$—$C(R^8, R^{8a})$;

$R^1$, $R^{1a}$, $R^2$, $R^{2a}$, $R^3$, $R^{3a}$, $R^4$, $R^{4a}$, $R^5$, $R^{5a}$, $R^6$, $R^7$, $R^{7a}$, $R^8$, $R^{8a}$ are independently selected from the group consisting of H; and $C_{1-4}$ alkyl; or Optionally, one or more of the pairs $R^{1a}/R^{4a}$, $R^{1a}/R^{5a}$, $R^{4a}/R^{5a}$, $R^{4a}/R^{5a}$, $R^{7a}/R^{8a}$ form a chemical bond;

Optionally, one or more of the pairs $R^1/R^{1a}$, $R^2/R^{2a}$, $R^4/R^{4a}$, $R^5/R^{5a}$, $R^7/R^{7a}$, $R^8/R^{8a}$ are joined together with the atom to which they are attached to form a $C_{3-7}$ cycloalkyl; or 4 to 7 membered heterocyclyl;

Optionally, one or more of the pairs $R^1/R^4$, $R^1/R^5$, $R^1/R^6$, $R^4/R^5$, $R^7/R^8$, $R^2/R^3$ are joined together with the atoms to which they are attached to form a ring A;

Optionally, $R^3/R^{3a}$ are joined together with the nitrogen atom to which they are attached to form a 4 to 7 membered heterocycle;

A is selected from the group consisting of phenyl; naphthyl; indenyl; indanyl; tetralinyl; $C_{3-10}$ cycloalkyl; 4 to 7 membered heterocyclyl; and 9 to 11 membered heterobicyclyl; and wherein $L^1$ is substituted with one group $L^2$-Z and optionally further substituted, provided that the hydrogen marked with the asterisk in formula (VI) is not replaced by a substituent;

wherein $L^2$ is a single chemical bond or a spacer; and

Z is the according to the invention.

Prodrug conjugates of this type are described in European Patent application EP-A 08150973.

"Alkyl" means a straight-chain or branched carbon chain. Each hydrogen of an alkyl carbon may be replaced by a substituent.

"$C_{1-4}$ alkyl" means an alkyl chain having 1-4 carbon atoms, e.g. if present at the end of a molecule: methyl, ethyl, n-propyl, isopropyl, n-butyl, isobutyl, sec-butyl tert-butyl, or e.g. —$CH_2$—, —$CH_2$—$CH_2$—, —$CH(CH_3)$—, —$CH_2$—$CH_2$—$CH_2$—, —$CH(C_2H_5)$—, —$C(CH_3)_2$—, when two moieties of a molecule are linked by the alkyl group. Each hydrogen of a $C_{1-4}$ alkyl carbon may be replaced by a substituent.

"$C_{1-6}$ alkyl" means an alkyl chain having 1-6 carbon atoms, e.g. if present at the end of a molecule: $C_{1-4}$ alkyl, methyl, ethyl, n-propyl, isopropyl, n-butyl, isobutyl, sec-butyl; tert-butyl, n-pentyl, n-hexyl, or e.g. —$CH_2$—, —$CH_2$—$CH_2$—, —$CH(CH_3)$—, —$CH_2$—$CH_2$—$CH_2$—, —$CH(C_2H_5)$—, —$C(CH_3)_2$—, when two moieties of a molecule are linked by the alkyl group. Each hydrogen of a $C_{1-6}$ alkyl carbon may be replaced by a substituent.

Accordingly, "$C_{1-18}$ alkyl" means an alkyl chain having 1 to 18 carbon atoms and "$C_{8-18}$ alkyl" means an alkyl chain having 8 to 18 carbon atoms. Accordingly, "$C_{1-50}$ alkyl" means an alkyl chain having 1 to 50 carbon atoms.

"$C_{2-50}$ alkenyl" means a branched or unbranched alkenyl chain having 2 to 50 carbon atoms, e.g. if present at the end of a molecule: —CH=$CH_2$, —CH=CH—$CH_3$, —$CH_2$—CH=$CH_2$, —CH=CH—$CH_2$—$CH_3$, —CH=CH—CH=$CH_2$, or e.g. —CH=CH—, when two moieties of a molecule are linked by the alkenyl group. Each hydrogen of a $C_{2-50}$ alkenyl carbon may be replaced by a substituent as further specified. Accordingly, the term "alkenyl" relates to a carbon chain with at least one carbon carbon double bond. Optionally, one or more triple bonds may occur.

"$C_{2-50}$ alkynyl" means a branched or unbranched alkynyl chain having 2 to 50 carbon atoms, e.g. if present at the end of a molecule: —C≡CH, —$CH_2$—C≡CH, $CH_2$—$CH_2$—C≡C—$CH_3$, or e.g. —C≡C— when two moieties of a molecule are linked by the alkynyl group. Each hydrogen of a $C_{2-50}$ alkynyl carbon may be replaced by a substituent as further specified. Accordingly, the term "alkynyl" relates to a carbon chain with at lest one carbon carbon triple bond. Optionally, one or more double bonds may occur.

"$C_{3-7}$ cycloalkyl" or "$C_{3-7}$ cycloalkyl ring" means a cyclic alkyl chain having 3 to 7 carbon atoms, which may have carbon-carbon double bonds being at least partially saturated, e.g. cyclopropyl, cyclobutyl, cyclopentyl, cyclohexyl, cyclohexenyl, cycloheptyl. Each hydrogen of a cycloalkyl carbon may be replaced by a substituent. The term "$C_{3-7}$ cycloalkyl" or "$C_{3-7}$ cycloalkyl ring" also includes bridged bicycles like norbonane or norbonene. Accordingly, "$C_{3-5}$ cycloalkyl" means a cycloalkyl having 3 to 5 carbon atoms and $C_{3-10}$ cycloalkyl having 3 to 10 carbon atoms.

Accordingly, "$C_{3-10}$ cycloalkyl" means a cyclic alkyl having 3 to 10 carbon atoms, e.g. $C_{3-7}$ cycloalkyl; cyclopropyl, cyclobutyl, cyclopentyl, cyclohexyl, cyclohexenyl, cycloheptyl, cyclooctyl, cyclononyl, cyclodecyl. The term "$C_{3-10}$ cycloalkyl" also includes at least partially saturated carbomono- and -bicycles.

"Halogen" means fluoro, chloro, bromo or iodo. It is generally preferred that halogen is fluoro or chloro.

"4 to 7 membered heterocyclyl" or "4 to 7 membered heterocycle" means a ring with 4, 5, 6 or 7 ring atoms that may contain up to the maximum number of double bonds (aromatic or non-aromatic ring which is fully, partially or un-saturated) wherein at least one ring atom up to 4 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for a 4 to 7 membered heterocycles are azetidine, oxetane, thietane, furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydrofuran, tetrahydrothiophene, pyrrolidine, imidazolidine, pyrazolidine, oxazolidine, isoxazolidine, thiazolidine, isothiazolidine, thiadiazolidine, sulfolane, pyran, dihydropyran, tetrahydropyran, imidazolidine, pyridine, pyridazine, pyrazine, pyrimidine, piperazine, piperidine, morpholine, tetrazole, triazole, triazolidine, tetrazolidine, diazepane, azepine or homopiperazine.

"9 to 11 membered heterobicyclyl" or "9 to 11 membered heterobicycle" means a heterocyclic system of two rings with 9 to 11 ring atoms, where at least one ring atom is shared by both rings and that may contain up to the maximum number of double bonds (aromatic or non-aromatic ring which is fully, partially or un-saturated) wherein at least one ring atom up to 6 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom. Examples for a 9 to 11 membered heterobicycle are indole, indoline, benzofuran, benzothiophene, benzoxazole, benzisoxazole, benzothiazole, benzisothiazole, benzimidazole, benzimidazoline, quinoline, quinazoline, dihydroquinazoline, quinoline, dihydroquinoline, tetrahydroquinoline, decahydroquinoline, isoquinoline, decahydroisoquinoline, tetrahydroisoquinoline, dihydroisoquinoline, benzazepine, purine or pteridine. The term 9 to 11 membered heterobicycle also includes spiro structures of two rings like 1,4-dioxa-8-azaspiro[4.5]decane or bridged heterocycles like 8-aza-bicyclo[3.2.1]octane.

Preferably, one or more further optional substituents are independently selected from the group consisting of halogen; CN; COOR$^9$; OR$^9$; C(O)R$^9$; C(O)N(R$^9$R$^{9a}$); S(O)$_2$N(R$^9$R$^{9a}$); S(O)N(R$^9$R$^{9a}$); S(O)$_2$R$^9$; S(O)R$^9$; N(R$^9$)S(O)$_2$N(R$^{9a}$R$^{9b}$); SR$^9$; N(R$^9$R$^{9a}$); NO$_2$; OC(O)R$^9$; N(R$^9$)C(O)R$^{9a}$; N(R$^9$)S(O)$_2$R$^{9a}$; N(R$^9$)S(O)R$^{9a}$; N(R$^9$)C(O)OR$^{9a}$; N(R$^9$)C(O)N(R$^{9a}$R$^{9b}$); OC(O)N(R$^9$R$^{9a}$); T; $C_{1-50}$ alkyl; $C_{2-50}$ alkenyl; or $C_{2-50}$ alkynyl, wherein T; $C_{1-50}$ alkyl; $C_{2-50}$ alkenyl; and $C_{2-50}$ alkynyl are optionally substituted with one or more R$^{10}$, which are the same or different and wherein $C_{1-50}$ alkyl; $C_{2-50}$ alkenyl; and $C_{2-50}$ alkynyl are optionally interrupted by one or more groups selected from the group consisting of T, —C(O)O—; —O—; —C(O)—; —C(O)N(R$^{11}$)—; —S(O)$_2$N(R$^{11}$)—; —S(O)N(R$^{11}$)—; —S(O)$_2$—; —S(O)—; —N(R$^{11}$)S(O)$_2$N(R$^{11a}$)—; —S—; —N(R$^{11}$)—; —OC(O)R$^{11}$; —N(R$^{11}$)C(O)—; —N(R$^{11}$)S(O)$_2$—; —N(R$^{11}$)S(O)—; —N(R$^{11}$)C(O)O—; —N(R$^{11}$)C(O)N(R$^{11a}$); and —OC(O)N(R$^{11}$R$^{11a}$);

R$^9$, R$^{9a}$, R$^{9b}$ are independently selected from the group consisting of H; T; and $C_{1-50}$ alkyl; $C_{2-50}$ alkenyl; or $C_{2-50}$ alkynyl, wherein T; $C_{1-50}$ alkyl; $C_{2-50}$ alkenyl; and $C_{2-50}$ alkynyl are optionally substituted with one or more R$^{10}$, which are the same or different and wherein $C_{1-50}$ alkyl; $C_{2-50}$ alkenyl; and $C_{2-50}$ alkynyl are optionally interrupted by one or more groups selected from the group consisting of T, —C(O)O—; —O—; —C(O)—; —C(O)N(R$^{11}$)—; —S(O)$_2$N(R$^{11}$)—; —S(O)N(R$^{11}$)—; —S(O)$_2$—; —S(O)—; —N(R$^{11}$)S(O)$_2$N(R$^{11a}$)—; —S—; —N(R$^{11}$)—; —OC(O)R$^{11}$; —N(R$^{11}$)C(O)—; —N(R$^{11}$)S(O)$_2$—; —N(R$^{11}$)S(O)—; —N(R$^{11}$)C(O)O—; —N(R$^{11}$)C(O)N(R$^{11a}$)—; and —OC(O)N(R$^{11}$R$^{11a}$);

T is selected from the group consisting of phenyl; naphthyl; indenyl; indanyl; tetralinyl; $C_{3-10}$ cycloalkyl; 4 to 7 membered heterocyclyl; or 9 to 11 membered heterobicyclyl, wherein T is optionally substituted with one or more R$^{10}$, which are the same or different;

R$^{10}$ is halogen; CN; oxo (=O); COOR$^{12}$; OR$^{12}$; C(O)R$^{12}$; C(O)N(R$^{12}$R$^{12a}$); S(O)$_2$N(R$^{12}$R$^{12a}$); S(O)N(R$^{12}$R$^{12a}$); S(O)$_2$ R$^{12}$; S(O)R$^{12}$; N(R$^{12}$)S(O)$_2$N(R$^{12a}$R$^{12b}$); SR$^{12}$; N(R$^{12}$R$^{12a}$); NO$_2$; OC(O)R$^{12}$; N(R$^{12}$)C(O)R$^{12a}$; N(R$^{12}$)S(O)$_2$R$^{12a}$; N(R$^{12}$)S(O)R$^{12a}$; N(R$^{12}$)C(O)OR$^{12a}$; N(R$^{12}$)C(O)N(R$^{12a}$R$^{12b}$); OC(O)N(R$^{12}$R$^{12a}$); or $C_{1-6}$ alkyl, wherein $C_{1-6}$ alkyl is optionally substituted with one or more halogen, which are the same or different;

$R^{11}, R^{11a}, R^{12}, R^{12a}, R^{12b}$ are independently selected from the group consisting of H; or $C_{1-6}$ alkyl, wherein $C_{1-6}$ alkyl is optionally substituted with one or more halogen, which are the same or different.

The term "interrupted" means that between two carbons a group is inserted or at the end of the carbon chain between the carbon and hydrogen.

$L^2$ is a single chemical bond or a spacer. In case $L^2$ is a spacer, it is preferably defined as the one or more optional substituents defined above, provided that $L^2$ is substituted with Z.

Accordingly, when $L^2$ is other than a single chemical bond, $L^2$-Z is $COOR^9$; $OR^9$; $C(O)R^9$; $C(O)N(R^9R^{9a})$; $S(O)_2$ $N(R^9R^{9a})$; $S(O)N(R^9R^{9a})$; $S(O)_2R^9$; $S(O)R^9$; $N(R^9)S(O)_2N$ $(R^{9a}R^{9b})$; $SR^9$; $N(R^9R^{9a})$; $OC(O)R^9$; $N(R^9)C(O)R^{9a}$; $N(R^9)$ $S(O)_2R^{9a}$; $N(R^9)S(O)R^{9a}$; $N(R^9)C(O)OR^{9a}$; $N(R^9)C(O)N$ $(R^{9a}R^{9b})$; $OC(O)N(R^9R^{9a})$; T; $C_{1-50}$ so alkyl; $C_{2-50}$ alkenyl; or $C_{2-50}$ alkynyl, wherein T; $C_{1-50}$ alkyl; $C_{2-50}$ alkenyl; and $C_{2-50}$ alkynyl are optionally substituted with one or more $R^{10}$, which are the same or different and wherein $C_{1-50}$ alkyl; $C_{2-50}$ alkenyl; and $C_{2-50}$ alkynyl are optionally interrupted by one or more groups selected from the group consisting of -T-, —C(O)O—; —O—; —C(O)—; —C(O)N($R^{11}$)—; —S(O)$_2$N($R^{11}$)—; —S(O)N($R^{11}$)—; —S(O)$_2$—; —S(O)—; —N($R^{11}$)S(O)$_2$N($R^{11a}$)—; —S—; —N($R^{11}$)—; —OC(O) $R^{11}$; —N($R^{11}$)C(O)—; —N($R^{11}$)S(O)$_2$—; —N($R^{11}$)S(O)—; —N($R^{11}$)C(O)O—; —N($R^{11}$)C(O)N($R^{11a}$)—; and —OC (O)N($R^{11}R^{11a}$);

$R^9, R^{9a}, R^{9b}$ are independently selected from the group consisting of H; Z; T; and $C_{1-50}$ alkyl; $C_{2-50}$ alkenyl; or $C_{2-50}$ alkynyl, wherein T; $C_{1-50}$ alkyl; $C_{2-50}$ alkenyl; and $C_{2-50}$ alkynyl are optionally substituted with one or more $R^{10}$, which are the same or different and wherein $C_{1-50}$ alkyl; $C_{2-50}$ alkenyl; and $C_{2-50}$ alkynyl are optionally interrupted by one or more groups selected from the group consisting of T, —C(O)O—; —O—; —C(O)—; —C(O)N($R^{11}$)—; —S(O)$_2$N($R^{11}$)—; —S(O)N($R^{11}$)—; —S(O)$_2$—; —S(O)—; —N($R^{11}$)S(O)$_2$N($R^{11a}$)—; —S—; —N($R^{11}$)—; —OC(O) $R^{11}$; —N($R^{11}$)C(O)—; —N($R^{11}$)S(O)$_2$—; —N($R^{11}$)S(O)—; —N($R^{11}$)C(O)O—; —N($R^{11}$)C(O)N($R^{11a}$)—; and —OC (O)N($R^{11}R^{11a}$);

T is selected from the group consisting of phenyl; naphthyl; indenyl; indanyl; tetralinyl; $C_{3-10}$ cycloalkyl; 4 to 7 membered heterocyclyl; or 9 to 11 membered heterobicyclyl, wherein t is optionally substituted with one or more $R^{10}$, which are the same or different;

$R^{10}$ is Z; halogen; CN; oxo (=O); $COOR^{12}$; $OR^{12}$; C(O) $R^{12}$; $C(O)N(R^{12}R^{12a})$; $S(O)_2N(R^{12}R^{12a})$; $S(O)N$ $(R^{12}R^{12a})$; $S(O)_2R^{12}$; $S(O)R^{12}$; $N(R^{12})S(O)_2N$ $(R^{12a}R^{12b})$; $SR^{12}$; $N(R^{12}R^{12a})$; $NO_2$; $OC(O)R^{12}$; $N(R^{12})$ $C(O)R^{12a}$; $N(R^{12})S(O)_2R^{12a}$; $N(R^{12})S(O)R^{12a}$; $N(R^{12})C$ $(O)OR^{12a}$; $N(R^{12})C(O)N(R^{12a}R^{12b})$; $OC(O)N(R^{12}R^{12a})$; or $C_{1-6}$ alkyl, wherein $C_{1-6}$ alkyl is optionally substituted with one or more halogen, which are the same or different;

$R^{11}, R^{11a}, R^{12}, R^{12a}, R^{12b}$ are independently selected from the group consisting of H; Z; or $C_{1-6}$ alkyl, wherein $C_{1-6}$ alkyl is optionally substituted with one or more halogen, which are the same or different;

provided that one of $R^9, R^{9a}, R^{9b}, R^{10}, R^{11}, R^{11a}, R^{12}, R^{12a}, R^{12b}$ is Z.

Preferred structures for formula (VI) are selected from the group consisting of

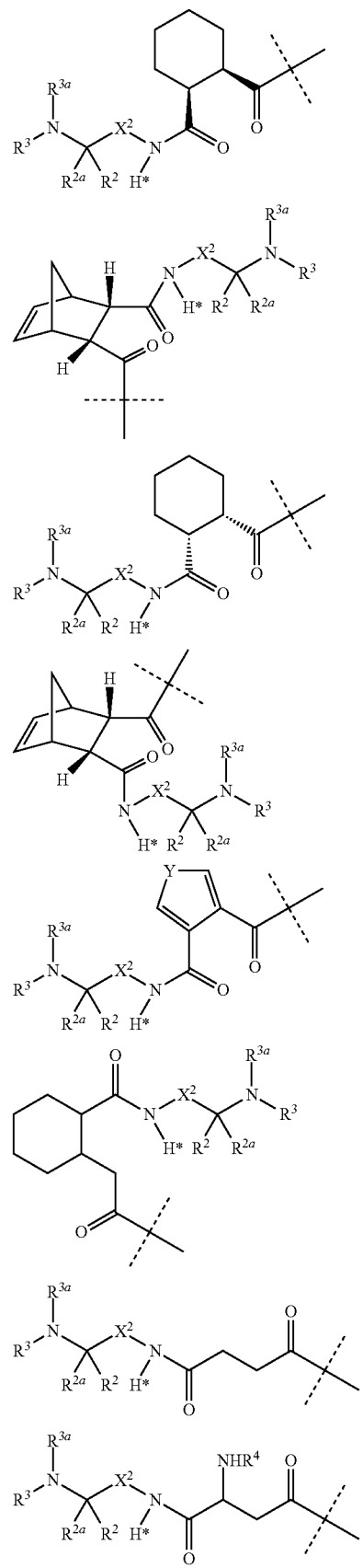

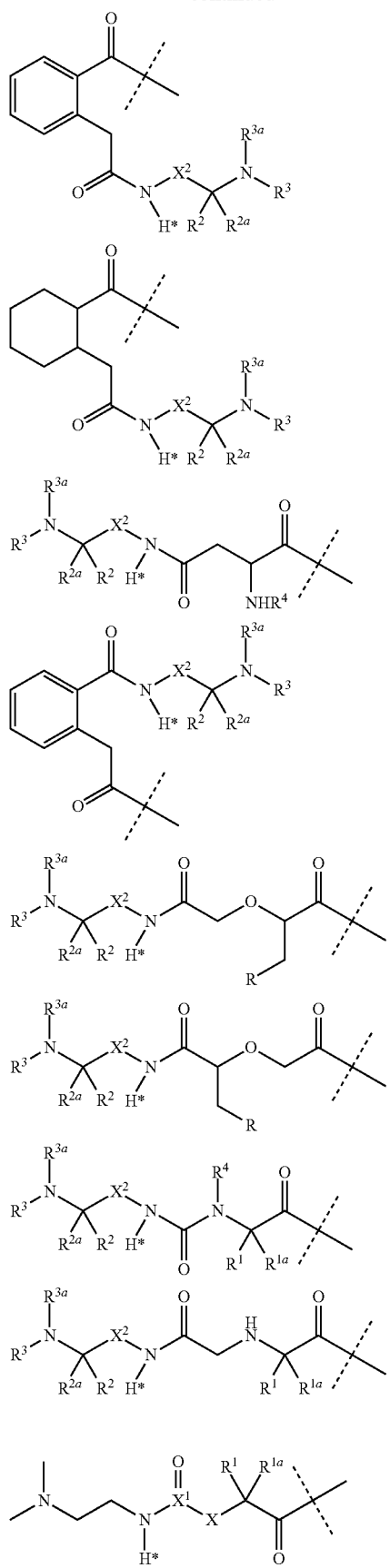
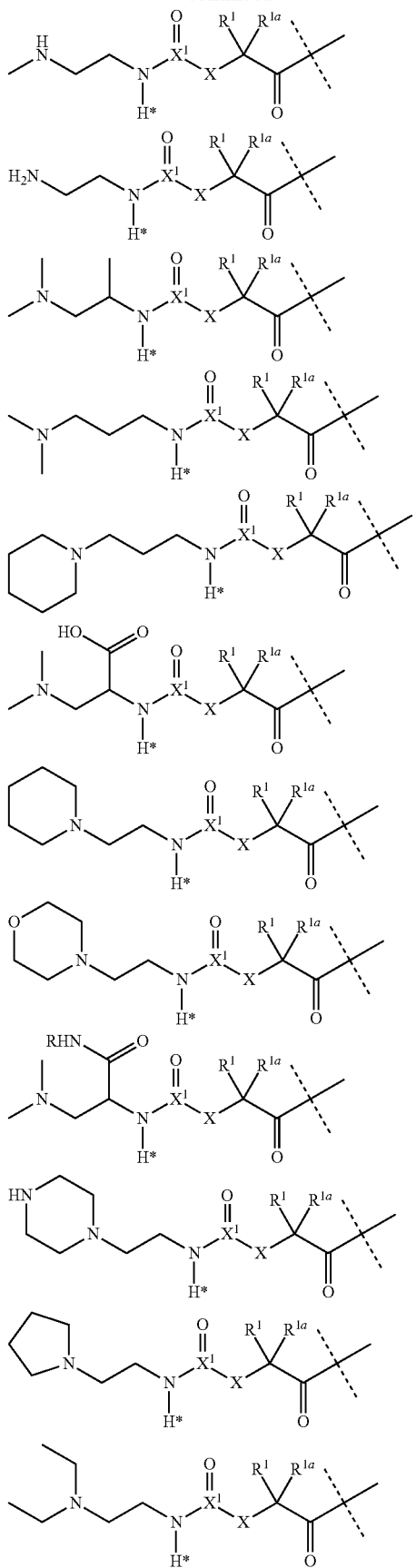

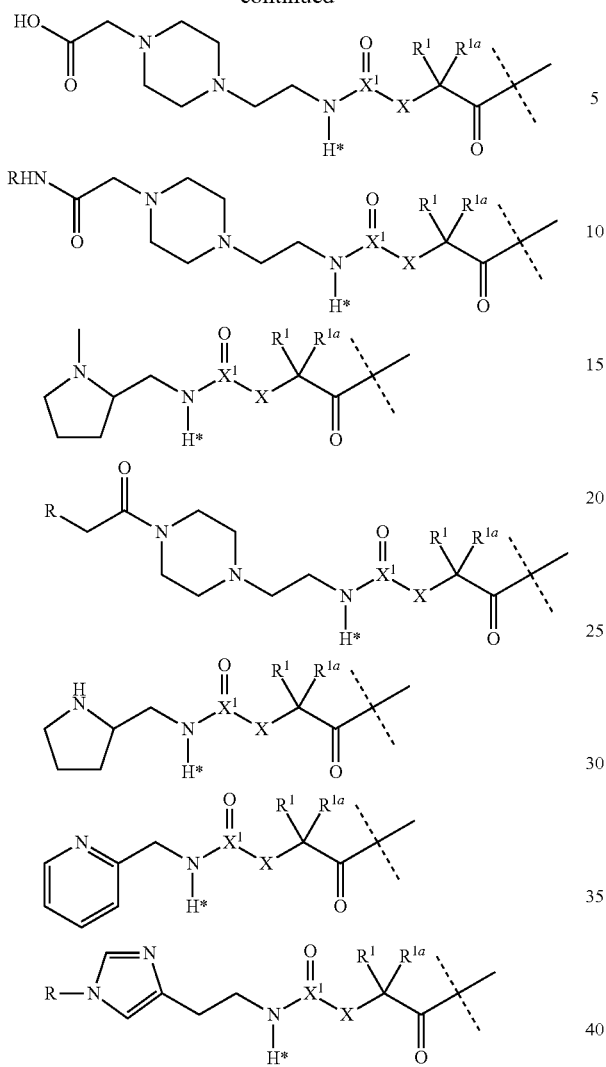
wherein R is H; or $C_{1-4}$ alkyl; Y is NH; O; or S; and $R^1$, $R^{1a}$, $R^2$, $R^{2a}$, $R^3$, $R^{3a}$, $R^4$, X, $X^1$, $X^2$ have the meaning as indicated above.
Even more preferred structures for formula (VI) are selected from the group consisting of
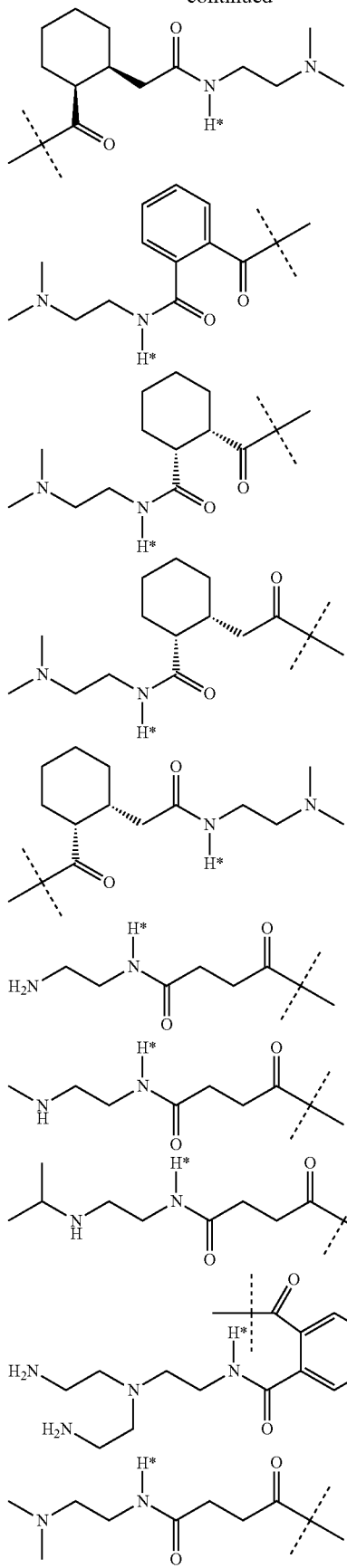

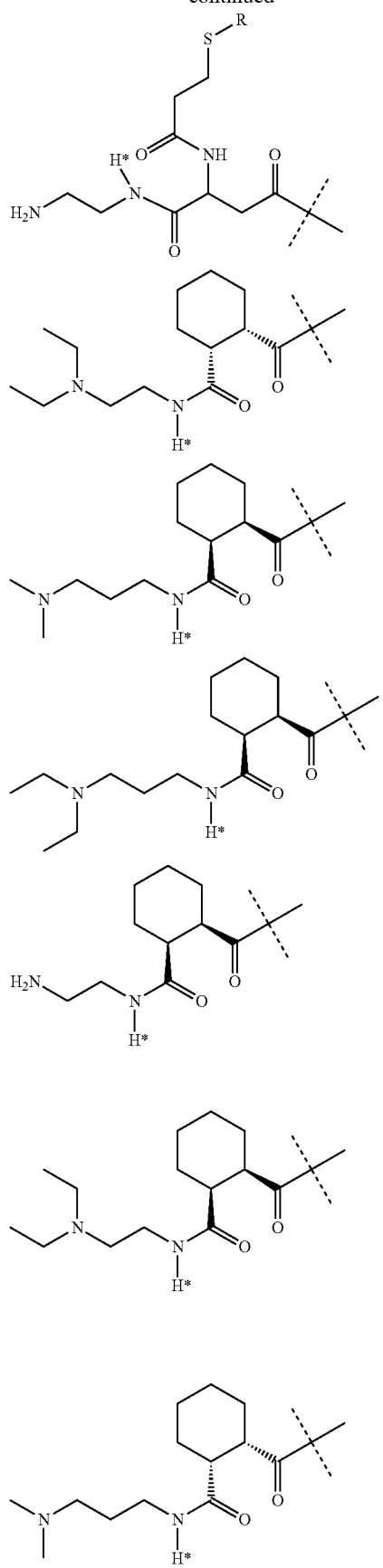
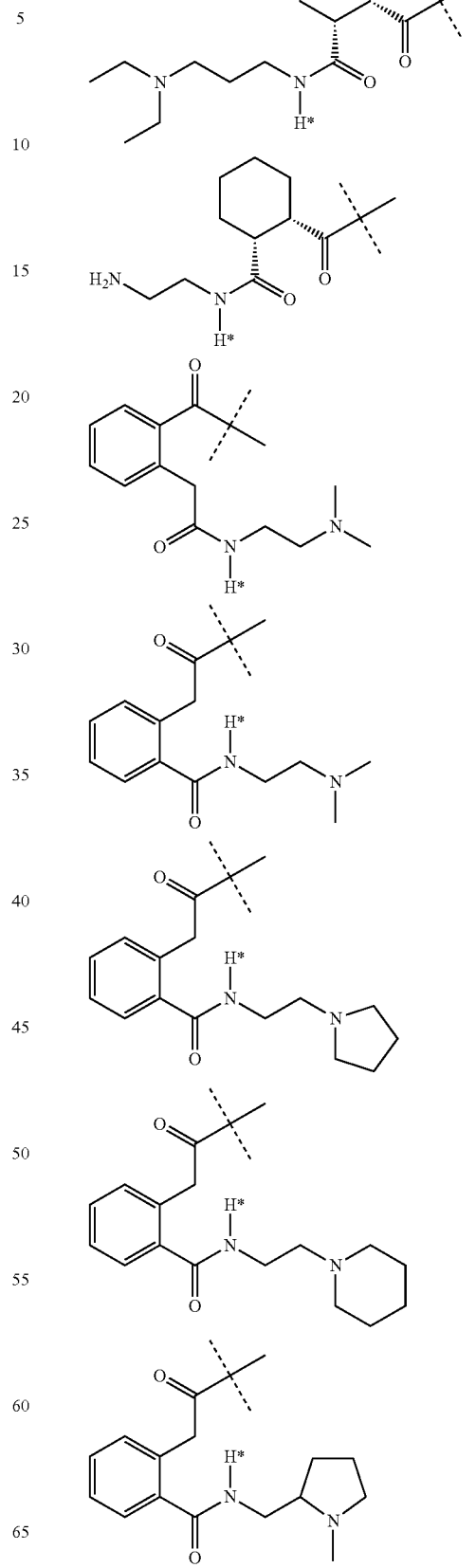

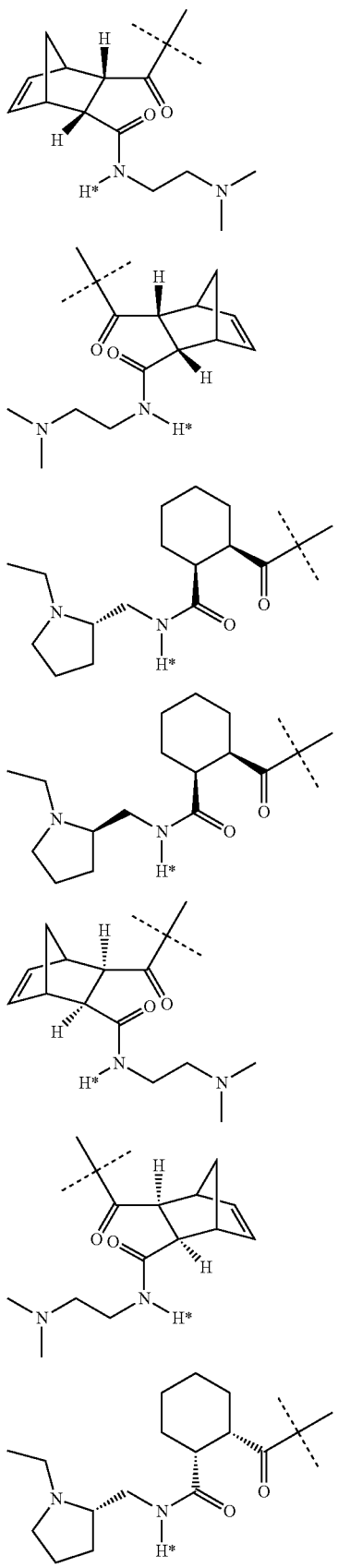
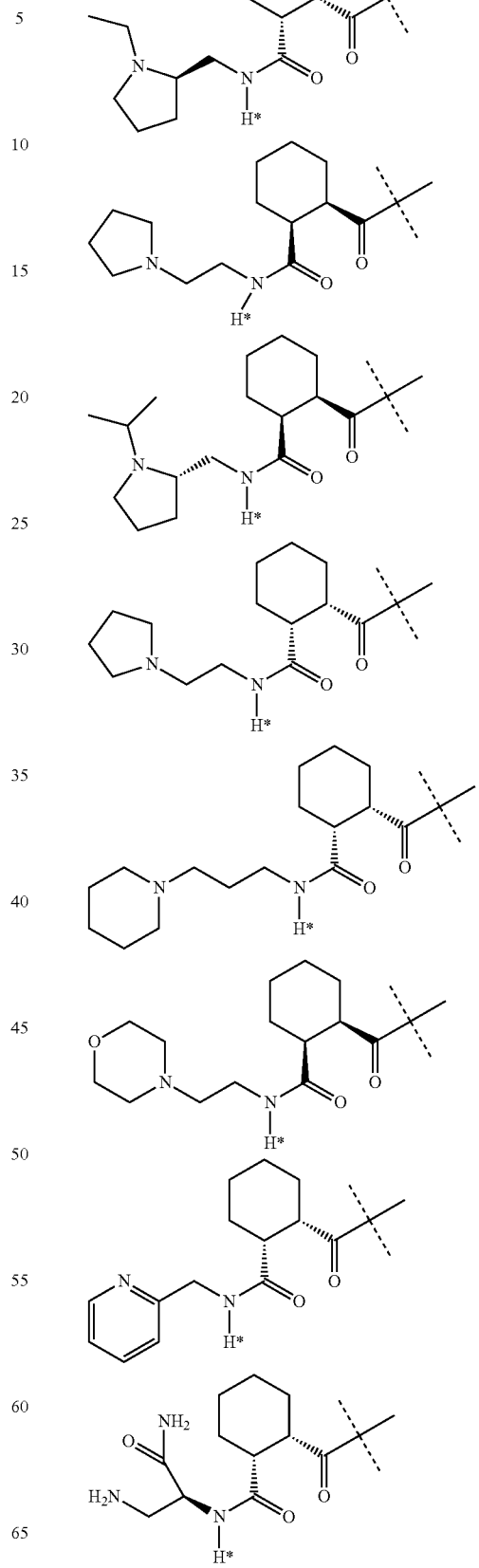

-continued
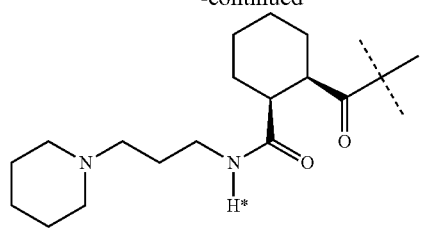
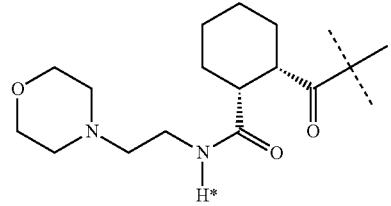
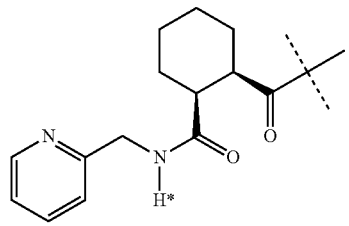
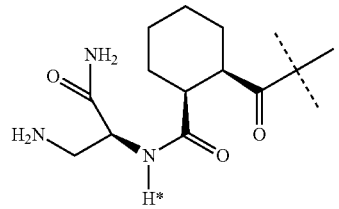
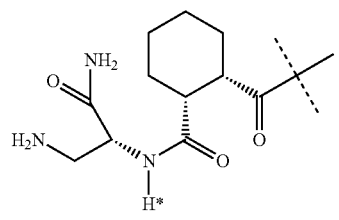
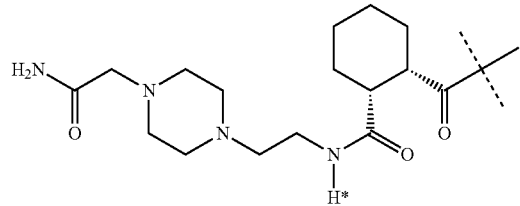
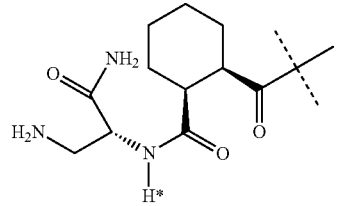
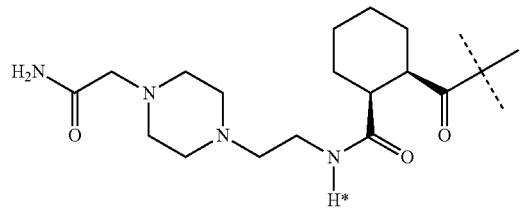
-continued
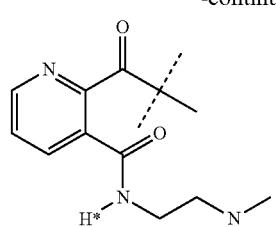
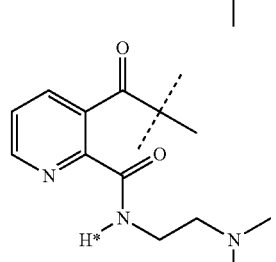
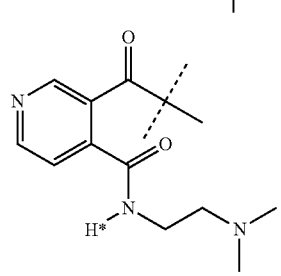
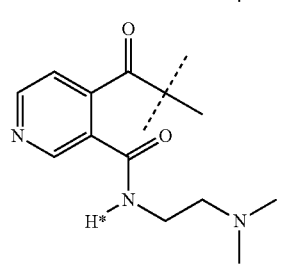
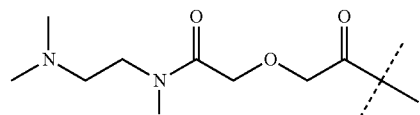
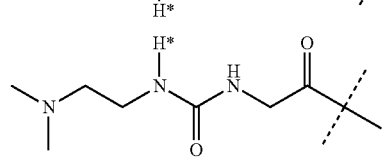
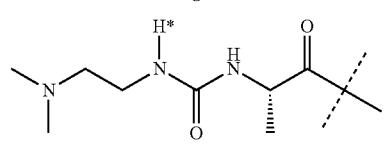
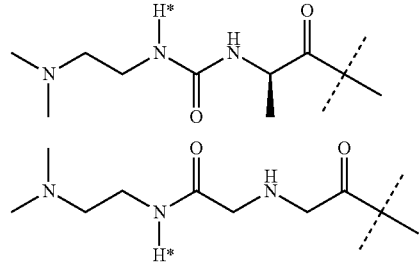

57
-continued
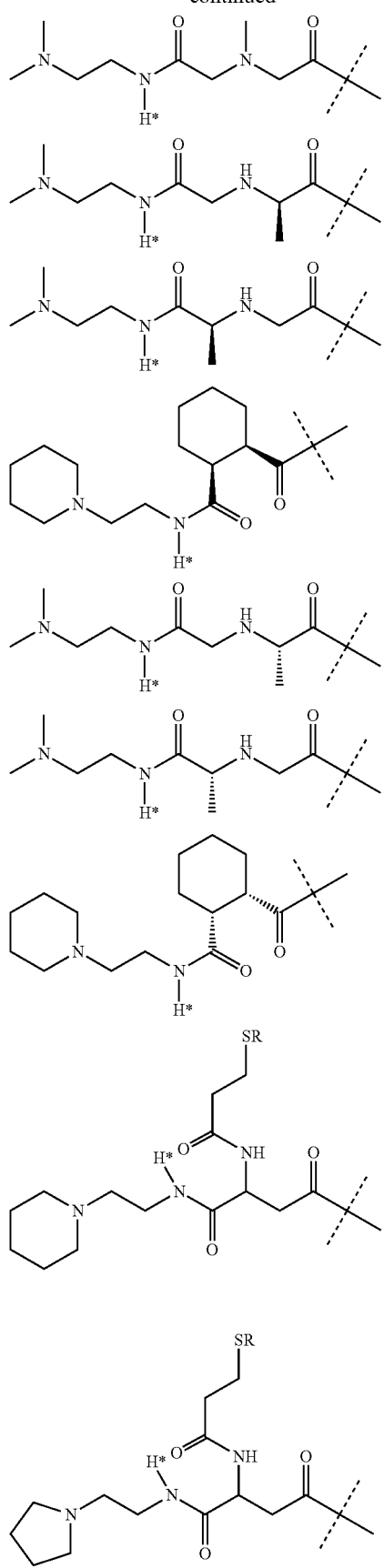
58
-continued
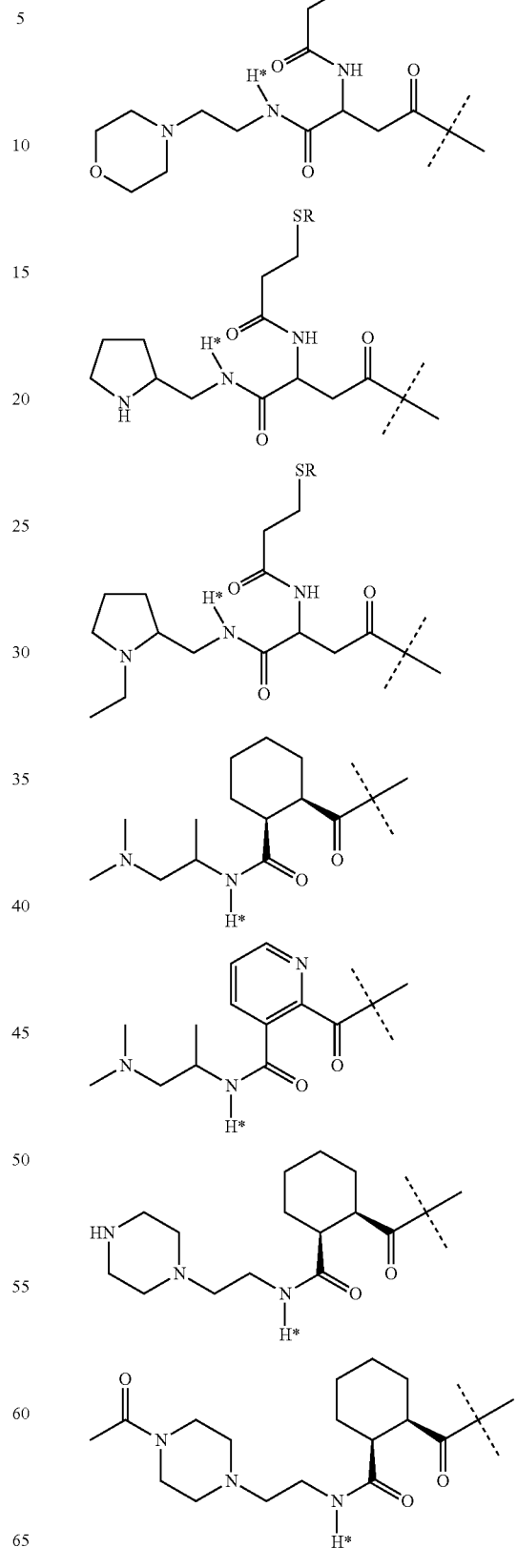

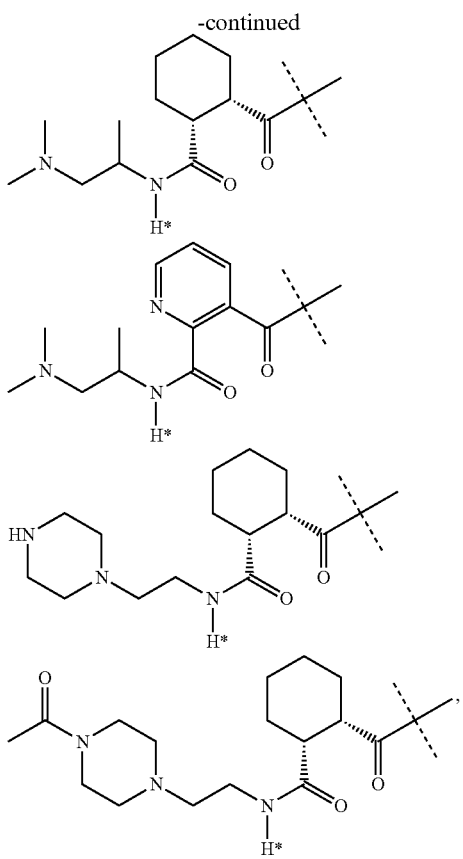

wherein R has the meaning as indicated above.

Further preferred prodrugs of the present invention are represented by a drug linker conjugate D-L, wherein D is an aromatic amine containing biologically active moiety; and L is a non-biologically active linker containing
  i) a moiety $L^1$ represented by formula (VII),

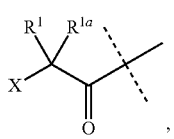
(VII)

wherein the dashed line indicates the attachment of $L^1$ to an aromatic amino group of D by forming an amide bond; and wherein X, $R^1$, and $R^{1a}$ of formula (VII) have the following meaning:

X is H or $C_{1-50}$ alkyl optionally interrupted by one or more groups selected from —NH—, —C(C$_{1-4}$ alkyl)-, —O—, —C(O)— or —C(O)NH—;

$R^1$ and $R^{1a}$ are independently selected from the group consisting of H and $C_{1-4}$ alkyl;

optionally, $L^1$ is further substituted.

ii) a moiety $L^2$, which is a chemical bond or a spacer, and $L^2$ is bound to a carrier group Z representing the hydrogel of the present invention,
   wherein $L^1$ is substituted with one $L^2$ moiety.

More preferably, X in formula (VII) includes one of the following fragments, wherein the dashed line on the right hand side indicates the attachment of $L^1$ to D by forming an amide bond with the aromatic amino group of D and the dashed line on the left hand side indicates the attachment to the rest of X and wherein $L^1$ is optionally further substituted:

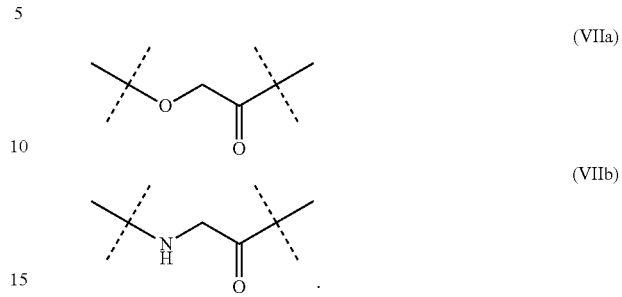

More preferably, X in formula (VII) includes one of the following fragments, wherein the dashed line on the right hand side indicates the attachment of $L^1$ to D by forming an amide bond with the aromatic amino group of D and the dashed line on the left hand side indicates the attachment to the rest of X:

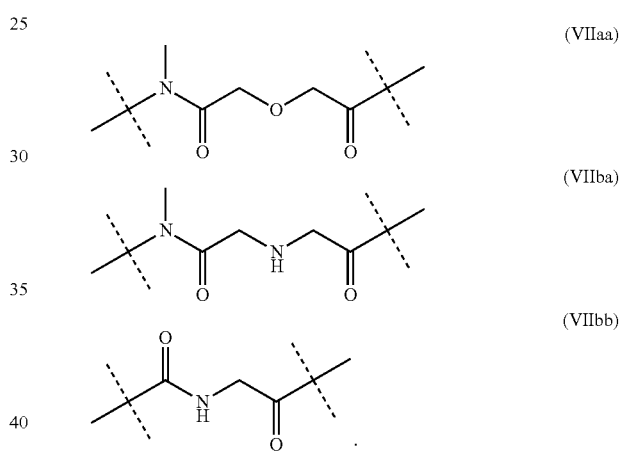

More preferably, L is a non-biologically active linker containing
  i) a moiety $L^1$ represented by formula (VIII),

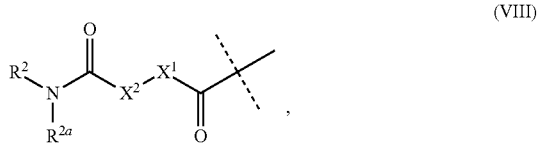
(VIII)

wherein the dashed line indicates the attachment of $L^1$ to an aromatic amino group of D by forming an amide bond; and wherein $X^1$, $X^2$, $R^2$, and $R^{2a}$ have the following meaning:

$X^1$ is $C(R^1R^{1a})$ or a cyclic fragment selected from $C_{3-7}$ cycloalkyl, 4 to 7 membered heterocyclyl, phenyl, naphthyl, indenyl, indanyl, tetralinyl, or 9 to 11 membered heterobicyclyl;

$X^2$ is a chemical bond or selected from $C(R^3R^{3a})$, $N(R^3)$, O, $C(R^3R^{3a})$—$C(R^4R^{4a})$, $C(R^3R^{3a})$—$N(R^4)$, $N(R^3)$—$C(R^4R^{4a})$, $C(R^3R^{3a})$—O, or O—$C(R^3R^{3a})$, wherein in case $X^1$ is a cyclic fragment, $X^2$ is a chemical bond, $C(R^3R^{3a})$, $N(R^3)$ or O;

optionally, in case X¹ is a cyclic fragment and X² is C(R³R³ᵃ), the order of the X¹ fragment and the X² fragment within L¹ may be changed;

R¹, R³ and R⁴ are independently selected from the group consisting of H, $C_{1-4}$ alkyl and —N(R⁵R⁵ᵃ);

R¹ᵃ, R², R²ᵃ, R³ᵃ, R⁴ᵃ and R⁵ᵃ are independently selected from the group consisting of H, and $C_{1-4}$ alkyl;

optionally, one of the pairs R²ᵃ/R², R²ᵃ/R³ᵃ, R²ᵃ/R⁴ᵃ are joined to form a 4 to 7 membered at least partially saturated heterocycle;

R⁵ is C(O)R⁶;

R⁶ is $C_{1-4}$ alkyl;

optionally, one of the pairs R¹ᵃ/R⁴ᵃ, R³ᵃ/R⁴ᵃ or R¹ᵃ/R³ᵃ form a chemical bond;

optionally, L¹ is further substituted.

ii) a moiety L², which is a chemical bond or a spacer, and L² is bound to a carrier group Z representing the hydrogel of the present invention, wherein L¹ is substituted with one L² moiety;

optionally, L is further substituted.

More preferably, the moiety L¹ is selected from

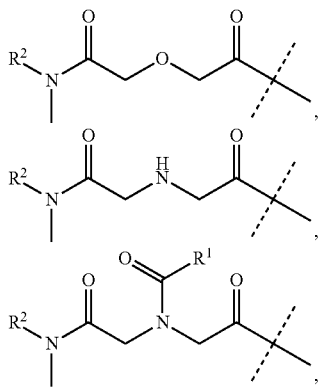

Preferably, in formula (VIII) R¹ᵃ, R², R²ᵃ, R³ᵃ, R⁴ᵃ and R⁵ᵃ are independently selected from the group consisting of H, and $C_{1-4}$ alkyl.

In another preferred embodiment, L is a non-biologically active linker containing i) a moiety L¹ represented by formula (IX),

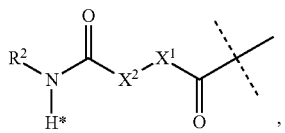
(IX)

wherein the dashed line indicates the attachment of L¹ to an aromatic amino group of D by forming an amide bond; and wherein X¹, X², and R² of formula (IX) have the following meaning X¹ is C(R¹R¹ᵃ) or a cyclic fragment selected from $C_{3-7}$ cycloalkyl, 4 to 7 membered heterocyclyl, phenyl, naphthyl, indenyl, indanyl, tetralinyl, or 9 to 11 membered heterobicyclyl, wherein in case X¹ is a cyclic fragment, said cyclic fragment is incorporated into L¹ via two adjacent ring atoms and the ring atom of X¹, which is adjacent to the carbon atom of the amide bond, is also a carbon atom;

X² is a chemical bond or selected from C(R³R³ᵃ), N(R³), O, C(R³R³ᵃ)—C(R⁴R⁴ᵃ), C(R³R³ᵃ)—N(R⁴), N(R³)—C(R⁴R⁴ᵃ), C(R³R³ᵃ)—O, or O—C(R³R³ᵃ), wherein in case X¹ is a cyclic fragment, X² is a chemical bond, C(R³R³ᵃ), N(R³) or O;

optionally, in case X¹ is a cyclic fragment and X² is C(R³R³ᵃ), the order of the X¹ fragment and the X² fragment within L¹ may be changed and the cyclic fragment is incorporated into L¹ via two adjacent ring atoms;

R¹, R³ and R⁴ are independently selected from the group consisting of H, $C_{1-4}$ alkyl and —N(R⁵R⁵ᵃ);

R¹ᵃ, R², R³ᵃ, R⁴ᵃ and R⁵ᵃ are independently selected from the group consisting of H, and $C_{1-4}$ alkyl;

R⁵ is C(O)R⁶;

R⁶ is $C_{1-4}$alkyl;

optionally, one of the pairs R¹ᵃ/R⁴ᵃ, R³ᵃ/R⁴ᵃ or R¹ᵃ/R³ᵃ form a chemical bond;

ii) a moiety L², which is a chemical bond or a spacer, and L² is bound to a carrier group Z representing the biodegradable hydrogel according to the invention, wherein L¹ is substituted with one L² moiety, provided that the hydrogen marked with the asterisk in formula (IX) is not replaced by L²;

optionally, L is further substituted.

More preferably, the moiety L¹ is selected from

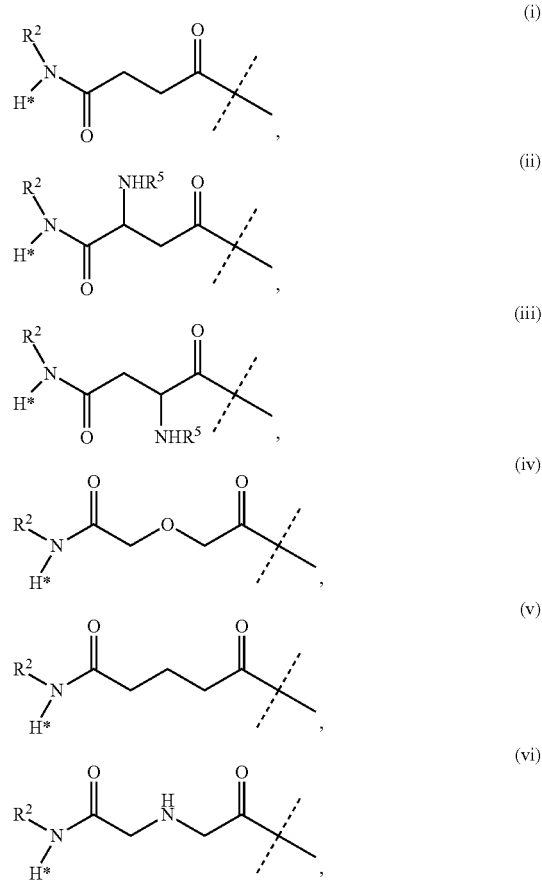

-continued
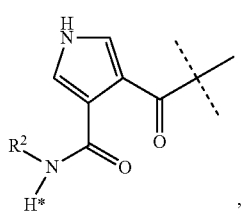
(vii)
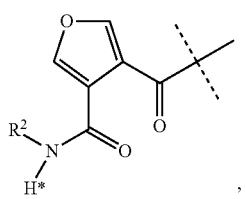
(viii)
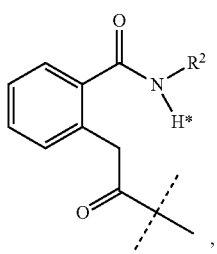
(ix)
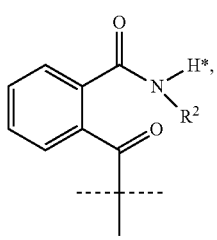
(x)
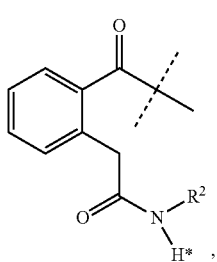
(xi)
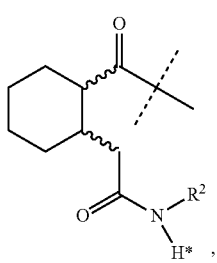
(xii)
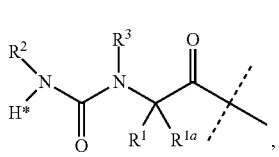
(xiii)
-continued
(xiv)
(xv)
(xvi)
(xvii)
(xviii)
(xvix)
(xx)

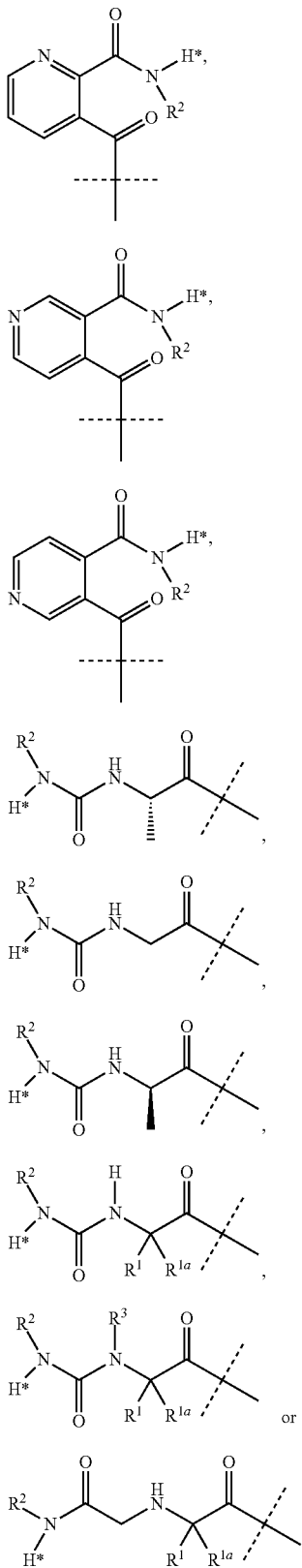

"Aromatic amine containing biologically active moiety D" means the part (moiety or fragment) of the drug linker conjugate D-L, which results after cleavage in a drug D-H (active agent) of (known) biological activity. In addition, the subterm "aromatic amine containing" means that the respective moiety D and analogously the corresponding drug D-H contain at least one aromatic fragment, which is substituted with at least one amino group.

The amino substituent of the aromatic fragment of D forms together with the carbonyl-fragment (—C(O)—) on the right hand side of $L^1$ (as depicted in formula (I)) an amide bond within the drug linker conjugate D-L. By consequence, the two parts D and L of the drug linker conjugate D-L are connected (chemically bound) by an amide fragment of the general structure $Y^1$—C(O)—N(R)—$Y^2$. $Y^1$ indicates the remaining parts of the moiety $L^1$ and $Y^2$ indicates the aromatic fragment of D. R is a substituent such as $C_{1-4}$ alkyl or preferably hydrogen. For example, said amide bond is indicated within formula (I) by the dashed line added diagonally on this bond.

"Non-biologically active linker" means a linker which does not show the pharmacological effects of the drug (D-H) derived from the biologically active moiety.

As indicated above, the $X^1$-fragment of the moiety $L^1$ represented by formula (IX) may also be a cyclic fragment such as $C_{3-7}$ cycloalkyl, phenyl or indanyl. In case $X^1$ is such a cyclic fragment, the respective cyclic fragment is incorporated into $L^1$ via two adjacent ring atoms (of said cyclic fragment). For example, if $X^1$ is phenyl, the phenyl fragment of $L^1$ is bound to the $X^2$ fragment of $L^1$ via a first (phenyl) ring atom being in a-position (adjacent) to a second (phenyl) ring atom, which itself is bound to the carbon atom of the carbonyl-fragment on the right hand side of $L^1$ according to formula (IX) (the carbonyl fragment which forms together with the aromatic amino group of D an amide bond).

"Alkyl" means a straight-chain or branched carbon chain (unsubstituted alkyl). Optionally, each hydrogen of an alkyl carbon may be replaced by a substituent.

"$C_{1-4}$ alkyl" means an alkyl chain having 1 to 4 carbon atoms (unsubstituted $C_{1-4}$ alkyl), e.g. if present at the end of a molecule: methyl, ethyl, n-propyl, isopropyl, n-butyl, isobutyl, sec-butyl tert-butyl, or e.g. —$CH_2$—, —$CH_2$—$CH_2$—, —CH($CH_3$)—, —$CH_2$—$CH_2$—$CH_2$—, —CH($C_2H_5$)—, —C($CH_3$)$_2$—, when two moieties of a molecule are linked by the alkyl group. Optionally, each hydrogen of a $C_{1-4}$ alkyl carbon may be replaced by a substituent. Accordingly, "$C_{1-50}$ alkyl" means an alkyl chain having 1 to 50 carbon atoms.

"$C_{2-50}$ alkenyl" means a branched or unbranched alkenyl chain having 2 to 50 carbon atoms (unsubstituted $C_{2-50}$ alkenyl), e.g. if present at the end of a molecule: —CH=$CH_2$, —CH=CH—$CH_3$, —$CH_2$—CH=$CH_2$, —CH=CH—$CH_2$—$CH_3$, —CH=CH—CH=$CH_2$, or e.g. —CH=CH—, when two moieties of a molecule are linked by the alkenyl group. Optionally, each hydrogen of a $C_{2-50}$ alkenyl carbon may be replaced by a substituent as further specified. Accordingly, the term "alkenyl" relates to a carbon chain with at least one carbon carbon double bond. Optionally, one or more triple bonds may occur.

"$C_{2-50}$ alkynyl" means a branched or unbranched alkynyl chain having 2 to 50 carbon atoms (unsubstituted $C_{2-50}$ alkynyl), e.g. if present at the end of a molecule: —C≡CH, —$CH_2$—C≡CH, $CH_2$—$CH_2$—C≡CH, $CH_2$—C≡C—$CH_3$, or e.g. —C≡C— when two moieties of a molecule are linked by the alkynyl group. Optionally, each hydrogen of a $C_{2-50}$ alkynyl carbon may be replaced by a substituent as further specified. Accordingly, the term "alkynyl" relates to a carbon chain with at lest one carbon carbon triple bond. Optionally, one or more double bonds may occur.

"$C_{3-7}$ cycloalkyl" or "$C_{3-7}$ cycloalkyl ring" means a cyclic alkyl chain having 3 to 7 carbon atoms, which may have carbon-carbon double bonds being at least partially saturated (unsubstituted $C_{3-7}$ cycloalkyl), e.g. cyclopropyl, cyclobutyl, cyclopentyl, cyclohexyl, cyclohexenyl, cycloheptyl. Optionally, each hydrogen of a cycloalkyl carbon may be replaced by a substituent. The term "$C_{3-7}$ cycloalkyl" or "$C_{3-7}$ cycloalkyl ring" also includes bridged bicycles like norbonane (norbonanyl) or norbonene (norbonenyl). Accordingly, "$C_{3-5}$ cycloalkyl" means a cycloalkyl having 3 to 5 carbon atoms.

"Halogen" means fluoro, chloro, bromo or iodo. It is generally preferred that halogen is fluoro or chloro.

"4 to 7 membered heterocyclyl" or "4 to 7 membered heterocycle" means a ring with 4, 5, 6 or 7 ring atoms that may contain up to the maximum number of double bonds (aromatic or non-aromatic ring which is fully, partially or un-saturated) wherein at least one ring atom up to 4 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom (unsubstituted 4 to 7 membered heterocyclyl). For the sake of completeness it is indicated that, for example, in case $X^1$ is 4 to 7 membered heterocyclyl, the respective additional requirements of $X^1$ have to be considered as well. This means that in this case the respective 4 to 7 membered heterocyclyl is incorporated into $L^1$ via two adjacent ring atoms and the ring atom of said 4 to 7 membered heterocyclyl, which is adjacent to the carbon atom of the amide bond, is also a carbon atom.

Examples for a 4 to 7 membered heterocycles are azetidine, oxetane, thietane, furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydrofuran, tetrahydrothiophene, pyrrolidine, imidazolidine, pyrazolidine, oxazolidine, isoxazolidine, thiazolidine, isothiazolidine, thiadiazolidine, sulfolane, pyran, dihydropyran, tetrahydropyran, imidazolidine, pyridine, pyridazine, pyrazine, pyrimidine, piperazine, piperidine, morpholine, tetrazole, triazole, triazolidine, tetrazolidine, diazepane, azepine or homopiperazine. Optionally, each hydrogen of a 4 to 7 membered heterocyclyl may be replaced by a substituent.

"9 to 11 membered heterobicyclyl" or "9 to 11 membered heterobicycle" means a heterocyclic system of two rings with 9 to 11 ring atoms, where at least one ring atom is shared by both rings and that may contain up to the maximum number of double bonds (aromatic or non-aromatic ring which is fully, partially or un-saturated) wherein at least one ring atom up to 6 ring atoms are replaced by a heteroatom selected from the group consisting of sulfur (including —S(O)—, —S(O)$_2$—), oxygen and nitrogen (including =N(O)—) and wherein the ring is linked to the rest of the molecule via a carbon or nitrogen atom (unsubstituted 9 to 11 membered heterobicyclyl). For the sake of completeness it is indicated that, for example, in case $X^1$ is 9 to 11 membered heterobicyclyl, the respective additional requirements of $X^1$ have to be considered as well. This means that in this case the respective 9 to 11 membered heterobicyclyl is incorporated into $L^1$ via two adjacent ring atoms and the ring atom of said 9 to 11 membered heterobicyclyl, which is adjacent to the carbon atom of the amide bond, is also a carbon atom.

Examples for a 9 to 11 membered heterobicycle are indole, indoline, benzofuran, benzothiophene, benzoxazole, benzisoxazole, benzothiazole, benzisothiazole, benzimidazole, benzimidazoline, quinoline, quinazoline, dihydroquinazoline, quinoline, dihydroquinoline, tetrahydroquinoline, decahydroquinoline, isoquinoline, decahydroisoquinoline, tetrahydroisoquinoline, dihydroisoquinoline, benzazepine, purine or pteridine. The term 9 to 11 membered heterobicycle also includes spiro structures of two rings like 1,4-dioxa-8-azaspiro[4.5]decane or bridged heterocycles like 8-aza-bicyclo[3.2.1]octane. Optionally, each hydrogen of a 9 to 11 membered heterobicyclyl may be replaced by a substituent.

The non-biologically active linker L contains a moiety $L^1$ represented by formula (IX) as depicted and defined above. Preferably, the moiety $L^1$ is defined as follows.

$X^1$ is $C(R^1R^{1a})$, cyclohexyl, phenyl, pyridinyl, norbonenyl, furanyl, pyrrolyl or thienyl, wherein in case $X^1$ is a cyclic fragment, said cyclic fragment is incorporated into $L^1$ via two adjacent ring atoms;

$X^2$ is a chemical bond or selected from $C(R^3R^{3a})$, $N(R^3)$, O, $C(R^3R^{3a})$—O or $C(R^3R^{3a})$—$C(R^4R^{4a})$;

$R^3$ and $R^4$ are independently selected from H, $C_{1-4}$ alkyl or —$N(R^5R^{5a})$;

$R^{1a}$, $R^{3a}$, $R^{4a}$ and $R^{5a}$ are independently selected from H or $C_{1-4}$ alkyl;

$R^2$ is $C_{1-4}$ alkyl;

$R^5$ is $C(O)R^6$;

$R^6$ is $C_{1-4}$ alkyl;

More preferably, the moiety $L^1$ is selected from

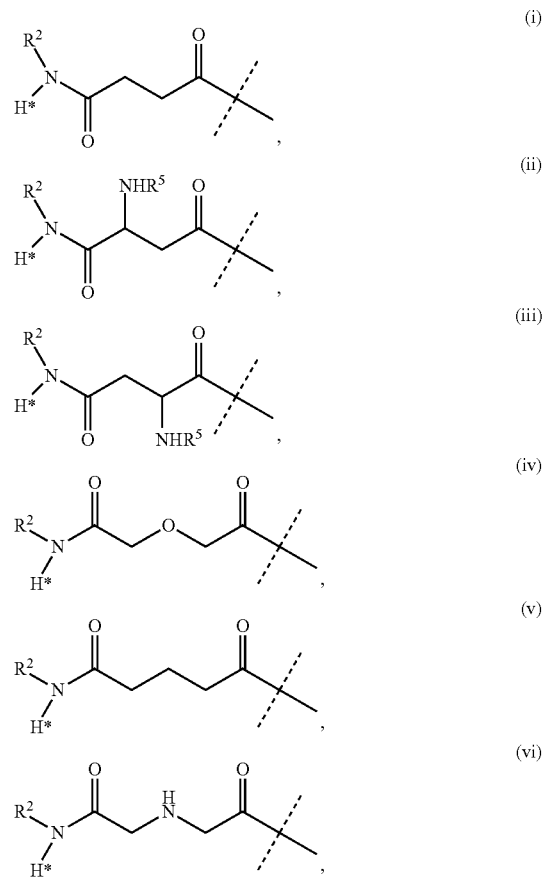

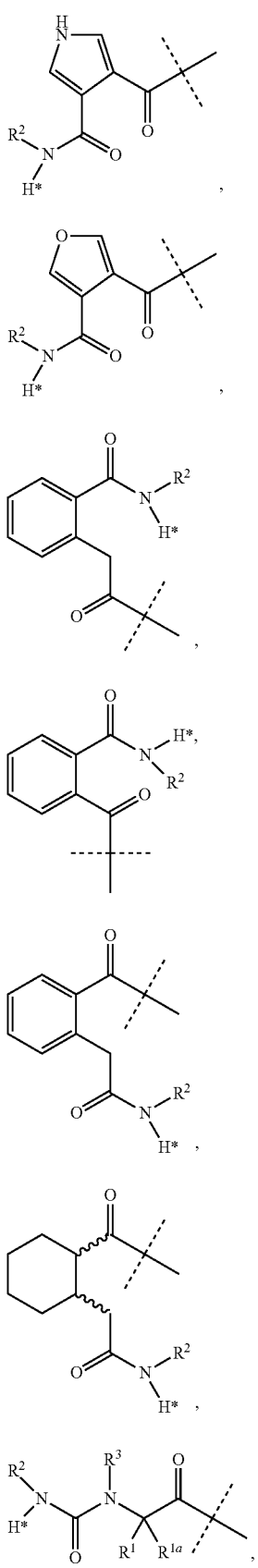
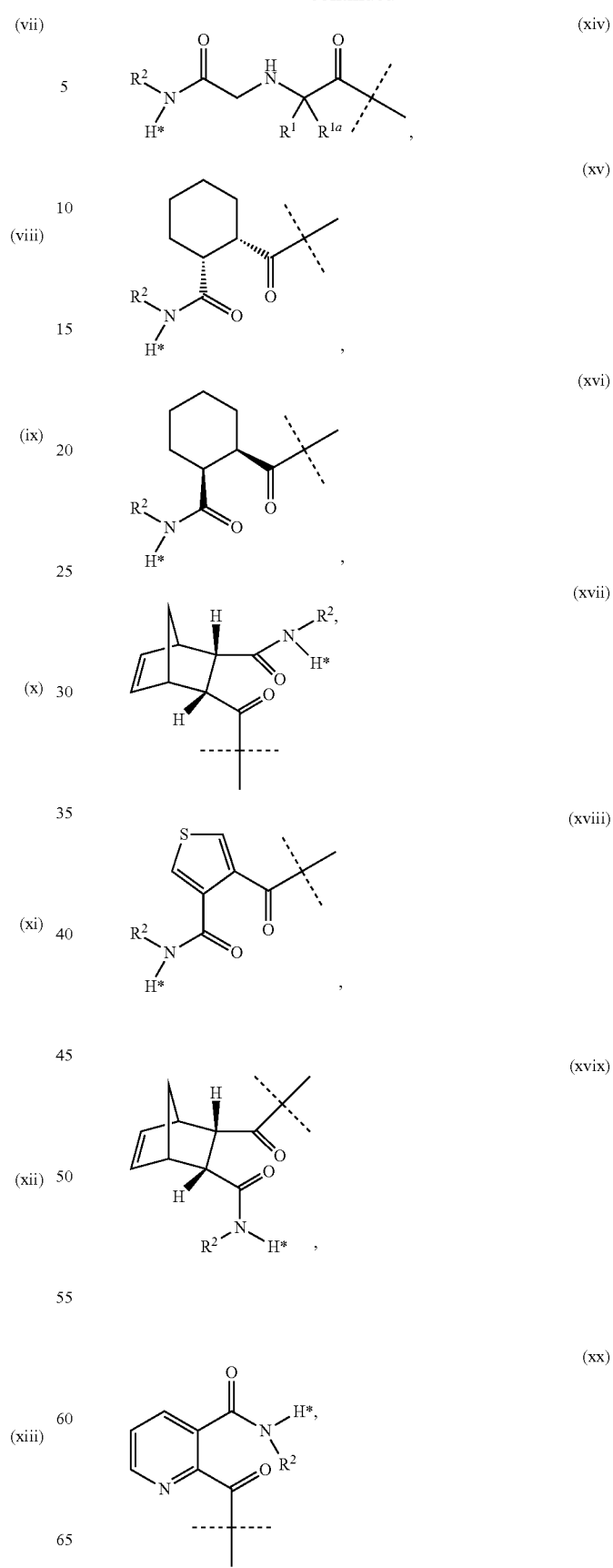

-continued

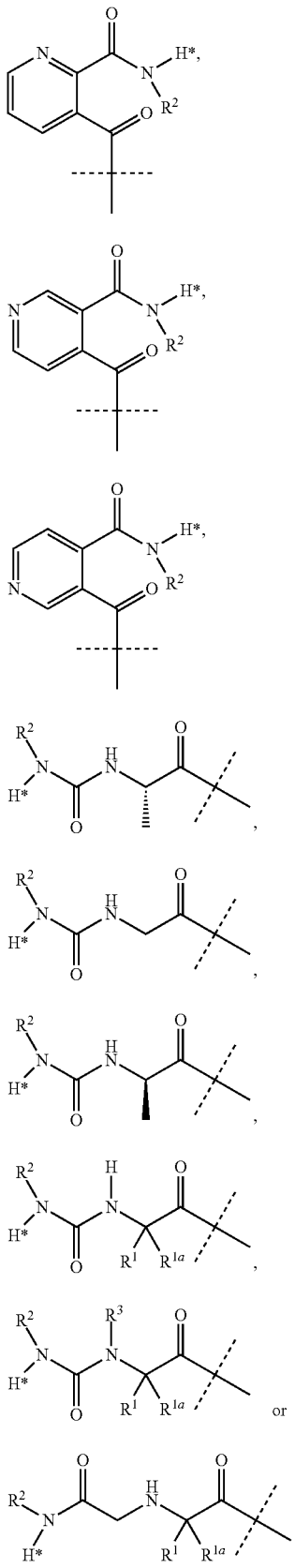

wherein
(xxi) $R^5$ is $C(O)R^6$;
$R^1$, $R^{1a}$, $R^2$, $R^3$ and $R^6$ are independently from each other $C_{1-4}$ alkyl; and
$L^1$ is substituted with one $L^2$ moiety, preferably $R^2$ is substituted with one $L^2$ moiety, i.e. the substitution of $L^1$ preferably occurs at $R^2$.

In yet another preferred embodiment, the preferred structure for a prodrug of the present invention is given by a prodrug conjugate (xxii)     $$D\text{-}O\text{—}Z^0 \qquad (X),$$

wherein
D is a hydroxyl group-containing biologically active moiety which is coupled to the moiety $Z^0$ through the oxygen of the hydroxyl group; and wherein $Z^0$ of formula (X) has the following meaning:
$Z^0$ is $C(O)\text{—}X^0\text{—}Z^1$; $C(O)O\text{—}X^0\text{—}Z^1$; $S(O)_2\text{—}X^0\text{—}Z^1$; $C(S)\text{—}X^0\text{—}Z^1$; $S(O)_2O\text{—}X^0\text{—}Z^1$; $S(O)_2N(R^1)\text{—}X^0\text{—}Z^1$; $CH(OR^1)\text{—}X^0\text{—}Z^1$; $C(OR^1)(OR^2)\text{—}X^0\text{—}Z^1$;
(xxiii) $C(O)N(R^1)\text{—}X^0\text{—}Z^1$; $P(=O)(OH)O\text{—}X^0\text{—}Z^1$; $P(=O)(OR^1)O\text{—}X^0\text{—}Z^1$; $P(=O)(SH)O\text{—}X^0\text{—}Z^1$; $P(=O)(SR^1)O\text{—}X^0\text{—}Z^1$; $P(=O)(OR^1)\text{—}X^0\text{—}Z^1$; $P(=S)(OH)O\text{—}X^0\text{—}Z^1$; $P(=S)(OR^1)O\text{—}X^0\text{—}Z^1$; $P(=S)(OH)N(R^1)\text{—}X^0\text{—}Z^1$; $P(=S)(OR^1)N(R^2)\text{—}X^0\text{—}Z^1$; $P(=O)(OH)N(R^1)\text{—}X^0\text{—}Z^1$; or $P(=O)(OR^1)N(R^2)\text{—}X^0\text{—}Z^1$;
$R^1$, $R^2$ are independently selected from the group consisting of $C_{1-6}$ alkyl; or $R^1$, $R^2$ jointly form a $C_{1-6}$ alkylene bridging group;
(xxiv) $X^0$ is $(X^{0A})_{m1}\text{-}(X^{0B})_{m2}$;
m1; m2 are independently 0; or 1;
$X^{0A}$ is $T^0$;
$X^{0B}$ is a branched or unbranched $C_{1-10}$ alkylene group which is unsubstituted or substituted with one or more $R^3$, which are the same or different;
(xxv) $R^3$ is halogen; CN; $C(O)R^4$; $C(O)OR^4$; $OR^4$; $C(O)R^4$; $C(O)N(R^4R^{4a})$; $S(O)_2N(R^4R^{4a})$; $S(O)N(R^4R^{4a})$; $S(O)_2R^4$; $S(O)R^4$; $N(R^4)S(O)_2N(R^{4a}R^{4b})$; $SR^4$; $N(R^4R^{4a})$; $NO_2$; $OC(O)R^4$; $N(R^4)C(O)R^{4a}$; $N(R^4)SO_2R^{4a}$; $N(R^4)S(O)R^{4a}$; $N(R^4)C(O)N(R^{4a}R^{4b})$; $N(R^4)C(O)OR^{4a}$; $OC(O)N(R^4R^{4a})$; or $T^0$;
(xxvi) $R^4$, $R^{4a}$, $R^{4b}$ are independently selected from the group consisting of H; $T^0$; $C_{1-4}$ alkyl; $C_{2-4}$ alkenyl; and $C_{2-4}$ alkynyl, wherein $C_{1-4}$ alkyl; $C_{2-4}$ alkenyl; and $C_{2-4}$ alkynyl are optionally substituted with one or more $R^5$, which are the same of different;
$R^5$ is halogen; CN; $C(O)R^6$; $C(O)OR^6$; $OR^6$; $C(O)R^6$;
(xxvii) $C(O)N(R^6R^{6a})$; $S(O)_2N(R^6R^{6a})$; $S(O)N(R^6R^{6a})$; $S(O)_2R^6$; $S(O)R^6$; $N(R^6)S(O)_2N(R^{6a}R^{6b})$; $SR^6$; $N(R^6R^{6a})$; $NO_2$; $OC(O)R^6$; $N(R^6)C(O)R^{6a}$; $N(R^6)SO_2R^{6a}$; $N(R^6)S(O)R^{6a}$; $N(R^6)C(O)N(R^{6a}R^{6b})$; $N(R^6)C(O)OR^{6a}$; $OC(O)N(R^6R^{6a})$;
(xxviii) $R^6$, $R^{6a}$, $R^{6b}$ are independently selected from the group consisting of H; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more halogen, which are the same of different;
$T^0$ is phenyl; naphthyl; azulenyl; indenyl; indanyl; $C_{3-7}$
(xxix) cycloalkyl; 3 to 7 membered heterocyclyl; or 8 to 11 membered heterobicyclyl, wherein $T^0$, is optionally substituted with one or more $R^7$, which are the same or different;
$R^7$ is halogen; CN; $COOR^8$; $OR^8$; $C(O)R^8$; $C(O)N(R^8R^{8a})$; $S(O)_2N(R^8R^{8a})$; $S(O)N(R^8R^{8a})$; $S(O)_2R^8$; $S(O)R^8$; $N(R^8)S(O)_2N(R^{8a}R^{8b})$; $SR^8$; $N(R^8R^{8a})$; $NO_2$; $OC(O)R^8$; $N(R^8)C(O)R^{8a}$; $N(R^8)S(O)_2R^{8a}$; $N(R^8)S(O)$ $R^{8a}$; $N(R^8)C(O)OR^{8a}$; $N(R^8)C(O)N(R^{8a}R^{8b})$; $OC(O)N(R^8R^{8a})$; oxo (=O), where the ring is at least partially saturated; $C_{1-6}$ alkyl; $C_{2-6}$ alkenyl; or $C_{2-6}$ alkynyl, wherein $C_{1-6}$ alkyl; $C_{2-6}$ alkenyl; and $C_{2-6}$ alkynyl are optionally substituted with one or more $R^9$, which are the same or different;

$R^8$, $R^{8a}$, $R^{8b}$ are independently selected from the group consisting of H; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more $R^{10}$, which are the same of different;

$R^9$, $R^{10}$ are independently selected from the group consisting of halogen; CN; $C(O)R^{11}$; $C(O)OR^{11}$; $OR^{11}$; $C(O)R^{11}$; $C(O)N(R^{11}R^{11a})$; $S(O)_2N(R^{11}R^{11a})$; $S(O)N(R^{11}R^{11a})$; $S(O)_2R^{11}$; $S(O)R^{11}$; $N(R^{11})S(O)_2N(R^{11a}R^{11b})$; $SR^{11}$; $N(R^{11}R^{11a})$; $NO_2$; $OC(O)R^{11}$; $N(R^{11})C(O)R^{11a}$; $N(R^{11})SO_2R^{11a}$; $N(R^{11})S(O)R^{11a}$; $N(R^{11})C(O)N(R^{11a}R^{11b})$; $N(R^{11})C(O)OR^{11a}$; and $OC(O)N(R^{11}R^{11a})$;

$R^{11}$, $R^{11a}$, $R^{11b}$ are independently selected from the group consisting of H; $C_{1-6}$ alkyl; $C_{2-6}$ alkenyl; and $C_{2-6}$ alkynyl, wherein $C_{1-6}$ alkyl; $C_{2-6}$ alkenyl; and $C_{2-6}$ alkynyl are optionally substituted with one or more halogen, which are the same of different;

$Z^1$ is a biodegradable hydrogel according to the present invention, which is covalently attached to $X^0$.

Such a hydroxyl-containing biologically active moiety D may be, for example, paliperidone.

Preferably, $Z^0$ is $C(O)-X^0-Z^1$; $C(O)O-X^0-Z^1$; or $S(O)_2-X^0-Z^1$. More preferably, $Z^0$ is $C(O)-X^0-Z^1$; or $C(O)O-X^0-Z^1$. Even more preferably, $Z^0$ is $C(O)-X^0-Z^1$.

Preferably, $X^0$ is unsubstituted.

Preferably, m1 is 0 and m2 is 1.

Preferably, $X^0-Z^0$ is $C(R^1R^2)CH_2-Z^0$, wherein $R^1$, $R^2$ are independently selected from the group consisting of H and $C_{1-4}$ alkyl, provided that at least one of $R^1$, $R^2$ is other than H; or $(CH_2)_n-Z^0$, wherein n is 3, 4, 5, 6, 7 or 8.

Preferably, the carrier $Z^1$ is covalently attached to $X^0$ via amide group.

In another preferred embodiment, L is a non-biologically active linker containing i) a moiety $L^1$ represented by formula (XI),

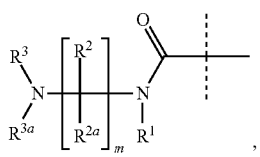
(XI)

wherein the dashed line indicates the attachment of $L^1$ to the aromatic hydroxyl group of the drug D by forming a carbamate group; and wherein $R^1$, $R^2$, $R^{2a}$, $R^3$, $R^{3a}$ and m of formula (XI) are defined as follows:

$R^1$ is selected from the group consisting of $C_{1-4}$ alkyl; heteroalkyl; $C_{3-7}$ cycloalkyl; and

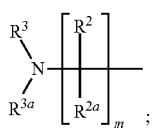
;

$R^2$, $R^{2a}$, $R^3$, $R^{3a}$ are independently selected from hydrogen, substituted or non-substituted linear, branched or cyclic $C_{1-4}$ alkyl or heteroalkyl;

m is independently 2, 3 or 4;

ii) a moiety $L^2$, which is a chemical bond or a spacer, and $L^2$ is bound to a hydrogel of the present invention, wherein $L^1$ is substituted with one $L^2$ moiety, optionally, L is further substituted.

In yet another preferred embodiment, L is a non-biologically active linker containing i) a moiety $L^1$ represented by formula (XII),

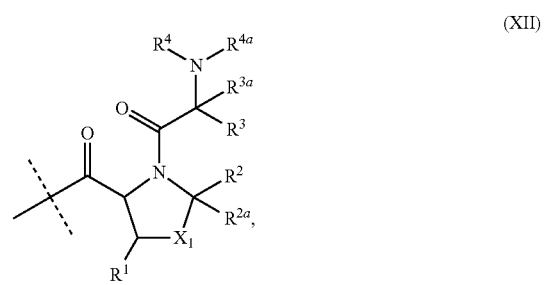
(XII)

wherein the dashed line indicates the attachment of $L^1$ to an aliphatic amino group of the drug D by forming an amide bond; and wherein $X_1$, $R^1$, $R^2$, $R^{2a}$, $R^3$, $R^{3a}$, $R^4$ and $R^{4a}$ of formula (XII) have the following meaning:

$X_1$ is selected from O, S or CH—$R^{1a}$, $R^1$ and $R^{1a}$ are independently selected from H, OH, $CH_3$ $R^2$, $R^{2a}$, $R^4$ and $R^{4a}$ are independently selected from H and $C_{1-4}$ alkyl, $R^3$, $R^{3a}$ are independently selected from H, $C_{1-4}$ alkyl, and $R^5$ $R^5$ is selected from

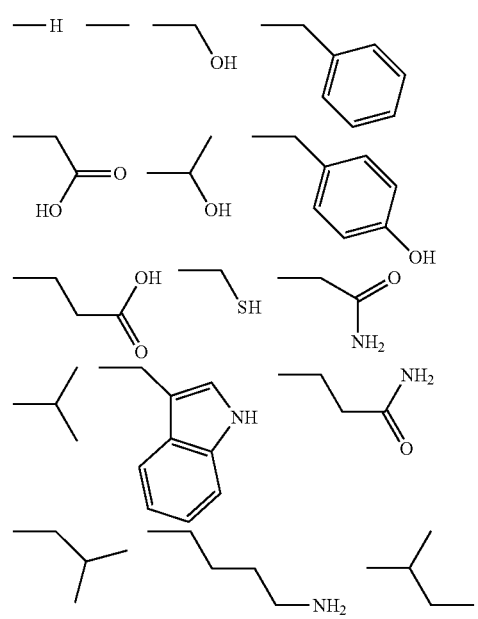

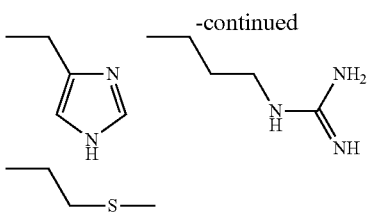

Preferably, one of the pair $R^3/R^{3a}$ is H and the other one is selected from $R^5$.

Preferably, one of $R^4/R^{4a}$ is H.

Optionally, one or more of the pairs $R^3/R^{3a}$, $R^4/R^{4a}$, $R^3/R^4$ may independently form one or more cyclic fragments selected from $C_{3-7}$ cycloalkyl, 4 to 7 membered heterocyclyl, or 9 to 11 membered heterobicyclyl.

Optionally, $R^3$, $R^{3a}$, $R^4$ and $R^{4a}$ are further substituted; suitable substituents are alkyl (such as $C_{1-6}$ alkyl), alkenyl (such as $C_{2-6}$ alkenyl), alkynyl (such as $C_{2-6}$ alkynyl), aryl (such as phenyl), heteroalkyl, heteroalkenyl, heteroalkynyl, heteroaryl (such as aromatic 4 to 7 membered heterocycle) or halogen moieties.

ii) a moiety $L^2$, which is a chemical bond or a spacer, and $L^2$ is bound to a hydrogel of the present invention, wherein $L^1$ is substituted with one $L^2$ moiety, optionally, L is further substituted.

Suitable substituents are alkyl (such as $C_{1-6}$ alkyl), alkenyl (such as $C_{2-6}$ alkenyl), alkynyl (such as $C_{2-6}$ alkynyl), aryl (such as phenyl), heteroalkyl, heteroalkenyl, heteroalkynyl, heteroaryl (such as aromatic 4 to 7 membered heterocycle) or halogen moieties.

In yet another preferred embodiment, L is a non-biologically active linker containing i) a moiety $L^1$ represented by formula (XIII),

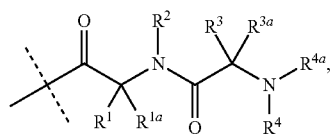

(XIII)

wherein the dashed line indicates the attachment of $L^1$ to an aromatic amino group of the drug D by forming an amide bond; and wherein $R^1$, $R^{1a}$, $R^2$, $R^{2a}$, $R^3$, $R^{3a}$, $R^4$ and $R^{4a}$ of formula (XIII) are defined as follows:

$R^1$, $R^{1a}$, $R^2$, $R^3$, $R^{3a}$, $R^4$ and $R^{4a}$ are independently selected from H and $C_{1-4}$ alkyl, optionally, any two of $R^1$, $R^{1a}$, $R^2$, $R^3$, $R^{3a}$, $R^4$ and $R^{4a}$ may independently form one or more cyclic fragments selected from $C_{3-7}$ cycloalkyl, 4 to 7 membered heterocyclyl, phenyl, naphthyl, indenyl, indanyl, tetralinyl, or 9 to 11 membered heterobicyclyl, optionally, $R^1$, $R^{1a}$, $R^2$, $R^3$, $R^{3a}$, $R^4$ and $R^{4a}$ are further substituted; suitable substituents are alkyl, such as $C_{1-6}$ alkyl; alkene, such as such as $C_{2-6}$ alkene; alkine, such as such as $C_{2-6}$ alkine; aryl, such as phenyl; heteroalkyl; heteroalkene; heteroalkine; heteroaryl such as aromatic 4 to 7 membered heterocycle; or halogen moieties.

ii) a moiety $L^2$, which is a chemical bond or a spacer, and $L^2$ is bound to a hydrogel of the present invention, wherein $L^1$ is substituted with one $L^2$ moiety, optionally, L is further substituted;

Suitable substituents are alkyl (such as $C_{1-6}$ alkyl), alkenyl (such as $C_{2-6}$ alkenyl), alkynyl (such as $C_{2-6}$ alkynyl), aryl (such as phenyl), heteroalkyl, heteroalkenyl, heteroalkynyl, heteroaryl (such as aromatic 4 to 7 membered heterocycle) or halogen moieties.

Preferably, one of $R^4$ or $R^{4a}$ is H.

Another preferred prodrug linker is described in U.S. Pat. No. 7,585,837. Such linker L is a non-biologically active linker containing i) a moiety $L^1$ represented by formula (XIV),

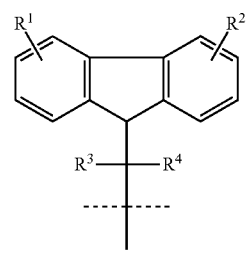

(XIV)

wherein the dashed line indicates the attachment of $L^1$ to a functional group of a drug D, wherein such functional group is selected from amino, carboxyl, phosphate, hydroxyl and mercapto; and wherein $R^1$, $R^2$, $R^3$ and $R^4$ of formula (XIV) are defined as follows:

$R^1$ and $R^2$ are independently selected from the group consisting of hydrogen, alkyl, alkoxy, alkoxyalkyl, aryl, alkaryl, aralkyl, halogen, nitro, —$SO_3H$, —$SO_2NHR^5$, amino, ammonium, carboxyl, $PO_3H_2$, and $OPO_3H_2$;

$R^3$, $R^4$, and $R^5$ are independently selected from the group consisting of hydrogen, alkyl, and aryl;

ii) a moiety $L^2$, which is a chemical bond or a spacer, and $L^2$ is bound to a hydrogel of the present invention, wherein $L^1$ is substituted with one $L^2$ moiety, optionally, L is further substituted;

Another preferred prodrug linker is described in the international application with the number WO-A 2002/089789. Such linker L is a shown in formula (XV):

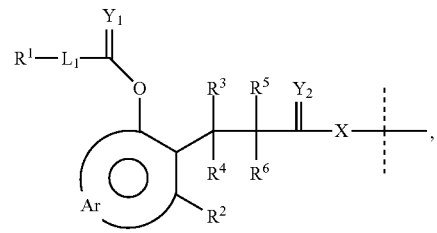

(XV)

wherein the dashed line indicates the attachment of L to a functional group of a drug D; and wherein X, Ar, L1, $Y_1$, $Y_2$, $R^1$, $R^2$, $R^3$, $R^4$, $R^5$, $R^6$ of formula (XV) are defined as follows:

$R^1$ is a hydrogel of the present invention;

$L_1$ is a bifunctional linking group;

$Y_1$ and $Y_2$ are independently O, S or $NR^7$;

$R^{1-7}$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy, and $C_{1-6}$ heteroalkoxy;

Ar is a moiety which when included in formula XI forms a multisubstituted aromatic hydrocarbon or a multi-substituted heterocyclic group;

Z is either a chemical bond or a moiety that is actively transported into a target cell, a hydrophobic moiety, or a combination thereof.

Another preferred prodrug linker for use with polynucleotide drugs, such as oligonucleotides, is described in WO-A 2008/034122. Such linker L is a shown in formula (XVI):

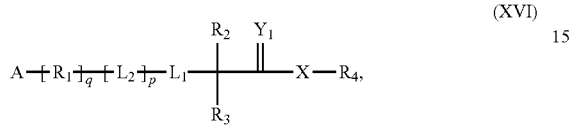   (XVI)

wherein A, $R_1$, $R_2$, $R_3$, $R_4$, $L_1$, $L_2$, $Y_1$, X, q and p of formula (XVI) are defined as follows:

A is a capping group or

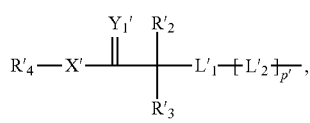

$R_1$ is a hydrogel according to the present invention;

$L_1$ and $L'_1$ are independently selected spacers having a free electron pair positioned four to ten atoms from $C(=Y_1)$ or $C(=Y'_1)$, preferably from about 4 to about 8, and most preferably from about 4 to 5 atoms from $C(=Y_1)$ or $C(=Y'_1)$;

$L_2$ and $L'_2$ are independently selected bifunctional linkers;

$Y_1$ and $Y'_1$ are independently O, S, or $NR_5$;

X and X' are independently O or S;

$R_2$, $R'_2$, $R_3$, $R'_3$, and $R_5$ are independently selected from among hydrogen, $C_{1-6}$ alkyl, $C_{2-6}$ alkenyl, $C_{2-6}$ alkynyl, $C_{3-19}$ branched alkyl, $C_{3-8}$ cycloalkyl, $C_{1-6}$ substituted alkyl, $C_{2-6}$ substituted alkenyl, $C_{2-6}$ substituted alkynyl, $C_{3-8}$ substituted cycloalkyl, aryl, substituted aryl, heteroaryl, substituted heteroaryl, $C_{1-6}$ heteroalkyl, substituted $C_{1-6}$ heteroalkyl, $C_{1-6}$ alkoxy, aryloxy, $C_{1-6}$ heteroalkoxy, heteroaryloxy, $C_{2-6}$ alkanoyl, arylcarbonyl, $C_{2-6}$ alkoxycarbonyl, aryloxycarbonyl, $C_{2-6}$ alkanoyloxy, arylcarbonyloxy, $C_{2-6}$ substituted alkanoyl, substituted arylcarbonyl, $C_{2-6}$ substituted alkanoyloxy, substituted aryloxycarbonyl, $C_{2-6}$ substituted alkanoyloxy and substituted arylcarbonyloxy, or $R_2$ together with $R_3$ and $R'_2$ together with $R'_3$ independently form a substituted or unsubstituted non-aromatic cyclohydrocarbon containing at least three carbons;

$R_4$ and $R'_4$ are independently selected polynucleotides and derivatives thereof;

(p) and (p') are independently zero or a positive integer, preferably zero or an integer from about 1 to about 3, more preferably zero or 1; and (q) and (q') are independently zero or 1, provided that $R_3$ is a substituted or unsubstituted hydrocarbon having at least three carbons when $R_2$ is H, and further provided that $L_1$ is not the same as $C(R_2)(R_3)$.

Another preferred prodrug linker for use with amine-containing drugs is described in WO-A 2001/47562. Such linker L is a shown in Formula (XVII):

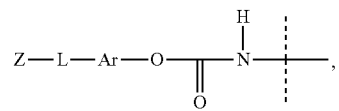   (XVII)

wherein the dashed line indicates the attachment of the linker L to the amine group of a drug D; and wherein Z, L and Ar of formula (XVII) have the meaning as follows:

Z is a hydrogel according to the present invention;

L is a covalent linkage, preferably a hydrolytically stable linkage;

Ar is an aromatic group;

Another preferred prodrug linker for use with heteroaromatic amine-containing biologically active moieties is described in the U.S. Pat. No. 7,393,953 B2. Such linker L is a shown in Formula (XVIII):

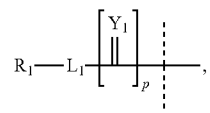   (XVIII)

wherein the dashed line indicates the attachment of the linker L to the heteroaromatic amine group of a drug D; and wherein $R_1$, $L_1$, $Y_1$, and p of formula (XVIII) have the meaning as follows:

$R_1$ is a hydrogel of the present invention;

$Y_1$ is O, S, or $NR_2$;

p is 0 or 1

$L_1$ is a bifunctional linker, such as, for example,

—NH($CH_2CH_2O$)$_n$($CH_2$)$_n$$NR_3$—,
—NH($CH_2CH_2O$)$_n$C(O)—,
—NH($CR_4R_5$)$_n$OC(O)—,
—C(O)($CR_4R_5$)$_n$NHC(O)($CR_8R_7$)$_q$$NR_3$—,
—C(O)O($CH_2$)$_n$O—
—C(O)($CR_4R_5$)$_n$$NR_3$—,
—C(O)NH($CH_2CH_2O$)$_n$($CH_2$)$_n$$NR_3$—,
—C(O)O—($CH_2CH_2O$)$_n$$NR_3$—,
—C(O)NH($CR_4R_5$)$_n$O—,
—C(O)O($CR_4R_5$)$_n$O—,
—C(O)NH($CH_2CH_2O$)$_n$—,

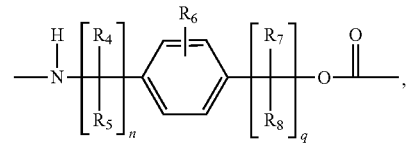

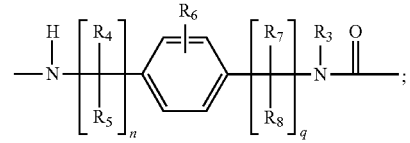

$R_2$, $R_3$, $R_4$, $R_5$, $R_7$ and $R_8$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy and $C_{1-6}$ heteroalkoxy;

$R_6$ is selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$alkoxy, phenoxy and $C_{1-6}$heteroalkoxy, $NO_2$, haloalkyl and halogen;

n and q are selected independently from each other and each is a positive integer.

The beforementioned linkers are suitable for use with a number of biologically active moieties. Suitable biologically active moieties are polypeptides, proteins, oligonucleotides, or small molecule biologically active moieties.

The biologically active moiety may comprise an amine, hydroxyl, carboxyl, phosphate, or mercapto group.

The biologically active moieties may be conjugated to the transient prodrug linker through a linkage formed by an amine, such as an aliphatic or aromatic amine; hydroxyl, such as an aliphatic or aromatic amine; carboxyl; phosphate; or mercapto group provided by the biologically active moiety.

Suitable aromatic amine containing biologically active moieties D are, for example, (−)-Carbovir, (±)-Hymenin, (±)-Norcisapride, (±)-Picumeterol, (R)-Aminoglutethimide, (R)-Clenbuterol, (S)-Aminoglutethimide, (S)-Clenbuterol, [6-p-aminophenylalanine]-angiotensin II, 10'-Demethoxystreptonigrin, 17-Aminogeldanamycin, 1-Aminoacridine, 1-Deazaadenine, 1-NA-PP 1, 1-NM-PP 1, 2,7-Diaminoacridine, 2,7-Dimethylproflavine, 2-Amino-6(5H)-phenanthridinone, 2-Aminoacridine, 2-amino-Carbanilide, 2-Aminohistamine, 2-Aminoperimidine, 2'-AMP, 2-Chloroadenosine, 2'-Deoxyxylotubercidin, 2-Sulfanilamidoimidazole, 3,4-Diaminocoumarin, 3'-Amino-4'-methoxyflavone, 3-Aminoacridine, 3-Aminopicolinic acid, 3-Deazaguanine, 4'-Aminoflavone, 4-Aminopyridine, 5'-ADP, 5-Aminoacridine, 5-amino-DL-Tryptophan, 5-Aminonicotinamide, 5'-AMP, 5'-ATP, 5-Chlorodeoxycytidine, 5'-CMP, 5-Dimethylamiloride, 5'-GDP, 5'-GMP, 5'-GTP, 5-Iodotubercidin, 5-Methylcytosine, 6-Aminoflavone, 6-Aminophenanthridine, 6-Aminothymine, 6-Benzylthioguanine, 6-Chlorotacrine, 6-Iodoamiloride, 7,8-Dihydroneopterin, 7-Aminonimetazepam, 7-Methoxytacrine, 7-Methyltacrine, 9-Deazaguanine, 9-Phenethyladenine, Abacavir, Acadesine, Acediasulfone, Acefurtiamine, Acetyl coenzyme A, Aciclovir, Actimid, Actinomycin, Acyclovir, Adefovir, Adenallene, Adenine, Adenophostin A, Adenosine, Adenosine monophosphate, Adenosine triphosphate, Adenosylhomocysteine, Aditeren, Afloqualone, Alamifovir, Albofungin, Alfuzosin, Allithiamine, Alpiropride, Amanozine, Ambasilide, Ambucaine, Amdoxovir, Ameltolide, Amethopterin, Amfenac, Amflutizole, Amicycline, Amidapsone, Amifampridine, Amiloride, Aminacrine, Aminoacridine, Aminoantipyrine, Aminobenzoate, Aminogenistein, Aminoglutethimide, Aminohippurate, Aminoisatin, Aminometradine, Aminonimetazepam, Aminophenylalanine, Aminopotentidine, Aminopterin, Aminopurvalanol A, Aminoquinuride, Aminosalicylic Acid, Amiphenazole, Amiphenosine, Amisometradine, Amisutpride, Amiterol, Amlexanox, Ammelin, Amonafide, Amoxecaine, Amphenidone, Amphethinile, Amphotalide, Amprenavir, Ampurine, Amrinone, AMT, Amthamine, Amtizole, Angustmycin A, Anileridine, Apadenoson, Apraclonidine, Apricitabine, Arafluorocytosine, Aramine, Arazide, Aristeromycin, Arprinocid, Ascamycin, Ascensil, Aspiculamycin, Atolide, Azabon, Azacitidine, Azaline B, Azamulin, Azanidazole, Azepexole, Aztreonam, Baquiloprim, Basedol, Batanopride, b-D-Adenosine, Bemitradine, Benfotiamine, Bentiamine, Benzamil, Benzocaine, Betoxycaine, Binodenoson, Biopterin, Bisbentiamine, Blasticidin, Bleomycin, Bleomycin A1, Bleomycin A2, Bleomycin A5, Bleomycin A6, Bleomycin DMA2, Brodimoprim, Bromfenac, Bromobuterol, Bromopride, Bropirimine, Buciclovir, Bunazosin, Butyrylthiamine disulfide, Cadeguomycin, cAMP, Candicidin, Capadenoson, Carbanilide, Carbodine, Carbovir, Carbutamide, Carumonam, CDP-dipalmitin, Cefcapenepivoxil, Cefclidin, Cefdaloxime, Cefdinir, Cefditoren, Cefempidone, Cefepime, Cefetamet, Cefetecol, Cefixime, Cefluprenam, Cefmatilen, Cefmenoxime, Cefodizime, Cefoselis, Cefotaxime, Cefotiam, Cefozopran, Cefpodoxime, Cefquinome, Cefrom, Ceftazidime, Cefteram, Ceftibuten, Ceftiofur, Ceftiolene, Ceftioxide, Ceftizoxime, Ceftobiprole, Ceftriaxone, Cefuzonam, Centazolone, Cetotiamine, cGMP, Chloroprocaine, Cidofovir, Cifostodine, Cipamfylline, Cisapride, Cladribine, Clafanone, Claforan, Clebopride, Clenbuterol, Clenproperol, Clofarabine, Clorsulon, Coelenteramine, Coenzyme A, Colchicamid, Coumarin 10, Coviracil, Crotonoside, Cyclobut A, Cyclobut G, Cycloclenbuterol, Cyclotiamine, Cytallene, Cytarabine, Cytarazid, Cytidine, Cytidine diphosphate, Cytidoline, CytosineD-(+)-Neopterin, Dactinomycin, D-Amethopterin, dAMP, Damvar, Daniquidone, Dapsone, Daptomycin, Daraprim, Darunavir, DATHF, Dazopride, dCMP, dCTP, Debromohymenialdisine, Decitabine, Declopramide, Deisopropylhydroxyatrazine, Delafloxacin, Delfantrine, Denavir, Deoxyadenosine, Deoxy-ATP, Deoxycytidine, Deoxyguanosine, Dephosphocoenzyme A, Dequalinium, Desbutylbumetanide, Desciclovir, Desoxyminoxidil, dGMP, dGTP, Diacethiamine, Diaminoacridine, Diaveridine, Dichlorobenzamil, Dichloromethotrexate, Dichlorophenarsine, Dideoxycytidine, Dihydrobiopterin, Dihydrofolic acid, Dimethialium, Dimethocaine, Dimethyl methotrexate, Dinalin, DL-5,6,7,8-Tetrahydrofolic acid, DL-Methotrexate, Dobupride, Dovitinib, Doxazosin, Draflazine, Edatrexate, Elpetrigine, Elvucitabine, Emtricitabine, Entecavir, Enviradene, Epcitabine, Epiroprim, Eritadenine, Etanterol, Etoxazene, Etaden, Ethylisopropylamiloride, Etoprine, Etoxazene, Etravirine, Etriciguat, FAD, Famciclovir, Fazarabine, Fenamol, Fepratset, Fiacitabine, Flucytosine, Fludara, Fludarabine, Fluocytosine, Folic acid, Formycin A, Fosamprenavir, Furalazine, Fursultiamine, Furyltriazine, Ganciclovir, Gancyclovir, Gastracid, Gemcitabine, Giracodazole, Gloximonam, Glybuthiazol, GSK 3B Inhibitor XII, GSK3BInhibitor XII, Guanine, Guanine arabinoside, Guanosine, Hexyl PABA, Hydroxymethylclenbuterol, Hydroxyprocaine, Hydroxytriamterene sulfate, Ibacitabine, Iclaprim, Imanixil, Imiquimod, Indanocine, Iobenzamic acid, Iocetamic acid, Iomeglamic acid, Iomeglamicacid, Ipidacrine, Iramine, Irsogladine, Isatoribine, Isobutamben, Isoritmon, Isosepiapterin, Ketoclenbuterol, Ketotrexate, Kopexil, Lamivudine, Lamotrigin, Lamotrigine, Lamtidine, Lappaconine, Lavendamycin, L-Cytidine, Lenalidomide, Leucinocaine, Leucovorin, L-g-Methylene-10-deazaminopterin, Linifanib, Lintopride, Lisadimate, Lobucavir, Lodenosine, Lomeguatrib, Lometrexol, Loxoribine, L-S-Adenosylmethionine, Mabuterol, Medeyol, Melarsenoxyd, Melarsoprol B, Mesalazine, Metabutethamine, Metabutoxycaine, Metahexamide, Metazosin, Methioprim, Methotrexate, Methylanthranilate, Metioprim, Metoclopramide, Metoprine, Minoxidil, Mirabegron, Mitomycin, Mivobulin, Mocetinostat, Monocain, Mosapride, Mutamycin, N-(p-Aminophenethyl)spiroperidol, N6-[2-(4-aminophenyl)ethyl]adenosine Role, NAD+, NADH, NADH2, NADP+, NADPH2, Naepaine, Naminterol, Naretin, Nebidrazine, NECA, Nelarabine, Nelzarabine, Neolamin, Neotropine, Nepafenac, Nerisopam, Neurofort, Nifurprazine, Nimustine, Nitrine, N-Methyltetrahydrofolic acid, Nolatrexed, Nomifensine, Norcisapride, N-Propionylprocainamide, N-Sulfanilylnorfloxacin, o-Aminophenylalanine, Octotiamine, Olamufloxacin, Ormetoprim, Orthocaine, Oximonam, Oxybuprocaine, p-Aminoantipyrine, p-Aminobenzoate, p-Amino-D-phenylalanine, Pancopride, Parsalmide, Pasdrazide, Pathocidine, Pelitrexol, Pemetrexed, Penciclovir, Peplomycin, Peralopride, Phenamil, Phenazone, Phenazopyridine, Phenyl p-aminobenzoate, Phenyl-PAS-Tebamin, Phleomycin D1, Pibutidine, Picumeterol, Pirazmonam, Piridocaine, Piritrexim, Porfiromycin, Pralatrexate, Pramipexole, Prazobind, Prazosin, Preladenant, Procainamide, Procaine, Proflavine, Proparacaine, Propoxycaine, Prosultiamine, Prucalopride, Pseudoisocytidine, Psicofuranine, Pteridoxamine, Pteroyltriglutamic acid, Pyramine, Pyrimethamine, Questiomycin, Quinelorane, Racivir, Regadenoson, Renoquid, Renzapride, Resiquimod, Resorcein, Retigabine, Reverset, Riluzole, Rociclovir, Rufocromomycin, S-Adenosylmethionine, Sangivamycin, Sapropterin, S-Doxazosin, Sepiapterine, Silversulfadiazine, Sinefungin, Sipatrigine, Sparfloxacin, Sparsomycin, Stearyl-CoA, Stearylsulfamide, Streptonigrin, Succisulfone, Sulfamonomethoxine, Sulamserod, Sulfabromomethazine, Sulfacetamide, Sulfachlorpyridazine, Sulfachrysoidine, Sulfaclomide, Sulfaclorazole, Sulfaclozine, Sulfacytine, Sulfadiasulfone, Sulfadiazine, Sulfadicramide, Sulfadimethoxine, Sulfadimidine, Sulfadoxine, Sulfaethoxypyridazine, Sulfaguanidine, Sulfaguanole, Sulfalene, Sulfamerazine, Sulfamethazine, Sulfamethizole, Sulfamethoxazole, Sulfamethoxydiazine, Sulfamethoxypyridazine, Sulfametomidine, Sulfametopyrazine, Sulfametrole, Sulfanilamide, Sulfanilamidoimidazole, Sulfanilylglycine, Sulfaperin, Sulfaphenazole, Sulfaproxyline, Sulfapyrazole, Sulfapyridine, Sulfasomizole, Sulfasymazine, Sulfathiadiazole, Sulfatroxazole, Sulfatrozole, Sulfisomidine, Sulfisoxazole, Tacedinaline, Tacrine, Talampanel, Talipexole, Talisomycin A, Tenofovir, Tenofovir disoproxil, Terazosin, Tetrahydrobiopterinm, Tetrahydrofolic acid, Tetroxoprim, Tezacitabine, Thiamine, Thiazosulfone, Thioguanine, Tiamiprine, Tigemonam, Timirdine, Tinoridine, Tiodazosin, Tirapazamine, Tiviciclovir, Tocladesine, Trancopal, Triacanthine, Triamterene, Triapine, Triciribine, Trimazosin, Trimethoprim, Trimetrexate, Tritoqualine, Troxacitabine, Tubercidin 5'-diphosphate, Tuvatidine, Tyrphostin AG 1112, Valacyclovir, Valganciclovir, Valopicitabine, Valtorcitabine, Velnacrine, Vengicide, Veradoline, Vidarabine, Viroxime, Vitaberin, Zalcitabine, Zhengguangmycin B2, Zinviroxime, Zorbamycin, Zoxazolamine, (±)-Saxitoxin, 2-Aminoperimidine, 6-Formylpterin, 8-13-Neurotensin, 8-Thioguanosine, 9-Deazaguanosine, 9-Desarginine-bradykinin, a4-10-Corticotropin, Afamelanotide, Agmatine, Alarelin, Ambazone, Amiloride, Aminopterine, Ampyrimine, Angiotensin, Angiotensin I, Angiotensin II, Antibiotic O-129, Antipain, Arginine, Argiprestocin, Astressin, Atriopeptin III, Aviptadil, Benzylisothiourea, Betacyamine, Bisindolylmaleimide IX, Bivalirudin, Blasticidin S, Bleomycin B2, Bombesin 14, Buformin, Camostat, Cariporide, Carperitide, Cecropin P 1, Cetrorelix, Cilengitide, Creapure, Cyanoginosin LR, Cyanoviridin RR, Dalargine, Damvar, Deazaminopterin, Defensin HNP 1, Deslorelin, Desmopressin, Dezaguanine, Dichloromethotrexate, Dihydrostreptomycin, Dimaprit, Dimethylamiloride, Diminazene, DL-Methotrexate, D-Methotrexate, Ebrotidine, Edatrexate, Eel Thyrocalcitonin, Elastatinal, Elcatonin, Enterostatin, Enviomycin, Eptifibatide, Ethylisopropylamiloride, Etilamide, Etoprine, Famotidine, Flupirtine, Furterene, Galanin, Galegin, Ghrelin, Glucagon, Gonadoliberin A, Guanethidine, Guanfacine, Guanoxan, Guanylthiourea, Gusperimus, Hexamidine, Histatin 5, Histrelin, Homoarginine, Icatibant, Imetit, Insulinotropin, Isocaramidine, Kallidin 10, Kemptide, Ketotrexate, Kiotorphin, Lactoferricin, Lamifiban, L-Bradykinin, Leucoverin, Leucovorin A, Leupeptin, Leuprolide, Lometrexol, Lutrelin, m-Chlorophenylbiguanide, Melagatran, Melanotan II, Melanotropin, Melittin, Metformin, Methotrexate dimethyl ester, Methotrexate monohydrate, Methoxtrexate, Methylisothiourea, Metoprine, Miacalcin, MIBG, Minoxidil, Mitoguazone, Mivobulin, Mivobulin isethionate, Moroxydine, Nafarelin, Neotine, Nesiritide, Netropsin, Neurotensin, N-Methyltetrahydrofolate, Nociceptin, Nolatrexed, Novastan, Panamidin, Pathocidine, Pebac, Peldesine, Pelitrexol, Pemetrexed, Pentamidine, Peramivir, Phenformine, Phenylbiguanide, Pig galanin, Pimagedine, Piritrexim, Pitressin, Porcine angiotensinogen, Porcine gastrin-releasing hormone, Porcine neuropeptide Y, Porcine PHI, Pralatrexate, Protein Humanin, Proteinase inhibitor E 64, Pyrimethamin, Quinespar, Rat atriopeptin, Rat atriopeptin, Resiquimod, Ribamidine, Rimorphin, Saralasin, Saxitoxin, Sermorelin, S-Ethylisothiourea, Spantide, Stallimycin, Stilbamidine, Streptomycin A, Substance P free acid, Sulfaguanidine, Synthetic LH-releasing hormone, Tallimustine, Teprotide, Tetracosactide, Tetrahydrobiopterin, Tetrahydrofolic acid, Thrombin receptor-activating peptide-14, Thymopentin, Tioguanin, Tiotidine, Tirapazamine, Triamteren, Trimetrexate, Tryptorelin, Tuberactinomycin B, Tuftsin, Urepearl, Viomycidin, Viprovex, Vitamin M, Xenopsin, Zanamivir, Zeocin, Ziconotide, Zoladex.

Preferably, suitable drugs with aromatic amine groups may be selected from the list containing (−)-Draflazine, (−)-Indocarbazostatin B, (+)-(R)-Pramipexole, (R)-(+)-Terazosin, (R)-Ganciclovir Cyclic Phosphonate, (R)-Sufinosine, (R)-Zacopride, (S)-Sufinosine, (S)-Zacopride Hydrochloride, 17-Aminogeldanamycin, 2-Aminoaristeromycin, 2-Aminoneplanocin A, 3-Chloroprocainamide, 3-Deazaadenosine, 4-Aminosalicylic Acid, 4-Chlorophenylthio-DADME-Immucillin-A, 5'-Homoneplanocin A, 5-Aminosalicylic Acid, 9-Aminocamptothecin, Abacavir Succinate, Abacavir Sulfate, Abanoquil Mesilate, Acadesine, Acriflavine, Acyclovir, Acyclovir Elaidate, Acyclovir Oleate, Adefovir, Adefovir Dipivoxil, Ademetionine Tosylate Sulfate, Adenallene, Adenophostin A, Adenophostin B, Adenosine, Afloqualone, Ageliferin Diacetate, Ageliferin Dihydrochloride, Alamifovir, Alfuzosin Hydrochloride, Ambaslide, Ambroxol Nitrate, Amdoxovir, Ameltolide, Amezinium Methylsulfate, Amfenac Sodium, Amiloride Hydrochloride, Aminoglutethimide, Amisulpride, Amoxanox, Amprenavir, Ampydin, Amrinone, Amselamine Hydrobromide, Amthamine, Anakinra, Apadenoson, Aplonidine Hydrochloride, Apricitabine, Azacytidine, Azalanstat, Aztreonam, Aztreonam L-Lysine, Balapiravir Hydrochloride, Batracylin, Belactin A, Benzocaine, Binodenoson, Bleomycin A2 Sulfate, Brodimoprim, Bromfenac Sodium, Bromhexine Hydrochloride, Bunazosin Hydrochloride, Capadenoson, Capeserod Hydrochloride, Carbovir, Carboxyamidotriazole, Carumonam Sodium, Cefcapene Pivoxil Hydrochloride, Cefdaloxime, Cefdaloxime Pentexil Tosilate, Cefdinir, Cefditoren Pivoxil, Cefepime, Cefetamet Pivoxil, Cefetecol, Cefixime, Cefluprenam, Cefmatilen Hydrochloride Hydrate, Cefmenoxime Hydrochloride, Cefodizime, Cefodizime Sodium, Cefoselis Sulfate, Cefotaxime Sodium, Cefotiam Hexetil, Cefotiam Hexetil Hydrochloride, Cefotiam Hydrochloride, Cefozopran, Cefozopran Hydrochloride, Cefpirome, Cefpodoxime Proxetil, Cefquinome, Ceftaroline, Ceftazidime, Cefteram Pivoxil, Ceftibuten, Ceftobiprole, Ceftobiprole Medocaril, Ceftrazonal Bopentil, Ceftrazonal Sodium, Ceftriaxone Sodium, Centanamycin, Cibrostatin 1, Cidofovir, Cimaterol, Cinitapride Hydrogen Tartrate, Cipamfylline, Cisapride Hydrate, Citicoline, Cladribine, Clitocine, Clofarabine, Clopidogrel Sulfate, Cycallene, Cyclic-Cidofovir, Cygalovir, Cystazosin, Cytarabine, Cytarabine Ocfosfate, Cytaramycin, Cytochlor, Dactinomycin, DADME-Immucillin-G, Dapropterin Dihydrochloride, Dapsone, Darbufelone Mesilate, Darunavir, Delafloxacin, Denufosol Tetrasodium, Deoxyvariolin B, Desacetylvinblastinehydrazide/Folate Conjugate, Detiviciclovir Diacetate, Dexelvucitabine, Dezocitidine, Diadenosine Tetraphosphate, Diaveridine, Dichlorobenzoprim, Dicloguamine Maleate, Dideoxycytidine, DI-VAL-L-DC, Docosyl Cidofovir, Dovitinib Lactate, Doxazosin Mesylate, Draflazine, DTPA-Adenosylcobalamin, Ecenofloxacin Hydrochloride, Eicosyl Cidofovir, Elacytarabine, Elpetrigine, Elvucitabine, Emtricitabine, Entecavir, Entinostat, Epinastine Hydrochloride, Epiroprim, Epofolate, Ethylthio-DADME-Immucillin-A, Ethynylcytidine, Etravirine, Etriciguat, Famciclovir, Filarizone, Flucytosine, Fludarabine Phosphate, Fluorobenzyltriamterene, Fluorominoxidil, Fluoroneplanocin A, Flupiritine Maleate, Folinic Acid, Fosamprenavir Calcium, Fosamprenavir Sodium, Freselestat, Ganciclovir, Ganciclovir Elaidic Acid, Ganciclovir Monophosphate, Ganciclovir Sodium, Gemcitabine, Gemcitabine Elaidate, Girodazole, Hepavir B, Heptaminol AMP Amidate, Hexadecyl Cidofovir, Hexadecyloxypropyl-Cidofovir, Hydroxyakalone, Iclaprim, Imiquimod, Immunosine, Indanocine, Isobatzelline A, Isobatzelline B, Isobatzelline C, Isobatzelline D, Lamivudine, Lamotrigine, Lenalidomide, Leucettamine A, Leucovorin Calcium, Levoleucovorin Calcium, Liblomycin, Linifanib, Lintopride, Lirexapride, Lobucavir, Lodenosine, Lomeguatrib, Lometrexol, Loxoribine, L-Simexonyl Homocysteine, Lymphostin, Mabuterol Hydrochloride, Makaluvamine A, Makaluvamine A, Makaluvamine B, Makaluvamine C, Managlinat Dialanetil, Meriolin-3, Metazosin, Methotrexate, Methylthio-DADME-Immucillin-A, Metoclopramide Hydrochloride, Midoriamin, Minoxidil, Mirabegron, Mitomycin, Mivobulin Isethionate, Mocetinostat Dihydrobromide, Mosapride Citrate, Mozenavir Mesilate, Neldazosin, Nelzarabine, Nepafenac, Nolatrexed Hydrochloride, NO-Mesalamine, Noraristeromycin, O6-Benzylguanine, Olamufloxacin, Olamufloxacin Mesilate, Omaciclovir, Oxyphenarsine, PalauÀmine, Pancopride, Peldesine, Pelitrexol, Pemetrexed Disodium, Penciclovir, Penicillin G Procaine, Peplomycin, Picumeterol Fumarate, Pimeloylanilide O-Aminoanilide, PMEO-5-ME-DAPY, Pralatrexate, Pramipexole Hydrochloride, Prazosin Hydrochloride, Prefolic A, Preladenant, Procainamide Hydrochloride, Procaine Hydrochloride, Prucalopride, Prucalopride Hydrochloride, Prucalopride Succinate, Pyriferone, Pyrimethamine, Quinelorane Hydrochloride, Razaxaban Hydrochloride, Regadenoson, Resiquimod, Retigabine Hydrochloride, Riluzole, Riociguat, Rociclovir, Rumycin 1, Rumycin 2, Sampirtine, Secobatzelline A, Secobatzelline B, Silver Sulfadiazine, Sipatrigine, Sonedenoson, Sotirimod, Sparfloxacin, Styloguanidine, Sufinosine, Surfen, Synadenol, Synguanol, Tacedinaline, Tacrine Hydrochloride, Talampanel, Talipexole Dihydrochloride, Talopterin, Tenofovir, Tenofovir DF, Terazosin Hydrochloride, Tetracosyl Cidofovir, Tezacitabine, TGP, Timirdine Diethanesulfonate, Torcitabine, Trantinterol Hydrochloride, Trichomycin A, Trimazosin Hydrochloride, Trimetrexate Glucuronate, Troxacitabine, Trybizine Hydrochloride, Valacyclovir, Valganciclovir Hydrochloride, Valomaciclovir Stearate, Valopicitabine, Velnacrine Maleate, Xylocydine.

Suitable drugs with an amine group may be selected from the group consisting of Aphidicolin Glycinate, Cetrorelix Acetate, Picumeterol Fumarate, (−)-Draflazine, (−)-Indocarbazostatin B, (+)-(23,24)-Dihydrodiscodermolide, (+)-(R)-Pramipexole, (R)-(+)-Amlodipine, (R)-(+)-Terazosin, (R)-Ganciclovir Cyclic Phosphonate, (R)-Sufinosine, (R)-Zacopride, (S)-(−)-Norketamine, (S)-Oxiracetam, (S)-Sufinosine, (S)-Zacopride Hydrochloride, [90Y]-DOTAGA-Substance P, [ARG(Me)9] MS-10, [D-TYR1,ARG(Me)9] MS-10, [D-TYR1,AzaGLY7,ARG(Me)9] MS-10, [D-TYR1] MS-10, [Psi(CH2NH)TPG4]Vancomycin Aglycon, [TRP19] MS-10, 111IN-Pentetreotide, 13-Deoxyadriamycin Hydrochloride, 17-Aminogeldanamycin, 19-O-Methylgeldanamycin, 1-Methyl-D-Tryptophan, 21-Aminoepothilone B, 2-Aminoaristeromycin, 2-Aminoneplanocin A, 3-Chloroprocainamide, 3-Deazaadenosine, 3-Matida, 4-Aminosalicylic Acid, 4-Chlorophenylthio-DADME-Immucillin-A, 5,4'-Diepiarbekacin, 5'-Homoneplanocin A, 5-Aminosalicylic Acid, 8(R)-Fluoroidarubicin Hydrochloride, 99MTC-C(RGDFK*)2Hynic, 9-Aminocamptothecin, A-42867 Pseudoaglycone, Abacavir Succinate, Abacavir Sulfate, Abanoquil Mesilate, Abarelix, Acadesine, Acriflavine, Acyclovir, Acyclovir Elaidate, Acyclovir Oleate, Acyline, Adefovir, Adefovir Dipivoxil, Ademetionine Tosylate Sulfate, Adenallene, Adenophostin A, Adenophostin B, Adenosine, Aerothricin 1, Aerothricin 16, Aerothricin 41, Aerothricin 45, Aerothricin 5, Aerothricin 50, Aerothricin 55, Afloqualone, Ageliferin Diacetate, Ageliferin Dihydrochloride, Aladapcin, Alamifovir, Alatrofloxacin Mesilate, Alendronic Acid Sodium Salt, Alestramustine, Alfuzosin Hydrochloride, Aliskiren Fumarate, Alogliptin Benzoate, Alpha-Methylnorepinephrine, Alpha-Methyltryptophan, Altemecidin, Alvespimycin Hydrochloride, Amantadine Hydrochloride, Ambasilide, Ambazone, Ambroxol Nitrate, Amdoxovir, Ameltolide, Amelubant, Amezinium Methylsulfate, Amfenac Sodium, Amidox, Amifostine Hydrate, Amikacin, Amiloride Hydrochloride, Aminocandin, Aminoglutethimide, Aminoguanidine, Aminolevulinic Acid Hexyl Ester, Aminolevulinic Acid Methyl Ester, Amisulpride, Amlodipine, Amlodipine Besylate, Amoxanox, Amoxicillin Pulsys, Amphotericin B, Ampicillin Sodium, Amprenavir, Ampydin, Amrinone, Amrubicin Hydrochloride, Amselamine Hydrobromide, Amthamine, Anakinra, Anamorelin Hydrochloride, Anatibant Mesilate, Angiopeptin Acetate, Anisperimus, Antagonist-G, Antide, Antide-1, Antide-2, Antide-3, Antileukinate, Apadenoson, Apixaban, Aplonidine Hydrochloride, Apoptozole 1, Apoptozole 2, Apoptozole 3, Apricitabine, Arbekacin, Arbekacin sulfate, Arborcandin A, Arborcandin B, Arborcandin C, Arborcandin D, Arborcandin E, Arborcandin F, Argatroban Monohydrate, Argimesna, Arginine Butyrate, Argiotoxin-636, Armodafinil, Arotinolol Hydrochloride, Arterolane Maleate, Aspoxicillin, Atenolol, Atosiban, Atreleuton, Avorelin, Azacytidine, Azalanstat, Azaromycin SC, Azelnidipine, Azetirelin, Azodicarbonamide, Azoxybacilin, Aztreonam, Aztreonam L-Lysine, Azumamide A, Baclofen, Bactobolin, Balapiravir Hydrochloride, Balhimycin, Barusiban, Batracylin, Belactin A, Belactosin A, Belactosin C, Benanomicin B, Benexate Cyclodextrin, Benzocaine, Besifloxacin Hydrochloride, Beta-Amyloid (12-20), Binodenoson, Bleomycin A2 Sulfate, Boceprevir, Bogorol A, Boholmycin, Brasilicardin A, Bremelanotide, Brivanib Alaninate, Brivaracetam, Brodimoprim, Bromfenac Sodium, Bromhexine Hydrochloride, Brostallicin Hydrochloride, Bunazosin Hydrochloride, Buserelin Acetate, Butabindide, Butamidine, Buteranol, Cabin 1, Calcium-Like Peptide 1, Calcium-Like Peptide 2, Cambrescidin 800, Cambrescidin 816, Cambrescidin 830, Cambrescidin 844, Camostat, Canfosamide Hydrochloride, Capadenoson, Capeserod Hydrochloride, Capravirine, Caprazamycin A, Caprazamycin B, Caprazamycin C, Caprazamycin E, Caprazamycin F, Capromorelin, Carafiban Maleate, Carbachol, Carbamazepine, Carbetocin, Carbovir, Carboxyamidotriazole, Cariporide Hydrochloride, Carisbamate, Carpipramine, Carumonam Sodium, Caspofungin Acetate, Cefaclor, Cefcanel Daloxate Hydrochloride, Cefcapene Pivoxil Hydrochloride, Cefdaloxime, Cefdaloxime Pentexil Tosilate, Cefdinir, Cefditoren Pivoxil, Cefepime, Cefetamet Pivoxil, Cefetecol, Cefixime, Cefluprenam, Cefmatilen Hydrochloride Hydrate, Cefmenoxime Hydrochloride, Cefminox Sodium, Cefodizime, Cefodizime Sodium, Cefoselis Sulfate, Cefotaxime Sodium, Cefotetan Disodium, Cefotiam Hexetil, Cefotiam Hexetil Hydrochloride, Cefotiam Hydrochloride, Cefoxitin, Cefozopran, Cefozopran Hydrochloride, Cefpirome, Cefpodoxime Proxetil, Cefprozil, Cefprozil Monohydrate, Cefquinome, Ceftaroline, Ceftazidime, Cefteram Pivoxil, Ceftibuten, Ceftobiprole, Ceftobiprole Medorcaril, Ceftrazonal Bopentil, Ceftrazonal Sodium, Ceftriaxone Sodium, Ceftrizoxime Alapivoxil, Cefuroxime, Cefuroxime Axetil, Cefuroxime Pivoxetil, Centanamycin, Cephalexin Monohydrate, Ceranapril, Ceruletide Diethylamine, Cetefloxacin, Chlorofusin, Chloroorienticin A, Chloroorienticin B, Chlorotetain, Cibrostatin 1, Cidofovir, Cilastatin Sodium, Cilengitide, Cimaterol, Cinitapride Hydrogen Tartrate, Cipamfylline, Circinamide, Cisapride Hydrate, Cispentacin, Citicoline, Citrullimycine A, Cladribine, Clitocine, Clofarabine, Clopidogrel Sulfate, Compound 301029, Coumamidine Gamma1, Coumamidine Gamma2, Cromoglycate Lisetil Hydrochloride, Cycallene, Cyclic-Cidofovir, Cycloserine, Cyclotheonamide A, Cyclothialidine, Cygalovir, Cypemycin, Cysmethynil, Cystamidin A, Cystamine, Cystazosin, Cystocin, Cytarabine, Cytarabine Ocfosfate, Cytaramycin, Cytochlor, Cytomodulin, Dabigatran, Dabigatran Etexilate, Dacopafant, Dactimicin, Dactinomycin, Dactylocycline A, Dactylocycline B, DADME-Immucillin-G, Dalargin, Danegaptide Hydrochloride, Dapropterin Dihydrochloride, Dapsone, Darbufelone Mesilate, Darifenacin Hydrobromide, Darinaparsin, Darunavir, Daunorubicin, Davasaicin, Davunetide, Debrisoquine Sulfate, Decahydromoenomycin A, Decaplanin, Deferoxamine, Degarelix Acetate, Delafloxacin, Delta-Aminolevulinic Acid Hydrochloride, Deltibant, Denagliptin Hydrochloride, Denibulin Hydrochloride, Denufosol Tetrasodium, Deoxymethylspergualin, Deoxynegamycin, Deoxyvariolin B, Desacetylvinblastinehydrazide/Folate Conjugate, Des-F-Sitagliptin, Desglugastrin Tromethamine, Deslorelin, Desmopressin Acetate, Detiviciclovir Diacetate, Dexelvucitabine, Dexibuprofen Lysine, Dextroamphetamine Sulfate, Dezinamide, Dezocitidine, Diadenosine Tetraphosphate, Diaveridine, Dichlorobenzoprim, Diclogua mine Maleate, Didemnin X, Didemnin Y, Dideoxycytidine, Difurazone, Dilevalol, Dilevalol Hydrochloride, Disermolide, Disopyramide Phosphate, DI-VAL-L-DC, Docosyl Cidofovir, Dolastatin 14, Dolastatin C, Donitriptan Hydrochloride, Donitriptan Mesilate, Dovitinib Lactate, Doxazosin Mesylate, Doxorubicin Hydrochloride, Doxycycline Hyclate, D-Penicillamine, Draflazine, Droxidopa, DTPA-Adenosylcobalamin, Ebrotidine, Ecenofloxacin Hydrochloride, Efegatran Sulfate Hydrate, Eflornithine Hydrochloride, Eglumegad Hydrate, Eicosyl Cidofovir, Elacytarabine, Elastatinal B, Elastatinal C, Elpetrigine, Elvucitabine, Emtricitabine, Enalkiren, Enigmol, Eniporide Mesilate, Entecavir, Entinostat, Epinastine Hydrochloride, Epiroprim, Epirubicin Hydrochloride, Epithalon, Epofolate, Epostatin, Epsilon Aminocaproic Acid, Eremomycin, Eribulin Mesylate, Erucamide, Esafloxacine Hydrochloride, Eslicarbazepine Acetate, Etaquine, Ethanolamine, Ethylthio-DADME-Immucillin-A, Ethynylcytidine, Etravirine, Etriciguat, Exalamide, Examorelin, Exatecan Mesilate, Ezatiostat Hydrochloride, Famciclovir, Famotidine, Famotidine Bismuth Citrate, Favipiravir, Feglymycin, Felbamate, Fenleuton, Fidarestat, Fidexaban, Filaminast, Filarizone, Fingolimod Hydrochloride, Flucytosine, Fludarabine Phosphate, Fluorobenzyltriamterene, Fluorominoxidil, Fluoroneplanocin A, Flupiritine Maleate, Fluvirucin B2, Fluvoxamine Maleate, Folinic Acid, Fortimicin A, Fosamprenavir Calcium, Fosamprenavir Sodium, Fosfomycin Trometamol, Fradafiban, Freselestat, Frovatriptan, Fudosteine, Furamidine, G1 Peptide, Gabadur, Gabapentin, Gabexate Mesilate, Galarubicin Hydrochloride, Galmic, Galnon, Ganciclovir, Ganciclovir Elaidic Acid, Ganciclovir Monophosphate, Ganciclovir Sodium, Ganirelix, Ganirelix Acetate, Garomefrine Hydrochloride, Gemcitabine, Gemcitabine Elaidate, Gemifloxacin Mesilate, Gilatide, Girodazole, Glaspimod, Glucosamine Sulfate, Gludopa, Glutathione Monoethylester, Glutathione Monoisopropylester, Glycine-Proline-Melphalan, Glycopin, Glycothiohexide alpha, Golotimod, Goserelin, Growth Factor Antagonist-116, Growth Hormone Releasing Peptid 2, Guanabenz Acetate, Guanadrel Sulfate, Guanethidine Monosulfate, Guanfacine Hydrochloride, Gusperimus Hydrochloride, Halovir A, Halovir B, Halovir C, Halovir D, Halovir E, Hayumicin B, Hayumicin C1, Hayumicin C2, Hayumicin D, Helvecardin A, Helvecardin B, Hepavir B, Heptaminol AMP Amidate, Hexa-D-Arginine, Hexadecyl Cidofovir, Hexadecyloxypropyl-Cidofovir, Histamine Dihydrochloride, Histaprodifen, Histrelin, Histrelin Acetate, Human Angiotensin II, Hydrostatin A, Hydroxyakalone, Hydroxyurea, Hypeptin, Ibutamoren Mesilate, Icatibant Acetate, Iclaprim, Icofungipen, Idarubicin Hydrochloride, Ilatreotide, Ilonidap, Imetit, Imidafenacin, Imidazenil, Imiquimod, Immunosine, Impentamine, Incyclinide, Indanocine, Indantadol Hydrochloride, Indoxam, Inogatran, Intrifiban, lobenguane[131I], Iodorubidazone (P), Iotriside, Isepamicin Sulfate, Isobatzelline A, Isobatzelline B, Isobatzelline C, Isobatzelline D, Isobutyramide, Isodoxorubicin, Isopropamide Iodide, Ispinesib Mesylate, Istaroxime, Janthinomycin A, Janthinomycin B, Janthinomycin C, Jaspine B, Kahalalide F, Kaitocephalin, Kanamycin, Karnamicin B1, Katanosin A, Katanosin B, Kistamicin A, L-4-Oxalysine, Labetalol Hydrochloride, Labradimil, Lagatide, Lamifiban, Lamivudine, Lamotrigine, Lanicemine 2(S)-Hydroxysuccinate, Lanicemine Hydrochloride, Lanomycin, Larazotide Acetate, Lazabemide Hydrochloride, L-Dopa Methyl Ester Hydrochloride, L-Dopamide, Lecirelin, Lenalidomide, Lenampicillin Hydrochloride, Leucettamine A, Leucovorin Calcium, Leuprolide Acetate, Leurubicin, Leustroducsin A, Leustroducsin B, Leustroducsin C, Leustroducsin H, Levetiracetam, Levodopa, Levodopa 3-O-Glucoside, Levodopa 4-O-Glucoside, Levoleucovorin Calcium, L-Histidinol, L-Homothiocitrulline, Liblomycin, Linagliptin, Linifanib, Lintopride, Lirexapride, Lirimilast, Lisinopril, L-Lysine-D-Amphetamine Dimesylate, Lobophorin A, Lobucavir, Lodenosine, Loloatin B, Lomeguatrib, Lometrexol, Lonafarnib, Loracarbef Hydrate, Loviride, Loxoribine, L-Simexonyl Homocysteine, L-Thiocitrulline, Lymphostin, Lysobactin, Mabuterol Hydrochloride, Makaluvamine A, Makaluvamine A, Makaluvamine B, Makaluvamine C, Managlinat Dialanetil, Matristatin A2, Melagatran, Melanotan II, Memantine Hydrochloride, Memno-Peptide A, Meprobamate, Meriolin-3, Mersacidin, Metaraminol, Metazosin, Metformin Hydrochloride, Methotrexate, Methyl Bestatin, Methyldopa, Methylthio-DADME-Immucillin-A, Metoclopramide Hydrochloride, Metyrosine, Mexiletine Hydrochloride, Micafungin Sodium, Midaxifylline, Mideplanin, Midoriamin, Milacamide Tartrate, Milacemide-[2H], Milnacipran Hydrochloride, Minamestane, Minocycline Hydrochloride, Minoxidil, Mirabegron, Mitomycin, Mivazerol, Mivobulin Isethionate, Mizoribine, Mocetinostat Dihydrobromide, Modafinil, Modafinil Sulfone, Moenomycin A Chloride Bismuth Salt, Mofegiline, Mofegiline Hydrochloride, Monamidocin, Monodansyl Cadaverine, Montirelin Tetrahydrate, Mosapride Citrate, Moxilubant, Moxilubant Maleate, Mozenavir Mesilate, M-Phenylene Ethynylene, Muraminomicin A, Muraminomicin B, Muraminomicin C, Muraminomicin D, Muraminomicin E1, Muraminomicin E2, Muraminomicin F, Muraminomicin G, Muraminomicin H, Muraminomicin I, Muraminomicin Z1, Muraminomicin Z2, Muraminomicin Z3, Muraminomicin Z4, Muramyl Dipeptide C, Mureidomycin A, Mureidomycin B, Mureidomycin C, Mureidomycin D, Mycestericin E, Myriocin, Nafamostat Mesylate, Nafarelin Acetate, Naglivan, Namitecan, Napsagatran, Nebostinel, Nebracetam Fumarate, Neldazosin, Nelzarabine, Nemonoxacin, Neomycin. B-Hexaarginine Conjugate, Neomycin-Acridine, Nepafenac, Nepicastat Hydrochloride, Neramexane Hydrochloride, Neridronic Acid, Netamiftide Trifluoroacetate, Netilmicin Sulfate, Nocathiacin I, Nocathiacin II, Nocathiacin III, Nocathiacin IV, NO-Gabapentin, Nolatrexed Hydrochloride, NO-Mesalamine, Noraristeromycin, Nuvanil, O6-Benzylguanine, Ocimumoside A, Octacosamicin A, Octacosamicin B, Octreother, Octreotide Acetate, Oglufanide Disodium, Olamufloxacin, Olamufloxacin Mesilate, Olcegepant, Olradipine Hydrochloride, Omaciclovir, Ombrabulin, Ombrabulin Hydrochloride, Onnamide A, Opiorphin, Orbofiban Acetate, Orienticin A, Orienticin B, Orienticin C, Orienticin D, Oritavancin, Oseltamivir Carboxylate, Oseltamivir Phosphate, Otamixaban, Otenabant Hydrochloride, Ovothiol A, Oxazofurin, Oxcarbazepine, Oxiglutatione Sodium, Oxiracetam, Oxolide, Oxynor, Oxyphenarsine, Ozarelix, Pachymedusa Dacnicolor Tryptophyllin-1, Paecilaminol, Pafuramidine Maleate, PalauÀmine, Paldimycin B, Pamidronate Sodium, Pancopride, Papuamide A, Papuamide B, Papuamide C, Papuamide D, Parasin I, Paromomycin, Pasireotide, Paulomycin, Paulomycin A2, Paulomycin B, Paulomycin C, Paulomycin D, Paulomycin E, Paulomycin F, Pazufloxacin, Pazufloxacin Mesilate, PEG-Vancomycin, Pelagiomicin C, Peldesine, Pelitrexol, Pemetrexed Disodium, Penciclovir, Penicillin G Procaine, Pentamidine Gluconate, Pentamidine Isethionate, Pentamidine Lactate, Peplomycin, Peramivir, Perphanazine 4-Aminobutyrate, Phakellistatin 5, PHE-ARG-Beta-Naphthylamide, Phentermine, Phortress, Pholine, Pibutidine Hydrochloride, Pimeloylanilide O-Aminoanilide, Piracetam, Pirarubicin, Pivampicillin, Pixantrone Maleate, Pluraflavin A, Pluraflavin B, Plusbacin A1, Plusbacin A2, Plusbacin A3, Plusbacin A4, Plusbacin B1, Plusbacin 82, Plusbacin B3, Plusbacin B4, PMEO-5-ME-DAPY, Pneumocandin A0, Pneumocandin BO, Pneumocandin BO 2-Phosphate, Pneumocandin D0, Polaprezinc, Polydiscamide A, Polymer Bound Human Leukocyte Elastase Inhibitor, Poststatin, PPI17-24, Pradimicin E, Pradimicin FA-2, Pralatrexate, Pramipexole Hydrochloride, Pranedipine Tartrate, Prazosin Hydrochloride, Prefolic A, Pregabalin, Preladenant, Primaquine Phosphate, Probestin, Procainamide Hydrochloride, Procaine Hydrochloride, Pro-Diazepam, Prostatin, Prucalopride, Prucalopride Hydrochloride, Prucalopride Succinate, Pseudomycin A', Pseudomycin B', Pyloricidin B, Pyradizomycin, Pyrazinamide, Pyrazinoylguanidine, Pyriferone, Pyrimethamine, Quinelorane Hydrochloride, R-(+)-Aminoindane, Ralfinamide, Ramoplanin A'1, Ramoplanin A'2, Ramoplanin A'3, Ramorelix, Ravidomycin N-oxide, Razaxaban Hydrochloride, Reblastatin, Regadenoson, Relcovaptan, Remacemide Hydrochloride, Resiquimod, Restricticin, Retaspimycin Hydrochloride, Retigabine Hydrochloride, Rhodopeptin C1, Rhodopeptin C2, Rhodopeptin C3, Rhodopeptin C4, Rhodostreptomycin A, Rhodostreptomycin B, Ribavirin, Ribavirin Eicosenate cis, Ribavirin Eicosenate trans, Ribavirin Elaidate, Ribavirin Oleate, Rilmazafone Hydrochloride Dihydrate, Riluzole, Rimacalib Hydrochloride, Rimeporide Hydrochloride, Riociguat, Ritipenem Acoxil, Robalzotan Hydrochloride, Robalzotan Tartrate Hydrate, Rociclovir, Romurtide, Rotigaptide, Roxifiban Acetate, Ruboxyl, Rufinamide, Rumycin 1, Rumycin 2, Sabarubicin Hydrochloride, Sabiporide Mesilate, Safinamide Mesilate, Safingol, Sagamacin, Sampatrilat, Sampirtine, Saprisartan, Saquinavir, Saquinavir Mesilate, Sardomizide Hydrochloride, Sardomozide, Saussureamine C, Saxagliptin, Secobatzelline A, Secobatzelline B, Seglitide, Selank, Seletracetam, Semapimod Hydrochloride, Senicapoc, Sepimostat Mesilate, Seproxetine, Seraspenide, Sevelamer Carbonate, Sevelamer Hydrochloride, Shepherdin, Sibrafiban, Silodosin, Silver Sulfadiazine, Sipatrigine, Sitafloxacin Hydrate, Sitagliptin Phosphate Monohydrate, S-Nitrosoglutathione, Sofigatran, Sonedenoson, Sotirimod, Sparfloxacin, Sperabillin A, Sperabillin B, Sperabillin C, Sperabillin D, Sphingofungin F, Spinorphin, Spisulosine, Squalamine Lactate, Streptomycin, Styloguanidine, Substance P(8-11), Sufinosine, Sulcephalosporin, Sulfostin, Sulphazocine, Sultamicilline Tosylate, Sunflower Trypsin Inhibitor-1, Surfen, Synadenol, Synguanol, Tabimorelin, Tacedinaline, Tacrine Hydrochloride, Tageflar, Talabostat, Talaglumetad Hydrochloride, Talampanel, Talipexole Dihydrochloride, Tallimustine Hydrochloride, Talopterin, Taltirelin, Tanespimycin, Tanogitran, Targinine, Technetium (99MTC) Depreotide, Teicoplanin-A2-1, Teicoplanin-A2-2, Teicoplanin-A2-3, Teicoplanin-A2-3, Teicoplanin-A2-5, Telavancin Hydrochloride, Telinavir, Temozolomide, Temurtide, Tenidap, Tenidap Sodium, Tenofovir, Tenofovir DF, Terazosin Hydrochloride, Tetracosyl Cidofovir, Tetracycline Hydrochloride, Tetrafibricin, Texenomycin A, Tezacitabine, TGP, Thioacet, Thiothio, Thrazarine, Thymoctonan, Thymopentin, Tiamdipine, Tigecycline, Tilarginine Hydrochloride, Timirdine Diethanesulfonate, Timodepressin, Tipifarnib, TNF-Alpha Protease Enzyme Inhibitor, Tobramycin, Tocamide Hydrochloride, Tokaramide A, Tomopenem, Topostatin, Torcitabine, Tosufloxacin, Tosufloxacin Tosilate, Tranexamic Acid, Trantinterol Hydrochloride, Tranylcypromine Sulfate, Trelanserin, Tresperimus Triflutate, Trichomycin A, Triciribine, Triciribine Phosphate, Trientine Hydrochloride, Trimazosin Hydrochloride, Trimetrexate Glucuronate, Trimexautide, Trimidox, Trovafloxacin, Trovafloxacin Hydrate, Trovafloxacin Hydrochloride Mesylate, Trovafloxacin Mesilate, Troxacitabine, Trybizine Hydrochloride, Tubastrine, Tuftsin, Tyroservatide, Tyrphostin 47, Ubenimex, Valacyclovir, Valganciclovir Hydrochloride, Valnemulin, Valomaciclovir Stearate, Valonomycin A, Valopicitabine, Valpromide, Valrocemide, Vamicamide, Vancomycin Hydrochloride, Vancoresmycin, Vapitadine Hydrochloride, Varespladib, Varespladib Methyl, Varespladib Mofetil, Velnacrine Maleate, Venorphin, Vigabatrin, Vilazodone Hydrochloride, Vindesine, Viramidine Hydrochloride, Viranamycin-B, Vitamin B3, W Peptide, Xemilofiban, Xylocydine, Zanamivir, Zileuton, Zoniporide Hydrochloride, Zorubicin Hydrochloride.

Suitable secondary amine-containing biologically active moieties may be selected from the group consisting of (−)-3-O-Acetylspectaline hydrochloride, (−)-3-O-tert-Bocspectaline hydrochloride, (−)-Cicloprolol, (−)-Norchloro-[18F]fluoro-homoepibatidine, (−)-Salbutamol hydrochloride, (−)-Salmeterol, (+)-(S)-Hydroxychloroquine, (+)-Isamoltan, (+)-R-Pramipexole, (R)-(+)-Amlodipine, (R)-Clevidipine, (R)-NSP-307, (R)-Teludipine, (R)-Thionisoxetine, (S)-Clevidipine, (S)—N-Desmethyltrimebutine, (S)-Noremopamil, [99Tc]Demobesin 4, [Glu10,Nle17,Nle30]-Pancreatic polypeptide (2-36), [Nle17,Nle30]-Pancreatic polypeptide(2-36), [psi[CH2NH]Tpg4]Vancomycin aglycon, 15bbeta-Methoxyardeemin, 3-Bromomethcathinone, 4,5-Dianilinophthalimide, 4-Hydroxyatomoxetine, 5-Methylurapidil, 7-Oxostaurosporine, 99 mTc-c(RGDfK*)2HYNIC, A-42867 pseudoaglycone, Abacavir succinate, Abacavir sulfate, Abarelix, Acarbose, Acebutolol hydrochloride, Aceclofenac, Acyline, Adaphostin, Adaprolol maleate, Adaprolol oxalate, Adecypenol, Adrogolide hydrochloride, Aglaiastatin C, Alchemix, Alinidine, Alkasar-18, Alminoprofen, Alniditan, alpha-Methylepinephrine, Alprafenone hydrochloride, Alprenolol hydrochloride, Alprenoxime hydrochloride, Altromycin A, Altromycin C, Alvespimycin hydrochloride, Ambroxol nitrate, Amfebutamone hydrochloride, Amibegron hydrochloride, Amifostine hydrate, Amineptine, Aminocandin, Aminochinol, Amitivir, Amlodipine, Amlodipine besylate, Amocarzine, Amodiaquine, Amosulalol hydrochloride, Amoxapine, Amsacrine, Anabasine hydrochloride, Anisperimus, Antide-1, Aranidipine, Araprofen, Arbutamine hydrochloride, Ardeemin, Arformoterol tartrate, Argatroban monohydrate, Argiopine, Arotinolol hydrochloride, Asperlicin E, Atenolol, Atevirdine mesylate, Azathioprine, Azelnidipine, Azepinostatin, Balamapimod, Balhimycin, Balofloxacin, Balofloxacin dihydrate, Bambuterol, Bamirastine hydrate, Banoxantrone, Baogongteng A, Barixibat, Barnidipine hydrochloride, Batoprazine, Batzelline A, Batzelline B, Batzelline C, Becampanel, Bederocin, Bedoradrine sulfate, Befunolol hydrochloride, Belactin B, Belotecan hydrochloride, Benazepril hydrochloride, Bendroflumethiazide, Benidipine hydrochloride, Berlafenone hydrochloride, Betaxolol hydrochloride, Bevantolol hydrochloride, Biemnidin, Bifemelane hydrochloride, Binospirone mesylate, Bioxalomycin alpha 1, Bis(7)-cognitin, Bisantrene hydrochloride, Bisnafide mesilate, Bisoprolol fumarate, Bitolterol mesylate, Bleomycin A2 sulfate, Boholmycin, Bopindolol, Bosutinib, Brinazarone, Brinzolamide, Bulaquine, Bumetanide, Buteranol, Butofilolol, Cadrofloxacin hydrochloride, Caldaret hydrate, Calindol Dihydrochloride, Capridine beta, Carmoterol hydrochloride, Carteolol hydrochloride, Carvedilol, Caspofungin acetate, Ceftaroline fosamil acetate, Ceftizoxime sodium, Ceftobiprole, Celiprolol hydrochloride, Cerebrocrast, Ceruletide diethylamine, Cevipabulin, Chinoin-169, Chloptosin, Chlordiazepoxide hydrochloride, Chloroorienticin A, Chloroorienticin B, Cilazapril, Cilnidipine, Ciluprevir, Cimaterol, Cinacalcet hydrochloride, Cinnamycin, Ciprofloxacin hydrochloride, Ciprofloxacin silver salt, Clevidipine butyrate, Clitocine, Clopenphendioxan, Cloranolol hydrochloride, Clozapine, Conantokin-R, Conophylline, Crisnatol mesilate, Cronidipine, Dabelotine mesilate, Dabigatran, Dabigatran etexilate, Dalbavancin, Dapivirine, Dapropterin dihydrochloride, Dasantafil, Debromoshermilamine, Decaplanin, Degarelix acetate, Delapril hydrochloride, Delavirdine mesilate, Delfaprazine hydrochloride, Delucemine hydrochloride, Demethylallosamidin, Demexiptiline hydrochloride, Denopamine, Deoxymethylspergualin, Deoxyspergualin Hydrochloride, Desacetylvinblastinehydrazide/folate conjugate, Desbutyl benflumetol, Desbutylhalofantrine hydrochloride, Desferri-salmycin A, Desferri-salmycin B, Desferri-salmycin C, Desferri-salmycin D, Desipramine hydrochloride, Desloratadine, Dexfenfluramine hydrochloride, Dexketoprofen meglumine, Dexmethylphenidate hydrochloride, Dexnguldipine hydrochloride, Dexsotalol, Diazepinomicin, Dichlorobenzoprim, Diclofenac potassium, Diclofenac sodium, Diclofenac zinc salt, Diethylnorspermine, Dihydrexidine, Dilevalol, Dilevalol hydrochloride, Dinapsoline, Dinoxyline, Dipivefrine hydrochloride, Discodermide, Discodermide acetate, Discorhabdin D, Discorhabdin P, Discorhabdin S, Discorhabdin T, Discorhabdin U, Dobutamine hydrochloride, Dobutamine phosphate, Dopexamine, Dopexamine hydrochloride, Doripenem, Dorzolamide hydrochloride, d-Pseudoephedrine hydrochloride, Droxinavir, Duloxetine hydrochloride, Duocarmycin A, Duocarmycin B1, Duocarmycin B2, Duocarmycin C1, Duocarmycin C2, Dynemicin A, Dynemicin C, Ebanicline, Ecteinascidin 1560, Ecteinascidin 722, Ecteinascidin 729, Ecteinascidin 736, Ecteinascidin 745, Ecteinascidin 770, Ecteinascidin 875, Efaroxan, Efegatran sulfate hydrate, Efepristin, Efonidipine hydrochloride ethanol, Elagolix sodium, Elansolid Cl, Elarofiban, Elbanizine, Elgodipine hydrochloride, Elinafide mesilate, Elinogrel potassium, Elnadipine, Enalapril maleate, Enalapril nitrate, Enalaprilat, Enazadrem, Enkastin (D), Enkastin (D), Enkastin (D), Enkastin AD, Enkastin AE, Enkastin ID, Enkastin IE, Enkastin VD, Enkastin VE, Enoxacin, Epibatidine, Epostatin, Eremomycin, Ersentilide, Ersentilide hydrochloride, Ertapenem sodium, Esculeogenin A, Esculeoside A, Esmolol hydrochloride, Esperamicin A1, Etamsylate, Ethoxy-idazoxan, Eugenodilol, Ezlopitant, Falnidamol, Farglitazar, Fasobegron hydrochloride, Fasudil hydrochloride, Felodipine, Fenoldopam mesilate, Fenoterol hydrobromide, Fepradinol, Ferroquine, Ferulinolol, Finafloxacin hydrochloride, Flecamide acetate, Florbetaben, Florbetapir F 18, Flufenoxine, Flumezapine, Fluodipine, Fluoxetine hydrochloride, Fluparoxan, Flupirtine maleate, Foetidine 1, Foetidine 2, Folinic acid, Formoterol fumarate, Forodesine hydrochloride, Fosaprepitant dimeglumine, Fosopamine, Frovatriptan, Furnidipine, Furosemide, Gaboxadol, Gadobenic acid dimeglumine salt, Gadopentetate dimeglumine, Gadoterate meglumine, Galactomycin I, Galactomycin II, Garenoxacin mesilate, Gatifloxacin, Gefitinib, Glucolanomycin, Glutapyrone, Gosogliptin hydrochloride, Grepafloxacin hydrochloride, Gypsetin, Halofuginone hydrobromide, Helvecardin A, Helvecardin B, Herquline B, Hesperadin, Himastatin, Hispidospermidin, Homoepibatidine, Hydrochlorothiazide, Hydroflumethiazide, Hydroxychloroquine sulfate, Ibopamine, Idazoxan hydrochloride, Iganidipine hydrochloride, Imidapril, Imidapril hydrochloride, Imidazoacridinone, Imisopasem manganese, Immepip, Immepyr, Incadronate, Indacaterol, Indantadol hydrochloride, Indeloxazine hydrochloride, Indolmycin, Inogatran, Intoplicine, Iofetamine hydrochloride I-123, Iptakalim hydrochloride, Isavuconazonium chloride hydrochloride, Isepamicin sulfate, Isofagomine tartrate, Isoquine, Ispronicline, Isradipine, Iturelix, Kaitocephalin, Ketamine hydrochloride, Kopsinine, Korupensamine A, Korupensamine B, Korupensamine C, Kosinostatin, Labedipinedilol A, Labedipinedilol B, Labetalol hydrochloride, Labradimil, Lacidipine, Ladasten, Ladostigil tartrate, Lagatide, Landiolol, Lapatinib ditosylate, Lenapenem hydrochloride, Lenapenem hydrochloride hydrate, Lerisetron, Leucovorin calcium, Levobetaxolol hydrochloride, Levobunolol hydrochloride, Levoleucovorin calcium, Levonebivolol, Liblomycin, Linaprazan, Lisinopril, Litoxetine, Lobenzarit sodium, Lodamin, Lofexidine hydrochloride, Lomefloxacin hydrochloride, Lorcaserin, Lotrafiban, Loviride, Lubazodone hydrochloride, Lumiracoxib, Mabuterol hydrochloride, Makaluvamine D, Makaluvamine E, Makaluvamine F, Makaluvone, Manidipine hydrochloride, Manifaxine hydrochloride, Manzamine B, Manzamine D, Maprotiline hydrochloride, Maropitant, Masnidipine hydrochloride, Mecamylamine hydrochloride, Meclofenamate sodium, Mefenamic acid, Mefloquine hydrochloride, Melagatran, Melogliptin, Meluadrine, Meluadrine tartrate, Memoquin, Mepindolol sulfate, Mepindolol transdermal patch, Meropenem, Methamphetamine hydrochloride, Methoctramine, Methyclothiazide, Methylhistaprodifen, Methylphenidate hydrochloride, Metipranolol, Metolazone, Metoprolol fumarate, Metoprolol succinate, Metoprolol tartrate, Mezacopride, Michellamine B, Microcin J25, Micronomicin sulfate, Midafotel, Milacemide-[2H], Minaprine hydrochloride, Mirabegron, Mitomycin, Mitoxantrone hydrochloride, Mivobulin isethionate, Modipafant, Moexipril hydrochloride, Moexiprilat, Montirelin tetrahydrate, Moranolin, Motesanib diphosphate, Moxifloxacin hydrochloride, Moxonidine hydrochloride hydrate, Muraminomicin I, Mureidomycin E, Mureidomycin F, Mureidomycins, N1,N8-Bisnorcymserine, Nadolol, Naproxen piperazine, Napsamycin A, Napsamycin B, Napsamycin C, Napsamycin D, Nardeterol, N-demethylated sildenafil, Nebivolol, Nemonapride, Neomycin-acridine, Neratinib, Netilmicin sulfate, Nicardipine hydrochloride, Nifedipine, Nifekalant hydrochloride, Niguldipine hydrochloride, Nilvadipine, Nimodipine, Nipradilol, Nisoldipine, Nitracrine dihydrochloride hydrate, Nitrendipine, Nitrofenac, Nitroso-nifedipine, Noberastine, Noberastine citrate, NO-ciprofloxacin, N-Octyl-beta-valienamine, Nolomirole hydrochloride, Norfloxacin, Norsegoline, Nortopixantrone hydrochloride, Nortriptyline hydrochloride, N-tert butyl isoquine, Oberadilol, Oberadilol monoethyl maleate, Odanacatib, Olanzapine, Olanzapine pamoate, Olradipine hydrochloride, Ontazolast, OPC-17083, Orbifloxacin, Orciprenaline sulphate, Orienticin A, Orienticin B, Orienticin C, Oritavancin, Osemozotan hydrochloride, Osutidine, Otenabant hydrochloride, Ovothiol B, Oxprenolol hydrochloride, Ozenoxacin, Pafenolol, Palau'amine, Palindore fumarate, Panobinostat, Parodilol hemifumarate, Parogrelil hydrochloride, Paroxetine, Paroxetine ascorbate, Paroxetine camsilate, Paroxetine hydrochloride, Paroxetine mesilate, Pazelliptine trihydrochloride, Pazelliptine trihydrochloride monohydrate, Pelitinib, Pelitrexol, Penbutolol sulfate, Penstostatin, Peplomycin, Perindopril, Perzinfotel, Phendioxan, Pibutidine hydrochloride, Picumeterol fumarate, Pindolol, Pirbuterol hydrochloride, Pittsburgh Compound B, Pixantrone maleate, Plerixafor hydrochloride, Polyglutamate camptothecin, Pozanicline hydrochloride, Pradimicin A, Pradimicin B, Pradimicin D, Pradimicin FA-1, Pradimicin FL, Pradimicin FS, Pradimicin L, Pradimicin S, Pradofloxacin, Pramipexole hydrochloride, Pranedipine tartrate, Pranidipine, Prefolic A, Premafloxacin, Premafloxacin hydrochloride, Premafloxacin magnesium, Primaquine phosphate, Prisotinol, Procaterol Hydrochloride Hemihydrate, Propafenone hydrochloride, Propranolol hydrochloride, Protriptyline hydrochloride, Proxodolol, Pumaprazole, Pyrindamycin A, Pyrindamycin B, Quinapril hydrochloride, Quinpramine, rac-Debromoflustramine E, Radezolid, Rafabegron, Ralfinamide, Ramipril, Rasagiline mesilate, Razupenem, Reboxetine mesilate, Repinotan, Repinotan hydrochloride, Reproterol hydrochloride, Retaspimycin hydrochloride, Retigabine hydrochloride, Rhodostreptomycin A, Rhodostreptomycin B, Rifabutin, Rilmenidine dihydrogen phosphate, Rimoterol hydrobromide, Risotilide, Rivanicline, Robenacoxib, Rolapitant hydrochloride, Safinamide mesilate, Sagandipine, Salbostatin, Salbutamol nitrate, Salbutamol sulfate, Salmaterol, Salmeterol xinafoate, Sarizotan hydrochloride, Saussureamine C, Sazetidine-A, Selodenoson, Sertraline, Sertraline hydrochloride, Setazindol, Sezolamide hydrochloride, Shishijimicin A, Shishijimicin B, Shishijimicin C, Sibanomicin, Sibenadet hydrochloride, Silodosin, Sitamaquine hydrochloride, Sivelestat sodium hydrate, Sofinicline, Solabegron hydrochloride, Solpecainol hydrochloride, Soraprazan, Sotalol hydrochloride, Sparfloxacin, Spermine dialdehyde, Spirapril, Spiroquinazoline, Squalamine lactate, Streptomycin, Stressinl-A, Sumanirole maleate, Suprofenac 1, Suprofenac 2, Suprofenac 3, Suronacrine maleate, Tafamidis meglumine, Tafenoquine succinate, Talarozole, Talibegron, Talibegron hydrochloride, Talniflumate, Talotrexin, Taltobulin, Taludipine hydrochloride, Tamsulosin hydrochloride, Tanespimycin, Tanogitran, Tauropyrone, Tazopsine, Tecalcet hydrochloride, Tecastemizole, Technetium (99mTc) apcitide, Technetium (99mTc) bicisate, Telatinib, Telavancin hydrochloride, Temacrazine mesilate, Temafloxacin hydrochloride, Temocapril hydrochloride, Terbutaline sulfate, Terodiline hydrochloride, Tertatolol hydrochloride, Tetracaine hydrochloride, Tetrahydrodercitin 1, Tetrindole, Tezampanel, Thiamet-G, Thiofedrine, Tiamdipine, Tiamenidine, Tianeptine sodium, Tiapafant, Tienoxolol hydrochloride, Tigecycline, Tilisolol hydrochloride, Timolol hemihydrate, Timolol maleate, Tinazoline hydrohloride, Tirofiban hydrochloride, Tizanidine hydrochloride, Toborinone, Tolfenamic acid, Tomatine, Tomoxetine hydrochloride, Topixantrone hydrochloride, Torasemide, Trabectedin, Trandolapril, Trandolaprilat, Trantinterol hydrochloride, Treprostinil diethanolamine, Tresperimus triflutate, Triacetyl dynemicin C, Trientine hydrochloride, Trifluproxim, Trimetazidine, Trimetrexate glucuronate, Trombodipine, Troxipide, Tulathromycin A, Tulathromycin B, Tulobuterol hydrochloride, Ufenamate, Ulifloxacin, Ulimorelin, Uncialamycin, Urapidil, Utibapril, Utibaprilat, Vabicaserin hydrochloride, Vancomycin hydrochloride, Vandetanib, Vanidipinedilol, Vaminolol, Vapitadine hydrochloride, Varenicline tartrate, Varlitinib, Vatalanib succinate, Vatanidipine, Vatanidipine hydrochloride, Vestipitant mesylate, Vicenistatin, Vildagliptin, Viloxazine hydrochloride, Vofopitant hydrochloride, Voglibose, Voreloxin, Xamoterol fumarate, Ximelagatran, Yttrium-90 edotreotide, Zabicipril hydrochloride, Zabiciprilat hydrochloride ( ) Zabofloxacin hydrochloride, Zanapezil fumarate, Zelandopam hydrochloride, Zilpaterol, Zolmitriptan.

Suitable amine-containing biologically active moieties may also be selected from the group consisting of Fab (fragment, antigen-binding), F(ab)2 fragments, Fc (fragment, crystallizable), pFc' fragment, Fv (fragment, variable), scFv (single-chain variable fragment), di-scFv/diabodies, bi-specific T-cell engager, CDRs (complementarity determining regions), single-domain antibodies (sdABs/Nanobodies), heavy chains (α, δ, ε, γ, µ) or heavy chain fragments, light chains (λ, κ) or light chain fragments, VH fragments (variable region of the heavy chain), VL fragments (variable region of the light chain), VHH fragments, VNAR fragments, shark-derived antibody fragments and affinity scaffold proteins, Kunitz domain-derived affinity scaffold proteins, centyrin-derived affinity scaffold proteins, ubiquitin-derived affinity scaffold proteins, lipocalin-derived affinity scaffold proteins, ankyrin-derived affinity scaffold proteins, Versa bodies (disulfide-rich affinity scaffold proteins), fibronectin-derived affinity scaffold proteins, cameloid-derived antibody fragments and affinity scaffold proteins, llama-derived antibody fragments and affinity scaffold proteins, transferrin-derived affinity scaffold proteins, Squash-type protease inhibitors with cysteine-knot scaffold-derived affinity scaffold proteins.

Suitable drugs containing aromatic hydroxyl groups are, for example, (−)-cis-Resorcylide, (−)-Indocarbazostatin B, (−)-Salmeterol, (−)-Subersic acid, (+)-alpha-Viniferin, (+)-Etorphine, (+)-Indocarbazostatin, (+)—SCH-351448, (R)-Gossypol, (S)-(+)-Curcuphenol, (S)-Methylnaltrexone bromide, [8]-Gingerol, [Arg(Me)9] MS-10, [D-Tyr1,Arg(Me)9] MS-10, [D-Tyr1,AzaGly7,Arg(Me)9] MS-10, [D-Tyr1] MS-10, [psi[CH2NH]Tpg4]Vancomycin aglycon, [Trp19] MS-10, 13-Deoxyadriamycin hydrochloride, 14-Methoxymetopon, 14-Phenylpropoxymetopon, 18,19-Dehydrobuprenorphine hydrochloride, 2,12-Dimethyleurotinone, 2'-Hydroxymatteucinol, 2-Methoxyestradiol, 2-Methyleurotinone, 3,5-Dicaffeoylquinic acid, 3-Bromodiosmetine, 3-Bromodiosmine, 3-Chlorodiosmetine, 3-Chlorodiosmine, 4',7,8-Trihydroxyisoflavone, 4-Aminosalicylic acid, 4-Hydroxyatomoxetine, 4-Iodopropofol, 5-Iodofredericamycin A, 5Z-7-Oxozeaenol, 6-Carboxygenistein, 6-O-mPEG4-Nalbupine, 6-O-mPEG5-Nalbuphine, 7-Methylcapillarisin, 8(R)-Fluoroidarubicin hydrochloride, 8',9'-Dehydroascochlorin, 8-Carboxy-iso-iantheran A, 8-Paradol, 8-Prenylapigenin, 8-Prenylnaringenin, 9-Hydroxycrisamicin A, A-42867 pseudoaglycone, Abarelix, Acacetin, Aclarubicin, Acolbifene hydrochloride, Acotiamide hydrochloride hydrate, Acrovestone, Actinoplanone A, Actinoplanone B, Aculeacin Agamma, Adaphostin, Adarotene, Adxanthromycin A, Aerothricin 1, Aerothricin 16, Aerothricin 41, Aerothricin 45, Aerothricin 50, Aerothricin 55, Ajulemic acid, Alchemix, Aldifen, alpha-Mangostin, alpha-Methylepinephrine, alpha-Methylnorepinephrine, Alpha-Peltatin, Altromycin A, Altromycin B, Altromycin C, Altromycin D, Altromycins, Alvimopan hydrate, Alvocidib hydrochloride, Amamistatin A, Amamistatin B, Amarogentin, Amelubant, Amidox, Aminocandin, Amodiaquine, Amoxicillin trihydrate, Amrubicin Hydrochloride, Amurensin H, Anguillosporal, Anidulafungin, Ankinomycin, Annamycin, Annulin C, Antimycin All, Antimycin A12, Antimycin A13, Antimycin A14, Antimycin A15, Antimycin A16, Apicularen A, Apicularen B, Apigenin, Apomine, Apomorphine hydrochloride, Arbidol, Arbutamine hydrochloride, Arformoterol tartrate, Artepillin C, Arzoxifene hydrochloride, Aspoxicillin, Atalaphillidine, Atalaphillinine, Atraric acid, Avorelin, Axitirome, Azaresveratrol, Azatoxin, Azepinostatin, Baicalein, Baicalin, Balhimycin, Balsalazide disodium, Banoxantrone, Bazedoxifene acetate, Bazedoxifene hydrochloride, Bedoradrine sulfate, Benadrostin, Benanomicin A, Benanomicin B, Benastatin A, Benastatin B, Benastatin C, Benastatin D, Benzbromarone, Berefrine, Berupipam maleate, beta-Mangostin, Biemnidin, Biochanin A, Bioxalomycin alpha 1, Bioxalomycin alpha2, Bismuth subsalicylate, Bisphenol, Bix, Bizelesin, Bogorol A, Brandisianin A, Brandisianin B, Brandisianin C, Brasilicardin A, Brevifolin carboxylic acid, Breynin A, Breynin B, Bromotopsentin, Buflomedil pyridoxaiphosphate, Buprenorphine hydrochloride, Buserelin acetate, Butein, Buteranol, Butorphan, Butorphanol tartrate, Calebin A, Calocoumarin A, Caloporoside D, Caloporoside E, Caloporoside F, Calphostin A, Calphostin B, Calphostin C, Calphostin D, Calphostin I, Capillarisin, Capsazepine, Carbazomadurin A, Carbazomadurin B, Carbetocin, Carbidopa, Carmoterol hydrochloride, Caspofungin acetate, Cassigalol A, Cefetecol, Cefoperazone sodium, Cefpiramide sodium, Cefprozil, Cefprozil monohydrate, Cetrorelix Acetate, Chaetatrosin A, Chafuroside, Chlooorienticin A, Chlooorienticin B, Chondramide A, Chondramide B, Chondramide C, Cinnatriacetin A, Cinnatriacetin B, cis-6-Shogaol, Citpressine I, Citreamicin-Alpha, Citreamicin-eta, Citrusinine-I, Clausenamine A, Combretastatin A-1, Combretastatin A-2, Combretastatin A-3, Combretastatin B-1, Combretastatin B-2, Combretastatin B-3, Combretastatin B-4, Combretastatin D-1, Combretastatin D-2, Complestatin, Coniferol Alcohol, Conophylline, Corynecandin, Cosalane, Crisamicin C, Crobenetine, Crobenetine hydrochloride, Curtisian A, Curtisian B, Curtisian D, Cyanidin Chloride Monohydrate, Cyclocommunol, Cycloproparadicicol, Cyclotheonamide A, Cyclothialidine, Cyrtominetin, Cytogenin, Cytosporone B, Cytotrienin I, Cytotrienin II, Dactylocycline A, Dactylocycline B, Dalargin, Dalbavancin, Damunacantal, Daphnodorin A, Daphnodorin B, Daphnodorin C ((−)-enantiomer), Darbufelone, Darbufelone mesilate, Daunorubicin, Daurichromenic acid, Davidigenin, Deacetyl moxisylyte hydrochloride, Decaplanin, Decyl gallate, Deferasirox, Dehydrozingerone, Deiphinidin, Denopamine, Deoxymulundocandin, Dersalazine, Desacetylravidomycin N-oxide, Desglugastrin tromethamine, Deslorelin, Desmopressin acetate, Desvenlafaxine succinate, Dexanabinot, Dextrorphan, Dexylosylbenanomycin A, D-Fluviabactin, Diazaphilonic acid, Diazepinomicin, Dieckol, Diflunisal, Dihydrexidine, Dihydroavenanthramide D, Dihydrogranaticin B, Dihydrohonokiol B, Dihydroraloxifene, Dilevalol, Dilevalol hydrochloride, Dinapsoline, Dinoxyline, Dioncoquinone A, Dioncoquinone B, Dipotassium gossypolate, Dobutamine hydrochloride, Dobutamine Phosphate, Dopexamine, Dopexamine hydrochloride, Dosmalfate, Doxorubicin Hydrochloride, Doxorubicin, Morpholinyl, DoxoTam 12, Doxycycline hyclate, Dronabinol, Droxidopa, Duocarmycin B1, Duocarmycin B2, Duocarmycin C1, Duocarmycin C2, Dutomycin, Dynemicin A, Dynemicin C, Econazole Sulfosalicylate, Ecopipam, Ecteinascidin 1560, Ecteinascidin 722, Ecteinascidin 729, Ecteinascidin 736, Ecteinascidin 745, Ecteinascidin 757, Ecteinascidin 770, Ecteinascidin 875, Edotecarin, Edotreotide yttrium, Eflucimibe, Eflumast, Elansolid C1, Eldacimibe, Ellagic acid-4-gallate, Elliptinium acetate, Elsibucol, Eltrombopag olamine, Emodin, Enazadrem, Enofelast, Entacapone, ent-Estriol, Epidoxoform, Epigallocatechin-3-gallate, Epirubicin hydrochloride, Eplivanserin, Eplivanserin fumarate, Eplivanserin mesilate, Epocarbazolin A, Epocarbazolin B, Eprotirome, Eptazocine hydrobromide, Erabulenol A, Erabulenol B, Eremomycin, Estetrol, Estradiol, Estriol, Etalocib sodium, Etamsylate, Ethinylestradiol, Ethyl gallate, Etoposide, Eurotinone, Euxanthone, Evernimicin, Exifone, Ezetimibe, Fadolmidine hydrochloride, Feglymycin, Fenoldopam mesilate, Fenoterol hydrobromide, Fidaxomicin, Fidexaban, Fluostatin A, Fluostatin B, Foetidine 1, Foetidine 2, Folipastatin, Formobactin, Formoterol fumarate, Fosopamine, Frederine, Fulvestrant, Furaquinocin A, Furaquinocin B, Fusacandin A, Fusacandin B, Fusidienol, Galactomycin I, Galactomycin II, Galarubicin hydrochloride, Galocitabine, Gambogic acid, gamma-Mangostin, gamma-Tocotrienol, Ganirelix, Ganirelix acetate, Garvalone C, Garveatin E, Garveatin F, Genistein-7-phosphate, Gigantol, Gilvusmycin, Glucopiericidinol A1, Glucopiericidinol A2, Gludopa, Glycothiohexide alpha, Goserelin, Granaticin B, Griseusin C, Hatomarubigin A, Hatomarubigin B, Hatomarubigin C, Hatomarubigin D, Hayumicin A, Hayumicin B, Hayumicin C1, Hayumicin C2, Hayumicin D, Heliquinomycin, Helvecardin A, Helvecardin B, Hericenal A, Hericenal B, Hericenal C, Hidrosmin, Histrelin, Histrelin acetate, Hongoquercin A, Hongoquercin B, Honokiol diepoxide, Honokiol diepoxide, Human angiotensin II, Hydromorphone methiodide, Hymenistatin 1, Hypeptin, Hypericin, Hyperoside, Icariin, Idarubicin hydrochloride, Idronoxil, Ifenprodil, Imidazoacridinone, Incyclinide, Indacaterol, Indanocine, Integracin A, Integracin B, Integracin C, Integramycin, Integrastatin A, Integrastatin B, Intoplicine, Iodochlorhydroxyquin, Iododiflunisal, Iodorubidazone (p), Iolopride (123I), Ioxipride, Iralukast, Iralukast sodium, Irciniastatin A, Irciniastatin B, Isalmadol, Isobavachalcone, Isodoxorubicin, Iso-iantheran A, Isoliquiritigenin, Isomolpan Hydrochloride, Isoquine, Isovanihuperzine A, Jadomycin B, Jasplakinolide, Kadsuphilin C, Kaitocephalin, Kampanol A, Kampanol B, Kanglemycin A, Kapurimycin A1, Kapurimycin A3, Kapurimycin A3, Kehokorin D, Kehokorin E, Kigamicin A, Kigamicin B, Kigamicin C, Kigamicin D, Kigamicin E, Kigamicinone, Kistamicin A, Klainetin A, Klainetin B, Kodaistatin A, Kodaistatin B, Kodaistatin C, Kodaistatin D, Korupensamine A, Korupensamine B, Korupensamine C, Korupensamine D, Kosinostatin, Labetalol hydrochloride, Laccaridione A, Lactonamycin, Lactosylphenyl trolox, Ladirubicin, Lamellarin alpha 20-sulfate sodium salt, Lamifiban, Lanreotide acetate, Lasofoxifene, Lasofoxifene tartrate, Latamoxef sodium, L-Chicoric acid, L-Dopamide, Lecirelin, Ledazerol, Leuprolide acetate, Leurubicin, Levalbuterol hydrochloride, Levodopa, Levodopa 3-O-glucoside, Levodopa 4-O-glucoside, Levorphanol tartrate, L-Fluviabactin, Lipiarmycin B3, Lipiarmycin B4, Liquiritin apioside, Lithospermic acid B magnesium salt, Lobatamide C, Lobatamide F, Loloatin B, Luminacin D, Luteolin, Macrocarpin A, Macrocarpin B, Makaluvamine D, Makaluvamine E, Malonoben, Maltolyl p-coumarate, Mannopeptimycin beta, Manzamine F, Marinopyrrole A, Marmelin, Masoprocol, Mastprom, Matteuorienate A, Matteuorienate B, Matteuorienate C, Medicarpin, Melevodopa hydrochloride, Mellein, Meluadrine, Meluadrine tartrate, Memno-peptide A, Meptazinol hydrochloride, Mesalazine, Metaraminol, Methanobactin, Methyl gallate, Methyldopa, Methylnaltrexone bromide, Metirosine, Micacocidin A, Micacocidin B, Micafungin sodium, Michellamine B, Mideplanin, Mimopezil, Minocycline hydrochloride, Miproxifene, Mitoxantrone hydrochloride, Mivazerol, Modecamide, Mollugin, Monohydroxyethylrutoside, Morphine Glucuronide, Morphine hydrochloride, Morphine sulfate, Moxifetin hydrogen maleate, Mumbaistatin, Mureidomycin A, Mureidomycin B, Mureidomycin C, Mureidomycin D, Mureidomycin E, Mureidomycin F, Mureidomycins, Mycophenolate Mofetil, Mycophenolic acid sodium salt, Myrciacitrin I, Myrciacitrin II, Myrciaphenone B, Myriceric acid A, Mytolbilin, Mytolbilin acid, Mytolbilin acid methyl ester, Mytolbilinol, Naamidine A, Nabilone, N-Acetylcolchinol, Nafarelin acetate, Nalbuphine hydrochloride, Nalfurafine hydrochloride, N-Allylsecoboldine, Nalmefene, Naloxone hydrochloride, Naltrexone hydrochloride, Naltrindole, Napsamycin A, Napsamycin B, Napsamycin C, Napsamycin D, Nardeterol, N-Cyclopentyl-tazopsine, Nebicapone, Nelfinavir mesilate, Nemorubicin, Neparensinol A, Neparensinol B, Neparensinol C, Nerfilin I, Nicanartine, Nitecapone, Nocardione A, Nocathiacin I, Nocathiacin III, Nocathiacin IV, NO-Mesalamine, Nordamunacantal, Nostocyclopeptide M1, Nothramicin, N-tert butyl isoquine, Obelmycin H, Ochromycinone, Octyl gallate, Odapipam acetate, O-Demethylchlorothricin, O-Demethylmurrayafoline A, Oenothein B, Okicenone, Olanzapine pamoate, Olcegepant, Olsalazine sodium, Onjixanthone I, Onjixanthone II, Oolonghomobisflavan A, Oolonghomobisflavan C, Orciprenaline sulphate, Orienticin A, Orienticin B, Orienticin C, Orienticin D, Oritavancin, Orniplabin, Orthosomycin A, Orthosomycin B, Orthosomycin C, Orthosomycin D, Orthosomycin E, Orthosomycin F, Orthosomycin G, Orthosomycin H, Osutidine, Oximidine III, Oxymetazoline hydrochloride, Oxymorphazole dihydrochloride, Oxymorphone hydrochloride, Oxyphenarsine, Ozarelix, Paeciloquinine A, Paeciloquinine D, Paeciloquinone B, Paeciloquinone D, Pancratistatin-3,4-cyclic phosphate sodium salt, Pannorin, Papuamide A, Papuamide B, Papuamide C, Papuamide D, Paracetamol, Parvisporin B, PEG-vancomycin, Penicillide, Pentazocine hydrochloride, Pepticinnamin E, Phaffiaol, Phakellistatin 7, Phakellistatin 8, Phakellistatin 9, Phenochalasin A, Phentolamine mesilate, Phlorofucofuroeckol, Phomopsichalasin, Phthalascidin, Physostigmine salicylate, Piceatannol, Pidobenzone, Pinocembrin, Pipendoxifene, Pirarubicin, Pittsburgh Compound B, Platencin, Platensimycin, Pluraflavin A, Pluraflavin B, Pluraflavin E, Pneumocandin A0, Pneumocandin B0, Pneumocandin B0 2-phosphate, Pneumocandin D0, Polyestradiol phosphate, Polyketomycin, Popolohuanone E, Pradimicin A, Pradimicin B, Pradimicin D, Pradimicin E, Pradimicin FA-1, Pradimicin FA-2, Pradimicin FL, Pradimicin FS ((+)-enantiomer), Pradimicin L, Pradimicin Q, Pradimicin S, Pradimicin T1, Pradimicin T2, Prinaberel, Probucol, Procaterol Hydrochloride Hemihydrate, Propofol, Propyl gallate, Protocatechuic acid, Protocatechuic aldehyde, Pseudohypericin, Purpuromycin, Pyrindamycin A, Pyrindamycin B, Quercetin-3-O-methyl ether, Quinagolide hydrochloride, Quinobene, rac-Apogossypolone, Rac-Tolterodine, Raloxifene hydrochloride, Ramoplanin A'1, Ramoplanin A'2, Ramoplanin A'3, Ramorelix, Ravidomycin N-oxide, Rawsonol, Reblastatin, Reproterol hydrochloride, Resobene, Resorthiomycin, Retaspimycin hydrochloride, Rhodiocyanoside B, Rhododaurichromanic acid A, Rifabutin, Rifalazil, Rifamexil, Rifampicin, Rifapentine, Rifaximin, Rimoterol hydrobromide, Riodoxol, Rohitukine, Rotigaptide, Rotigotine, Roxindole Mesilate, Ruboxyl, Rufigallol, Rumycin 1, Rumycin 2, Russuphelin A, Sabarubicin hydrochloride, Saintopin, Saintopin E, Sakyomicin A, Sakyomicin E, Salazopyridazin, Salbutamol nitrate, Salbutamol sulfate, Salcaprozic acid sodium salt, Salicylazobenzoic acid, Salicylihalamide A, Salicylihalamide B, Saliphenylhalamide, Salmaterol, Salmeterol xinafoate, Saloxin, Salvianolic acid L, Sampatrilat, Sanglifehrin A, Sanglifehrin B, Sanglifehrin C, Sanglifehrin D, Saptomycin D, Sapurimycin, Saricandin, Secoisolariciresinol diglucoside, Seglitide, Semorphone hydrochloride, Shishijimicin A, Shishijimicin B, Shishijimicin C, Sibenadet hydrochloride, Silychristin, Sinomenine, Sivifene, Siwenmycin, Sootepenseone, Spinorphin, Spinosulfate A, Spinosulfate B, Spiroximicin, Stachybocin A, Stachybocin B, Stachybocin C, Stachybotrin C, Stachybotrydial, Staplabin, Sterenin A, Sterenin C, Sterenin D, Streptopyrrole, Succinobucol, Sulfasalazine, Sulphazocine, Susalimod, Symbioimine, Syriacusin A, Syriacusin B, Syriacusin C, Tageflar, Taiwanhomoflavone A, TAP-doxorubicin, Tapentadol hydrochloride, Taramanon A, Tazofelone, Tazopsine, Tebufelone, Technetium Tc 99m depreotide, Teicoplanin-A2-1, Teicoplanin-A2-2, Teicoplanin-A2-3, Teicoplanin-A2-3, Teicoplanin-A2-5, Telavancin hydrochloride, Temoporfin, Teniposide, Tenuifoliside A, Tenuifoliside B, Tenuifoliside C, Terbutaline sulfate, Terprenin, Tetracycline hydrochloride, Tetragalloylquinic acid, Tetrahydrocurcumin, Tetra hydroechinocandin B, Tetrahydroswertianolin, Thenorphine, Theophylline rutoside, Thiazinotrienomycin B, Thiazinotrienomycin F, Thiazinotrienomycin G, Thielavin G, Thielocin B3, Thymopentin, Tigecycline, Tipelukast, Tocotrienol, Tokaramide A, Tolcapone, Tolterodine Tartrate, Topotecan Acetate, Topotecan Hydrochloride, Topsentine B1, Trabectedin, trans-Resveratrol, Traxoprodil, Traxoprodil mesylate, Trimidox, Triphendiol, Troglitazone, Tubastrine, Tubulysin A, Tubulysin B, Tubulysin C, Tucaresol, Tyropeptin A10, Tyropeptin A6, Tyropeptin A9, Tyroservatide, Tyrphostin 47, Uncarinic acid A, Uncarinic acid B, Uncialamycin, Valrubicin, Vancomycin hydrochloride, Veinamitol, Venorphin, Verticillatine, Vexibinol, Vialinin B, Vinaxanthone, W Peptide, Wiedendiol A, Wiedendiol B, Woodorien, Xamoterol Fumarate, Xanthoangelol E, Xanthofulvin, Xanthomegnin, Xipamide, Yatakemycin, Zelandopam hydrochloride, Zorubicin hydrochloride.

Suitable drugs with a hydroxyl group may be selected fromt the group consisting of (−)-(2R*,3R*,11bS*)-Dihydrotetrabenazine, (−)-(2R*,3S*,11bR*)-Dihydrotetrabenazine, (−)-2-(2-Bromohexadecanoyl)paclitaxel, (−)-4',5'-Didemethoxypicropodophyllin, (−)-4'-Demethoxypicropodophyllin, (−)-9-Dehydrogalanthaminium bromide, (−)-Calicheamicinone, (−)-Cicloprolol, (−)-cis-Resorcylide, (−)-Indocarbazostatin B, (−)-Kendomycin, (−)-Kolavenol, (−)-Salmeterol, (−)-Subersic acid, (+)-(2R*,3R*,11bS*)-Dihydrotetrabenazine, (+)-(2R*,3S*,11bR*)-Dihydrotetrabenazine, (+)-(S)-Hydroxychloroquine, (+)-23,24-Dihydrodiscodermolide, (+)-Almuheptolide A, (+)-alpha-Viniferin, (+)-Azacalanolide A, (+)-Dihydrocalanolide A, (+)-Etorphine, (+)-Indocarbazostatin, (+)-Isamoltan, (+)—SCH-351448, (+)-Sotalol, (E)-p-Coumaroylquinic acid, (R)-Almokalant, (R)-Dixyrazine dihydrochloride, (R)-Gossypol, (R)-Sulfinosine, (S)-(+)-Curcuphenol, (S)-Almokalant, (S)-Methylnaltrexone bromide, (S)-Oxiracetam, (S)-Sulfinosine, (Z)-Indenaprost, [8]-Gingerol, [Arg(Me)9] MS-10, [D-Tyr1,Arg(Me)9] MS-10, [D-Tyr1,AzaGly7,Arg(Me)9] MS-10, [D-Tyr1] MS-10, [N-Melle4]-cyclosporin, [psi[CH2NH]Tpg4]Vancomycin aglycon, [Trp19] MS-10, 111In-Pentetreotide, 11-Hydroxyepothilone D, 11-Keto-Beta-Boswellic Acid, 13-Deoxyadriamycin hydrochloride, 14alpha-Lipoyl andrographolide, 14beta-Hydroxydocetaxel-1,14-acetonide, 14beta-Hydroxytaxotere, 14-Demethylmycoticin A, 14-Hydroxyclarithromycin, 14-Isobutanoylandrographolide, 14-Methoxymetopon, 14-Phenylpropoxymetopon, 14-Pivaloylandrographolide, 15-Methylepothilone B, 16-Methyloxazolomycin, 17-Aminogeldanamycin, 17beta-Hydroxywortmannin, 18,19-Dehydrobuprenorphine hydrochloride, 18-Hydroxycoronaridine, 19-O-Demethylscytophycin C, 19-O-Methylgeldanamycin, 1alpha,25-Dihydroxyvitamin D3-23,26-lactone, 1alpha-Hydroxyvitamin D4, 1-Oxorapamycin, 2,12-Dimethyleurotinone, 21-Aminoepothilone B, 22-Ene-25-oxavitamin D, 22-Oxacalcitriol, 24(S)-Ocotillol, 24-Deoxyascomycin, 25-Anhydrocimigenol-3-O-beta-D-xylopyranoside, 26-Fluoroepothilone, 2-Aminoaristeromycin, 2-Aminoneplanocin A, 2'-Hydroxymatteucinol, 2-Methoxyestradiol, 2-Methyleurotinone, 2'-Palmitoylpaclitaxel, 3,5-Dicaffeoylquinic acid, 3,7a-Diepialexine, 36-Dihydroisorolliniastatin 1,3-Allyl farnesol, 3-Bromodiosmetine, 3-Bromodiosmine, 3-Chlorodiosmetine, 3-Chlorodiosmine, 3-Deazaadenosine, 3-Epimaxacalcitol, 4,6-diene-Cer, 4',7,8-Trihydroxyisoflavone, 41-Demethylhomooligomycin B, 44-Homooligomycin B, 4-Aminosalicylic acid, 4-Chlorophenylthio-DADMe-immucillin-A, 4-Demethylepothilone B, 4-Demethylpenclomedine, 4'-Ethynylstavudine, 4-Hydroxyatomoxetine, 4"-Hydroxymevastatin lactone, 4-Iodopropofol, 5(R)-Hydroxytriptolide, 5,4'-Diepiarbekacin, 5,6-Dehydroascomycin, 5'-Epiequisetin, 5-Ethylthioribose, 5-Iodofredericamycin A, 5-N-Acetyl-15balpha-hydroxyardeemin, 5-Phenylthioacyclouridine, 5-Thiaepothilone, 5Z-7-Oxozeaenol, 6alpha-7-Epipaclitaxel, 6alpha-Fluoroursodeoxycholic acid, 6-Carboxygenistein, 6'-Homoneplanocin A, 6-Hydroxyscytophycin B, 6-O-mPEG4-Nalbupine, 6-O-mPEG5-Nalbuphine, 7,7a-Diepialexine, 7-Chlorokynurenic acid, 7-Deoxytaxol, 7-Methylcapillarisin, 8(R)-Fluoroidarubicin hydrochloride, 8',9'-Dehydroascochlorin, 8-Carboxy-iso-iantheran A, 8-Paradol, 8-Prenylapigenin, 8-Prenylnaringenin, 9,11-Dehydrocortexolone 17alpha-butyrate, 9,9-Dihydrotaxol, 9-[18F]Fluoropropyl-(+)-dihydrotetrabenazine, 99mTc-c(RGDfK*)2HYNIC, 9-Aminocamptothecin, 9-Hydroxycrisamicin A, 9-Hydroxyrisperidone, A-42867 pseudoaglycone, Abacavir succinate, Abacavir sulfate, Abaperidone hydrochloride, Abarelix, Abietaquinone methide, Abiraterone, Acacetin, Acadesine, Acarbose, Acaterin, Acebutolol hydrochloride, Acemannan, Aceneuramic acid sodium salt, Aciclovir, Aclarubicin, Acolbifene hydrochloride, Acotiamide hydrochloride hydrate, Acrovestone, Actinoplanone A, Actinoplanone B, Aculeacin Agamma, Acyline, Adamantyl globotriaosylceramide, Adaphostin, Adaprolol maleate, Adaprolol Oxalate, Adarotene, Adecypenol, Adelmidrol, Ademetionine tosylate sulfate, Adenophostin A, Adenophostin B, Adenosine, Adlupulon, Adxanthromycin A, Aerothricin 1, Aerothricin 41, Aerothricin 45, Aerothricin 5, Aerothricin 50, Aerothricin 55, Afeletecan hydrochloride, Agelasphin 517, Agelasphin 564, Aglaiastatin A, Aglaiastatin B, Ajulemic acid, Albaconazole, Albifylline, Albithiazolium bromide, Albocycline K3, Alchemix, Alclometasone dipropionate, Alcuronium chloride, Aldecalmycin, Aldifen, Alemcinal, Alfacalcidol, Alisamycin, Aliskiren fumarate, Alkasar-18, Allixin, Almokalant, Alogliptin benzoate, alpha-C-Galactosylceramide, alpha-Galactosylceramide, alpha-Galactosylceramide-BODIPY, alpha-Lactosylceramide, alpha-Mangostin, alpha-Methylepinephrine, alpha-Methylnorepinephrine, Alpha-Peltatin, alpha-Pyrone I, Alprafenone hydrochloride, Alprenolol hydrochloride, Alprostadil, Altemicidin, Altorhyrtin C, Altromycin A, Altromycin B, Altromycin C, Altromycin D, Altromycins, Alvespimycin hydrochloride, Alvimopan hydrate, Alvocidib hydrochloride, Amamistatin A, Amamistatin B, Amarogentin, Ambroxol nitrate, Amdoxovir, Amelometasone, Amelubant, Amibegron hydrochloride, Amidox, Amikacin, Aminocandin, Amlexanox, Ammocidin A, Amodiaquine, Amosulalol Hydrochloride, Amoxicillin trihydrate, Amphidinolide E, Amphidinolide T1, Amphinidin A, Amphotericin B, Amprenavir, Amrubicin Hydrochloride, Amurensin H, Amycolamicin, Amycomycin, Anandamide, Andenallene, ANDREA-1, Androstanolone, Anguillosporal, Anguinomycin C, Anguinomycin D, Anidulafungin, Ankinomycin, Annamycin, Annocherimolin, Annulin C, Antheliatin, Antide, Antide-1, Antide-2, Antide-3, Antiflammin-1, Antiflammin-3, Antimycin A11, Antimycin A12, Antimycin A13, Antimycin A14, Antimycin A15, Antimycin A16, Apadenoson, Apalcillin sodium, Apaziquone, Aphidicolin, Aphidicolin Glycinate, Apicularen A, Apicularen B, Apigenin, Aplaviroc hydrochloride, Apomine, Apomorphine hydrochloride, Apricitabine, Aragusterol A, Aragusterol C, Aranorosin, Aranorosinol A, Aranorosinol B, Aranose, Arbekacin, Arbekacin sulfate, Arbidol, Arborcandin A, Arborcandin B, Arborcandin C, Arborcandin D, Arborcandin E, Arborcandin F, Arbutamine hydrochloride, Archazolid A, Archazolid B, Arformoterol tartrate, Argiotoxin-636, Arimoclomol maleate, Arisostatin A, Arisugacin A, Arotinolol hydrochloride, Artepillin C, Artilide fumarate, Arundifungin, Arzoxifene hydrochloride, Ascosteroside, Asiatic acid, Asiaticoside, Asimadoline, Asperlicin B, Asperlicin E, Aspoxicillin, Assamicin I, Assamicin II, Astromicin sulfate, Atalaphillidine, Atalaphillinine, Atazanavir sulfate, Atenolol, Atigliflozin, Atorvastatin, Atorvastatin calcium, Atorvastatin-Aliskiren, Atosiban, Atovaquone, Atraric acid, Atrinositol, Auristatin E, Aurothioglucose, Australifungin, Australine, Avicenol A, Avicequinone A, Avicin D, Avicin G, Avorelin, Axitirome, Azacitidine, Azaresveratrol, Azaromycin SC, Azatoxin, Azelastine embonate, Azepinostatin, Azithromycin, Azithromycin Copper Complex, Bactobolin, Bafilomycin A1, Bafilomycin C1, Baicalein, Baicalin, Balhimycin, Balofloxacin, Balofloxacin dihydrate, Balsalazide disodium, Bambuterol, Banoxantrone, Baogongteng A, Barixibat, Barusiban, Bazedoxifene acetate, Bazedoxifene hydrochloride, Becatecarin, Beciparcil, Beclometasone dipropionate, Becocalcidiol, Bedoradrine sulfate, Befloxatone, Befunolol hydrochloride, Begacestat, Belactin B, Belotecan hydrochloride, Benadrostin, Benanomicin A, Benanomicin B, Benastatin A, Benastatin B, Benastatin C, Benastatin D, Benexate cyclodextrin, Bengazole A, Bengazole B, Benzbromarone, Beraprost sodium, Berefrine, Berupipam maleate, Bervastatin, Besifloxacin hydrochloride, Beta-Boswellic Acid, beta-Mangostin, Betamethasone butyrate propionate, Betamethasone dipropionate, Beta-Sialosylcholesterol Sodium Salt, Betaxolol hydrochloride, Bevantolol hydrochloride, Biapenem, Biemnidin, Bimatoprost, Bimoclomol, Bimoclomol 1-oxide, Bimosiamose, Binfloxacin, Binodenoson, Biochanin A, Bioxalomycin alpha 1, Bioxalomycin alpha2, Bipranol hydrochloride, Bisabosqual B, Bisabosqual D, Bismuth subsalicylate, Bisoprolol fumarate, Bisphenol, Bitolterol mesylate, Bix, Bizelesin, Bleomycin A2 sulfate, Bogorol A, Bohemine, Boholmycin, Bolinaquinone, Borrelidin, Bosentan, Brandisianin A, Brandisianin B, Brandisianin C, Brasilicardin A, Brasilinolide A, Brasilinolide B, Brecanavir, Breflate, Brevifolin carboxylic acid, Breynin A, Breynin B, Brivanib, Brivudine, Bromotopsentin, Bryostatin 1, Bryostatin 10, Bryostatin 11, Bryostatin 12, Bryostatin 13, Bryostatin 9, Budesonide, Buflomedil pyridoxalphosphate, Bungeolic acid, Buprenorphine hydrochloride, Buserelin acetate, Butalactin, Butein, Buteranol, Butixocort, Butofilolol, Butorphan, Butorphanol tartrate, Byssochlamysol, Cabazitaxel, Cabin 1, Cadralazine, Cadrofloxacin hydrochloride, Caffeine citrate, Calanolide A, Calanolide B, Calbistrin A, Calbistrin B, Calbistrin C, Calbistrin D, Calcipotriol, Calcitriol, Calcium-like peptide 1, Calebin A, Calocoumarin A, Caloporoside B, Caloporoside C, Caloporoside D, Caloporoside E, Caloporoside F, Calphostin A, Calphostin B, Calphostin C, Calphostin D, Calphostin I, Calteridol calcium, Cambrescidin 800, Cambrescidin 816, Cambrescidin 830, Cambrescidin 844, Camiglibose, Campestanol ascorbyl phosphate, Canadensol, Canagliflozin, Candelalide B, Candelalide C, Cangrelor tetrasodium, Canventol, Capadenoson, Capecitabine, Capillarisin, Caprazamycin A, Caprazamycin B, Caprazamycin C, Caprazamycin E, Caprazamycin F, Capridine beta, Capsazepine, Carabersat, Carbazomadurin A, Carbazomadurin B, Carbetocin, Carbidopa, Carbovir, Caribaeoside, Carisbamate, Carmoterol hydrochloride, Carpesterol, Carquinostatin A, Carsatrin, Carteolol hydrochloride, Carteramine A, Carvastatin, Carvedilol, Caspofungin acetate, Cassigalol A, Castanospermine, Cefbuperazone sodium, Cefcanel, Cefetecol, Cefonicid sodium, Cefoperazone sodium, Cefoselis sulfate, Cefpiramide sodium, Cefprozil, Cefprozil monohydrate, Celgosivir, Celikalim, Celiprolol hydrochloride, Cephalostatin 1, Cephalostatin 2, Cephalostatin 3, Cephalostatin 4, Cephalostatin 7, Cephalostatin 8, Cephalostatin 9, Ceramidastin, Cerebroside A, Cerebroside B, Cerebroside C, Cerebroside D, Cerivastatin sodium, Ceruletide diethylamine, Cetefloxacin, Cethromycin, Cetrorelix Acetate, Chackol, Chaetoatrosin A, Chafuroside, Chenodeoxycholic acid, Chetocin, Chinoin-169, Chloptosin, Chlorazicomycin, Chlorofusin, Chlorogentisylquinone, Chloroorienticin A, Chloroorienticin B, Cholerae Autoinducer-1, Choline alfoscerate, Chondramide A, Chondramide B, Chondramide C, Ciclesonide, Cicletanine, Cidofovir, Cimaterol, Cimetropium bromide, Cinatrin A, Cinatrin B, Cinatrin C1, Cinatrin C2, Cinnabaramide A, Cinnatriacetin A, Cinnatriacetin B, Cinolazepam, Ciprofloxacin hydrochloride, Ciprokiren, cis-6-Shogaol, Citicoline, Citpressine I, Citreamicin-Alpha, Citreamicin-eta, Citropeptin, Citrullimycine A, Citrusinine-I, Cladribine, Clarithromycin, Clausenamine A, Clavaric acid, Clavarinone, Clavulanate potassium, Clazosentan, Clevudine, Clindamycin hydrochloride, Clitocine, Clobenoside, Clofarabine, Clopithepin, Cloranolol hydrochloride, Cocositol, Colabomycin A, Coleneuramide, Coleophomone B, Colestimide, Colforsin, Colforsin daproate hydrochloride, Colletoic acid, Colupulon, Combretastatin A-1, Combretastatin A-2, Combretastatin A-3, Combretastatin B-1, Combretastatin B-2, Combretastatin B-3, Combretastatin B-4, Combretastatin D-1, Combretastatin D-2, Complestatin, Conagenin, Coniferol Alcohol, Coniosetin, Conocurvone, Conophylline, Contignasterol, Contulakin G, Cortexolone 17alpha-propionate, Corynecandin, Cosalane, Cositecan, Costatolide, Coumamidine Gammal, Coumamidine Gamma2, Crassicauline A, Crellastatin A, Crisamicin C, Crisnatol mesilate, Crobenetine, Crobenetine hydrochloride, Cromakalim, Crossoptine A, Crossoptine B, Curtisian A, Curtisian B, Curtisian D, Curvularol, Cyanidin Chloride Monohydrate, Cyclamenol, Cyclandelate, Cyclipostin A, Cyclocommunol, Cyclohexanediol, Cyclomarin A, Cyclooctatin, Cycloplatam, Cycloproparadicicol, Cyclosporin A, Cyclosporin J, Cyclotheonamide A, Cyclothialidine, Cygalovir, Cypemycin, Cyrtominetin, Cystocin, Cystothiazole C, Cystothiazole D, Cystothiazole F, Cytallene, Cytarabine, Cytaramycin, Cytoblastin, Cytochalasin B, Cytochlor, Cytogenin, Cytosporic acid, Cytosporone B, Cytostatin, Cytotrienin I, Cytotrienin II, Cytotrienin III, Cytotrienin IV, Cytoxazone, DACH-Pt(II)-bis-ascorbate, Dacinostat, Dactimicin, Dactylfungin A, Dactylfungin B, Dactylocycline A, Dactylocycline B, Dactylorhin B, DADMe-Immucillin-G, DADMe-Immucillin-H, Dalargin, Dalbavancin, Dalfopristin mesilate, Dalvastatin, Damunacantal, Danofloxacin, Dapagliflozin, Daphnodorin A, Daphnodorin B, Daphnodorin C ((−)-enantiomer), Dapropterin dihydrochloride, Darbufelone, Darbufelone mesilate, Darunavir, Dasantafil, Dasatinib, Daunorubicin, Daurichromenic acid, Davidigenin, Davunetide, Deacetyl moxisylyte hydrochloride, Decahydromoenomycin A, Decaplanin, Decarestrictine C, Decarestrictine D, Decatromicin A, Decatromicin B, Decitabine, Decursinol, Decyl gallate, Deferasirox, Deferiprone, Deflazacort, Deforolimus, Degarelix acetate, Dehydelone, Dehydrodolastatin-13, Dehydrozingerone, Delafloxacin, Delaminomycin A, Delaminomycin B, Delaminomycin C, Delimotecan sodium, Delphinidin, delta-Tocopherol glucoside, Deltibant, Demethimmunomycin, Demethomycin, Demethylallosamidin, Demethylasterriquinone B-1, Denopamine, Denufosol tetrasodium, Deoxyenterocin, Deoxylaidlomycin, Deoxymulundocandin, Deoxynojirimycin, Deoxyspergualin Hydrochloride, Deprodone propionate, Dersalazine, Desacetyleleutherobin, Desacetylravidomycin N-oxide, Desacetylvinblastinehydrazide, Desacetylvinblastinehydrazide/folate conjugate, Desbutyl benflumetol, Desbutylhalofantrine hydrochloride, Desferri-danoxamine, Desferri-nordanoxamine, Desferri-salmycin A, Desferri-salmycin B, Desferri-salmycin C, Desferri-salmycin D, Desglugastrin tromethamine, Desisobutyrylciclesonide, Deslorelin, Desmethyleleutherobin, Desmin-370, Desmopressin acetate, Desoxyepothilone B, Desoxyepothilone F, Desoxylaulimalide, Desvenlafaxine succinate, Dexamethasone, Dexamethasone beloxil, Dexamethasone cipecilate, Dexamethasone Palmitate, Dexamethasone sodium phosphate, Dexanabinol, Dexelvucitabine, Dextrorphan, Dexylosylbenanomycin A, D-Fluviabactin, DHA-paclitaxel, Diadenosine tetraphosphate, Diazaphilonic acid, Diazepinomicin, Dicoumarol, Dictyostatin 1, Didemnin X, Didemnin Y, Dideoxyinosine, Dieckol, Diepoxin-sigma, Diflomotecan, Diflunisal, Digalactosyldiacylglycerol, Digoxin, Diheteropeptin, Dihydrexidine, Dihydroavenanthramide D, Dihydrocostatolide, Dihydroeponemycin, Dihydrogranaticin B, Dihydroheptaprenol, Dihydrohonokiol B, Dihydroisosteviol, Dihydroraloxifene, Dilevalol, Dilevalol hydrochloride, Dilmapimod, Dimelamol, Dimethandrolone, Dimethylcurcumin, di-mPEG5-Atazanavir, Dinaphine, Dinapsoline, Dinoxyline, Dioncoquinone A, Dioncoquinone B, Dioxolane thymine nucleoside, Dipivefrine hydrochloride, Dipotassium gossypolate, Dipyridamole, Dipyridamole beta-cyclodextrin complex, Diquafosol tetrasodium, Dirithromycin, Discodermide, Discodermide acetate, Disermolide, Disodium cromproxate, Disodium lettusate, Disorazol E1, Dobutamine hydrochloride, Dobutamine Phosphate, Docetaxel, Docosanol, Docosyl cidofovir, Dofequidar fumarate, Dolastatin 13, Dopexamine, Dopexamine hydrochloride, Doqualast, Doramectin, Doranidazole, Doretinel, Doripenem, Dorrigocin A, Dorrigocin B, Dosmalfate, Dovitinib Lactate, Doxefazepam, Doxercalciferol, Doxifluridine, Doxorubicin Hydrochloride, Doxorubicin, Morpholinyl, DoxoTam 12, Doxycycline hyclate, Dridocamide, Dronabinol, Droxidopa, Droxinavir, DTPA-adenosylcobalamin, Duocarmycin B1, Duocarmycin B2, Duocarmycin C1, Duocarmycin C2, Duramycin, Dutomycin, Dynemicin A, Dynemicin C, Ecdysterone, Ecenofloxacin hydrochloride, Ecomustine, Econazole Sulfosalicylate, Ecopipam, Ecraprost, Ecteinascidin 1560, Ecteinascidin 722, Ecteinascidin 729, Ecteinascidin 736, Ecteinascidin 745, Ecteinascidin 757, Ecteinascidin 770, Ecteinascidin 875, Edotecarin, Edotreotide yttrium, Efepristin, Eflucimibe, Eflumast, Eicosyl cidofovir, Elacytarabine, Elansolid C1, Eldacimibe, Eldecalcitol, Eleutherobin, Eleutheroside B, Eliprodil, Elisapterosin B, Ellagic acid-4-gallate, Elliptinium acetate, Elocalcitol, Elomotecan hydrochloride, Elsibucol, Eltanolone, Eltrombopag olamine, Elvitegravir, Elvucitabine, Emakalim, Embelin, Emestrin C, Emodin, Emtricitabine, Enalkiren, Enazadrem, Enfumafungin, Englerin A, Enigmol, Enkastin (D), Enkastin AD, Enkastin AE, Enkastin ID, Enkastin IE, Enkastin VD, Enkastin VE, Enocitabine, Enofelast, Enoloxone, Enoxacin, Enprostil, Enrasentan, Enrofloxacin, Entacapone, Entecavir, ent-Estriol, Eperezolid, Eperezolid N-oxide, Epervudine, Epicochlioquinone A, Epidoxoform, Epigallocatechin-3-gallate, Epirubicin hydrochloride, Epispongiadiol, Eplivanserin, Eplivanserin fumarate, Eplivanserin mesilate, Epocarbazolin A, Epocarbazolin B, Epofolate, Eponemycin, Epoprostenol sodium, Epothilone A, Epothilone A N-oxide, Epothilone B N-oxide, Epothilone E, Epoxomicin, Epoxyvibsanin B, Eprotirome, Eptaloprost, Eptastatin sodium, Eptastigmine Tartrate, Eptazocine hydrobromide, Erabulenol A, Erabulenol B, Erectumin A, Eremomycin, Eremophyllene A, Eribulin mesilate, Eriocalyxin B, Eritoran tetrasodium, Ersentilide, Ersentilide hydrochloride, Ertapenem sodium, Eryloside A, Eryloside F, Erythritol, Erythrodiol, Erythromycin, Erythromycin Acistrate, Erythromycin salnacedin, Erythromycin stinoprate, Esafloxacin Hydrochloride, Esculeogenin A, Esculeoside A, Esmolol hydrochloride, Espatropate hydrate, Esperatrucin, Estetrol, Estradiol, Estradiol acetate, Estren, Estriol, Etalocib sodium, Etamsylate, Ethanolamine, Ethinylestradiol, Ethyl gallate, Ethylthio-DADMe-immucillin-A, Ethynylcytidine, Etiprednol dicloacetate, Etoposide, Etoposide phosphate disodium salt, Eugenodilol, Eugenosedin A, Euphodendroidin D, Eurotinone, Euxanthone, Evernimicin, Everolimus, Exatecan mesilate, Exifone, Ezetimibe, Ezetimibe glucuronide, Fadolmidine hydrochloride, Faeriefungin A, Faeriefungin B, Fandofloxacin hydrochloride, Faropenem medoxomil, Faropenem sodium, Fasobegron hydrochloride, Fattiviracin A1, Favipiravir, Febradinol, Febuprol, Feglymycin, Fenoldopam mesilate, Fenoterol hydrobromide, Ferpifosate sodium, Ferulinolol, Fesoterodine fumarate, Fexofenadine hydrochloride, Fidaxomicin, Fidexaban, Filibuvir, Fimbrigal P, Finafloxacin hydrochloride, Fingolimod hydrochloride, Finrozole, Fleroxacin, Flomoxef Sodium, Flopristin, Floxuridine, Fludarabine phosphate, Fludelone, Fludeoxyglucose (18F), Flunisolide, Flunoprost, Fluocinonide, Fluoroindolocarbazole A, Fluoroindolocarbazole B, Fluoroindolocarbazole C, Fluoroneplanocin A, Fluostatin A, Fluostatin B, Flupentixol hydrochloride, Fluphenazine hydrochloride, Flurithromycin, Fluticasone furoate, Fluticasone propionate, Fluvastatin sodium, Fluvirucin B2, Foetidine 1, Foetidine 2, Folinic acid, Folipastatin, Fondaparinux sodium, Formamicin, Formestane, Formobactin, Formosyn A, Formoterol fumarate, Forodesine hydrochloride, Fosopamine, Fosteabine sodium hydrate, Frederine, Fucoxanthin, Fudosteine, Fuladectin component A3, Fuladectin component A4, Fulvestrant, Fumagalone, Furaquinocin A, Furaquinocin B, Fusacandin A, Fusacandin B, Fuscoside B, Fusidate silver, Fusidienol, Gaboxadol, Gabusectin, Gabusectin methyl ester, Gadobutrol, Gadocoletic acid trisodium salt, Gadomelitol, Gadoterate meglumine, Gadoteridol, Galactomycin I, Galactomycin II, Galactosyllactose, Galamustine hydrochloride, Galantamine hydrobromide, Galarubicin hydrochloride, Galocitabine, Gambogic acid, gamma-Mangostin, gamma-Tocotrienol, Ganciclovir, Ganciclovir elaidic acid, Ganciclovir monophosphate, Ganciclovir Sodium, Ganefromycin Alpha, Ganefromycin Beta, Ganglioside GM1, Ganirelix, Ganirelix acetate, Ganoderic acid X, Garenoxacin mesilate, Garomefrine hydrochloride, Garvalone C, Garveatin E, Garveatin F, Gatifloxacin, Gemcitabine, Gemcitabine elaidate, Gemeprost, Gemifloxacin mesilate, Genipin, Genistein-7-phosphate, Gigantol, Gilatide, Gilvusmycin, Gimestat, Girodazole, Glaucocalyxin A, Glemanserin, Glenvastatin, Glidobactin PF-1, Glucarolactam potassium, Glucolanomycin, Glucolipsin A, Glucolipsin B, Glucopiericidinol A1, Glucopiericidinol A2, Glucosamine sulfate, Gludopa, Glufosfamide, Glycopin, Glycothiohexide alpha, Glycyrrhizinic acid, Gomphostenin, Goodyeroside A, Goodyeroside B, Goralatide, Goserelin, Granaticin B, Grepafloxacin hydrochloride, Griseusin C, Halistatin 1, Halistatin 2, Halistatin 3, Halobetasol propionate, Halofantrine hydrochloride, Halofuginone hydrobromide, Halometasone, Halopredone Acetate, Halovir A, Halovir B, Halovir C, Halovir D, Halovir E, Halxazone, Haperforine Bl, Hatomamicin, Hatomarubigin A, Hatomarubigin B, Hatomarubigin C, Hatomarubigin D, Hattalin, Hayumicin A, Hayumicin B, Hayumicin C1, Hayumicin C2, Hayumicin D, Hederacolchiside E, Heliquinomycin, Helvecardin A, Helvecardin B, Heptaminol AMP Amidate, Hericenal A, Hericenal B, Hericenal C, Hexadecyl cidofovir, Hexadecyloxypropyl-cidofovir, Hexafluorocalcitriol, Hidrosmin, Himastatin, Histrelin, Histrelin acetate, Hongoquercin A, Hongoquercin B, Honokiol diepoxide, Human angiotensin II, Hyaluronate sodium, Hydrocortisone Aceponate, Hydromorphone methiodide, Hydrostatin A, Hydroxyakalone, Hydroxychloroquine sulfate, Hydroxymycotrienin A, Hydroxymycotrienin B, Hydroxyphoslactomycin B, Hydroxyzine hydrochloride, Hymenistatin 1, Hypeptin, Hypericin, Hyperoside, Hypocholamide, Hypocholaride, Ibutilide fumarate, Icariin, Icatibant acetate, Idarubicin hydrochloride, Idebenone, Idremcinal, Idronoxil, Ifenprodil, Ilatreotide, Iliparcil, Ilonidap, Iloprost, Imidazoacridinone, Imipenem, Immunosine, Implitapide, Incyclinide, Indacaterol, Indanaprost (S), Indanocine, Indinavir sulfate, Indomethacin-Simvastatin, Indynaprost, Ingenol mebutate, Inophyllum B, Inophyllum P, Inosiplex, Integracide A, Integracide B, Integracin A, Integracin B, Integracin C, Integramycin, Integrastatin A, Integrastatin B, Intoplicine, Iobitridol, Iodixanol, Iodochlorhydroxyquin, Iododiflunisal, Iodorubidazone (p), Iofratol, Iohexyl, Iolopride (123I), Iomeprol, Iopamidol, Iopentol, Iopromide, Iolotriside, Iotrol, Ioversol, Ioxilan, Ioxipride, Ipratropium bromide, Iralukast, Iralukast sodium, Irciniastatin A, Irciniastatin B, Irinotecan hydrochloride, Irofulven, Isalmadol, Isepamicin sulfate, Isobavachalcone, Isodoxorubicin, Isoeleutherobin A, Isofagomine tartrate, Isofloxythepin, Isohomohalichondrin B, Iso-iantheran A, Isoliquiritigenin, Isomolpan Hydrochloride, Isoquine, Isosorbide 5-mononitrate, Isospongiadiol, Isovanihuperzine A, Isoxazoledehydelone, Isoxazolefludelone, Itavastatin calcium, Itrocinonide, Ixabepilone, Jadomycin B, Janthinomycin A, Janthinomycin B, Janthinomycin C, Jasplakinolide, Jorumycin, Kadsuphilin C, Kahalalide F, Kaitocephalin, Kampanol A, Kampanol B, Kanamycin, Kanglemycin A, Kansuinin B, kappa-Conotoxin P VIIA, Kapurimycin A1, Kapurimycin A3, Karalicin, Karnamicin B1, Katanosin A, Katanosin B, Kehokorin D, Kehokorin E, Khafrefungin, Kifunensine, Kigamicin A, Kigamicin B, Kigamicin C, Kigamicin D, Kigamicin E, Kigamicinone, Kijimicin, Kinsenoside, Kistamicin A, Klainetin A, Klainetin B, Kobifuranone B, Kobiin, Kodaistatin A, Kodaistatin B, Kodaistatin C, Kodaistatin D, Korupensamine A, Korupensamine B, Korupensamine C, Korupensamine D, Kosinostatin, Kuehneromycin A, Kurasoin B, Kynostatin-227, Kynostatin-272, Labedipinedilol A, Labedipinedilol B, Labetalol hydrochloride, Labradimil, Laccaridione A, Lactonamycin, Lactosylphenyl trolox, Ladirubicin, Lagatide, Laherradurin, Lamellarin alpha 20-sulfate sodium salt, Lamifiban, Lamivudine, Landiolol, Lanreotide acetate, Lanthiopeptin, Larotaxel dihydrate, Lasinavir, Lasofoxifene, Lasofoxifene tartrate, Lasonolide A, Latamoxef sodium, Latanoprost, Latrunculin S, Lavanduquinocin, L-Chicoric acid, L-Dopamide, Lecirelin, Ledazerol, Leinamycin, Lemuteporphin, Lenapenem hydrochloride, Lenapenem hydrochloride hydrate, Leptofuranin A, Leptofuranin B, Lersivirine, Lestaurtinib, Leuprolide acetate, Leurubicin, Leustroducsin A, Leustroducsin B, Leustroducsin C, Leustroducsin H, Levalbuterol hydrochloride, Levobetaxolol hydrochloride, Levobunolol hydrochloride, Levodopa, Levodopa 3-O-glucoside, Levodopa 4-O-glucoside, Levodropropizine, Levofloxacin, Levonadifloxacin arginine salt, Levonebivolol, Levorphanol tartrate, Lexacalcitol, L-Fluviabactin, L-Histidinol, Liblomycin, Licoricesaponin C2, Lificiguat, Limaprost alfadex, Linaprazan, Linopristin, Lipiarmycin B3, Lipiarmycin B4, Liquiritin apioside, Lisofylline, Lithospermic acid B magnesium salt, Lobatamide C, Lobatamide F, Lobophorin A, Lobophorin B, Lobucavir, Lodenafil, Lodenosine, Loloatin B, Lomefloxacin hydrochloride, Lometrexol, Longestin, Lopinavir, Lorazepam, Lormetazepam, Lornoxicam, Losartan, Losartan potassium, Losigamone, Loteprednol etabonate, Lovastatin, Loxoribine, L-threitol ceramide, L-threo-C6-pyridinium-ceramide-bromide, Lubeluzole, Lumefantrine, Luminacin D, Lupulone, Lurtotecan, Luteolin, Lu-Tex bis(gluconate), Lysobactin, Mabuterol hydrochloride, Macquarimycin B, Macrocarpin A, Macrocarpin B, Macrolactine M, Madecassic acid, Madecassoside, Makaluvamine D, Makaluvamine E, Malonoben, Maltolyl p-coumarate, Manitimus, Mannopeptimycin alpha, Mannopeptimycin beta, Mannopeptimycin delta, Mannopeptimycin epsilon, Mannopeptimycin gamma, Manoalide, Manumycin A, Manumycin B, Manumycin C, Manumycin E, Manumycin F, Manumycin G, Manzamine F, Marbofloxacin, Maribavir, Marimastat, Marinopyrrole A, Marmelin, Maslinic acid, Masoprocol, Mastprom, Matteuorienate A, Matteuorienate B, Matteuorienate C, Mazokalim, Medicarpin, Mefloquine hydrochloride, Megovalicin A, Megovalicin B, Megovalicin C, Megovalicin D, Megovalicin G, Megovalicin H, Melevodopa hydrochloride, Mellein, Meloxicam, Meluadrine, Meluadrine tartrate, Memno-peptide A, Mepindolol sulfate, Mepindolol transdermal patch, Meptazinol hydrochloride, Meropenem, Mesalazine, Metaraminol, Metesind glucuronate, Methanobactin, Methoxatone, Methscopolamine bromide, Methyl bestatin, Methyl gallate, Methyldopa, Methylnaltrexone bromide, Methylprednisolone, Methylprednisolone aceponate, Methylprednisolone suleptanate, Methylthio-DADMe-immucillin-A, Methysergide maleate, Metildigoxin, Metipranolol, Metirosine, Metoprolol Fumarate, Metoprolol succinate, Metoprolol tartrate, Metrifonate, Metronidazole, Micacocidin A, Micacocidin B, Micafungin sodium, Michellamine B, Michigazone, Microbisporicin A2, Microcolin A, Micronomicin sulfate, Midecamycin acetate, Mideplanin, Miglitol, Miglustat, Milataxel, Milbemycin alpha-9, Milrinone Lactate, Mimopezil, Minerval, Minocycline hydrochloride, Miporamicin, Mipragoside, Miproxifene, Mirabegron, Mirodenafil hydrochloride, Misakinolide, Misoprostol, Mitemcinal fumarate, Mitoxantrone hydrochloride, Mivazerol, Mizoribine, Modecamide, Modithromycin, Moenomycin A chloride bismuth salt, Mollugin, Mometasone furoate, Momordin Ic, Monamidocin, Monlicin A, Monogalactosyldiacylglycerol, Monohydroxyethylrutoside, Monophosphoryl lipid A, Montelukast sodium, Morphine Glucuronide, Morphine hydrochloride, Morphine sulfate, Motexafin gadolinium, Motexafin lutetium, Moxidectin, Moxifetin hydrogen maleate, Moxifloxacin hydrochloride, Mozenavir mesilate, Multiforisin A, Mumbaistatin, Mupirocin, Muraminomicin A, Muraminomicin B, Muraminomicin C, Muraminomicin D, Muraminomicin E1, Muraminomicin E2, Muraminomicin F, Muraminomicin G, Muraminomicin H, Muraminomicin I, Muraminomicin Z1, Muraminomicin Z2, Muraminomicin Z3, Muraminomicin Z4, Muramyl dipeptide C, Mureidomycin A, Mureidomycin B, Mureidomycin C, Mureidomycin D, Mureidomycin E, Mureidomycin F, Mureidomycins, Mycalamide A, Mycestericin E, Mycolactone A, Mycolactone B, Mycophenolate Mofetil, Mycophenolic acid sodium salt, Myrciacitrin I, Myrciacitrin II, Myrciaphenone B, Myriceric acid A, Mytolbilin, Mytolbilin acid, Mytolbilin acid methyl ester, Mytolbilinol, N4-Hexadecyl-dC-AZT, N-9-Oxadecyl-6-methyl-DGJ, Naamidine A, Nabilone, N-Acetylcolchinol, N-Acetylsperamycin A1, N-Acetylsperamycin A1B, N-Acetylsperamycin A2, Nadifloxacin, Nadolol, Nafarelin acetate, Naftopidil, Nafuredin, Nafuredin-gamma, Nagstatin, Nalbuphine hydrochloride, Nalfurafine hydrochloride, N-Allylsecoboldine, Nalmefene, Naloxone hydrochloride, Naltrexone hydrochloride, Naltrindole, Namitecan, Napsamycin A, Napsamycin B, Napsamycin C, Napsamycin D, Nardeterol, Naroparcil, Navuridine, N-Cyclopentyl-tazopsine, Nebicapone, Nebivolol, Nectrisine, Neldazosin, Nelfinavir mesilate, Nelivaptan, Nelzarabine, Nemifitide ditriflutate, Nemonoxacin, Nemorubicin, Neocimicigenoside A, Neocimicigenoside B, Neolaulimalide, Neomycin B-arginine conjugate, Neomycinacridine, Nepadutant, Neparensinol A, Neparensinol B, Neparensinol C, Nerfilin I, Neristatin 1, Nesbuvir, Netilmicin sulfate, Netivudine, Neu5Ac2en, Ngercheumicin A, Ngercheumicin B, N-hexacosanol, Nicanartine, Nifekalant hydrochloride, Nileprost beta-cyclodextrin clathrate, Nipradolol, Nitecapone, Nitropravastatin, N-Nonyl-deoxygalactojirimycin, Nocardione A, Nocathiacin I, Nocathiacin II, Nocathiacin III, Nocathiacin IV, N-Octyl-beta-valienamine, NO-hydrocortisone, Noladin ether, NO-Mesalamine, Nooglutil, Noraristeromycin, Nordamunacantal, Norfloxacin, Norfloxacin succinil, Nortopixantrone hydrochloride, Nostocyclopeptide M1, Nothramicin, NO-Ursodeoxycholic acid, N-Retinoyl-D-glucosamine, N-tert butyl isoquine, Nubiotic 2, Nutlin-2, Obelmycin H, Oberadilol, Oberadilol Monoethyl Maleate, Obeticholic acid, Ochromycinone, Ocimumoside A, Ocimumoside B, Octacosamicin A, Octacosamicin B, Octreotide Acetate, Octyl gallate, Odapipam acetate, O-Demethylchlorothricin, O-Demethylmurrayafoline A, Odiparcil, Oenothein B, Ofloxacin, Okicenone, Olamufloxacin, Olamufloxacin mesilate, Olanzapine pamoate, Olcegepant, Oleanolic acid, Oleoyl-L-Valinol amide, Olsalazine sodium, Omaciclovir, Ombrabulin, Ombrabulin hydrochloride, Onjixanthone I, Onjixanthone II, Onnamide A, Oolonghomobisflavan A, Oolonghomobisflavan C, OPC-17083, Opiorphin, Opipramol hydrochloride, Orbifloxacin, Orciprenaline sulphate, Orienticin A, Orienticin B, Orienticin C, Orienticin D, Oritavancin, Orniplabin, Ornoprostil, Ortataxel, Orthosomycin A, Orthosomycin B, Orthosomycin C, Orthosomycin D, Orthosomycin E, Orthosomycin F, Orthosomycin G, Orthosomycin H, Ospemifene, Osutidine, Oxaspirol A, Oxaspirol B, Oxazepam, Oxazofurin, Oxeclosporin, Oximidine III, Oxiracetam, Oxitropium bromide, Oxolide, Oxprenolol hydrochloride, Oxymetazoline hydrochloride, Oxymethacyl, Oxymorphazole dihydrochloride, Oxymorphone hydrochloride, Oxynor, Oxyphenarsine, Ozarelix, Ozenoxacin, Pachastrissamine, Pachymedusa dacnicolor Tryptophyllin-1, Paciforgine, Paclitaxel, Paclitaxel ceribate, Paecilaminol, Paeciloquinine A, Paeciloquinine D, Paeciloquinone B, Paeciloquinone D, Pafenolol, Palau'amine, Paldimycin B, Palinavir, Palmidrol, Pamapimod, Pamaqueside, Pancratistatin disodium phosphate, Pancratistatin-3,4-cyclic phosphate sodium salt, Panipenem, Pannorin, Pantethine, Papuamide A, Papuamide B, Papuamide C, Papuamide D, Paquinimod, Paracetamol, Parasin I, Paricalcitol, Parodilol Hemifumarate, Paromomycin, Parvisporin B, Patellazole A, Patellazole B, Patellazole C, Patupilone, Paulomycin, Paulomycin A2, Paulomycin B, Paulomycin C, Paulomycin D, Paulomycin E, Paulomycin F, Pazufloxacin, Pazufloxacin mesilate, Pefloxacin, PEG40000-Paclitaxel, PEG5000-Paclitaxel, PEG-conjugated camptothecin, PEG-vancomycin, Pelitrexol, Peloruside A, Penasterol, Penbutolol sulfate, Penciclovir, Penicillide, Pentazocine hydrochloride, Pentostatin, Peplomycin, Pepticinnamin E, Peramivir, Percyquinnin, Periciazine, Perillyl alcohol, Perphenazine, Persin, Petrosaspongiolide M, PG-camptothecin, Phaffiaol, Phakellistatin 7, Phakellistatin 8, Phakellistatin 9, Phaseolinone, Phenochalasin A, Phenprocoumon, Phentolamine mesilate, Philinopside A, Phlorofucofuroeckol, Phomactin A, Phomactin B, Phomoidride A, Phomopsichalasin, Phorboxazole A, Phorboxazole B, Phospholine, Phthalascidin, Physostigmine salicylate, Piceatannol, Picumeterol fumarate, Pidobenzone, Pimecrolimus, Pimilprost, Pindolol, Pinitol, Pinocembrin, Pipendoxifene, Pipotiazine, Pirarubicin, Pirbuterol hydrochloride, Pirfenoxone, Pirodomast, Pironetin, Piroxicam, Pittsburgh Compound B, Pladienolide A, Pladienolide B, Pladienolide C, Pladienolide D, Pladienolide E, Plantagoside, Platencin, Platensimycin, Plaunotol, Plevitrexed, Plitidepsin, Pluraflavin A, Pluraflavin B, Pluraflavin E, Plusbacin A1, Plusbacin A2, Plusbacin A3, Plusbacin A4, Plusbacin B1, Plusbacin B2, Plusbacin B3, Plusbacin B4, Pneumocandin A0, Pneumocandin B0, Pneumocandin B0 2-phosphate, Pneumocandin D0, Podophyllotoxin, Polyestradiol phosphate, Polyketomycin, Polymer bound human leukocyte elastase inhibitor, Ponalrestat, Popolohuanone E, Posaconazole, Posizolid, Potassium embelate, Pradimicin A, Pradimicin B, Pradimicin D, Pradimicin E, Pradimicin FA-1, Pradimicin FA-2, Pradimicin FL, Pradimicin FS ((+)-enantiomer), Pradimicin L, Pradimicin Q, Pradimicin S, Pradimicin T1, Pradimicin T2, Pradofloxacin, Prasterone, Prednicarbate, Prednisolone, Prednisolone acetate, Prednisolone farnesylate, Prednisone, Prefolic A, Premafloxacin, Premafloxacin hydrochloride, Preussin, Prinaberel, Prisotinol, Pristinamycin IA, Pristinamycin IIA, Proamipide, Probestin, Probucol, Procaterol Hydrochloride Hemihydrate, Prolylmeridamycin, Propafenone hydrochloride, Propeptin T, Propofol, Propranolol hydrochloride, Propyl gallate, Prostanit, Prostatin, Prostratin, Protocatechuic acid, Protocatechuic aldehyde, Proxodolol, Prulifloxacin, Prulifloxacin Hydrochloride, Prulifloxacin Mesylate, Pseudoephedrine hydrochloride, Pseudohypericin, Pseudomycin A', Pseudomycin B', Purpuromycin, Purvalanol A, Pycnanthuquinone A, Pycnanthuquinone B, Pyloricidin B, Pyridavone, Pyrindamycin A, Pyrindamycin B, Pyripyropene A, Pyripyropene B, Pyripyropene C, Pyripyropene D, Pyrrolosporin A, Quartromicin A1, Quartromicin A2, Quartromicin A3, Quartromicin D1, Quartromicin D2, Quartromicin D3, Quercetin-3-O-methyl ether, Quetiapine fumarate, Quinagolide hydrochloride, Quinidine, Quinobene, Quinoxapeptin C, Quinupristin Mesilate, rac-Apogossypolone, Rac-Tolterodine, Rafabegron, Raloxifene hydrochloride, Raltitrexed, Raluridine, Rameswaralide, Ramoplanin Ramoplanin A'2, Ramoplanin A'3, Ramorelix, Ranimustine, Ranolazine, Rapamycin, Ravidomycin N-oxide, Rawsonol, Razupenem, Rebamipide bismuth citrate tetramethyledamine, Reblastin, Regadenoson, Remikiren mesilate, Remiprostol, Remogliflozin etabonate, Repandiol, Reproterol hydrochloride, Resobene, Resorthiomycin, Retapamulin, Retaspimycin hydrochloride, Revatropate, Reveromycin A, Rhodiocyanoside A, Rhodiocyanoside B, Rhododaurichromanic acid A, Rhodostreptomycin A, Rhodostreptomycin B, Ribavirin, Ribavirin eicosenate cis, Ribavirin eicosenate trans, Ribavirin elaidate, Ribavirin oleate, Rifabutin, Rifalazil, Rifamexil, Rifampicin, Rifapentine, Rifaximin, Rilmakalim hemihydrate, Rimexolone, Rimoterol hydrobromide, Riodoxol, Ritipenem acoxil, Ritonavir, Rivastigmine tartrate, Rivenprost, Rocagloic acid, Rocuronium bromide, Rofleponide, Rofleponide palmitate, Rohitukine, Rokitamycin, Rolliniastatin 1, Romurtide, Roquinimex, Rosaprostol sodium, Roscovitine, Roselipin 1A, Roselipin 1B, Roselipin 2A, Roselipin 2B, Rostafuroxine, Rosuvastatin calcium, Rosuvastatin sodium, Rotigaptide, Rotigotine, Roxatidine bismuth citrate, Roxindole Mesilate, Roxithromycin, Rubiginone A1, Rubiginone A2, Rubiginone B1, Rubiginone C1, Rubitecan, Ruboxyl, Rufigallol, Rufloxacin Gluconate, Rufloxacin hydrochloride, Rumycin 1, Rumycin 2, Russuphelin A, Sabarubicin hydrochloride, Safingol, Saintopin, Saintopin E, Saishin N, Sakyomicin A, Sakyomicin E, Salazopyridazin, Salbostatin, Salbutamol nitrate, Salbutamol sulfate, Salcaprozic acid sodium salt, Salicylazobenzoic acid, Salicylihalamide A, Salicylihalamide B, Salinamide A, Salinosporamide A, Saliphenylhalamide, Salmaterol, Salmeterol xinafoate, Saloxin, Salvianolic acid 1, Samaderine X, Sampatrilat, Sanfetrinem, Sanfetrinem cilexetil, Sanfetrinem sodium, Sanglifehrin A, Sanglifehrin B, Sanglifehrin C, Sanglifehrin D, Sapacitabine, Saptomycin D, Sapurimycin, Saquinavir, Saquinavir mesilate, Sarcophytol A, Sarcophytol B, Saricandin, Saussureamine D, Saussureamine E, Sazetidine-A, Scopinast fumarate, Scopolamine, Scyphostatin, Secalciferol, Secobatzelline A, Secobatzelline B, Secoisolariciresinol diglucoside, Securioside A, Securioside B, Seglitide, Selamectin, Selank, Selodenoson, Semagacestat, Semduramicin, Semorphone hydrochloride, Seocalcitol, Seprilose, Sergliflozin etabonate, Serofendic acid, Sessiloside, Setamycin, Setazindol, Shepherdin, Shishijimicin A, Shishijimicin B, Shishijimicin C, Sialosylcholesterol-Alpha Sodium Salt, Sibanomicin, Sibenadet hydrochloride, Sibiskoside, Sildenafil citrate, Silodosin, Siltenzepine, Silychristin, Simotaxel, Simvastatin, Sinomenine, Sitafloxacin hydrate, Sitostanol ascorbyl phosphate, Sivifene, Siwenmycin, Sizofuran, Smilagenin, Socorromycin, Sodium cromoglycate, Sodium oxybate, Solabegron hydrochloride, Solpecainol hydrochloride, Sonedenoson, Sootepenseone, Soraprazan, Sorbicillactone A, Sorivudine, so-Simvastatin-6-one, Sotalol hydrochloride, Sparfloxacin, Sparoxomycin A1, Sparoxomycin A2, Sperabillin A, Sperabillin B, Sperabillin C, Sperabillin D, Sphingofungin F, Spinorphin, Spinosulfate A, Spinosulfate B, Spirocardin A, Spirocardin B, Spiroximicin, Spiruchostatin A, Spiruchostatin B, Spisulosine, Spongiadiol, Spongistatin 1, Spongistatin 3, Spongistatin 4, Spongistatin 5, Spongistatin 6, Spongistatin 7, Spongistatin 8, Spongistatin 9, Sporeamicin A, Sporeamicin B, Squalamine lactate, Squalestatin I, Stachybocin A, Stachybocin B, Stachybocin C, Stachybotrin C, Stachybotrydial, Staplabin, Starrhizin, Stavudine, Stelleramacrin A, Stelleramacrin B, Sterenin A, Sterenin C, Sterenin D, Streptomycin, Streptopyrrole, Styloguanidine, Suberosenol A, Succinobucol, Sugammadex sodium, Sulfasalazine, Sulfinosine, Sulfircin C, Sulopenem, Sulopenem etzadroxil, Sulphazocine, Sulphoquinovosyldiacylglycerol, Sulprostone, Sulukast, Sunflower trypsin inhibitor-1, Suplatast tosilate, Suronacrine maleate, Susalimod, Swiftiapregnene, Symbioimine, Synadenol, Synguanol, Syriacusin A, Syriacusin B, Syriacusin C, Syzygiol, Tacalcitol, Tacapenem pivoxil, Taccalonolide E, Tacrolimus, Tafluprost, Tageflar, Taiwanhomoflavone A, Takanawaene A, Takanawaene B, Takanawaene C, Talibegron, Talibegron hydrochloride, Talnetant, Tamandarin A, Tamandarin B, Tamolarizine Hydrochloride, Tanespimycin, TAP-doxorubicin, Tapentadol hydrochloride, Taramanon A, Tasquinimod, Taurohyodeoxycholic acid, Tautomycin, Taxuyunnanine, Tazofelone, Tazopsine, Tebipenem, Tebipenem cilexetil, Tebipenem pivoxil, Tebufelone, Tecadenoson, Technetium Tc 99m depreotide, Teicoplanin-A2-1, Teicoplanin-A2-2, Teicoplanin-A2-3, Teicoplanin-A2-5, Telavancin hydrochloride, Telbivudine, Telinavir, Telithromycin, Temafloxacin hydrochloride, Temazepam, Temoporfin, Tempol, Temsirolimus, Temurtide, Tenidap, Teniposide, Tenoxicam, Tenuifoliside A, Tenuifoliside B, Tenuifoliside C, Tenuifoliside D, Terbutaline sulfate, Terestigmine tartrate, Terfenadine, Teriflunomide, Terlakiren, Ternatin, Terprenin, Terreulactone A, Terreulactone B, Terreulactone C, Terreulactone D, Tertatolol hydrochloride, Tesetaxel, Testosterone glucoside, Tetracosyl cidofovir, Tetracycline hydrochloride, Tetrafibricin, Tetragalloylquinic acid, Tetrahydrocortisol, Tetra hydrocurcumin, Tetrahydroechinocandin B, Tetrahydroswertianolin, Tetrahydroxyquinone, Tetromycin A, Tetromycin B, Tetronothiodin, Texenomycin A, Tezacita bine, Tezosentan, Tezosentan disodium, Thenorphine, Theopederin D, Theoperidin E, Theophylline rutoside, Thermozymocidin, Thiamet-G, Thiamphenicol, Thiarubrine E, Thiarubrine F, Thiarubrine G, Thiarubrine H, Thiazinotrienomycin B, Thiazinotrienomycin F, Thiazinotrienomycin G, Thiazohalostatin, Thielavin G, Thielocin B3, Thiofedrine, Thiomarinol, Thiomarinol B, Thiomarinol C, Thiomarinol D, Thiomarinol E, Thiomarinol F, Thioviridamide, Thioxamycin, Thrazarine, Thymallene, Thymectacin, Thymopentin, Tidembersat, Tienoxolol hydrochloride, Tigecycline, Tilisolol hydrochloride, Timolol hemihydrate, Timolol maleate, Tipelukast, Tipranavir, Tiqueside, Tisocalcitate, Tixocortol buryrate propionate, Toborinone, Tobramycin, Tocotrienol, Tokaramide A, Tolcapone, Toloxatone, Tolterodine Tartrate, Tolvaptan, Tolytoxin, Tomatine, Tomeglovir, Tonabersat, Topixantrone hydrochloride, Topotecan Acetate, Topotecane Hydrochloride, Topovale, Topsentine B1, Torcitabine, Torezolid, Tosedostat, Tosufloxacin, Tosufloxacin Tosilate, Trabectedin, Tradecamide, trans-Resveratrol, Trantinterol hydrochloride, Travoprost, Traxoprodil, Traxoprodil mesylate, Trecadrine, Trecetilide fumarate, Treprostinil diethanolamine, Treprostinil sodium, Triamcinolone acetonide, Triamcinolone hexacetonide, Trichodimerol, Trichomycin A, Trichostatin D, Triciferol, Triciribine, Triciribine phosphate, Trifluridine, Trilostane, Trimegestone, Trimidox, Trimoprostil, Triphendiol, Tripterin, Triptolide, Troglitazone, Trovafloxacin, Trovafloxacin hydrate, Trovafloxacin hydrochloride mesylate, Trovafloxacin mesilate, Troxacitabine, Tsukubamycin A, Tubastrine, Tubelactomicin A, Tuberactomycin B, Tuberactomycin D, Tuberactomycin E, Tubingensin B, Tubulysin A, Tubulysin B, Tubulysin C, Tucaresol, Tuftsin, Tulathromycin A, Tulathromycin B, Tulobuterol hydrochloride, Turbostatin 1, Turbostatin 2, Turbostatin 3, Turbostatin 4, Tyropeptin A10, Tyropeptin A6, Tyropeptin A9, Tyroservatide, Tyrphostin 47, Ubenimex, Ukrain, Ulifloxacin, Uncarinic acid A, Uncarinic acid B, Uncialamycin, Unoprostone, Unoprostone isopropyl ester, Ursodeoxycholic acid, Ustilipid A, Ustilipid B, Ustilipid C, Uvalol, Vadimezan, Valganciclovir hydrochloride, Valnemulin, Valonomycin A, Valopicitabine, Valrubicin, Vancomycin hydrochloride, Vancoresmycin, Vanidipinedilol, Vaminolol, Variapeptin, Vebufloxacin, Veinamitol, Velnacrine Maleate, Velusetrag, Venorphin, Vermisporin, Vernakalant hydrochloride, Verticillatine, Vexibinol, Vialinin B, Vicenistatin, Vinaxanthone, Vindesine, Vinfosiltine sulfate, Vinleucinol, Vinylamycin, Viquidacin, Viramidine Hydrochloride, Viranamycin-A, Viranamycin-B, Viscosin, Vitilevuamide, Voclosporin, Voglibose, Volinanserin, Volpristin, Voreloxin, W Peptide, Wiedendiol A, Wiedendiol B, Woodorien, Xamoterol Fumarate, Xanthoangelol E, Xanthofulvin, Xanthomegnin, Xenovulene A, Xipamide, Xylocydine, Yatakemycin, Yohimbine, Zabofloxacin hydrochloride, Zahavin B, Zalcitabine, Zampanolide, Zanamivir, Zankiren, Zaragozic acid D3, Zelandopam hydrochloride, Z-Eleutherobin, Zenarestat, Zidovudine, Zilascorb (2H), Zilpaterol, Zonampanel, Zorubicin hydrochloride, Zosuquidar trihydrochloride, Zotarolimus, Zoticasone propionate, Zuclopenthixol hydrochloride.

Suitable drugs with carboxyl groups may be be selected from the list containing (−)-Subersic acid, (+)-Deoxoartelinic acid, (+)-Hemipalmitoylcarnitinium, (+)-Indobufen, (+)-SCH-351448, (E)-p-Coumaroylquinic acid, (Z)-Indenaprost, [111In-DTPA-Pro1,Tyr4]bombesin, [90Y]-DOTAGA-substance P, [psi[CH2NH]Tpg4]Vancomycin aglycon, 111In-Pentetreotide, 11-Keto-Beta-Boswellic Acid, 15-Methoxypinusolidic acid, 1-Methyl-D-tryptophan, 3,5-Dicaffeoylquinic acid, 3-MATIDA, 3-O-Acetyloleanolic acid, 4-Aminosalicylic acid, 6alpha-Fluoroursodeoxycholic acid, 6-Carboxygenistein, 7-Chlorokynurenic acid, 8-Carboxy-iso-iantheran A, 99mTc-c(RGDfK*)2HYNIC, A-42867 pseudoaglycone, Aceclofenac, Acemetacin, Aceneuramic acid sodium salt, Acetyl-11-Keto-Beta-Boswellic Acid, Acetyl-Beta-Boswellic Acid, Acetylcysteine, Achimillic Acids, Acipimox, Acitazanolast, Acrivastine, Actarit, Adapalene, Adarotene, Ademetionine tosylate sulfate, Adxanthromycin A, Ajulemic acid, Alacepril, Aladapcin, Aleglitazar, Alitretinoin, Alminoprofen, Alogliptin benzoate, alpha-Linolenic acid, alpha-Lipoic acid, alpha-Methyltryptophan, Alprostadil, Altemicidin, Alutacenoic acid B, Alvimopan hydrate, Amiglumide, Amineptine, Aminocaproic acid, Aminolevulinic acid hydrochloride, Amlexanox, Amoxicillin trihydrate, Amphotericin B, Amsilarotene, Anakinra, Antiflammin-1, Antiflammin-2, Antiflammin-3, Apalcillin sodium, Aplaviroc hydrochloride, Argatroban monohydrate, Argimesna, Artelinate, Artepillin C, Artesunate, Arundifungin, Ascosteroside, Asiatic acid, Aspirin, Aspoxicillin, Assamicin I, Assamicin II, Ataluren, Atorvastatin, Atorvastatin calcium, Atrasentan, Azaromycin SC, Azelaic Acid, Azepinostatin, Azilsartan, Azoxybacilin, Aztreonam, Aztreonam L-lysine, Azumamide E, Baclofen, Bafilomycin C1, Baicalin, Balhimycin, Balofloxacin, Balofloxacin dihydrate, Balsalazide disodium, Bamirastine hydrate, Belactosin A, Belactosin C, Benanomicin A, Benanomicin B, Benastatin A, Benastatin B, Benazepril hydrochloride, Benthocyanin A, Bepotastine besilate, Beraprost sodium, Besifloxacin hydrochloride, Beta-Boswellic Acid, beta-Hydroxy beta-methylbutyrate, Betamipron, Beta-Sialosylcholesterol Sodium Salt, Bevirimat, Bexarotene, Bezafibrate, Biapenem, Bilastine, Bimosiamose, Bindarit, Binfloxacin, Biphenyl-indanone A, Boc-Belactosin A, Borrelidin, Brasilicardin A, Brasilinolide A, Bremelanotide, Brevifolin carboxylic acid, Bucillamine, Bumetanide, Bungeolic acid, Buprenorphine hemiadipate, Buprenorphine-Val-carbamate, Butibufen, Butoctamide hemisuccinate, Butyzamide, Cabin 1, Cadrofloxacin hydrochloride, Calbistrin A, Calbistrin B, Calbistrin C, Calbistrin D, Calcium-like peptide 1, Calcium-like peptide 2, Caloporoside B, Caloporoside C, Caloporoside D, Caloporoside E, Caloporoside F, Calpinactam, Calteridol calcium, Camprofen, Candesartan, Candoxatril, Candoxatrilat, Canfosfamide hydrochloride, Canrenoate potassium, Caprazamycin A, Caprazamycin B, Caprazamycin C, Caprazamycin E, Caprazamycin F, Captopril, Carbidopa, Carmoxirole hydrochloride, Carprofen, Cefaclor, Cefalexin monohydrate, Cefbuperazone sodium, Cefcanel, Cefdaloxime, Cefdinir, Cefetecol, Cefixime, Cefmatilen hydrochloride hydrate, Cefmenoxime hydrochloride, Cefminox sodium, Cefodizime, Cefonicid sodium, Cefoperazone sodium, Cefoselis sulfate, Cefotiam hydrochloride, Cefoxitin, Cefpimizole sodium, Cefpiramide sodium, Cefprozil, Cefprozil monohydrate, Ceftaroline fosamil acetate, Ceftazidime, Ceftibuten, Ceftobiprole, Cefuroxime, Ceranapril, Cerivastatin sodium, Ceruletide diethylamine, Cetefloxacin, Cetirizine hydrochloride, Chenodeoxycholic acid, Chinoin-169, Chlorambucil, Chloroorienticin A, Chloroorienticin B, Choline fenofibrate, Choline thioctate, Chrolactomycin, Cilastatin sodium, Cilazapril, Cilengitide, Cilomilast, Ciluprevir, Cinaciguat, Cinalukast, Cinatrin A, Cinatrin B, Cinatrin C1, Cinatrin C2, Cinatrin C3, Cinnatriacetin A, Cinnatriacetin B, Ciprofibrate, Ciprofloxacin hydrochloride, Circinamide, Cispentacin, Citrullimycine A, Clavaric acid, Clavulanate potassium, Clinofibrate, Clopidogrel Sulfate, Colletoic acid, Complestatin, Conagenin, Cosalane, Creatine phosphate, Cyclocreatine, Cycloplatam, Cyclothialidine, Cytomodulin, Cytosporic acid, Dabigatran, Daglutril, Dalargin, Dalbavancin, Danegaptide hydrochloride, Danofloxacin, Darinaparsin, Darusentan, Daurichromenic acid, Davunetide, Decahydromoenomycin A, Decaplanin, Decatromicin A, Decatromicin B, Deferasirox, Delafloxacin, Delapril Hydrochloride, Deltibant, Deoxylaidlomycin, Deoxynegamycin, Dersalazine, Desacetylvinblastinehydrazide/folate conjugate, Desferri-danoxamine, Desferri-nordanoxamine, Desglugastrin tromethamine, Desmin-370, Dexibuprofen, Dexibuprofen lysine, Dexketoprofen, Dexketoprofen choline, Dexketoprofen D,L-lysine, Dexketoprofen lysine, Dexketoprofen meglumine, Dexketoprofen trometamol, Dexloxiglumide, Dexpemedolac, dextro-Ciprofibrate, Dexylosylbenanomycin A, Diacerein, Diazaphilonic acid, Di-Calciphor, Difenoxin, Diflunisal, Dihydroavenanthramide D, Dihydrogranaticin B, Dihydroisosteviol, Dihydrolipoic acid, Disalazine, Disila-bexarotene, Disodium cromproxate, Disodium lettusate, Doqualast, Doripenem, Dormitroban, Dorrigocin A, Dorrigocin B, Droxidopa, DTPA-adenosylcobalamin, Duramycin, Dynemicin A, Ecabet Sodium, Ecenofloxacin hydrochloride, Econazole Sulfosalicylate, Edetic acid, Edotreotide yttrium, Efletirizine, Eflornithine hydrochloride, Eglumetad hydrate, Elansolid C1, Elarofiban, Elastatinal B, Elastatinal C, Elsibucol, Eltrombopag olamine, Elvitegravir, Emricasan, Enalapril maleate, Enalapril nitrate, Enalaprilat, Enfumafungin, Enkastin (D), Enkastin AD, Enkastin AE, Enkastin ID, Enkastin IE, Enkastin VD, Enkastin VE, Enoloxone, Enoxacin, Enrasentan, Enrofloxacin, Epalrestat, Epidioxymanadic acid A, Epidioxymanadic acid B, Epithalon, Epofolate, Epoprostenol sodium, Epostatin, Epristeride, Eprosartan mesilate, Eprotirome, Eptaloprost, Eptastatin sodium, Eptastigmine Tartrate, Eptifibatide, Erdosteine, Eremomycin, Ertapenem sodium, Ertiprotafib, Eryloside F, Esafloxacin Hydrochloride, Esonarimod, Etacrynic acid, Etalocib sodium, Etodolac, Etretin, Evatanepag, Evernimicin, Exisulind, Ezetimibe glucuronide, Fandofloxacin hydrochloride, Faranoxi, Farglitazar, Faropenem sodium, Fasobegron hydrochloride, Febuxostat, Feglymycin, Felbinac, Felbinac Lysine Salt, Fenbufen, Fexofenadine hydrochloride, Fidexaban, Finafloxacin hydrochloride, Fleroxacin, Flobufen, Flomoxef Sodium, Flunoprost, Flunoxaprofen, Flurbiprofen, Fluvastatin sodium, Folinic acid, Fondaparinux sodium, Fosfosal, Fradafiban, Frusemide, Fudosteine, Furprofen, G1 peptide, Gabadur, Gabapentin, Gabapentin enacarbil, Gabusectin, Gadobenic acid dimeglumine salt, Gadobutrol, Gadocoletic acid trisodium salt, Gadodenterate, Gadomelitol, Gadopentetate dimeglumine, Gadoterate meglumine, Gadoteridol, Gambogic acid, Gamendazole, Gamma-Linolenic Acid, Ganefromycin Alpha, Ganefromycin Beta, Ganglioside GM1, Ganoderic acid X, Garenoxacin mesilate, Gastrazole, Gatifloxacin, Gemfibrozil, Gemifloxacin mesilate, Gemopatrilat, Gilatide, Gimatecan, Giripladib, Glaspimod, Glucarolactam potassium, Gludopa, Glutathione Monoethyl Ester, Glutathione Monoisopropyl Ester, Glycine-proline-Melphalan, Glycopin, Glycyrrhizinic acid, Golotimod, Goodyeroside B, Goralatide, Grepafloxacin hydrochloride, GS-143, Haterumadioxin A, Haterumadioxin B, Helvecardin A, Helvecardin B, Heptelidic acid chlorohydrin, Hericenal A, Hericenal B, Hericenal C, Homoindanomycin, Hongoquercin A, Hongoquercin B, Human angiotensin II, Hyaluronate sodium, Hydrostatin A, Ibuprofen, Icatibant acetate, Icofungipen, Idrapril, Ifetroban, Ilepatril, Iloprost, Imidapril, Imidapril hydrochloride, Imiglitazar, Imipenem, Indanaprost (S), Indanomycin, Indeglitazar, Indobufen, Indole-3-propionic acid, Indometacin, Indomethacin trometamol, Indoxam, Indynaprost, Inogatran, Inosiplex, Iododiflunisal, Iodofiltic acid-[123I], Iodostearic Acid, Iralukast, Iralukast sodium, Isalsteine, Isobongkrekic acid, Isotretinoin, Itavastatin calcium, Itriglumide, Kaitocephalin, Kanglemycin A, Kapurimycin A1, Kapurimycin A3, Ketoprofen, Ketoprofen lysine, Ketorolac, Ketorolac tromethamine, Khafrefungin, Kijimicin, Kistamicin A, L-4-Oxalysine, Labradimil, Lamectacin, Lamifiban, Lanthiopeptin, Lapaquistat acetate, Larazotide acetate, Laropiprant, Latamoxef sodium, L-Chicoric acid, Lenapenem hydrochloride, Lenapenem hydrochloride hydrate, Levocabastine hydrochloride, Levocetirizine dihydrochloride, levo-Ciprofibrate, Levodopa, Levodopa 3-O-glucoside, Levodopa 4-O-glucoside, Levofloxacin, Levonadifloxacin arginine salt, L-Homothiocitrulline, Licofelone, Licorice-saponin C2, Lidorestat, Limaprost alfadex, Limazocic, Linoleic acid 18:2w6-cis,9-cis, Linotroban, Lintitript, Lipohexin, Lisinopril, Lithium succinate, Lithospermic acid B magnesium salt, Loloatin B, Lomefloxacin hydrochloride, Lometrexol, Longestin, Lonidamine, Loracarbef hydrate, Lorglumide, Lotrafiban, Loxiglumide, L-Simexonyl homocysteine, L-Thiocitrulline, Lubiprostone, Lumiracoxib, Lu-Tex bis (gluconate), Lysinated-betulonic acid, Lysine acetylsalicylate, Macrocarpin B, Madecassic acid, Maracenin A1, Maracenin A2, Maracenin B1, Maracenin B2, Maracenin C1, Maracenin C2, Maracenin D1, Maracenin D2, Marbofloxacin, Maslinic acid, Matristatin A1, Matristatin A2, Matteuorienate A, Matteuorienate B, Matteuorienate C, Mebrofenin, Meclinertant, Mefenamic acid, Melagatran, Memnopeptide A, Meptazinol-Val-carbamate, Meropenem, Mersacidin, Mesalazine, Metesind glucuronate, Methanobactin, Methotrexate, Methoxatin, Methyldopa, Methylenolactocin, Methylhomoindanomycin, Metiapril, Metirosine, Micacocidin A, Micacocidin B, Midafotel, Midoriamin, Milrinone Lactate, Minerval, Mipitroban, Mispyric acid, Mixanpril, Moenomycin A chloride bismuth salt, Moexipril hydrochloride, Moexiprilat, Mofezolac, Momordin Ic, Monamidocin, Monoethanolamine oleate, Montelukast sodium, Morphine Glucuronide, Moxifloxacin hydrochloride, Mumbaistatin, Mupirocin, Muraglitazar, Muraminomicin A, Muraminomicin B, Muraminomicin C, Muraminomicin D, Muraminomicin E1, Muraminomicin E2, Muraminomicin F, Muraminomicin G, Muraminomicin H, Muraminomicin I, Muraminomicin Z1, Muraminomicin Z2, Muraminomicin Z3, Muraminomicin Z4, Mureidomycin A, Mureidomycin B, Mureidomycin C, Mureidomycin D, Mureidomycin E, Mureidomycin F, Mureidomycins, Mycaperoxide A, Mycaperoxide B, Mycestericin E, Mycophenolic acid sodium salt, Myriceric acid A, Mytolbilin acid, Nadifloxacin, Nafagrel hydrochloride, Nafagrel hydrochloride hemihydrate, Nagstatin, Napirimus, Napsagatran, Napsamycin A, Napsamycin B, Napsamycin C, Napsamycin D, Nateglinide, Naveglitazar, Nebostinel, Nemonoxacin, Neu5Ac2en, Niacin, Niglizin, Nileprost beta-cyclodextrin clathrate, Nooglutil, Norfloxacin, Norfloxacin succinil, Obeticholic acid, Octacosamicin A, Octacosamicin B, O-Demethylchlorothricin, Ofloxacin, Olamufloxacin, Olamufloxacin mesilate, Olanzapine pamoate, Oleanolic acid, Olmesartan, Olopatadine Hydrochloride, Olsalazine sodium, Omapatrilat, Onnamide A, OPC-17083, Opiorphin, Orbifloxacin, Oreganic acid, Orienticin A, Orienticin B, Orienticin C, Orienticin D, Oritavancin, Orniplabin, Oseltamivir carboxylate, Ovothiol A, Ovothiol B, Ovothiol C, Oxaprozin, Oxeglitazar, Oxiglutatione sodium, Oxymorphone-Val-carbamate, Oxynor, Ozagrel hydrochloride, Ozenoxacin, Pactimibe, Padoporfin, Paeciloquinone B, Paeciloquinone D, Paldimycin B, Palovarotene, Panipenem, Parasin I, Parinaric acid, Paulomycin, Paulomycin A2, Paulomycin B, Paulomycin C, Paulomycin D, Paulomycin E, Paulomycin F, Pazufloxacin, Pazufloxacin mesilate, Pefloxacin, PEG-vancomycin, Pelagiomicin C, Peliglitazar, Pelitrexol, Pelretin, Penasterol, Penicillamine, Peramivir, Perindopril, PG-camptothecin, Phomallenic acid C, Phomoidride A, Phomoidride B, Phosphinic cyclocreatine, Phosphosalsalate, Physostigmine salicylate, Pibaxizine, Pidotimod, Piraxostat, Piretanide, Pirfenoxone, Pirprofen, Pivagabine, Pixantrone maleate, Plakotenin, Platencin, Platensimycin, Plevitrexed, Pluraflavin E, Plusbacin A1, Plusbacin A2, Plusbacin A3, Plusbacin A4, Plusbacin B1, Plusbacin B2, Plusbacin B3, Plusbacin B4, Polyalthidin, Pomisartan, Ponalrestat, Poststatin, PPI17-24, Pradimicin A, Pradimicin B, Pradimicin D, Pradimicin E, Pradimicin FA-1, Pradimicin FA-2, Pradimicin FL, Pradimicin FS ((+)-enantiomer), Pradimicin L, Pradimicin Q, Pradimicin S, Pradimicin T1, Pradimicin T2, Pradofloxacin, Pralatrexate, Pranoprofen, Prefolic A, Pregabalin, Premafloxacin, Premafloxacin hydrochloride, Prezatide copper acetate, Proamipide, Probenecid, Probestin, Procysteine, Proglumide, Propagermanium, Propofol hemisuccinate, Prostatin, Prostratin succinate, Protocatechuic acid, Protoporphyrin IX gallium(III) complex, Prulifloxacin, Prulifloxacin Hydrochloride, Prulifloxacin Mesylate, Pseudomycin A', Pseudomycin B', Pycnanthuquinone A, Pycnanthuquinone B, Pyloricidin B, Pyridazomycin, Pyrrolosporin A, Quiflapon Sodium, Quinapril hydrochloride, Quinlukast, Rafabegron, Ragaglitazar, Raltitrexed, Ramatroban, Ramipril, Raxofelast, Razupenem, Rebamipide bismuth citrate tetramethyledamine, Rebamipide bismuth L-tartrate tetramethyledamine, Repaglinide, Resobene, Reveromycin A, Rhododaurichromanic acid A, Ridogrel, Robenacoxib, Rocagloic acid, Rolafagrel, Romazarit, Romurtide, Rosaprostol sodium, Rosuvastatin calcium, Rosuvastatin sodium, Rufloxacin Gluconate, Rufloxacin hydrochloride, Rumycin 1, Rumycin 2, Salazopyridazin, Salcaprozic acid sodium salt, Salicylazobenzoic acid, S-Allylmercaptocaptopril, Salmisteine, Salvianolic acid L, Samixogrel, Sampatrilat, Sanfetrinem, Sanfetrinem sodium, Sapurimycin, Sarpogrelate hydrochloride, Saussureamine A, Saussureamine B, Saussureamine C, Saussureamine D, Saussureamine E, Scabronine G, Scopadulcic acid B, Securioside A, Securioside B, Selank, Semduramicin, Seocalcitol, Seratrodast, Serofendic acid, Sessiloside, Shepherdin, Sialosylcholesterol-Alpha Sodium Salt, Sitafloxacin hydrate, S-Nitrosocaptopril, S-Nitrosoglutathione, Sodelglitazar, Sodium cromoglycate, Sodium oxybate, Sofalcone, Solabegron hydrochloride, Sorbicillactone A, Sparfloxacin, Sphingofungin F, Spinorphin, Spirapril, Spiriprostil, Spiroglumide, Spiroximicin, Squalestatin I, Stachybocin A, Stachybocin B, Stachybocin C, Staplabin, Starrhizin, Sterenin D, Subtilopentadecanoic acid, Succinobucol, Sufotidine bismuth citrate, Sugammadex sodium, Sulfasalazine, Sulindac, Sulopenem, Sulukast, Sunflower trypsin inhibitor-1, Susalimod, Tafamidis meglumine, Tageflar, Talaglumetad hydrochloride, Talibegron, Talibegron hydrochloride, Talopterin, Taltobulin, Tamibarotene, Tanogitran, Tanomastat, TAP-doxorubicin, Tarenflurbil, Targinine, Tazarotenic Acid, Tebipenem, Teicoplanin-A2-1, Teicoplanin-A2-2, Teicoplanin-A2-3, Teicoplanin-A2-5, Telavancin hydrochloride, Telmesteine, Telmisartan, Temafloxacin hydrochloride, Temocapril hydrochloride, Temurtide, Tenosal, Terbogrel, Terestigmine tartrate, Terikalant fumarate, Tesaglitazar, Tetomilast, Tetradecylselenoacetic acid, Tetrafibricin, Tetragalloylquinic acid, Tetrahydroechinocandin B, Tetronothiodin, Tezampanel, Thermozymocidin, Thiazohalostatin, Thielavin G, Thielocin, Thielocin B3, Thiofoscarnet, Thioxamycin, Thrazarine, Thymic humoral factor gamma-2, Thymopentin, Tiagabine hydrochloride, Tibenelast, Ticolubant, Tilarginine hydrochloride, Tiliquinatine, Timodepressin, Tipelukast, Tiplasinin, Tirofiban hydrochloride, Tisartan, Tolfenamic acid, Tolmetin, Tolrestatin, Tomopenem, Tosufloxacin, Tosufloxacin Tosilate, Trandolapril, Trandolaprilat, Tranexamic acid, Tranilast, Treprostinil diethanolamine, Treprostinil sodium, Tretinoin, Triacetylshikimic acid, Trichomycin A, Triflusal, Trimexautide, Trimoprostil, Tripterin, Tropesin, Trovafloxacin, Trovafloxacin hydrate, Trovafloxacin hydrochloride mesylate, Trovafloxacin mesilate, Tubelactomicin A, Tuberactomycin D, Tuberactomycin E, Tubulysin A, Tubulysin B, Tubulysin C, Tucaresol, Tuftsin, Turbinaric acid, Tyroservatide, Ubenimex, Ulifloxacin, Uncarinic acid A, Uncarinic acid B, Unoprostone, Ursodeoxycholic acid, Ursolic acid phosphate, Utibapril, Utibaprilat, Vadimezan, Valonomycin A, Valproate Semisodium, Valproic acid, Valsartan, Vancomycin hydrochloride, Varespladib, Vebufloxacin, Vedaprofen, Veliflapon, Verlukast, Vinaxanthone, Viquidacin, Viranamycin-A, Viscosin, Vitilevuamide, Voreloxin, W Peptide, Xanthofulvin, Zabicipril Hydrochloride, Zabiciprilat Hydrochloride, Zabofloxacin hydrochloride, Zaltoprofen, Zanamivir, Zaragozic acid D3, Zenarestat, Zofenoprilat, Zofenoprilat arginine, Zolasartan, Zonampanel.

Suitable drugs with a phosphate group may be selected fromt the group consisting of Adenophostin A, Adenophostin B, Atrinositol, Buflomedil pyridoxalphosphate, Cytostatin, Fludarabine phosphate, Fosfluconazole, Fosfonochlorin, Fosfosal, Fosopamine, Fosquidone, Fostamatinib, Ganciclovir monophosphate, Genistein-7-phosphate, Hydroxyphoslactomycin B, Leustroducsin A, Leustroducsin B, Leustroducsin C, Leustroducsin H, Mangafodipir trisodium, Menadiol sodium diphosphate, Miproxifene phosphate, Monophosphoryl lipid A, Phospholine, Phosphosalsalate, Pneumocandin B0 2-phosphate, Tafluposide, Triciribine phosphate, Ursolic acid phosphate.

Suitable drugs with a thiol group may be selected fromt the group consisting of Acetylcysteine, Antileukinate, Argimesna, Bucillamine, Butixocort, Captopril, Dihydrolipoic acid, Gemopatrilat, Glutathione monoethyl ester, Glutathione monoisopropyl ester, Midoriamin, Omapatrilat, Ovothiol A, Ovothiol B, Ovothiol C, Penicillamine, Rebimastat, Shepherdin, Zofenoprilat, Zofenoprilat arginine.

FIG. 6 shows a schematic drawing of a relevant section of a hydrogel comprising permanent linkages of the backbone moieties with a transient prodrug linker to which a biologically active moiety is covalently attached. A hyperbranched moiety (oval, "Hyp") comprises permanent bonds (white diamonds) to either the transient prodrug linker (black arrow) or a spacer moiety connected to a backbone moiety and on the other side connected to a crosslinking moiety (thick black line). The thin black line indicates a PEG-based polymeric chain extending from a branching core (not shown). Dashed lines indicate the attachment to a larger moiety, which was not fully drawn.

FIG. 6a shows the direct linkage of a transient prodrug linker to the hyperbranched moiety, whereas FIG. 6b shows an indirect linkage of the transient prodrug linker to the hyperbranched moiey. In FIG. 6b the transient prodrug linker is coupled to the hyperbranched moiety through a spacer moiety (thick grey line), which is coupled to the transient prodrug linker through a permanent bond (white diamond). In each case, the drug moiety (large white circle) is coupled to the transient prodrug linker through a biodegradable linkage (white arrow).

Hydrogel Degradation

The degradation of the biodegradable hydrogel according to the invention is a multi-step reaction where a multitude of degradable bonds is cleaved resulting in degradation products which may be water-soluble or water-insoluble. However, water-insoluble degradation products may further comprise degradable bonds so that they can be cleaved in that water-soluble degradation products are obtained. These water-soluble degradation products may comprise one or more backbone moieties. It is understood that released backbone moieties may, for instance, be permanently conjugated to spacer or blocking or linker groups or affinity groups and/or prodrug linker degradation products and that also water-soluble degradation products may comprise degradable bonds.

The structures of the branching core, PEG-based polymeric chains, hyperbranched dendritic moieties and moieties attached to the hyperbranched dendritic moieties can be inferred from the corresponding descriptions provided in the sections covering the different hydrogels of the present invention. It is understood that the structure of a degradant depends on the type of hydrogel according to the invention undergoing degradation.

The total amount of backbone moieties can be measured in solution after complete degradation of the hydrogel according to the invention, and during degradation, fractions of soluble backbone degradation products can be separated from the insoluble hydrogel according to the invention and can be quantified without interference from other soluble degradation products released from the hydrogel according to the invention. A hydrogel object according to the invention may be separated from excess water of buffer of physiological osmolality by sedimentation or centrifugation. Centrifugation may be performed in such way that the supernatant provides for at least 10% of the volume of the swollen hydrogel according to the invention. Soluble hydrogel degradation products remain in the aqueous supernatant after such sedimentation or centrifugation step, and water-soluble degradation products comprising one or more backbone moieties are detectable by subjecting aliquots of such supernatant to suitable separation and/or analytical methods.

Preferably, water-soluble degradation products may be separated from water-insoluble degradation products by filtration through 0.45 μm filters, after which the water-soluble degradation products can be found in the flow-through. Water-soluble degradation products may also be separated from water-insoluble degradation products by a combination of a centrifugation and a filtration step.

For instance the backbone moieties may carry groups that exhibit UV absorption at wavelengths where other degradation products do not exhibit UV absorption. Such selectively UV-absorbing groups may be structural components of the backbone moiety such as amide bonds or may be introduced into the backbone by attachment to its reactive functional groups by means of aromatic ring systems such as indoyl groups.

FIG. 7 shows a schematic drawing of different degradation products. The exemplary degradation product of FIG. 7a results from the degradation of a biodegradable hydrogel carrying conjugate functional groups. From a central branching core (C) extend four PEG-based polymeric chains (thin black lines), at which ends hyperbranched dendritic moieties ("Hyp"; ovals) are attached. Said hyperbranched dendritic moieties contain a number of permanent linkages (white diamonds) to either spacer moieties connected to a backbone moiety and on the other side connected to a crosslinking moiety (asterisk) or to conjugates such as affinity ligands or chelating groups (black ovals). Dashed lines indicate the attachment to a larger moiety which is not shown.

The exemplary degradation product of FIG. 7b results from the degradation of a hydrogel carrying prodrugs. From a central branching core (C) extend four PEG-based polymeric chains (thin black lines), at which ends hyperbranched dendritic moieties ("Hyp"; ovals) are attached. Said hyperbranched dendritic moieties contain a number of permanent linkages to either spacer moieties connected to a backbone moiety and on the other side connected to a crosslinking moiety (asterisk) or to spacer moieties (white rectangle) which are connected to transient prodrug linkers (black arrow). It is understood that said spacer moiety is optional and depends on the type of hydrogel according to the invention. Dashed lines indicate the attachment to a larger moiety which is not shown.

It is understood that the hyperbranched dendritic moieties of the degradation products comprise more permanent linkages to spacer moieties connected to a backbone moiety and on the other side connected to a crosslinking moiety, conjugates or transient prodrug linkers than shown in FIGS. 7a and 7b.

Synthesis of Biodegradable Reactive Hydrogels

Biodegradable reactive hydrogels may be prepared by a variety of different methods. Such methods are described e.g. in WO-A 2006/003014. One particular synthesis process based on either radical or ionic polymerization is based on using a crosslinking macromonomer or crosslinking monomer—the so-called crosslinker reagents,—carrying at least two interconnectable functional groups and a functional macromonomer—the so-called backbone reagent. The backbone reagents carries at least one interconnectable functional group and at least one chemical functional group which is not intended to participate in the polymerization step. Additional diluent monomers may or may not be present. Copolymerization of these components results in a hydrogel according to the invention containing reactive functional groups provided by the backbone moiety. In order to ensure that the reactive functional group is available for reactions after completion of the polymerization, the conditions for the interconnecting polymerization are chosen such that the reactive functional groups are not modified. Alternatively, the reactive functional groups may be protected by use of a reversible protecting group known to the person skilled in the art, which is removed after the polymerization. Useful interconnectable functional groups include but are not limited to radically polymerizable groups like vinyl, vinylbenzene, acrylate, acrylamide, methacylate, methacrylamide and ionically polymerizable groups like oxetane, aziridine, and oxirane.

In an alternative method of preparation, the biodegradable hydrogel according to the invention is generated through chemical ligation reactions. In one alternative, the starting material is one macromolecular starting material with complementary functionalities which undergo a reaction such as a condensation or addition reaction, which is a heteromultifunctional backbone reagent, comprising a number of polymerizable functional groups.

Alternatively, the biodegradable hydrogel according to the invention may be formed from two or more macromolecular starting materials with complementary functionalities which undergo a reaction such as a condensation or addition reaction. One of these starting materials is a crosslinker reagent with at least two identical polymerizable functional groups and the other starting material is a homo-multifunctional or heteromultifunctional backbone reagent, also comprising a number of polymerizable functional groups.

Suitable polymerizable functional groups present on the crosslinker reagent include terminal primary and secondary amino, carboxylic acid and derivatives, maleimide, thiol, hydroxyl and other alpha,beta unsaturated Michael acceptors like vinylsulfone groups. Suitable polymerizable functional groups present in the backbone reagent include but are not limited to primary and secondary amino, carboxylic acid and derivatives, maleimide, thiol, hydroxyl and other alpha, beta unsaturated Michael acceptors like vinylsulfone groups.

If the crosslinker reagent polymerizable functional groups are used substoichiometrically with respect to backbone polymerizable functional groups, the resulting biodegradable hydrogel according to the invention will be a reactive biodegradable hydrogel with free reactive functional groups attached to the backbone structure, i.e. to backbone moieties.

Synthesis of Hydrogel Prodrugs

The hydrogel prodrug of the present invention can be prepared starting from the reactive biodegradable hydrogel or the modified reactive biodegradable hydrogel of the present invention by convenient methods known in the art. It is clear to a practitioner in the art that several routes exist. For example, the prodrug linker mentioned above, to which the biologically active moiety is covalently attached, can be reacted with the reactive functional groups of the hydrogel of the present invention with or without already bearing the active moiety in part or as whole.

Optionally, a prodrug linker may be first conjugated to a biologically active moiety and the resulting biologically active moiety-prodrug linker conjugate may then react with the biodegradable hydrogel's reactive functional groups. Alternatively, after activation of one of the reactive functional groups of the prodrug linker, the linker-hydrogel conjugate may be contacted with the biologically active moiety in the second reaction step and excess biologically active moiety (e.g. excess drug) may be removed by washing and filtration after conjugation of the biologically active moiety to the hydrogel-bound prodrug linker. Despite the large size of the pore of the hydrogel according to the invention, the biologically active moiety remains bound inside the biodegradable hydrogel according to the invention by the covalent attachment of a suitable chemical functional group present on the biologically active moiety to the second chemical functional group of the prodrug linker.

Preferably, the covalent attachment formed between the reactive functional groups provided by the backbone moieties and the chemical functional groups of the prodrug linker are permanent bonds. Suitable reactive functional groups for attachment of the prodrug linker to the reactive biodegradable hydrogel include but are not limited to carboxylic acid and derivatives, carbonate and derivatives, hydroxyl, hydrazine, hydroxylamine, maleamic acid and derivatives, ketone, amino, aldehyde, thiol and disulfide.

A preferred process for the preparation of a prodrug according to the present invention is as follows:

A preferred starting material for the backbone reagent synthesis is a 4-arm PEG tetra amine or 8-arm PEG octa amine, with the PEG reagent having a molecular weight ranging from 2000 to 10000 Dalton, most preferably fom 2000 to 5000 Da. To such multi-arm PEG-derivatives, lysine residues are coupled sequentially to form the hyperbranched backbone reagent. It is understood that the lysines can be partially or fully protected by protective groups during the coupling steps and that also the final backbone reagent may contain protective groups. A preferred building block is bis-boc lysine. Alternatively, instead of sequential additions of lysine residues, a dendritic poly-lysine moiety may be assembled first and subsequently coupled to the 4-arm PEG tetra amine or 8-arm PEG octa amine. It is desirable to obtain backbone reagent carrying 32 amino groups, consequently seven lysines would be attached to each arm of a 4-arm PEG, or five lysines would be attached to each arm of a 8-arm PEG.

In another embodiment, the multi-arm PEG derivative is a tetra- or octa carboxy PEG. In this case, the dendritic moieties may be generated from glutamic or aspartic acid, and the resulting backbone reagent would carry 32 carboxy groups. It is understood that all or a fraction of the backbone reagent's reactive functional groups may be present in a free form, as salts or conjugated to protecting groups. It is understood that due to practical reasons the backbone reagent's number of lysines per PEG-arm will be between six and seven, more preferably approximately seven.

A preferred backbone reagent is shown below:

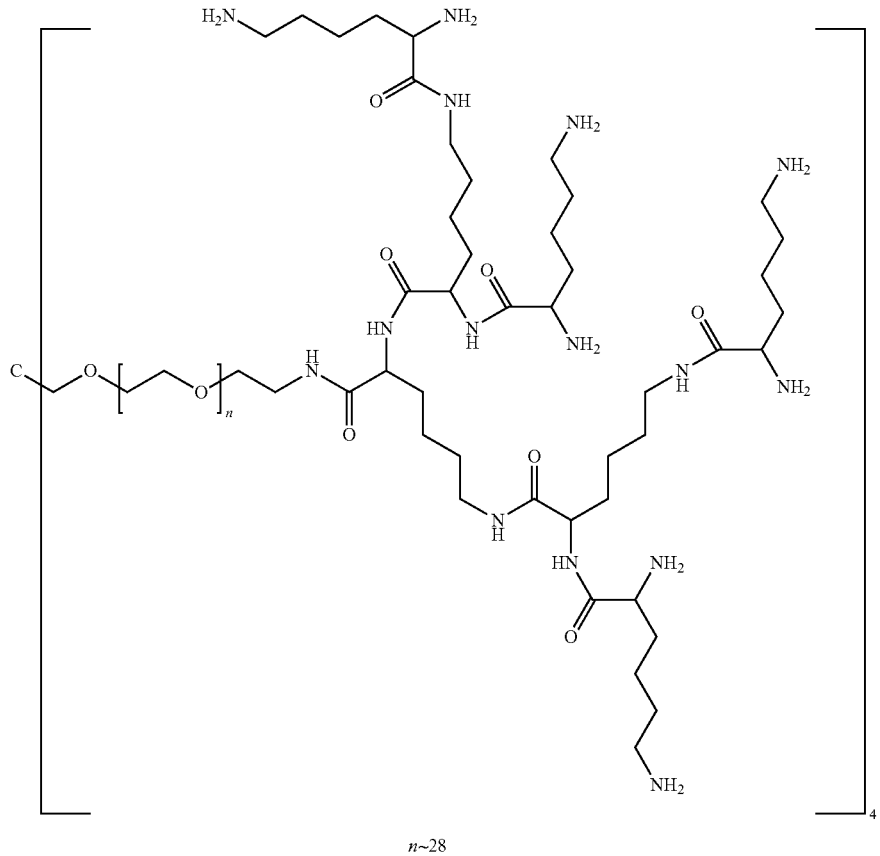

$n{\sim}28$

Synthesis of the crosslinker reagent starts from a linear PEG with a molecular weight ranging from 0.2 to 5 kDa, more preferably from 0.6 to 2 kDa, which is esterified with a half ester of a dicarboxylic acid, most adipic acid or glutaric acid. Preferred protecting group for half ester formation is the benzylic group. The resulting bis dicarboxylic acid PEG half esters are converted into more reactive carboxy compounds such as acyl chlorides or active esters, e.g. pentafluorophenyl or N-hydroxysuccinimide esters, most preferred N-hydroxysuccinimde esters, of which a preferred structur is shown below.

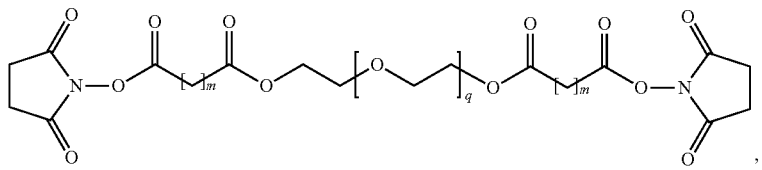

wherein each m independently is an integer ranging from 2 to 4, and q is an integer of from 3 to 100.

More preferred is the following structure:

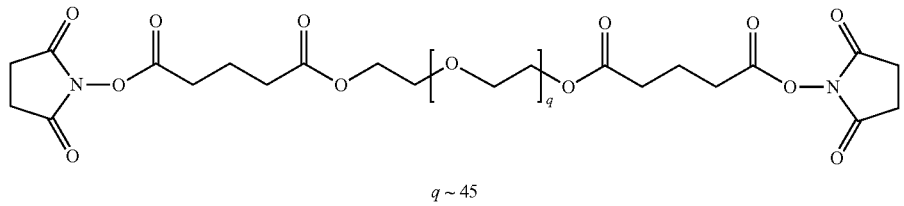

q ~ 45

Alternatively, the bis-dicarboxylic acid PEG half esters may be activated in the presence of a coupling agent such as DCC or HOBt or PyBOP.

In an alternative embodiment, the backbone reagent carries carboxyl groups and the corresponding crosslinker reagent would be selected from ester-containing amino-terminated PEG-chains.

Backbone reagent and crosslinker reagent may be polymerized to form the hydrogel according to the invention using inverse emulsion polymerization. After selecting the desired stoichiometry between backbone and crosslinker polymerizable functional groups, backbone and crosslinker are dissolved in DMSO and a suitable emulgator with an appropriately selected HLB value, preferably Arlacel P135, is employed to form an inverse emulsion using a mechanical stirrer and controlling the stirring speed. Polymerization is initiated by the addition of a suitable base, preferably by N,N,N',N'-tetramethylethylene diamine. After stirring for an appropriate amount of time, the reaction is quenched by the addition of an acid, such as acetic acid and water. The beads are harvested, washed, and fractionated according to particle size by mechanical sieving. Optionally, protecting groups may be removed at this stage.

In an alternative embodiment of this invention, multi-functional moieties are coupled to the reactive functional groups of the polymerized reactive biodegradable hydrogel to increase the number of reactive functional groups which allows to increase the drug load of the biodegradable hydrogel according to the invention. Such multi-functional moieties may be provided by suitably substituted derivatives of lysine, dilysine, trilysine, tetralysine, pentalysine, hexylysine, heptalysine, or oligolysine, low-molecular weight PEI, ornithine, diaminobutyric acid. Preferably, the multi-functional moiety is lysine.

Further, such hydrogel according to the invention may be functionalized with a spacer carrying the same reactive functional group, for instance, amino groups may be introduced into the modified reactive biodegradable hydrogel by coupling a heterobifunctional spacer, such as suitably activated COOH-(EG)$_6$-NH-fmoc, and removing the fmoc-protecting group.

In one embodiment, a drug compound may be directly reacted with a reactive biodegradable hydrogel to form a covalent transient linkage resulting in a hydrogel prodrug according to the invention. Such transient linkage between drug and biodegradable hydrogel according to the invention is preferably a carbamate, ester, amide or carbonate.

In another embodiment, a drug compound is first conjugated to a spacer in such a fashion that the linkage between drug compound and spacer is a covalent transient linkage such as a carbamate, ester, amide or carbonate linkage, and is subsequently reacted with the reactive biodegradable hydrogel form a prodrug according to the invention.

In yet another embodiment, a drug compound is first conjugated to a linker in such a fashion that the linkage between drug compound and linker is a covalent transient linkage such as a carbamate, ester, amide or carbonate linkage, and is subsequently reacted with a reactive biodegradable hydrogel to form a prodrug according to the invention.

Further, such biodegradable hydrogel according to the invention may be functionalized with a spacer carrying a different reactive functional group than provided by the biodegradable hydrogel according to the invention. For instance, maleimide reactive functional groups may be introduced into the hydrogel according to the invention by coupling a suitable heterobifunctional spacer such as Mal-(EG)$_6$-NHS to the biodegradable hydrogel according to the invention. Such modified reactive biodegradable hydrogel can be further conjugated to drug-linker reagents, carrying a reactive thiol group on the linker moiety to form carrier-linked prodrugs according to the present invention.

After loading the drug-linker conjugate to the functionalized maleimido group-containing modified reactive biodegradable hydrogel, all remaining reactive functional groups are capped with suitable blocking reagents, such as mercaptoethanol, to prevent undesired side-reactions.

In a preferred embodiment of the invention, drug linker conjugates, where the drug moiety comprises a disulfide (—S—S—) linkage and where a free thiol group is connected to the linker moiety, are reacted with a maleimide-functionalized hydrogel at temperatures between room temperature and 4° C., more preferred at room temperature, in a buffered aqueous solution of pH 2-5, preferably pH 2.5-4.5, more preferably pH 3.0-4.0. Subsequently, a resulting drug-linker-hydrogel conjugate is treated with a low molecular weight compound comprising a thiol group, preferably with a thiol-containing compound of 34-500 Da, most preferably with mercaptoethanol at temperatures between room temperature and 4° C., more preferred at room temperature, in a buffered aqueous solution of pH 2-5, preferably pH 2.5-4.0, more preferably pH 2.5-3.5.

In another preferred embodiment of the invention, drug linker conjugates, where the drug moiety comprises a disulfide (—S—S—) linkage and where a maleimide group is connected to the linker moiety, are reacted with a thiol-functionalized hydrogel according to the invention at temperatures between room temperature and 4° C., more preferred at room temperature, in a buffered aqueous solution of pH 2-5, preferably pH 2.5-4.5, more preferably pH 3.0-4.0. Subsequently, the corresponding resulting drug-linker-hydrogel conjugate is treated with a low molecular weight compound comprising a maleimide group, preferably a maleimide-containing compound of 100-300 Da, eg N-ethyl-maleimide, at temperatures between room temperature and 4° C., more preferred at room temperature, in a buffered aqueous solution of pH 2-5, preferably pH 2.5-4.0, more preferably pH 2.5-3.5.

In another preferred embodiment of the invention, drug linker conjugates where a free thiol group is connected to the linker moiety, are reacted with a maleimide-functionalized hydrogel at temperatures between room temperature and 4° C., more preferred at room temperature, in a buffered aqueous solution of pH 5.5-8, preferably pH 6.5-7.5. Subsequently, a resulting drug-linker-hydrogel conjugate is treated with a low molecular weight compound comprising a thiol group, preferably with a thiol-containing compound of 34-500 Da, most preferably with mercaptoethanol at temperatures between room temperature and 4° C., more preferred at room temperature, in a buffered aqueous solution of pH 5.5-8, preferably pH 6.5-7.5.

In another preferred embodiment of the invention, drug linker conjugates, where a maleimide group is connected to the linker moiety, are reacted with a thiol-functionalized hydrogel according to the invention at temperatures between room temperature and 4° C., more preferred at room temperature, in a buffered aqueous solution of pH 5.5-8, preferably pH 6.5-7.5. Subsequently, the corresponding resulting drug-linker-hydrogel conjugate is treated with a low molecular weight compound comprising a maleimide group, preferably a maleimide-containing compound of 100-300 Da, eg N-ethyl-maleimide, at temperatures between room temperature and 4° C., more preferred at room temperature, in a buffered aqueous solution of pH 5.5-8, preferably 6.5-7.5.

A particularly preferred method for the preparation of a prodrug of the present invention comprises the steps of
  (a) reacting a compound of formula $C(A'-X^1)_4$, wherein $A'-X^1$ represents A before its binding to Hyp or a precursor of Hyp and $X^1$ is a suitable chemical functional group, with a compound of formula $Hyp'-X^2$, wherein $Hyp'-X^2$ represents Hyp before its binding to A or a precursor of Hyp and $X^2$ is a suitable chemical functional group to react with $X^1$;
  (b) optionally reacting the resulting compound from step (a) in one or more further steps to yield a compound of formula $C(A-Hyp)_4$ having at least four chemical functional groups;
  (c) reacting the at least four chemical functional groups of the resulting compound from step (b) with a poly (ethylene glycol) based crosslinker precursor reagent, wherein the crosslinker precursor reagent is used in a sub-stoichiometric amount compared to the total number of functional groups of $C(A-Hyp)_4$ to yield a hydrogel according to the invention;
  (d) reacting remaining un-reacted reactive functional groups (representing the reactive functional groups of the backbone comprised in the reactive biodegradable hydrogel of the present invention) in the hydrogel backbone of step (c) with a covalent conjugate of biologically active moiety and transient prodrug linker or first reacting the un-reacted reactive functional groups with the transient prodrug linker and subsequently with the biologically active moiety;
  (e) optionally capping remaining un-reacted reactive functional groups to yield a prodrug of the present invention.

Specifically, hydrogels of the present invention are synthesized as follows:

For bulk polymerization, backbone reagent and crosslinker reagent are mixed in a ratio amine/active ester of 2:1 to 1.05:1.

Both backbone reagent and crosslinker reagent are dissolved in DMSO to give a solution with a concentration of 5 to 50 g per 100 mL, preferably 7.5 to 20 g per 100 ml and most preferably 10 to 20 g per 100 ml.

To effect polymerization, 2 to 10% (vol.) N,N,N',N'-tertramethylethylene diamine (TMEDA) are added to the DMSO solution containing crosslinker reagent and backbone reagent and the mixture is shaken for 1 to 20 sec and left standing. The mixture solidifies within less than 1 min.

Such hydrogel according to the invention is preferably comminuted by mechanical processes such as stirring, crushing, cutting pressing, or milling, and optionally sieving.

For emulsion polymerization, the reaction mixture is comprised of the dispersed phase and the continuous phase.

For the dispersed phase, backbone reagent and crosslinker reagent are mixed in a ratio amine/active ester of 2:1 to 1.05:1 and are dissolved in DMSO to give a to give a solution with a concentration of 5 to 50 g per 100 mL, preferably 7.5 to 20 g per 100 ml and most preferably 10 to 20 g per 100 ml.

The continuous phase is any solvent, that is not miscible with DMSO, not basic, aprotic and shows a viscosity lower than 10 Pa*s. Preferably, the solvent is not miscible with DMSO, not basic, aprotic, shows a viscosity lower than 2 Pa*s and is non-toxic. More preferably, the solvent is a saturated linear or branched hydrocarbon with 5 to 10 carbon atoms. Most preferably, the solvent is n-heptane.

To form an emulsion of the dispersed phase in the continuous phase, an emulsifier is added to the continuous phase before adding the dispersed phase. The amount of emulsifier is 2 to 50 mg per mL dispersed phase, more preferably 5 to 20 mg per mL dispersed phase, most preferably 10 mg per mL dispersed phase.

The emulsifier has an HLB-value of 3 to 8. Preferably, the emulsifier is a triester of sorbitol and a fatty acid or an poly(hydroxyl fatty acid)-poly(ethylene glycol) conjugate. More preferably, the emulsifier is an poly(hydroxy-fatty acid)-polyethylene glycol conjugate, with a linear poly(ethylene glycol) of a molecular weight in the range of from 0.5 kDa to 5 kDa and poly(hydroxy-fatty acid) units of a molecular weight in the range of from 0.5 kDa to 3 kDa on each end of the chain. Most preferably, the emulsifier is poly(ethylene glycol) dipolyhydroxy stearate, Cithrol DPHS (Cithrol DPHS, former Arlacel P135, Croda International Plc)

Droplets of the dispersed phase are generated by stirring with an axial flow impeller with a geometry similar to stirrers such as Isojet, Intermig, Propeller (EKATO Rühr- and Mischtechnik GmbH, Germany)), most preferably similar to Isojet with a diameter of 50 to 90% of the reactor diameter. Preferably, stirring is initated before addition of the dispersed phase. Stirrer speed is set to 0.6 to 1.7 m/s. The dispersed phase is added at room temperature, and the concentration of the disperse phase is 2% to 70%, preferably 5 to 50%, more preferably 10 to 40%, and most preferably 20 to 35% of the total reaction volume. The mixture of dispersed phase, emulsifier and continuous phase is stirred for 5 to 60 min before adding the base to the effect polymerization.

5 to 10 equivalents (referred to each amide bond to be formed) of a base are added to the mixture of dispersed and continuous phase. The base is aprotic, non nucleophilic and soluble in the disperse phase. Preferably, the base is aprotic, non nucleophilic, well soluble in both disperse phase and DMSO. More preferably, the base is aprotic, non nucleophilic, well soluble in both disperse phase and DMSO, an amine base and non-toxic. Most preferably, the base is N,N,N',N'-tertramethylethylene diamine (TMEDA). Stirring in the presence of base is continued for 1 to 16 h.

During stirring, droplets of dispersed phase are hardened to become crosslinked hydrogel beads according to the invention which can be collected and fractionation according to size is performed on a vibrational continuous sieving machine with a 75 µm and a 32 µm deck to give hydrogel microparticles according to the invention.

Biodegradable hydrogels of the present invention are obtained from the above-described preparation method in form of micro-particles. In a preferred embodiment of the invention, the reactive biodegradable hydrogel is a shaped article such as a coating, mesh or a stent or a microparticle. Most preferably, the biodegradable hydrogels comprising conjugate functional groups or the hydrogel-connected drug linker prodrug conjugates are formed into microparticulate beads which can be administered as subcutaneous or intramuscular injectably by means of a standard syringe. Such soft beads may have a diameter of between 1 and 500 micrometer. Preferably, such biodegradable hydrogels comprising conjugate functional groups or the biodegradable hydrogel-connected drug-linker prodrug conjugates have a diameter of between 10 and 100 micrometer if suspended in an isotonic aqueous formulation buffer, most preferably a diameter of between 20 and 100 micrometer, most preferably a diameter of between 25 and 80 micrometer.

Preferably, such beaded biodegradable hydrogels comprising conjugate functional groups or the biodegradable hydrogel-connected drug-linker prodrug conjugates can be administered by injection through a needle smaller than 0.6 mm inner diameter, preferably through a needle smaller than 0.3 mm inner diameter, more preferably through a needle small than 0.25 mm inner diameter, even more preferably through a needle smaller than 0.2 mm inner diameter, and most preferably through a needle small than 0.16 mm inner diameter.

It is understood that the terms "can be administered by injection", "injectable" or "injectability" refer to a combination of factors such as a certain force applied to a plunger of a syringe containing the biodegradable hydrogel according to the invention swollen in a liquid at a certain concentration (w/v) and at a certain temperature, a needle of a given inner diameter connected to the outlet of such syringe, and the time required to extrude a certain volume of the biodegradable hydrogel according to the invention from the syringe through the needle.

In order to provide for injectability, a volume of 1 mL of biodegradable hydrogel according to the invention swollen in water to a concentration of at least 5% (w/v) and contained in a syringe holding a plunger of a diameter of 4.7 mm can be extruded at room temperature within 10 seconds by applying a force of less than 50 Newton.

Preferably injectability is achieved for a biodegradable hydrogel according to the invention swollen in water to a concentration of ca. 10% (w/v).

Another aspect of the present invention is a pharmaceutical composition comprising a hydrogel prodrug of the present invention or a pharmaceutical salt thereof together with a pharmaceutically acceptable excipient.

Yet another aspect of the present invention is a hydrogel prodrug of the present invention or a pharmaceutical composition of the present invention for use as a medicament.

In case the hydrogel prodrugs according to the invention contain one or more acidic or basic groups, the invention also comprises their corresponding pharmaceutically or toxicologically acceptable salts, in particular their pharmaceutically utilizable salts. Thus, the hydrogel prodrugs according to the invention which contain acidic groups can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. Hydrogel prodrugs according to the invention which contain one or more basic groups, i.e. groups which can be protonated, can be present and can be used according to the invention in the form of their addition salts with inorganic or organic acids. Examples for suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. If the hydrogel prodrugs according to the invention simultaneously contain acidic and basic groups in the molecule, the invention also includes, in addition to the salt forms mentioned, inner salts or betaines (zwitterions). The respective salts can be obtained by customary methods which are known to the person skilled in the art like, for example by contacting these with an organic or inorganic acid or base in a solvent or dispersant, or by anion exchange or cation exchange with other salts. The present invention also includes all salts of the prodrugs which, owing to low physiological compatibility, are not directly suitable for use in pharmaceuticals but which can be used, for example, as intermediates for chemical reactions or for the preparation of pharmaceutically acceptable salts.

The term "pharmaceutically acceptable" means approved by a regulatory agency such as the EMEA (Europe) and/or the FDA (US) and/or any other national regulatory agency for use in animals, preferably in humans.

"Pharmaceutical composition" means one or more active ingredients, and one or more inert ingredients, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable excipient (pharmaceutically acceptable carrier).

The term "excipient" refers to a diluent, adjuvant, or vehicle with which the therapeutic is administered. Such pharmaceutical excipient can be sterile liquids, such as water and oils, including those of petroleum, animal, vegetable or synthetic origin, including but not limited to peanut oil, soybean oil, mineral oil, sesame oil and the like. Water is a preferred excipient when the pharmaceutical composition is administered orally. Saline and aqueous dextrose are preferred excipients when the pharmaceutical composition is administered intravenously. Saline solutions and aqueous dextrose and glycerol solutions are preferably employed as liquid excipients for injectable solutions. Suitable pharmaceutical excipients include starch, glucose, lactose, sucrose, mannitol, trehalose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, pH buffering agents, like, for example, acetate, succinate, tris, carbonate, phosphate, HEPES (4-(2-hydroxyethyl)-1-piperazineethanesulfonic acid), MES (2-(N-morpholino)ethanesulfonic acid), or can contain detergents, like Tween, poloxamers, poloxamines, CHAPS, Igepal, or amino acids like, for example, glycine, lysine, or histidine. These compositions can take the form of solutions, suspensions, emulsions, tablets, pills, capsules, powders, sustained-release formulations and the like. The composition can be formulated as a suppository, with traditional binders and excipients such as triglycerides. Oral formulation can include standard excipients such as pharmaceutical grades of mannitol, lactose, starch, magnesium stearate, sodium saccharine, cellulose, magnesium carbonate, etc. Examples of suitable pharmaceutical excipients are described in "Remington's Pharmaceutical Sciences" by E. W. Martin. Such compositions will contain a therapeutically effective amount of the therapeutic (drug or active ingredient), preferably in purified form, together with a suitable amount of excipient so as to provide the form for proper administration to the patient. The formulation should suit the mode of administration.

Yet another aspect of the present invention is a method of treating, controlling, delaying or preventing in a mammalian patient, preferably in a human, in need of the treatment of one or more conditions comprising administering to said patient a therapeutically effective amount of a hydrogel prodrug of the present invention or a pharmaceutical composition of the present invention or a pharmaceutically acceptable salt thereof.

EXAMPLES

Materials and Methods

Materials: Side chain protected Exendin-4 (J. Eng et al., *J. Biol. Chem.* 1992, 267(11), 7402-7405) on Rink amide resin was obtained from Peptide Specialty Laboratories GmbH, Heidelberg, Germany. Human insulin was obtained from Biocon Ltd., Bangalore, India.

Amino 4-arm PEG5000 was obtained from JenKem Technology, Beijing, P. R. China). Amino 4-arm PEG2000 was obtained from CreativePEGWorks, Winston Salem, N.C., USA N-(3-maleimidopropyl)-21-amino-4,7,10,13,16,19-hexaoxa-heneicosanoic acid NHS ester (Mal-PEG6-NHS) was obtained from Celares GmbH, Berlin, Germany.

2-Chlorotrityl chloride resin, HATU and amino acids were from Merck Biosciences GmbH, Schwalbach/Ts, Germany, if not stated otherwise. Fmoc-Asp(OH)—OMe was obtained from Bachem AG, Bubendorf, Switzerland. S-Trityl-6-mercaptohexanoic acid (Trt-MHA) was obtained from PolyPeptide (France).

All other chemicals were from Sigma-ALDRICH Chemie GmbH, Taufkirchen, Germany.

Solid phase synthesis was performed on 2-Chlorotrityl chloride (TCP) resin with a loading of 1.3 mmol/g. Syringes equipped with polypropylene frits were used as reaction vessels.

Loading of the first amino acid to resins was performed according to manufacturer's instructions.

Fmoc Deprotection:

For Fmoc protecting-group removal, the resin was agitated with 2/2/96 (v/v/v) piperidine/DBU/DMF (two times, 10 min each) and washed with DMF (ten times).

Mmt Deprotection:

For Mmt protecting-group removal, the resin was treated with HFIP/DCM 1/9 (v/v) (15 times, 1 min each) and washed with DCM (ten times).

Standard Coupling Condition for Acids:

Coupling of acids (aliphatic acids, Fmoc-amino acids) to free amino groups on resin was achieved by agitating resin with 3 eq of acid, 3 eq PyBOP and 6 eq DIEA in relation to free amino groups on resin (calculated based on theoretical loading of the resin) in DMF at room temperature. After 1 hour resin was washed with DMF (10 times).

Cleavage Protocol for 2-Chlorotrityl Chloride Resin:

Upon completed synthesis, the resin was washed with DCM, dried in vacuo and treated two times for 30 minutes with 6/4 (v/v) DCM/HFIP. Eluates were combined, volatiles were removed under a nitrogen stream and product was purified by RP-HPLC. HPLC fractions containing product were combined and lyophilized.

Amine containing products obtained as TFA salts were converted to the corresponding HCl salts using ion exchange resin (Discovery DSC-SAX, Supelco, USA). This step was performed in case the residual TFA was expected to interfere with e.g. subsequent coupling reactions.

RP-HPLC Purification:

RP-HPLC was done on a 100×20 mm and 100×40 mm C18 ReproSil-Pur 300 ODS-3 5µ column (Dr. Maisch, Ammerbuch, Germany) connected to a Waters 600 HPLC System and Waters 2487 Absorbance detector. Linear gradients of solution A (0.1% TFA in $H_2O$) and solution B (0.1% TFA in acetonitrile) were used. HPLC fractions containing product were lyophilized.

For hydrogel beads, syringes equipped with polypropylene frits were used as reaction vessels or for washing steps.

Analytics

Electrospray ionization mass spectrometry (ESI-MS) was performed on a Thermo Fisher Orbitrap Discovery instrument equipped with Waters Acquity HPLC System.

MS spectra of PEG products showed a series of $(CH_2CH_2O)_n$ moieties due to polydispersity of PEG staring materials. For easier interpretation only one single representative m/z signal is given in the examples.

Size exclusion chromatography (SEC) was performed using an Amersham Bioscience AEKTAbasic system equipped with a Superdex200 5/150 GL column (Amersham Bioscience/GE Healthcare) equipped with a 0.45 µm inlet filter, if not stated otherwise. 20 mM sodium phosphate, 140 mM NaCl, pH 7.4, was used as mobile phase.

Example 1

Synthesis of Backbone Reagent 1g and 1h

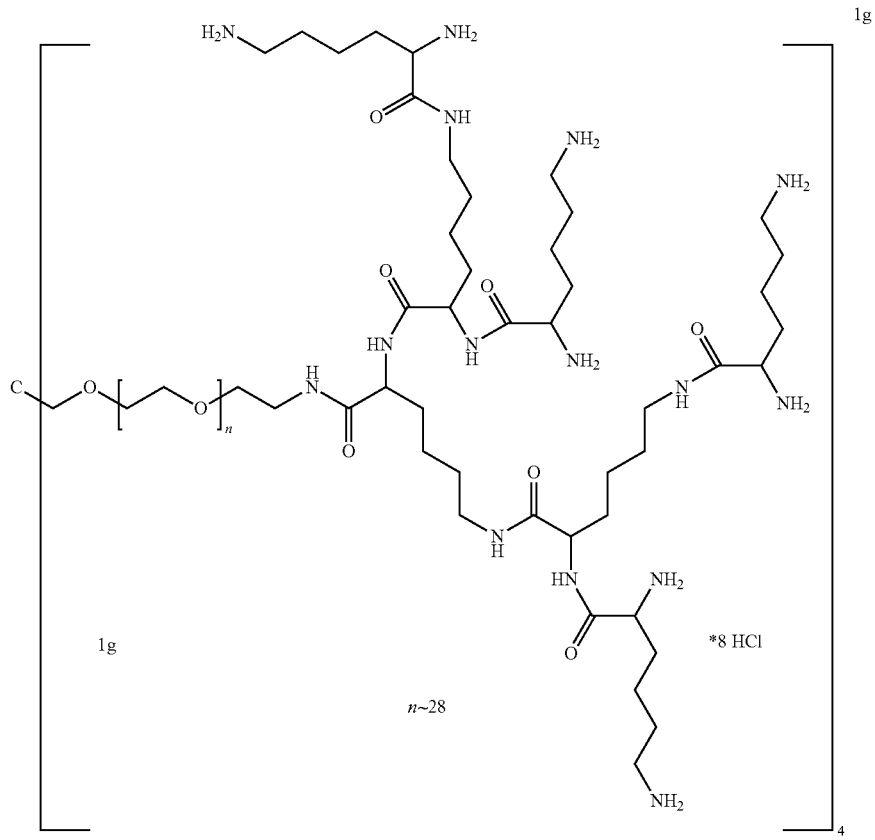

Backbone reagent 1g was synthesized from Amino 4-arm PEG5000 1a according to following scheme:

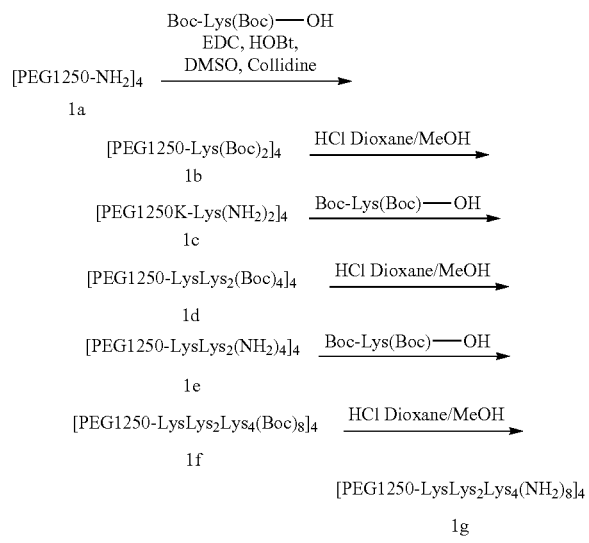

For synthesis of compound 1b, 4-Arm-PEG5000 tetraamine 1a (MW ca. 5200 g/mol, 5.20 g, 1.00 mmol, HCl salt) was dissolved in 20 mL of DMSO (anhydrous). Boc-Lys(Boc)-OH (2.17 g, 6.25 mmol) in 5 mL of DMSO (anhydrous), EDC HCl (1.15 g, 6.00 mmol), HOBt·H$_2$O (0.96 g, 6.25 mmol), and collidine (5.20 mL, 40 mmol) were added. The reaction mixture was stirred for 30 min at RT.

The reaction mixture was diluted with 1200 mL of dichloromethane and washed with 600 mL of 0.1 N H$_2$SO$_4$ (2×), brine (1×), 0.1 M NaOH (2×), and 1/1 (v/v) brine/water (4×). Aqueous layers were reextracted with 500 mL of DCM. Organic phases were dried over Na$_2$SO$_4$, filtered and evaporated to give 6.3 g of crude product 1b as colorless oil. Compound 1b was purified by RP-HPLC.

Yield 3.85 g (59%) colorless glassy product 1b.

MS: m/z 1294.4=[M+5H]$^{5+}$ (calculated=1294.6).

Compound 1c was obtained by stirring of 3.40 g of compound 1b (0.521 mmol) in 5 mL of methanol and 9 mL of 4 N HCl in dioxane at RT for 15 min. Volatiles were removed in vacuo. The product was used in the next step without further purification.

MS: m/z 1151.9=[M+5H]$^{5+}$ (calculated=1152.0).

For synthesis of compound 1d, 3.26 g of compound 1c (0.54 mmol) were dissolved in 15 mL of DMSO (anhydrous). 2.99 g Boc-Lys(Boc)-OH (8.64 mmol) in 15 mL DMSO (anhydrous), 1.55 g EDC HCl (8.1 mmol), 1.24 g HOBt·H$_2$O (8.1 mmol), and 5.62 mL of collidine (43 mmol) were added. The reaction mixture was stirred for 30 min at RT.

Reaction mixture was diluted with 800 mL DCM and washed with 400 mL of 0.1 N $H_2SO_4$ (2×), brine (1×), 0.1 M NaOH (2×), and 1/1 (v/v) brine/water (4×). Aqueous layers were reextracted with 800 mL of DCM. Organic phases were dried with $Na_2SO_4$, filtered and evaporated to give a glassy crude product.

Product was dissolved in DCM and precipitated with cooled (−18° C.) diethylether. This procedure was repeated twice and the precipitate was dried in vacuo.

Yield: 4.01 g (89%) colorless glassy product 1d, which was used in the next step without further purification.

MS: m/z 1405.4=$[M+6H]^{6+}$ (calculated=1405.4).

Compound 1e was obtained by stirring a solution of compound 1d (3.96 g, 0.47 mmol) in 7 mL of methanol and 20 mL of 4 N HCl in dioxane at RT for 15 min. Volatiles were removed in vacuo. The product was used in the next step without further purification.

MS: m/z 969.6=$[M+7H]^{7+}$ (calculated=969.7).

For the synthesis of compound 1f, compound 1e (3.55 g, 0.48 mmol) was dissolved in 20 mL of DMSO (anhydrous). Boc-Lys(Boc)-OH (5.32 g, 15.4 mmol) in 18.8 mL of DMSO (anhydrous), EDC HCl (2.76 g, 14.4 mmol), HOBt.$H_2O$ (2.20 g, 14.4 mmol), and 10.0 mL of collidine (76.8 mmol) were added. The reaction mixture was stirred for 60 min at RT.

The reaction mixture was diluted with 800 mL of DCM and washed with 400 mL of 0.1 N $H_2SO_4$ (2×), brine (1×), 0.1 M NaOH (2×), and 1/1 (v/v) brine/water (4×). Aqueous layers were reextracted with 800 mL of DCM. Organic phases were dried over $Na_2SO_4$, filtered and evaporated to give crude product 1f as colorless oil.

Product was dissolved in DCM and precipitated with cooled (−18° C.) diethylther. This step was repeated twice and the precipitate was dried in vacuo.

Yield 4.72 g (82%) colourless glassy product 1f which was used in the next step without further purification.

MS: m/z 1505.3=$[M+8H]^{8+}$ (calculated=1505.4).

Backbone reagent 1g was obtained by stirring a solution of compound 1f (MW ca 12035 g/mol, 4.72 g, 0.39 mmol) in 20 mL of methanol and 40 mL of 4 N HCl in dioxane at RT for 30 min. Volatiles were removed in vacuo.

Yield 3.91 g (100%), glassy product backbone reagent 1g.

MS: m/z 977.2=$[M+9H]^{9+}$ (calculated=977.4).

Synthesis of Backbone Reagent 1h

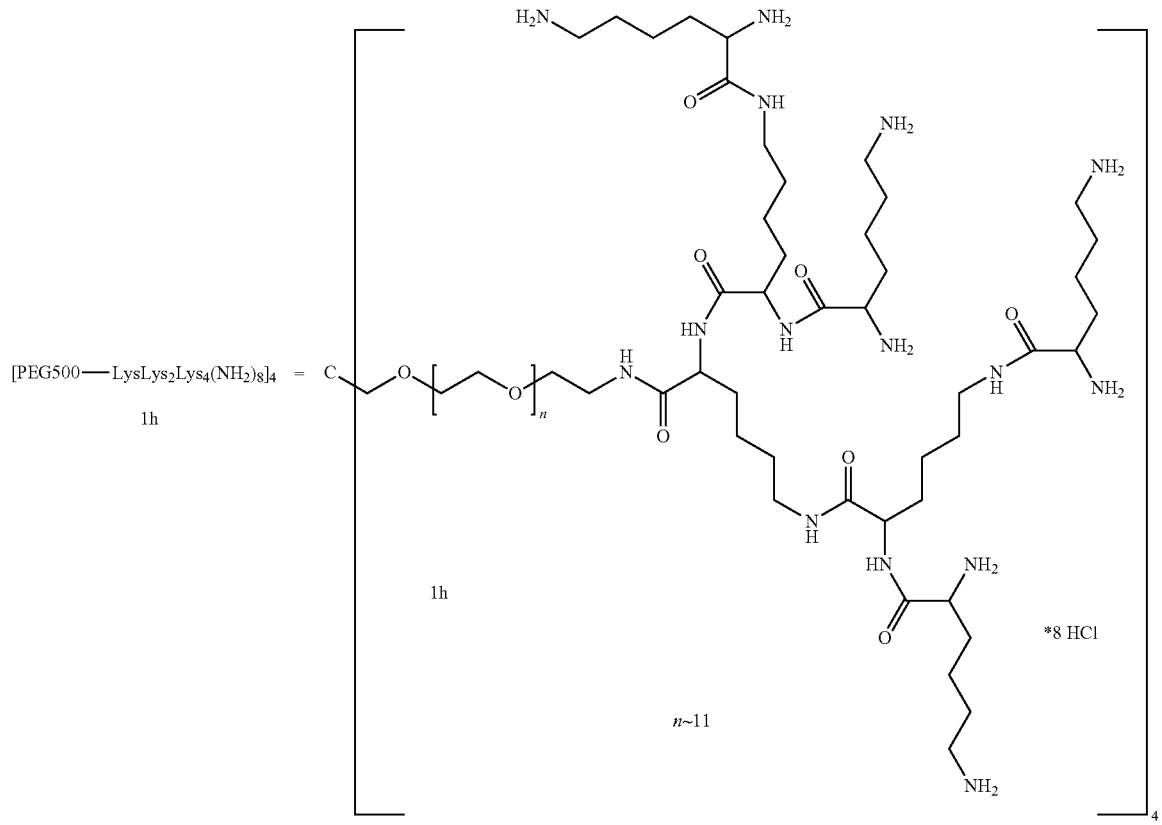

Backbone reagent 1h was synthesized as described for 1g except for the use of 4-arm PEG2000 instead of 4-arm PEG5000.

MS: m/z 719.4=$[M+8H]^{8+}$ (calculated=719.5).

Example 2

Synthesis of Crosslinker Reagents 2d, 2e, 2f, and 2g

Crosslinker reagent 2d was prepared from adipic acid mono benzyl ester (English, Arthur R. et al., *Journal of Medicinal Chemistry*, 1990, 33(1), 344-347) and PEG2000 according to the following scheme:

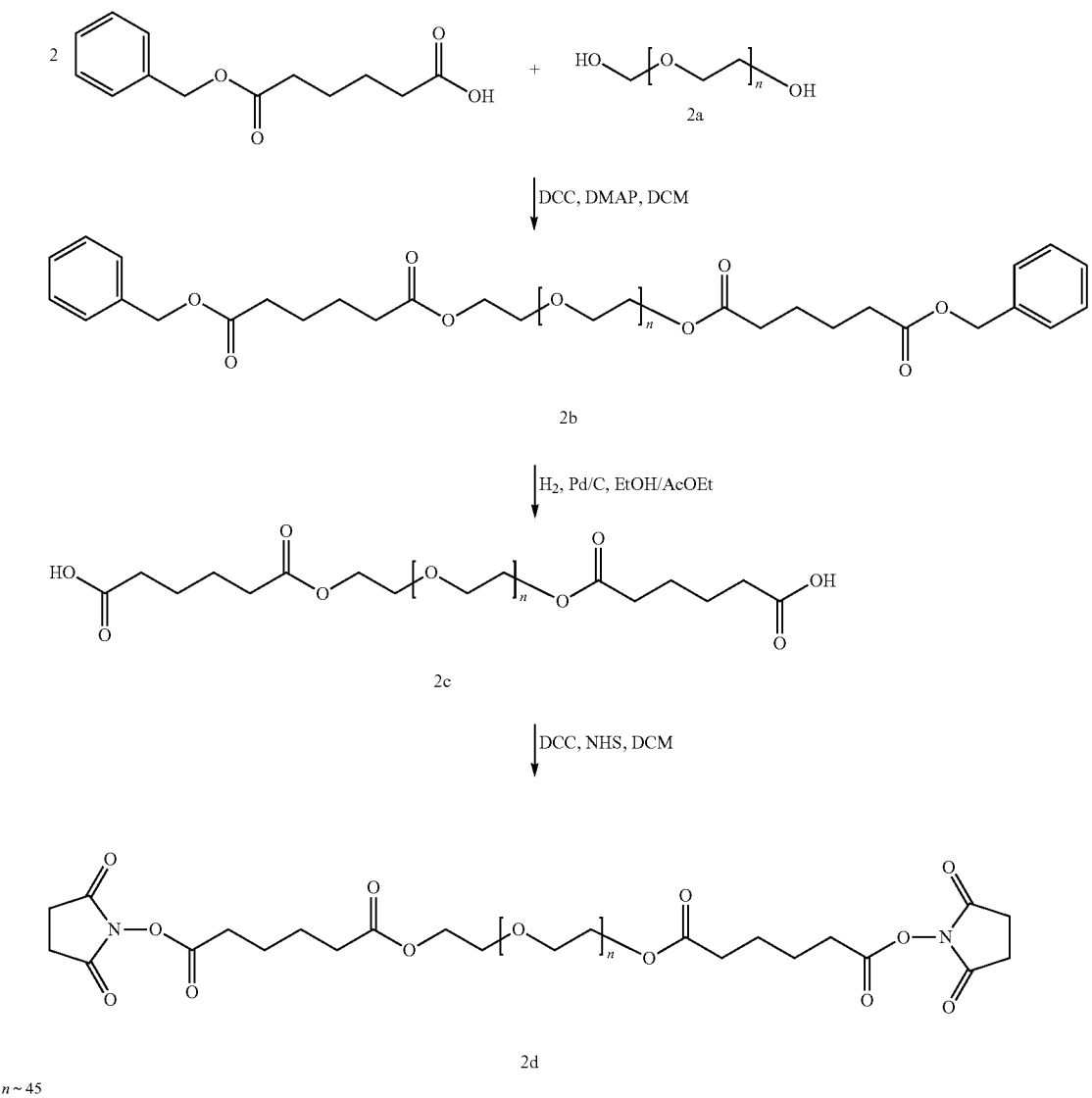

$n \sim 45$

A solution of PEG2000 (2a) (11.0 g, 5.5 mmol) and benzyl adipate half-ester (4.8 g, 20.6 mmol) in dichloromethane (90.0 mL) was cooled to 0° C. Dicyclohexylcarbodiimide (4.47 g, 21.7 mmol) was added followed by a catalytic amount of DMAP (5 mg) and the solution was stirred and allowed to reach room temperature overnight (12 h). The flask was stored at +4° C. for 5 h. The solid was filtered and the solvent completely removed by destillation in vacuo. The residue was dissolved in 1000 mL 1/1(v/v) ether/ethyl acetate and stored at RT for 2 hours while a small amount of a flaky solid was formed. The solid was removed by filtration through a pad of Celite®. The solution was stored in a tightly closed flask at −30° C. in the freezer for 12 h until crystallisation was complete. The crystalline product was filtered through a glass frit and washed with cooled ether (−30° C.). The filter cake was dried in vacuo. Yield: 11.6 g (86%) 2b as a colorless solid. The product was used without further purification in the next step.

MS: m/z 813.1=[M+3H]$^{3+}$ (calculated=813.3)

In a 500 mL glass autoclave PEG2000-bis-adipic acid-bis-benzyl ester 2b (13.3 g, 5.5 mmol) was dissolved in ethyl acetate (180 mL) and 10% Palladium on charcoal (0.4 g) was added. The solution was hydrogenated at 6 bar, 40° C. until consumption of hydrogen had ceased (5-12 h). Catalyst was removed by filtration through a pad of Celite® and the solvent was evaporated in vacuo. Yield: 12.3 g (quantitative) 2c as yellowish oil. The product was used without further purification in the next step.

MS: m/z 753.1=[M+3H]$^{3+}$ (calculated=753.2)

A solution of PEG2000-bis-adipic acid half ester 2c (9.43 g, 4.18 mmol), N-hydroxysuccinimide (1.92 g, 16.7 mmol) and dicyclohexylcarbodiimide (3.44 g, 16.7 mmol) in 75 mL of DVM (anhydrous) was stirred over night at room temperature. The reaction mixture was cooled to 0° C. and precipitate was filtered off. DCM was evaporated and the residue was recystallized from THF.

Yield: 8.73 g (85%) crosslinker reagent 2d as colorless solid.

MS: m/z 817.8=[M+3H]$^{3+}$ (calculated=817.9).

Synthesis of 2e

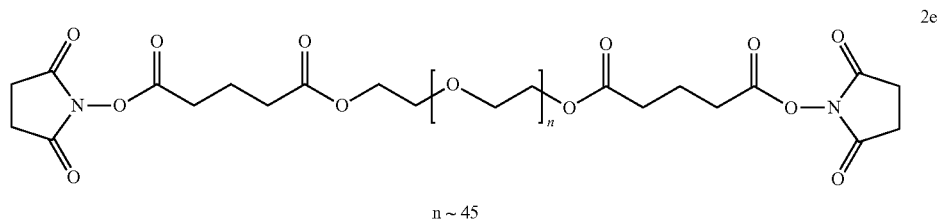

n ~ 45

2e was synthesized as described for 2d except for the use of glutaric acid instead of adipic acid MS: m/z 764.4=[M+3H]$^{3+}$ (calculated=764.5).

Synthesis of 2f

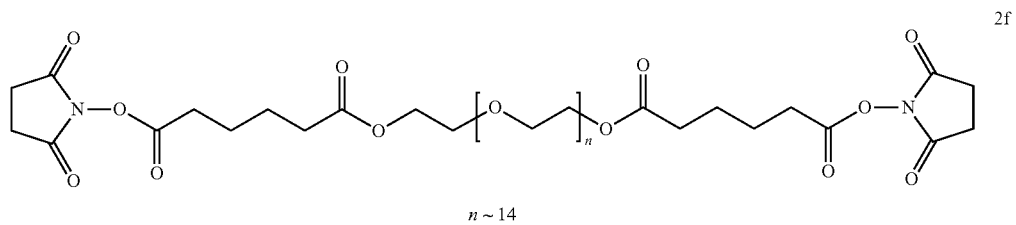

n ~ 14

2f was synthesized as described for 2d except for the use of PEG600 instead of PEG2000

MS: m/z 997.5=[M+H]$^{+}$ (calculated=997.8)

Synthesis of 2g

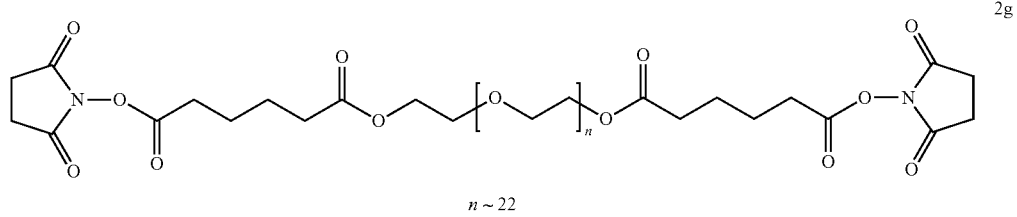

n ~ 22

2g was synthesized as described for 2d except for the use of PEG1000 instead of PEG2000

MS: m/z 697.4=[M+2H]$^{2+}$ (calculated=697.3)

Example 3

Preparation of Hydrogel Beads 3a, 3b, 3c, 3d, and 3e Containing Free Amino Groups A solution of 275 mg 1g and 866 mg 2d in 14 mL DMSO was added to a solution of 100 mg Arlacel P135 (Croda International Plc) in 60 mL heptane. The mixture was stirred at 700 rpm with a custom metal stirrer for 10 min at RT to form a suspension. 1.0 mL N,N,N',N'-tetramethylethylene diamine (TMEDA) was added to effect polymerization. After 2 h, the stirrer speed was reduced to 400 rpm and the mixture was stirred for additional 16 h. 1.5 mL of acetic acid were added and then after 10 min 50 mL of water were added. After 5 min, the stirrer was stopped and the aqueous phase was drained.

For bead size fractionation, the water-hydrogel suspension was wet-sieved on 75, 50, 40, 32 and 20 µm steel sieves. Bead fractions that were retained on the 32, 40, and 50 µm sieves were pooled and washed 3 times with water, 10 times with ethanol and dried for 16 h at 0.1 mbar to give 3a as a white powder.

3b was prepared as described for 3a except for the use of 300 mg 1g, 900 mg 2d, 10.8 ml DMSO, 1.1 ml TMEDA, and 1.6 ml acetic acid.

3c was prepared as described for 3a except for the use of 322 mg 1h, 350 mg 2f, 2.9 ml DMSO, 1.6 ml TMEDA, 2.4 ml acetic acid and a stirring speed of 1000 rpm.

3d was prepared as described for 3a except for the use of 300 mg 1g, 810 mg 2e, 6.3 ml DMSO, 1.1 ml TMEDA, 1.6 ml acetic acid and a stirring speed of 1000 rpm.

3e was prepared as described for 3a except for the use of 1200 mg 1g, 3840 mg 2d, 28.6 ml DMSO, 425 mg Arlacel P135, 100 mL heptane and 4.3 ml TMEDA. For workup, 6.6 ml acetic acid were added and then after 10 min 50 mL of water and 50 mL of saturated aqueous sodium chloride solution were added.

Amino group content of hydrogel was determined by conjugation of a fmoc-amino acid to the free amino groups on the hydrogel and subsequent fmoc-determination as described by Gude, M., J. Ryf, et al. *Letters in Peptide Science* 9(4): 203-206 (2002).

The amino group contents of the various hydrogels were determined to be between 0.13 and 1.1 mmol/g.

Example 4

Preparation of Maleimide Functionalized Hydrogel Beads 4a, 4b, 4c, and 4d, and Determination of Maleimide Substitution A solution of 600 mg Mal-PEG6-NHS (1.0 mmol) in 4.5 mL 2/1 (v/v) acetonitrile/water was added to 200 mg dry hydrogel beads 3a. 500 µL sodium phosphate buffer (pH 7.4, 0.5 M) was added and the suspension was agitated for 30 min at room temperature. Beads 4a were washed five times each with 2/1 (v/v) acetonitrile/water, methanol and 1/1/0.001 (v/v/v/) acetonitrile/water/TFA. For determination of maleimide content, an aliquot of hydrogel beads 4a was lyophilized and weighed out. Another aliquot of hydrogel beads 4a was reacted with excess mercaptoethanol (in 50 mM sodium phosphate buffer, 30 min at RT), and mercaptoethanol consumption was detected by Ellman test (Ellman, G. L. et al., *Biochem. Pharmacol.*, 1961, 7, 88-95). Maleimide content was determined to be 0.13 mmol/g dry hydrogel.

4b and 4c and 4d were prepared as described above except for the use of 3b and 3c and 3e, respectively.

Loading 4b: 0.14 mmol/g
Loading 4c: 0.9 mmol/g
Loading 4d: 0.13 mmol/g

Example 5

Preparation of Indole Acetic Acid Labeled Hydrogel 5

A solution of 15 mg 3-indole acetic acid (87 µmol), 14 µL N,N'-diisopropylcarbodiimide (87 µmol) and 27 mg 1-hydroxybenzotriazole hydrate (174 µmmol) in 0.4 mL DMF was added to 15 mg dry hydrogel beads 3d in a syringe equipped with a filter frit. The suspension was agitated for 1 h at room temperature. 5 was washed five times with DMF and incubated 5 min with a solution of 0.05 mL piperidine in 1 mL DMF at room temperature. 5 was washed five times with DMF, five times with dichloromethane, five times with ethanol and dried in vacuo.

Example 6

Preparation of Desthiobiotin Conjugated Hydrogel 6

Desthiobiotin conjugated hydrogel 6 was prepared from 3b and desthiobiotin as described for 5 except for the use of desthiobiotin and 3b instead of indole acetic acid and 3a.

Example 7

Synthesis of Linker Reagent 7

Fmoc-Asp(OMe)OH (150 mg, 0.41 mmol), $H_2N$—$(CH_2)_2$—$N(CH_3)$-boc (36 µL, 0.34 mmol), HATU (156 mg, 0.41 mmol) and DIEA (214 µL, 1.23 mmol) were dissolved in 1 mL DMF. The mixture was stirred for 1.5 h at RT, acidified with AcOH (100 µL) and purified by RP-HPLC.

Yield: 119 mg (0.23 mmol)

MS Fmoc-Asp(OMe)CO(NH(CH$_2$)$_2$N(CH$_3$)-boc): m/z 548.4=[M+Na]$^+$ (calculated=548.3)

Fmoc-Asp(OMe)CO(NH(CH$_2$)$_2$N(CH$_3$)-boc) (119 mg, 0.23 mmol) was dissolved in DMF (1.0 mL), piperidine (50 µL) and DBU (15 µL) were added and the mixture was stirred for 45 min at RT. AcOH (100 µL) was added and NH$_2$-Asp(OMe)CO(NH(CH$_2$)$_2$N(CH$_3$)-boc) was purified by RP-HPLC.

Yield: 73 mg (0.18 mmol, TFA salt)

MS NH$_2$-Asp(OMe)CO(NH(CH$_2$)$_2$N(CH$_3$)-boc): m/z 326.2=[M+Na]$^+$ (calculated=326.2)

6-Tritylmercaptohexanoic acid (102 mg, 0.26 mmol), (PfpO)$_2$CO (103 mg, 0.26 mmol) and collidine (170 µL, 1.31 mmol) were dissolved in DMSO (1 mL). The mixture was stirred for 1 h and afterwards added to a solution of NH$_2$-Asp(OMe)CO(NH(CH$_2$)$_2$N(CH$_3$)-boc) (73 mg, 0.18 mmol) in DMF (1.0 mL). The mixture was stirred for 1 h, acidified with AcOH (100 µL) and TrtS(CH$_2$)$_5$CONH-Asp(OMe)CO(NH(CH$_2$)$_2$N(CH$_3$)-boc) was purified by RP-HPLC.

Yield: 61 mg (0.09 mmol)

MS TrtS(CH$_2$)$_5$CONH-Asp(OMe)CO(NH(CH$_2$)$_2$N(CH$_3$)-boc): m/z 698.5=[M+Na]$^+$ (calculated=698.3)

TrtS(CH$_2$)$_5$CONH-Asp(OMe)CO(NH(CH$_2$)$_2$N(CH$_3$)-boc) (61 mg, 0.09 mmol) was dissolved in 9:1 dioxane/H$_2$O (1.0 mL), LiOH (4.3 mg, 0.18 mmol) was added and the mixture was stirred at 60° C. for 1 h. AcOH (50 µL) was added and 7 was purified by RP-HPLC.

Yield: 53 mg (0.08 mmol)

MS 7: m/z 684.4=[M+Na]$^+$ (calculated=684.3 g/mol)

Example 8

Synthesis of Linker-Exendin Conjugate 8

7 (22 mg, 33 µmol), PyBOP (23 mg, 44 µmol) and DIEA (31 µL, 0.18 mmol) were dissolved in DMF (600 µL) and immediately added to 220 mg (22 µmol) resin bound, side chain protected exendin with free N-terminus. After incubation for 1.5 h at RT, the resin was washed with 10×DMF, 10×DCM and dried in vacuo. The product was cleaved from the resin and purified by RP-HPLC.

Yield: 15.2 mg

MS 8: m/z 1496.7=[M+3H]$^{3+}$ (calculated=1497)

Example 9

Preparation of Exendin-Linker-Hydrogel Prodrug 9

Hydrogel 4b (600 µL suspended in acetonitrile/water/TFA 1/1/0.001 (v/v/v), 7.3 µmol maleimido groups) was added to a solution of exendin-linker-thiol 8 (15.2 mg, 3.4 µmol) in 500 µL acetonitrile/water/TFA 1/1/0.001 (v/v/v). Phosphate buffer (300 µL, pH 7.4, 0.5 M) was added and the sample was incubated at RT for 15 min. Complete consumption of thiol was confirmed by Ellman test. Mercaptoethanol (10 µL, 146 µmol) was added and the sample was incubated at rt for 10 min. The hydrogel 9 was washed (10 times) with acetonitrile/water 1/1 (v/v) and stored in 0.1% AcOH at 4° C.

Example 10

Synthesis of Linker Reagent 10d

Linker reagent 10d was synthesized according to the following scheme:

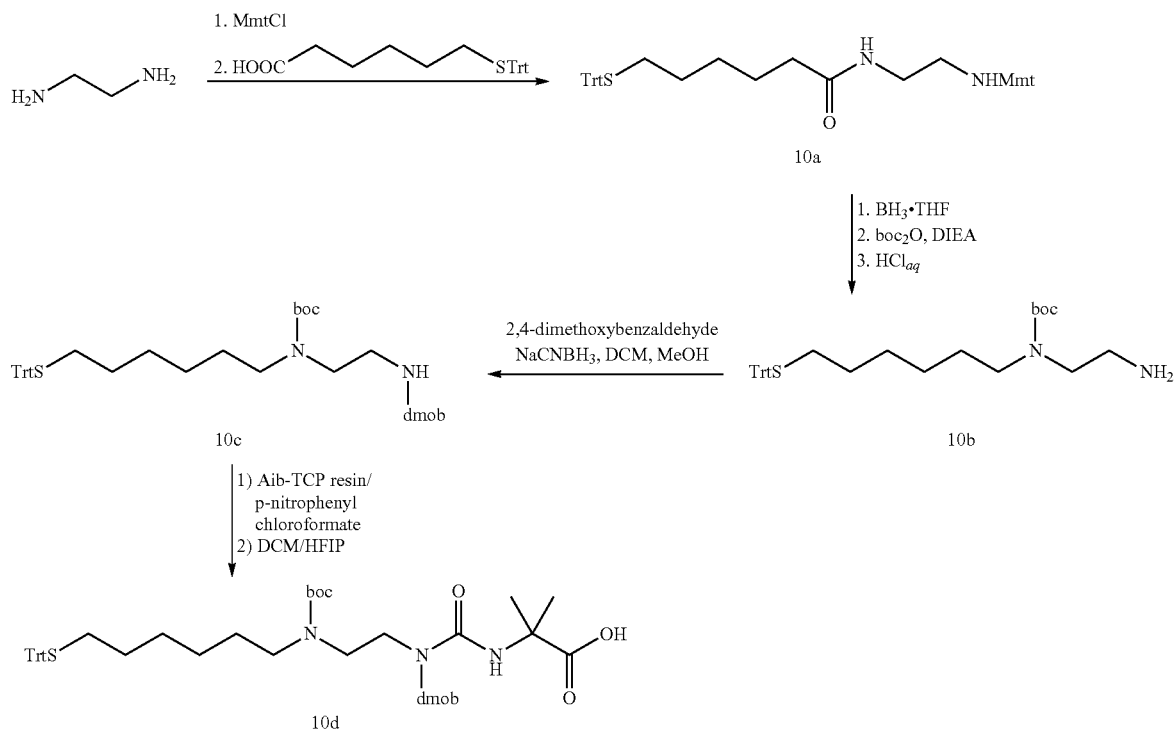

Synthesis of Linker Reagent Intermediate 5a

4-Methoxytrityl chloride (3 g, 9.71 mmol) was dissolved in DCM (20 mL) and added dropwise to a solution of ethylenediamine (6.5 mL, 97.1 mmol) in DCM (20 mL). After two hours the solution was poured into diethyl ether (300 mL) and washed three times with 30/1 (v/v) brine/0.1 M NaOH solution (50 ml each) and once with brine (50 mL). The organic phase was dried over $Na_2SO_4$ and volatiles were removed under reduced pressure to obtain the Mmt-protected intermediate (3.18 g, 9.56 mmol).

The Mmt-protected intermediate (3.18 g, 9.56 mmol) was dissolved in anhydrous DCM (30 mL). 6-(Tritylmercapto)-hexanoic acid (4.48 g, 11.47 mmol), PyBOP (5.67 g, 11.47 mmol) and DIEA (5.0 ml, 28.68 mmol) were added and the mixture was agitated for 30 min at RT. The solution was diluted with diethyl ether (250 mL) and washed three times with 30/1 (v/v) brine/0.1 M NaOH solution (50 mL each) and once with brine (50 mL). The organic phase was dried over $Na_2SO_4$ and volatiles were removed under reduced pressure. 10a was purified by flash chromatography.

Yield: 5.69 g (8.09 mmol).

MS: m/z 705.4=$[M+H]^+$ (calculated=705.0).

Synthesis of Linker Reagent Intermediate 10b

To a solution of 10a (3.19 g, 4.53 mmol) in anhydrous THF (50 mL) was added $BH_3$.THF (1 M solution, 8.5 mL, 8.5 mmol) and the solution was stirred for 16 hours at RT. Further $BH_3$.THF (1 M solution, 14 mL, 14 mmol) was added and stirred for 16 hours at RT. The reaction was quenched by addition of methanol (8.5 mL), N,N-dimethyl-ethylenediamine (3 mL, 27.2 mmol) was added and the solution was heated to reflux and stirred for three hours. The mixture was diluted with ethyl acetate (300 mL) at RT, washed with saturated, aqueous $Na_2CO_3$ solution (2×100 mL) and saturated, aqueous $NaHCO_3$ solution (2×100 mL). The organic phase was dried over $Na_2SO_4$ and volatiles were evaporated at reduced pressure to obtain the crude amine intermediate (3.22 g).

The amine intermediate was dissolved in DCM (5 mL), $Boc_2O$ (2.97 g, 13.69 mmol) dissolved in DCM (5 mL) and DIEA (3.95 mL, 22.65 mmol) were added and the mixture was agitated at RT for 30 min. The mitxture was purified by flash chromatography to obtain the crude Boc- and Mmt-protected intermediate (3g).

MS: m/z 791.4=$[M+H]^+$, 519.3=$[M-Mmt+H]^+$ (calculated=791.1).

0.4 M aqueous HCl (48 mL) was added to a solution of the Boc- and Mmt-protected intermediate in acetonitrile (45 mL). The mixture was diluted with acetonitrile (10 mL) and stirred for one hour at RT. Subsequently, the pH value of the reaction mixture was adjusted to 5.5 by addition of 5 M NaOH solution, acetonitrile was removed under reduced pressure and the aqueous solution was extracted with DCM (4×100 mL). The combined organic phases were dried over Na$_2$SO$_4$ and volatiles were removed under reduced pressure. Crude 5b was used without further purification.

Yield: 2.52 g (3.19 mmol).

MS: m/z 519.3=[M+H]$^+$ (calculated=519.8 g/mol).

Synthesis of Linker Reagent Intermediate 10c 10b (780 mg, 0.98 mmol, ~65% purity) and NaCNBH$_3$ (128 mg, 1.97 mmol) were dissolved in anhydrous methanol (13 mL). A solution of 2,4-dimethoxybenzaldehyde (195 mg, 1.17 mmol) in DCM (2 mL) was added, and the mixture was stirred for 2 h at RT. The solvents were evaporated under reduced pressure, and the crude product was dissolved in DCM and washed with saturated NaCO$_3$ solution. The aqueous phase was extracted three times with DCM, and the combined organic phases were washed with brine, dried over MgSO$_4$ and concentrated under reduced pressure. 10c was purified by flash chromatography using DCM and MeOH as eluents.

Yield: 343 mg (0.512 mmol).

MS: m/z 669.37=[M+H]$^+$, (calculated=669.95).

Synthesis of Linker Reagent 10d

Fmoc-Aib-loaded TCP resin (980 mg, ~0.9 mmol) was deprotected with DMF/piperidine, washed with DMF (5 times) and DCM (6 times) and dried in vacuo. The resin was treated with a solution of p-nitrophenyl chloroformate (364 mg, 1.81 mmol) and collidine (398 µL, 3.0 mmol) in anhydrous THF (6 mL) and shaken for 30 min. The reagent solution was removed by filtration and the resin was washed with THF (5 times) before a solution of amine 5c (490 mg, 0.7 mmol) and DIEA (1.23 mL, 7.1 mmol) in anhydrous THF (6 mL) was added. After shaking for 18 h at RT, the reagent solution was removed by filtration and the resin was washed with DCM (5 times). The linker was cleaved from the resin and purified by RP-HPLC. Product fractions were brought to pH 6 by addition of sat. aq. NaHCO$_3$ and concentrated under reduced pressure. The resulting slurry was partitioned between saturated aqueous NaCl and DCM; and the aqueous layer was extracted with DCM. The combined organic fractions were concentrated to dryness to afford linker reagent 10d.

Yield: 230 mg, (0.29 mmol).

MS m/z 798.41=[M+H]$^+$, (calculated=798.41).

Example 11

Synthesis of αA1-Conjugated Insulin-Linker Conjugate 11b

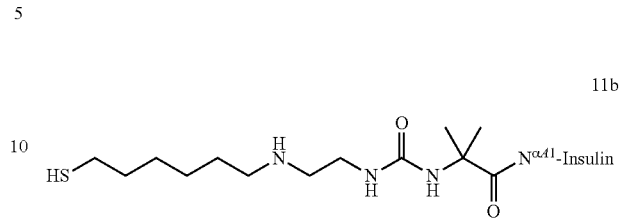

11b

Synthesis of Protected Insulin Linker Conjugate 11a

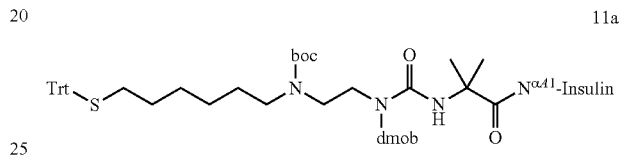

11a

Linker reagent 10d was dissolved in DCM (20 mg/mL) and activated with carbodiimide-resin (1.9 mmol/g, 10 eq.) for 1 h. The solution of the activated linker reagent was added to a solution of insulin (1.2 eq.) and DIEA (3.5 eq.) in DMSO (100 mg insulin/mL), and the mixture was shaken at RT for 45 min. The solution was acidified with acetic acid, the DCM was evaporated under reduced pressure, and N$^{\alpha A1}$-conjugated protected insulin-linker conjugate 11a was purified by RP-HPLC.

Lyophilized 11a was treated with a mixture of 90/10/2/2 (v/v/v/v) HFIP/TFA/water/triethylsilane (2 mL/100 mg of 11a) for 45 min at RT. The reaction mixture was diluted with water, and all volatiles were removed under a stream of nitrogen. N$^{\alpha A1}$-conjugated insulin-linker conjugate 11b was purified by RP-HPLC.

Yield: 139 mg (0.023 mmol) from 62 mg (0.078 mmol) linker 10d

MS: m/z 1524.45=[M+4H]$^{4+}$ (calculated=1524.75).

Example 12

Preparation of Insulin-Linker-Hydrogel Prodrug 12

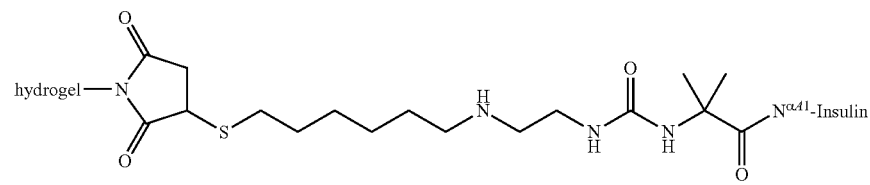

12

Dry maleimide functionalized hydrogel 4a (82 mg, 10.3 µmol maleimido groups) was filled into a syringe equipped with a filter. A solution of insulin-linker-thiol 11b (27.8 mg, 4.6 µmol) in 1.0 mL acetonitrile/water/TFA 1/1/0.001 (v/v/v) was added and the suspension was incubated for 5 min at RT. Acetate buffer (0.4 mL, pH 4.8, 1.0 M) was added and the sample was incubated at RT for 1 h. Consumption of thiol was monitored by Ellman test. Hydrogel was washed 10 times with 1/0.43/0.001 (v/v/v) acetonitrile/water/TFA and 2 times with 1/1/0.2/0.25 (v/v/v/v) 1.0 M sarcosine pH 7.4/ acetonitrile/0.5 M phosphate buffer pH 7.4/water. Finally, the hydrogel was suspended in the sarcosine solution and incubated for 2 h at RT.

Insulin-linker-hydrogel 12 was washed 10 times with acetonitrile/water/TFA 1/1/0.001 (v/v/v) and stored at 4° C.

Insulin loading of 12: 175 mg insulin/g insulin-linker-hydrogel

Example 13

Synthesis of Pramipexole Linker Conjugate 13b

Synthesis of Pramipexole Glycin Intermediate 13a

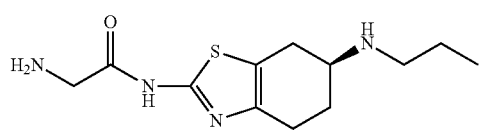

13a

Boc-Gly-OH (659 mg, 3.76 mmol), PyBOP (2.35 g, 4.51 mmol) and N-methyl morpholine (4.14 mL, 37.6 mmol) were dissolved in DMSO (20 mL). Pramipexole dihydrochloride (2.14 g, 7.52 mmol) was added, and the mixture was stirred for 1 h. After complete reaction the solution was diluted with 300 mL 1 M NaOH solution, saturated with NaCl, and extracted with DCM (8×70 mL). The combined organic phases were dried over $MgSO_4$, the solvent was evaporated under reduced pressure, and the residue purified by RP-HPLC. After lyophilisation 721 mg (1.49 mmol, TFA salt) of the Boc protected derivative were obtained.

MS: m/z 369.2=$[M+H]^+$, 737.4=$[2M+H]^+$ (calculated=369.5 g/mol).

For boc deprotection, the intermediate was dissolved in 3 M methanolic HCl (10 mL), concentrated aqueous HCl (400 μL) was added, and the mixture was agitated for 4 h. The solvent was removed under reduced pressure and 13a was dried in vacuo.

Yield: 490 mg (1.44 mmol, double HCl salt).

MS: m/z 269.1=$[M+H]^+$ (calculated=269.4).

Synthesis of 13b

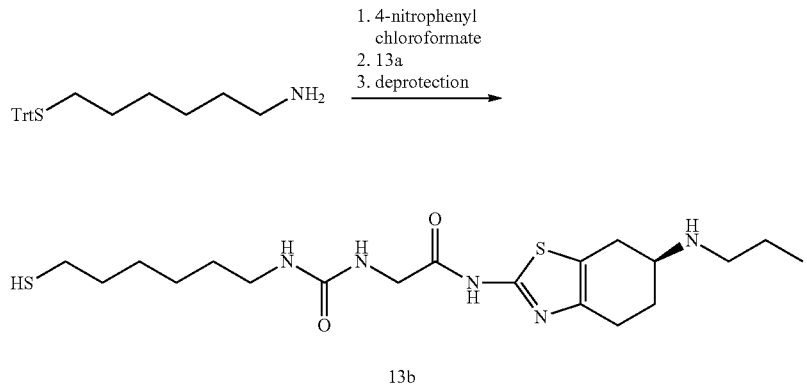

13b 6-(Tritylmercapto)hexane-1-amine (1.21 g, 3.22 mmol) and p-nitrophenyl chloroformate (0.78 g, 3.86 mmol) were suspended in dry THF (15 mL). DIEA (841 μL, 4.83 mmol) was added, and the resulting solution was stirred at room temperature for 2 h. After acidification by addition of acetic acid the solvent was evaporated under reduced pressure, and the residue was purified by RP-HPLC. 1.21 g (2.25 mmol) p-nitrophenyl carbamate were obtained after lyophilisation.

The carbamate (801 mg, 1.48 mmol) was dissolved in DMSO (4.4 mL) and added dropwise to a stirred solution of 13a (490 mg, 1.44 mmol) and DIEA (800 μL, 4.60 mmol) in DMSO (7 mL) within 30 min. The mixture was agitated for 4.5 h at room temperature. Upon complete reaction the solution was diluted with 0.5 M NaOH solution (300 mL) and extracted with DCM (6×70 mL). The combined organic phases were dried over $MgSO_4$, the solvent was evaporated under reduced pressure, and the conjugate was purified by RP-HPLC to obtain 254 mg (0.323 mmol, TFA salt) of the trityl protected intermediate.

MS: m/z 670.3=$[M+H]^+$ (calculated=670.0 g/mol).

For deprotection the intermediate (248 mg, 0.32 mmol) was incubated in HFIP (6 mL) and TES (240 μL) for 30 min at room temperature. Volatiles were evaporated, and 13b was purified by RP-HPLC.

Yield: 167 mg (0.31 mmol, TFA salt).

MS: m/z 428.2=$[M+H]^+$ (calculated=428.6 g/mol)

Example 14

Synthesis of Hydrogel-Linker-Pramipexole Conjugate 14a and 14b

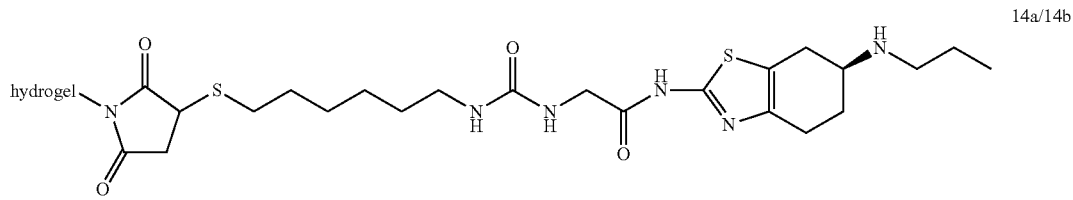

Maleimide-derivatized hydrogel microparticles 4a (100 µL. loading 30 µmol/mL, 3 µmol) were reacted with compound 13b (2.3 mg, 4.3 µmol) in 1/1 acetonitrile/water (420 µL) and 0.5 M phosphate buffer pH 7.4 (52 µL) for 10 min at RT. The hydrogel was washed 20 times with 1/1 acetonitrile/water. Remaining maleimides where reacted with 2-mercaptoethanol (34 µL, 0.48 mmol) in 1/1 acetonitrile/water (3 mL) and 0.5 M phosphate buffer pH 7.4 (0.4 mL) for 10 min at RT. The loaded hydrogel was washed 20 times with 1/1 acetonitrile/water, 20 times with phosphate buffer pH 7.4 and incubated in the same buffer (1.5 mL) at 37° C.

Pramipexole loading 14a: 27 mg/g

High loaded pramipexole linker hydrogel 14b was prepared as described above except for the use of 88 mg 13b and 100 mg 4c.

Pramipexole loading 14b: 152 mg/g

Example 15

Preparation of Mercaptoethanol Blocked Maleimide Derivatized Hydrogel Beads 15

2 mL of a solution of mercaptoethanol (0.7 M in 1/1/0.001 acetonitrile/water/TFA (v/v/v)) was added to 100 mg 4b suspended in 1/1/0.001 acetonitrile/water/TFA (v/v/v). The solution was adjusted to pH 7.0 with phosphate buffer (pH 7.4, 0.5 M) and the mixture was agitated for 30 min at RT. 15 was washed with acetonitrile/water/TFA 1/1/0.001 (10 times).

Example 16

Release Kinetics In Vitro

Drug-linker-hydrogel 9, 12, and 14a, respectively, (containing approximately 1 mg drug) were suspended in 2 ml 60 mM sodium phosphate, 3 mM EDTA, 0.01% Tween-20, pH 7.4, and incubated at 37° C. Suspensions were centrifuged at time intervals and supernatant was analyzed by RP-HPLC at 215 nm and ESI-MS (for 9 and 12) or by absorbance measurement at 263 nm (for 14a). UV-signals correlating to liberated drug were integrated (9 and 12) or directly used (14a) and plotted against incubation time.

Curve-fitting software was applied to estimate the corresponding halftime of release.

In vitro half-lives of 14 d, 18 d, and 8 d were determined for 9, 12, and 14a, respectively. In vitro release kinetics of 9 at pH 7.4 and 37° C. is shown in FIG. 8.

Example 17

In Vitro Degradation of 15 at pH 9 and 37° C.

Accelerated hydrolysis of hydrogel beads 15 was affected by incubating 5 mg 15 in 2.0 ml 0.5 M sodium borate buffer, pH 9.0 at 37° C. Samples were taken at time intervals and analyzed by size exclusion chromatography. UV-signals corresponding to hydrogel released water-soluble degradation products comprising one or more backbone moieties (corresponding to reactive functional groups) were integrated and plotted against incubation time, see FIG. 9.

The time period for the complete degradation of the hydrogel by hydrolysis of the degradable bonds into water-soluble degradation products comprising one or more backbone moieties was found to be 94 hours which is 1.45 fold longer than the time period of the release of the first 10 mol-% of water soluble degradation products comprising one or more backbone moieties (which corresponds in this hydrogel material to the first 10 mol-% of reactive functional groups) which was found to be 65 hours.

Example 18

In Vitro Degradation of 15 at pH 7.4 and 37° C.

Hydrolysis of hydrogel beads 15 was affected by incubating 5 mg 15 in 2.0 ml 100 mM sodium phosphate, 3 mM EDTA, pH 7.4 at 37° C. Samples were taken at time intervals and analyzed by SEC (see Materials and Methods). UV-signals corresponding to hydrogel released water-soluble degradation products comprising one or more backbone moieties (corresponding to reactive functional groups) were integrated and plotted against incubation time, see FIG. 10.

The time period for the complete degradation of the hydrogel by hydrolysis of the degradable bonds into water-soluble degradation products comprising one or more backbone moieties was found to be 117 days which is 1.43 fold longer than the time period of the release of the first 10 mol-% of water soluble degradation products comprising one or more backbone moieties (which corresponds in this hydrogel material to the first 10 mol-% of reactive functional groups) which was found to be 82 days. This ratio of 1.43 is essentially identical to the value of 1.45 (see example 17) for the accelerated conditions at pH 9 showing that accelerated conditions can be used for the degradation analysis of hydrogel samples.

Example 19

In Vitro Degradation of 5 at pH 9 and 37° C.

Hydrolysis of hydrogel beads 5 was affected by incubating 5 mg 5 in 2.0 ml 0.5 M sodium borate buffer, pH 9.0 at 37° C. Samples were taken at time intervals and analyzed by SEC (see Materials and Methods). UV-signals at 280 nm corresponding to hydrogel released water-soluble degradation products containing indole-acetyl labelled reactive functional groups comprising were integrated and plotted against incubation time, see FIG. 11.

The time period for the complete degradation of the hydrogel by hydrolysis of the degradable bonds into water-soluble degradation products comprising one or more backbone moieties comprising indole-acetyl labelled reactive functional groups was found to be 75 h which is 1.44 longer than the time period of the release of the first 10 mol-% of indole-acetyl labelled reactive functional groups which was found to be 52 h (FIG. 11)

Example 20

Synthesis of Paliperidone Dicarboxylic Acid Hemiesters

General Procedure for Synthesis of Paliperidone-Esters

Paliperidone (1 eq) was dissolved in dry DCM and tritethylamine (4.4 eq), a catalytic amount of DMAP and the suitable cyclic anhydride (4 eq) were successively added. The reaction mixture was then allowed to stir for 1 h at room temperature. Volatiles were removed and the resulting mixture was diluted with ACN/water 1/1+0.1% TFA and acidified until pH reached about 4. The respective product was purified by RP-HPLC and HPLC fractions containing product were lyophilized.

Synthesis of Intermediate (16a)

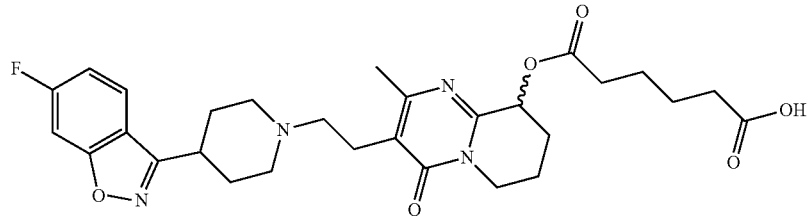

16a 16a was synthesized as described according to the general procedure for the synthesis of paliperidone-esters from 50 mg of paliperidone and adipic anhydride to afford a white solid.
Yield: 68 mg (0.102 mmol, 87%, TFA salt).
MS: m/z 555.3=[M+H]$^+$. (calculated=555.6)

Synthesis of Intermediate (16b)

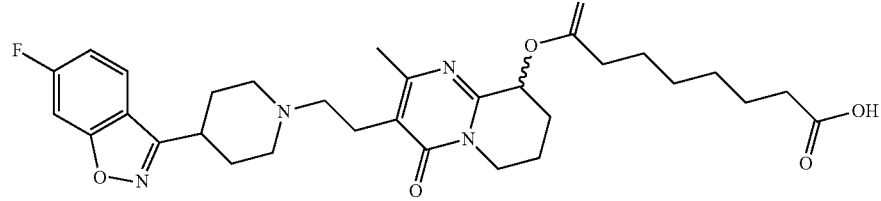

16b 16b was synthesized from 130 mg of paliperidone and suberic anhydride according to the general procedure, leading to a white solid.
Yield: 93 mg (0.133 mmol, 43%, TFA salt).
MS: m/z 583.3=[M+H]$^+$ (calculated=583.7)

Synthesis of Intermediate (16c)

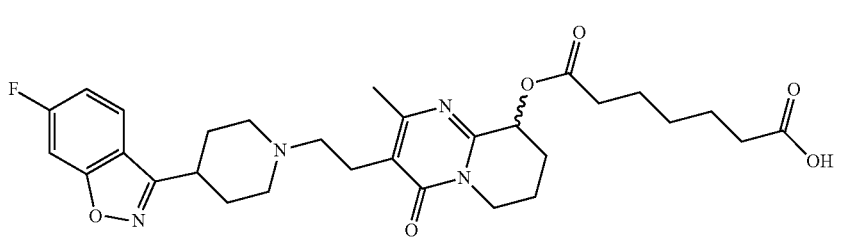

16c was synthesized from 500 mg of paliperidone and pimelic anhydride to yield a white solid.

Yield: 483 mg (0.799 mmol, 68%, HCl salt).
MS: m/z 569.3=[M+H]$^+$ (calculated=569.7)

Example 21

Preparation of Hydrogel Beads (17a), (17b), and (17c) Containing Free Amino Groups A solution of 720 mg 1g and 1180 mg 2d in 7.3 mL DMSO was added to a solution of 300 mg Arlacel P135 (Croda International Plc) in 60 mL heptane. The mixture was stirred at 1200 rpm with a custom metal stirrer for 10 min at RT to form a suspension. 2.6 mL N,N,N',N'-tetramethylethylene diamine (TMEDA) was added to effect polymerization. After 2 h, the stirrer speed was reduced to 500 rpm and the mixture was stirred for additional 16 h. 4 mL of acetic acid were added and then after 10 min 50 mL of water were added. After 5 min, the stirrer was stopped and the aqueous phase was drained.

For bead size fractionation, the water-hydrogel suspension was wet-sieved on 75, 50, 40, 32 and 20 μm steel sieves. Bead fractions that were retained on the 32, 40, and 50 μm sieves were pooled and washed 3 times with water, 10 times with ethanol and dried for 16 h at 0.1 mbar to give 17a as a white powder.

17b was prepared as described for 17a except for the use of 900 mg 1g, 886 mg 2g, 6.7 ml DMSO, 3.2 ml TMEDA, 5.0 ml acetic acid and a stirring speed of 1500 rpm.

17c was prepared as described for 17a except for the use of 1200 mg 1h, 1300 mg 2f, 9.9 ml DMSO, 6.1 ml TMEDA, 9.4 ml acetic acid and a stirring speed of 1000 rpm.

Example 22

Synthesis of Ado-Modified Hydrogels (18a), (18b), and (18c) and Lys-Modified Hydrogel (18d)

Ado-Modified Hydrogels (18a, 18b, 18c)

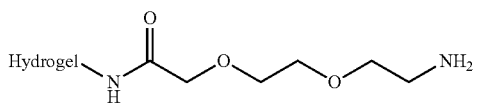

Hydrogel 17a, 17b, and 17c, respectively, in a syringe equipped with a polypropylene frit was washed with 1% diisopropylethylamine solution in DMF and ten times with DMF.

Fmoc-Ado-OH coupling was then performed by agitating 17a, 17b, and 17c, respectively, with 3.5 eq of fmoc-Ado-OH, 3.5 eq of PyBOP and 8.75 eq of DIPEA in DMF (using 0.2 mmol/mL fmoc-Ado-OH concentration). After 45 min, hydrogel was washed with DMF (10 times), then with DCM (10 times). Fmoc-deprotection was achieved by agitating the hydrogel two times with a 96/2/2 DMF/piperidine/DBU (v/v) solution for 5 min each. 18a, 18b, and 18c, respectively, was then washed with DMF (10 times) and ethanol (10 times) and finally dried in vacuo.

Lys-Modified Hydrogel (18d)

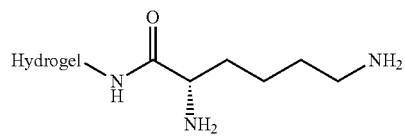

Hydrogel 17a in a syringe equipped with a polypropylene frit was washed with 1% diisopropylethylamine solution in DMF and ten times with DMF.

Fmoc-Lys(Fmoc)-OH coupling was then performed by agitating 17a with 3.5 eq of Fmoc-Lys(Fmoc)-OH, 3.5 eq of PyBOP and 8.75 eq of DIPEA in DMF (using 0.2 mmol/mL fmoc-Lys-OH concentration). After 45 min, hydrogel was washed with DMF (10 times), then with DCM (10 times).

Fmoc-deprotection was achieved by agitating the hydrogel two times with a 96/2/2 DMF/piperidine/DBU (v/v) solution for 5 min each. 18d was then washed with DMF (10 times) and ethanol (10 times) and finally dried in vacuo.

Example 23

Synthesis of Paliperidone-Linker-Hydrogel (19a), (19b), (19c), (19d), (19e), (19f) and (19g)

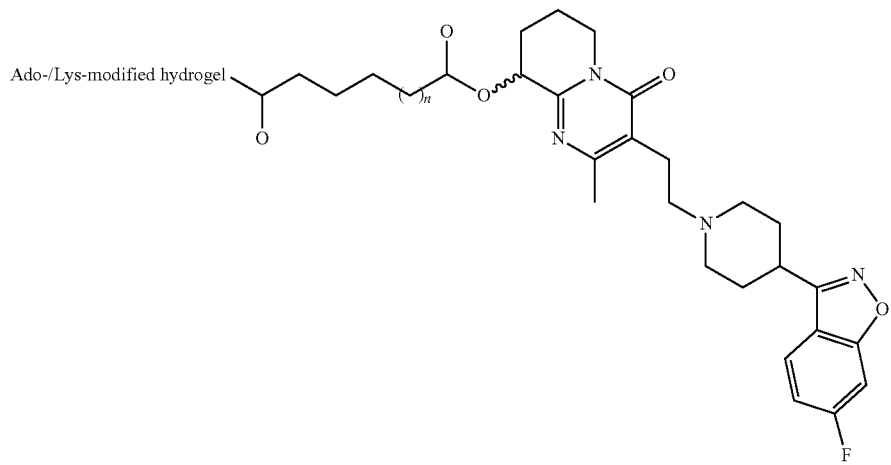

19a, 19b, 19c, 19d, 19e, 19f, 19g

General Protocol for Paliperdione-Linker Coupling 18c (1 eq amine content) was weighed into a syringe equipped with a polypropylene frit and agitated with 3 eq of paliperidone-ester 16a, 3 eq of PyBOP, and 7.5 eq of DIPEA in dry DMF (using 0.2 mmol/mL concentration of paliperidone-ester 16a) for 2 h. Paliperidone-linker-hydrogel 19a was washed with DMF (8 times), then with a 96/2/2 v/v DMF/piperidine/DBU solution (10 times), then further washed with DMF (10 times) and finally with a ACN/water 1/1+0.1% TFA solution (10 times). Paliperidone loading was determined by total hydrolysis of paliperidone-linker-hydrogel samples at pH 12 for 4 h at 37° C. and quantification of released paliperidone by HPLC and detection at 280 nm using a paliperidone calibration curve.

19b, 19c, 19d, 19e, 19f and 19g, respectively, were synthesized as described above except for the use of hydrogel 18c, 18a, 18b, 18a, 18d and 18d, respectively, and paliperdione ester 16b, 16a, 16a, 16c, 16a and 16c, respectively.

Loading of different paliperidone-linker-hydrogel conjugates is summarized in table 1:

TABLE 1

| Compound | Hydrogel | Paliperidone-linker | Yield (mg) | Paliperidone loading (% w/w) |
|---|---|---|---|---|
| 19a | 18c | 16a | 15 | 27% |
| 19b | 18c | 16b | 59 | 33% |
| 19c | 18a | 16a | 52 | 24% |
| 19d | 18b | 16a | 245 | 18% |
| 19e | 18a | 16c | 104 | 23% |
| 19f | 18d | 16a | 170 | 38% |
| 19g | 18d | 16c | 177 | 38% |

Paliperidone-linker hydrogel was suspended in PBS buffer.
Paliperidone concentration in paliperidone-linker hydrogel suspension (w/v):
19f: 100 mg/ml
19g: 112 mg/ml

Example 24

In Vitro Release Kinetics

In Vitro Release Studies at pH 7.4

Paliperdione-linker-hydrogel samples (19a through 19g, respectively) (in duplicate) containing approximately 0.85 mg paliperidone were washed three times with pH 7.4 phosphate buffer (60 mM, 3 mM EDTA, 0.01% Tween-20) and filled-up to 1.5 mL using the same buffer. Samples were incubated at 37° C. and aliquots of supernatant were analyzed at various time points by HPLC and detection at 280 nm. Peaks corresponding to released paliperidone were integrated and paliperidone amount calculated by comparison with a calibration curve. Amount released paliperdone was plotted versus time and half-life of release was determined using curve-fitting software assuming first-order release kinetics.

In vitro release kinetics of 19a is shown in FIG. 12.

Half-life times of other hydrogel linkers mentioned in Table 1 are disclosed in the following table (Table 2):

TABLE 2

| Ref. | $t_{1/2}$ (d) |
|---|---|
| 19a | 17 |
| 19b | 53 |
| 19c | 19 |
| 19d | 15 |
| 19e | 28 |
| 19f | 28 |
| 19g | 44 |

Example 25

Paliperidone Pharmacokinetics Study in Rat

The pharmacokinetics of 19c was determined by measuring the plasma paliperidone concentration after subcutaneous application of a single dose into rats.

One group consisting of 5 male Wistar rats (200-250 g) was used to study the plasma paliperidone levels over a period of 28 days. Each of the animals received a single subcutaneous injection of 500 µL 19c suspension in acetate buffer pH 5, containing 7 mg paliperidone (14 mg paliperidone/ml). Per animal and time point 200 µL of blood was withdrawn sublingually to obtain 100 µL Li-Heparin plasma. Samples were collected before application and after 4 h, 2, 4, 7, 11, 14, 18, 21, 25 and 28 days post injection. Plasma samples were frozen within 15 min after blood withdrawal and stored at −80° C. until assayed.

The quantification of plasma paliperidone concentrations were carried out using a Waters Acquity HPLC coupled to a Thermo LTQ Orbitrap Discovery mass spectrometer via an ESI probe and with Waters BEH C18 (50×2.1 mm I.D., 1.7 µm particle size) as analytical column (mobile phase A: 10 mM ammonium formate pH 4.0, mobile phase B: acetonitrile, T=45° C.). The gradient system comprised a linear gradient from 10% B to 50% B in 4 min, an isocratic washing phase with 95% B (1.5 min), and a reconditioning phase (2.5 min) with a flow rate of 0.25 mL/min. Detection of the ions was performed in the selected reaction monitoring (SRM) mode, monitoring the transition pairs at the m/z 427.2 precursor ions to the m/z 207.1 product ion ions for paliperidone and m/z 376.1 precursor ions to the m/z 165.1 product ions for the internal standard (IS) haloperidol.

Blood samples were obtained following s.c. injections of hydrogel-paliperidone into heparinized tubes at different time points. Plasma was harvested by centrifuging the blood and stored frozen at −80° C. until analysis. After addition of aq. NaOH (50 µL, 0.5 M NaOH) the thawed plasma samples (~95 µL) were spiked with 220 pg haloperidol (10 µl of an aqueous haloperidol solution c=22 pg/µL) and extracted with diethyl ether (2×500 µL). The aqueous layer was frozen in a liquid nitrogen bath and the organic layer was transferred to a separate tube. The solvent of the combined organic phase was removed in a stream of nitrogen at 40° C. and the residue was dried in vacuo. The residues at different time points were dissolved in mobile phase A:mobile phase B=7:3 (v/v) (100 µL) and aliquots (15 µL) were injected into the HPLC-MS system.

The calibration curve was acquired by plotting the peak area of paliperidone against the nominal amount of calibration standards. The results were fitted to linear regression analysis using $1/X^2$ as weighting factor.

The paliperidone peak areas of the quantification experiments at different time points were weighted relatively to the ratio mean peak area IS of all experiments/peak area IS. The resulting peak areas were used to calculate the paliperidone concentration in rat plasma (ng mL$^{-1}$).

No burst of paliperidone and a sustained release of paliperidone over 28 days was observed.

The results are shown in FIG. 13.

The pharmocokinetics of 19e were measured as described for 19c. The results are shown in FIG. 14.

Example 26

Alternative Synthetic Route for 1g

For synthesis of compound 1b, to a 45° C. suspension of 4-Arm-PEG5000 tetraamine (1a) (50.0 g, 10.0 mmol) in 250 mL of iPrOH (anhydrous), boc-Lys(boc)-OSu (26.6 g, 60.0 mmol) and DIEA (20.9 mL, 120 mmol) were added and the mixture was stirred for 30 min.

Subsequently, n-propylamine (2.48 mL, 30.0 mmol) was added. After 5 min the solution was diluted with 1000 mL of MTBE and stored overnight at −20° C. without stirring. Approximately 500 mL of the supernatant were decanted off and discarded. 300 mL of cold MTBE were added and after 1 min shaking the product was collected by filtration through a glass filter and washed with 500 mL of cold MTBE. The product was dried in vacuo for 16 h.

Yield: 65.6 g (74%) 1b as a white lumpy solid
MS: m/z=937.4=[M+7H]$^{7+}$ (calculated=937.6).

Compound 1c was obtained by stirring of compound 1b from the previous step (48.8 g, 7.44 mmol) in 156 mL of 2-propanol at 40° C. A mixture of 196 mL of 2-propanol and 78.3 mL of acetylchloride was added under stirring within 1-2 min. The solution was stirred at 40° C. for 30 min and cooled to −30° C. overnight without stirring. 100 mL of cold MTBE were added, the suspension was shaken for 1 min and cooled for 1 h at −30° C. The product was collected by filtration through a glass filter and washed with 200 mL of cold MTBE. The product was dried in vacuo for 16 h.

Yield: 38.9 g (86%) 1c as a white powder which
MS: m/z=960.1 [M+6H]$^{6+}$ (calculated=960.2).

For synthesis of compound 1d, to a 45° C. suspension of 1c from the previous step (19.0 g, 3.14 mmol) in 80 ml 2-propanol were added boc-Lys(boc)-OSu (16.7 g, 37.7 mmol) and DIEA (13.1 mL, 75.4 mmol) and the mixture was stirred for 30 min at 45° C. Subsequently, n-propylamine (1.56 mL, 18.9 mmol) was added. After 5 min the solution was precipitated with 600 mL of cold MTBE and centrifugated (3000 min$^{-1}$, 1 min) The precipitate was dried in vacuo for 1 h and dissolved in 400 mL THF. 200 mL of diethyl ether were added and the product was cooled to −30° C. for 16 h without stirring. The suspension was filtered through a glass filter and washed with 300 mL cold MTBE. The product was dried in vacuo for 16 h.

Yield: 21.0 g (80%) 1d as a white
MS: m/z 1405.4=[M+6H]$^{6+}$ (calculated=1405.4).

Compound 1e was obtained by dissolving compound 1d from the previous step (15.6 g, 1.86 mmol) in in 3 N HCl in methanol (81 mL, 243 mmol) and stirring for 90 min at 40° C. 200 mL of MeOH and 700 mL of iPrOH were added and the mixture was stored for 2 h at −30° C. For completeness of crystallization, 100 mL of MTBE were added and the suspension was stored at −30° C. overnight. 250 mL of cold MTBE were added, the suspension was shaken for 1 min and filtered through a glass filter and washed with 100 mL of cold MTBE. The product was dried in vacuo.

Yield: 13.2 g (96%) 1e as a white powder
MS: m/z=679.1=[M+10H]$^{10+}$ (calculated=679.1).

For the synthesis of compound 1f, to a 45° C. suspension of 1e from the previous step, (8.22 g, 1.12 mmol) in 165 ml 2-propanol were added boc-Lys(boc)-OSu (11.9 g, 26.8 mmol) and DIEA (9.34 mL, 53.6 mmol) and the mixture was stirred for 30 min. Subsequently, n-propylamine (1.47 mL, 17.9 mmol) was added. After 5 min the solution was cooled to −18° C. for 2 h, then 165 mL of cold MTBE were added, the suspension was shaken for 1 min and filtered through a glass filter. Subsequently, the filter cake was washed with 4×200 mL of cold MTBE/iPrOH 4:1 and 1×200 mL of cold MTBE. The product was dried in vacuo for 16 h.

Yield: 12.8 g, MW (90%) 1f as a pale yellow lumpy solid
MS: m/z 1505.3=[M+8H]$^{8+}$ (calculated=1505.4).

Backbone reagent 1g was obtained by dissolving 4Arm-PEG5 kDa(-LysLys$_2$Lys$_4$(boc)$_8$)$_4$ (1f) (15.5 g, 1.29 mmol) in 30 mL of MeOH and cooling to 0° C. 4 N HCl in dioxane (120 mL, 480 mmol, cooled to 0° C.) was added within 3 min and the ice bath was removed. After 20 min, 3 N HCl in methanol (200 mL, 600 mmol, cooled to 0° C.) was added within 15 min and the solution was stirred for 10 min at room temperature. The product solution was precipitated with 480 mL of cold MTBE and centrifugated at 3000 rpm for 1 min. The precipitate was dried in vacuo for 1 h and redissolved in 90 mL of MeOH, precipitated with 240 mL of cold MTBE and the suspension was centrifugated at 3000 rpm for 1 min again. The product was dried in vacuo Yield: 11.5 g (89%) as a pale yellow flakes.

MS: m/z=1104.9 [M+8H]$^{8+}$ (calculated=1104.9).

Example 27

Derivatization Procedure for Multi-Amino Functionalized Pegs, Including 1g, for Analysis on Reverse Phase HPLC Amino-functionalized PEG derivatives with multiple amino groups are difficult to analyze by RP-HPLC, since they typically elute early, show broad peaks, and have a very weak absorption by UV detection. Therefore, the purity of these PEG derivatives cannot be directly analyzed by RP-HPLC as impurities are typically not resolved from the main peak. Derivatization with 3-methoxy-4-nitrobenzoic acid yields in aromatic amides which show sharper peaks and a better resolution upon RP-HPLC analysis. Furthermore, UV detection at 340 nm allows for direct relative quantification of amino group content of different species present in the amino-functionalized PEG derivative.

3-Methoxy-4-nitrobenzoic acid N-succinimidyl ester was synthesized from 3-methoxy-4-nitrobenzoic acid, N-hydroxysuccinimide and dicyclohexylcarbodiimide in dichloromethane and purified by reverse phase HPLC.

PEG-solution: 10 mg of the multi-amino functionalized PEG is dissolved in 90 µL of DMSO Derivatization reagent solution: 5 mg 3-Methoxy-4-nitrobenzoic acid N-succinimidyl ester are dissolved in 65 µL of DMSO.

To 25 µL PEG-solution the derivatization reagent solution (2 eq per free amino group) and diisopropylethyl amine (3 eq per free amino group) was added and the mixture was shaken for 15 min. 500 µL of acetonitrile and then 800 µL of 0.1 N NaOH were added and the mixture was shaken for further 60 minutes. 10 µL of the solution were acidified with 5 µL of acetic acid and diluted with 100 µL of acetonitrile/water/trifluoroacetic acid (TFA) 90:10:0.1 (v/v/v) and analyzed by reverse phase HPLC (eluent: 0.05% TFA in water/0.04% TFA in acetonitrile).

Example 28

Synthesis of Paracetamol Conjugate 20

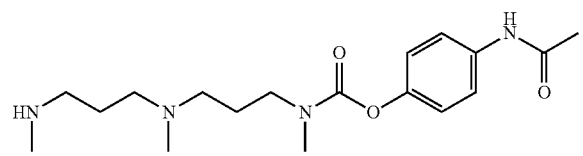

20

Paracetamol (1 mmol) was dissolved in 10 ml of THF and nitrophenyl-chloroformate (1.1 mmol) and DIEA (1.1 mmol) were added. After 30 min, N,N-bis[3-(methylamino)propyl]methylamine (2 mmol) was added and reaction mixture was stirred at room temperature for 30 min. 20 was purified by RP-HPLC.

Yield 83 mg (14%).

MS: m/z=351.26 [M+H]$^+$.

Example 29

Synthesis of Linker-Paracetamol Conjugate 21

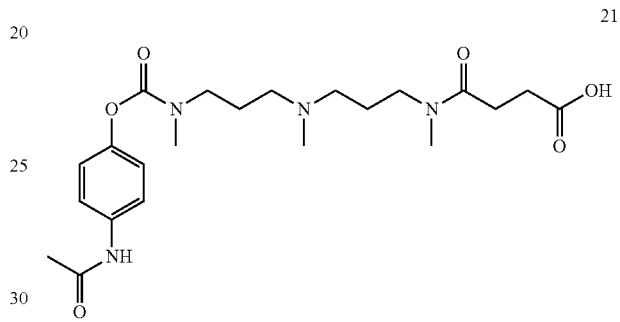

21

To a solution of 20 (17 µmol) in DMF (300 µL) were added solid succinic anhydride (65 µmol) and DIEA (173 µmol), and the mixture was stirred at 60° C. for 50 min. 21 was purified by RP-HPLC. Yield: 7.7 mg (79%).

Example 30

Synthesis of Hydrogel-Paracetamol Conjugate 22

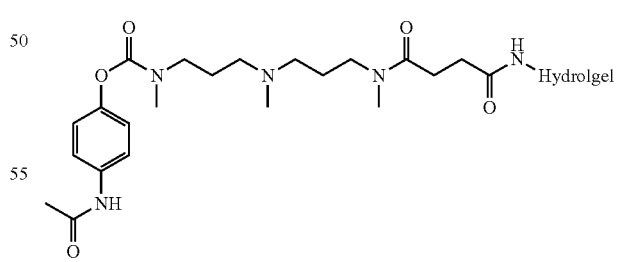

22

100 mg amine-functionalized hydrogel 3e (0.13 mmol amine/g dry hydrogel) was suspended in DMF. A solution of 21 (6 µmol), PyBOP (22 µmol) and DIEA (31 µmol) in DMF (0.5 mL) was added, and the mixture was shaken at 22° C. for 2 h. The resulting loaded hydrogel was washed with DMF (10 times), dichloromethane (10 times) and ethanol (5 times) and was dried in vacuo.

Example 31

Synthesis of Linker-Paracetamol Conjugate 23

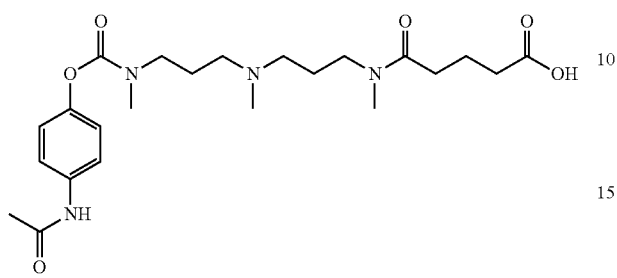

To a solution of 20 (17 µmol) in DMF (300 µL) were added solid glutaric anhydride (79 µmol) and DIEA (173 µmol), and the mixture was stirred at 60° C. for 50 min. 23 was purified by RP-HPLC.

Yield: 6.4 mg (64%).

Example 32

Synthesis of Hydrogel-Paracetamol Conjugate 24

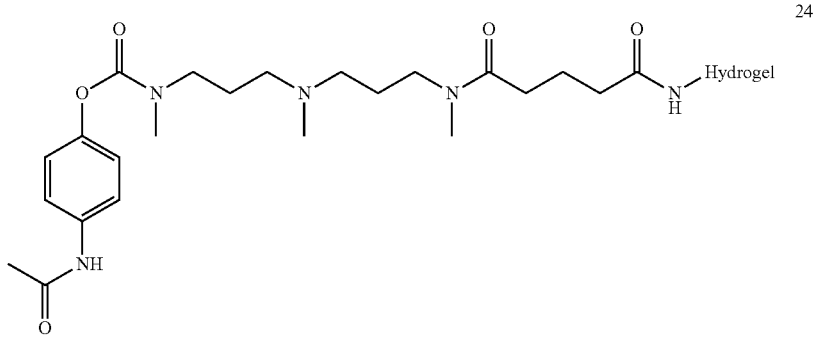

80 mg amine-functionalized hydrogel 3e (0.13 mmol amine/g dry hydrogel) was suspended in DMF. A solution of 23 (5 µmol), PyBOP (19 µmol) and DIEA (27 µmol) in DMF (0.5 mL) was added, and the mixture was shaken at 22° C. for 3 h. The resulting loaded hydrogel was washed with DMF (10 times), dichloromethane (10 times) and ethanol (5 times) and was dried in vacuo.

Example 33

Release of Paracetamol In Vitro

Hydrogel-paracetamol conjugates 22 and 24 were dissolved in 60 mM sodium phosphate, pH 7.4, and incubated at 37° C. Aliquots of the supernatant were analyzed by RP-HPLC at 242 nm and MS for released paracetamol. MS showed release of unmodified paracetamol.

$t_{1/2}$ (22)=19 d.
$t_{1/2}$ (24)=15 d.

Example 34

Synthesis of Cetirizine-Ester 25

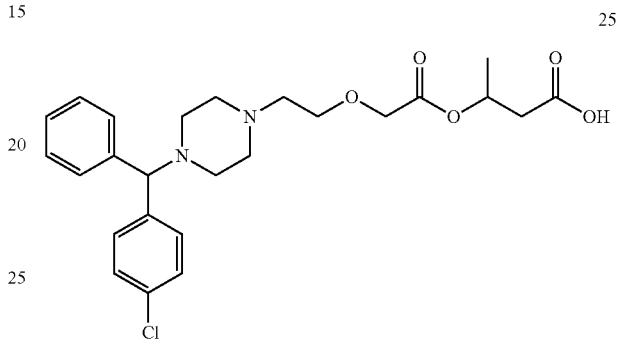

3-Hydroxy butyric acid (0.56 mmol) was loaded onto 2-chlorotrityl resin (0.35 mmol) according to manufacturer's instructions.

The resin was washed with dichloromethane (7 times), DMF (7 times) and dichloromethane (7 times). A solution of Cetirizine dihydrochloride (1.25 mmol), DIC (1.46 mmol), HOSu (1.39 mmol) and DIEA (3.13 mmol) in dichloromethane (3 mL) was added to the resin and incubated for 15 h. Intermediate 25 was cleaved from the resin by addition of a solution of HFIP (2 ml) in dichloromethane (3 mL) and incubation for 10 min. This step was repeated once, and all volatiles were removed from the combined eluates under a stream of nitrogen. Product 25 (yield 2%) was purified by RP-HPLC and analyzed by RP-HPLC-MS.

Example 35

Synthesis of Cetirizine Hydrogel Conjugate 26

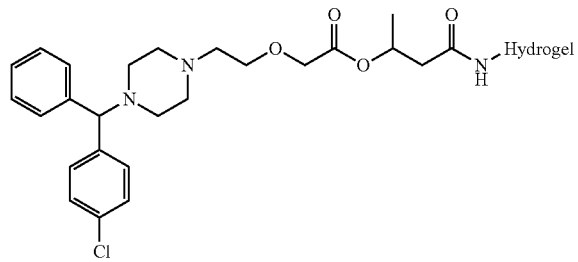

26

100 mg amine-functionalized hydrogel 3e (0.13 mmol amine/g dry hydrogel) was suspended in DMF (0.6 mL). A solution of 25 (7.1 μmol), PyBOP (23 μmol) and DIEA (28 μmol) in DMF (0.6 mL) was added to the hydrogel suspension, and the mixture was incubated for 3 h. The solution was discarded, and the hydrogel was washed with DMF (7 times) and ethanol (5 times) and dried in vacuo.

Example 36

Cetirizine Release In Vitro

Release of Cetirizine from 26 was accomplished by hydrolysis in 60 mM sodium phosphate buffer at pH 7.4 and 37° C. Unmodified Cetirizine is released as assessed by RP-HPLC/MS.

$t_{1/2} = 31$ h.

Example 37

Synthesis of Linker Reagent 27f

Linker reagent 27f was synthesized according to the following procedure:

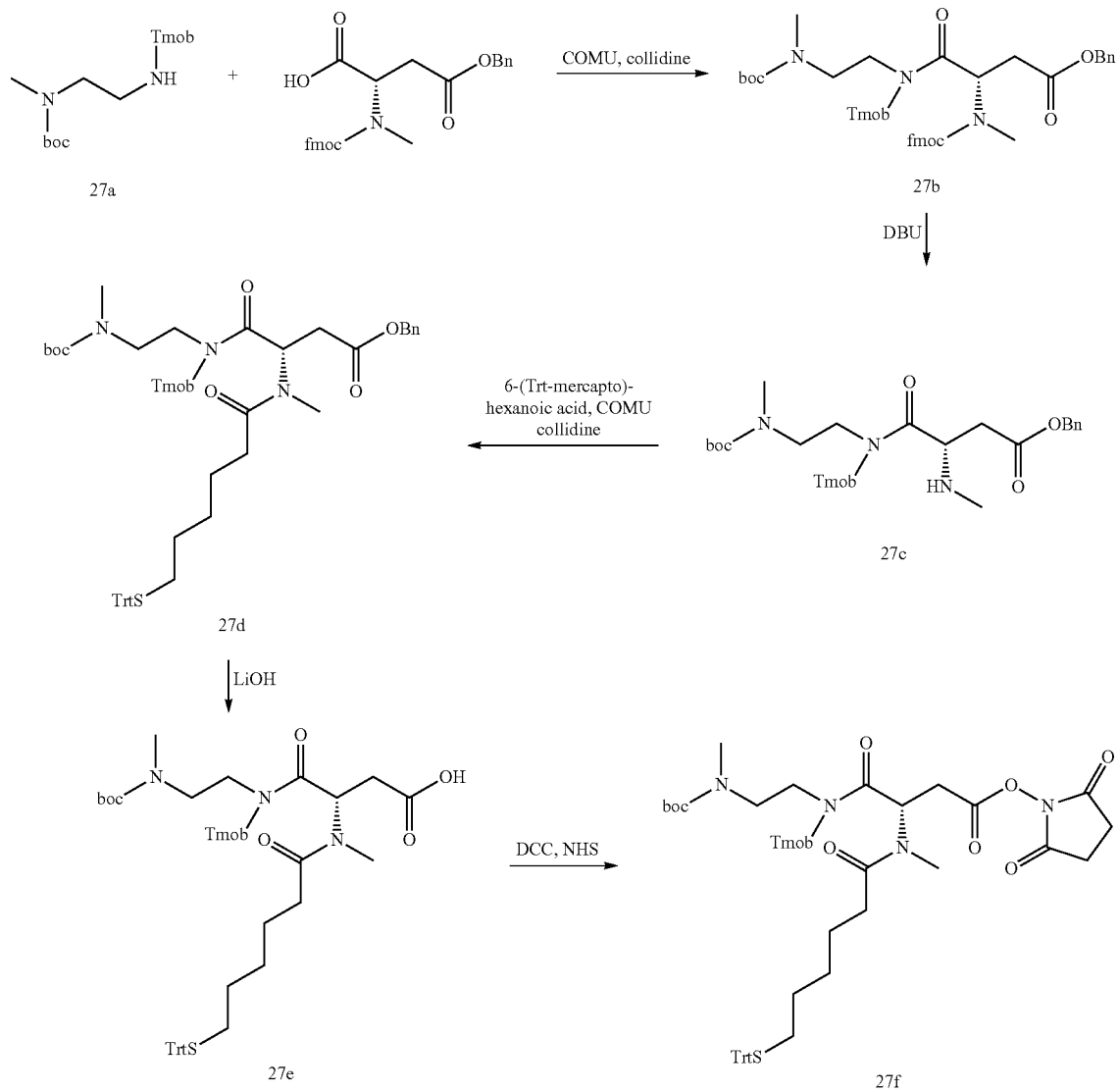

To a solution of N-Methyl-N-boc-ethylenediamine (2 g, 11.48 mmol) and NaCNBH$_3$ (819 mg, 12.63 mmol) in MeOH (20 mL) was added 2,4,6-trimethoxybenzaldehyde (2.08 mg, 10.61 mmol) portion wise. The mixture was stirred at RT for 90 min, acidified with 3 M HCl (4 mL) and stirred further 15 min. The reaction mixture was added to saturated NaHCO$_3$ solution (200 mL) and extracted 5× with CH$_2$Cl$_2$. The combined organic phases were dried over Na$_2$SO$_4$ and the solvents were evaporated in vacuo. The resulting N-Methyl-N-boc-N'-tmob-ethylenediamine (27a) was completely dried in high vacuum and used in the next reaction step without further purification.

Yield: 3.76 g (11.48 mmol, 89% purity, 27a: double Tmob protected product=8:1)

MS: m/z 355.22=[M+H]$^+$, (calculated=354.21).

To a solution of 27a (2 g, 5.65 mmol) in CH$_2$Cl$_2$ (24 ml) COMU (4.84 g, 11.3 mmol), N-Fmoc-N-Me-Asp(OBn)-OH (2.08 g, 4.52 mmol) and collidine (2.65 mL, 20.34 mmol) were added. The reaction mixture was stirred for 3 h at RT, diluted with CH$_2$CL$_2$ (250 mL) and washed 3× with 0.1 M H$_2$SO$_4$ (100 ml) and 3× with brine (100 ml). The aqueous phases were reextracted with CH$_2$Cl$_2$ (100 ml). The combined organic phases were dried over Na$_2$SO$_4$, filtrated and the residue concentrated to a volume of 24 mL. 27b was purified using flash chromatography.

Yield: 5.31 g (148%, 6.66 mmol)

MS: m/z 796.38=[M+H]$^+$, (calculated=795.37).

To a solution of 27b [5.31 g, max. 4.51 mmol ref. to N-Fmoc-N-Me-Asp(OBn)-OH] in THF (60 mL) DBU (1.8 mL, 3% v/v) was added. The solution was stirred for 12 min at RT, diluted with CH$_2$Cl$_2$ (400 ml) and washed 3× with 0.1 M H$_2$SO$_4$ (150 ml) and 3× with brine (150 ml). The aqueous phases were re extracted with CH$_2$Cl$_2$ (100 ml). The combined organic phases were dried over Na$_2$SO$_4$ and filtrated. 27c was isolated upon evaporation of the solvent and used in the next reaction without further purification.

MS: m/z 574.31=[M+H]$^+$, (calculated=573.30).

27c (5.31 g, 4.51 mmol, crude) was dissolved in MeCN (26 mL) and COMU (3.87 g, 9.04 mmol), 6-Tritylmercaptohexanoic acid (2.12 g, 5.42 mmol) and collidine (2.35 mL, 18.08 mmol) were added. The reaction mixture was stirred for 4 h at RT, diluted with CH$_2$Cl$_2$ (400 ml) and washed 3× with 0.1 M H$_2$SO$_4$ (100 ml) and 3× with brine (100 ml). The aqueous phases were reextracted with CH$_2$Cl$_2$ (100 ml). The combined organic phases were dried over Na$_2$SO$_4$, filtrated and 7i was isolated upon evaporation of the solvent. Product 27d was purified using flash chromatography.

Yield: 2.63 g (62%, 94% purity)

MS: m/z 856.41=[M+H]$^+$, (calculated=855.41).

To a solution of 27d (2.63 g, 2.78 mmol) in i-PrOH (33 mL) and H$_2$O (11 mL) was added LiOH (267 mg, 11.12 mmol) and the reaction mixture was stirred for 70 min at RT. The mixture was diluted with CH$_2$Cl$_2$ (200 ml) and washed 3× with 0.1 M H$_2$SO$_4$ (50 ml) and 3× with brine (50 ml). The aqueous phases were re-extracted with CH$_2$Cl$_2$ (100 ml). The combined organic phases were dried over Na$_2$SO$_4$, filtrated and 27e was isolated upon evaporation of the solvent. 27e was purified using flash chromatography.

Yield: 2.1 g (88%)

MS: m/z 878.4=[M+Na]$^+$, (calculated=878.40).

To a solution of 27e (170 mg, 0.198 mmol) in anhydrous DCM (4 mL) were added DCC (123 mg, 0.59 mmol), and a catalytic amount of DMAP. After 5 min N-hydroxysuccinimide (114 mg, 0.99 mmol) was added and the reaction mixture was stirred at RT for 1 h. The reaction mixture was filtered, the solvent was removed in vacuo and the residue was taken up in 90% acetonitrile plus 0.1% TFA (3.4 ml). The crude mixture was purified by RP-HPLC. Product fractions were neutralized with 0.5 M pH 7.4 phosphate buffer and concentrated. The remaining aqueous phase was extracted with DCM and 27f was isolated upon evaporation of the solvent.

Yield: 154 mg (81%)

MS: m/z 953.4=[M+H]$^+$, (calculated=953.43).

Example 38

Synthesis of N$^{\varepsilon B29}$-Insulin Linker Conjugate 28

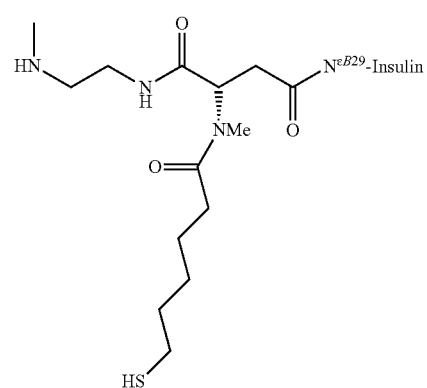

Insulin (644 mg, 0.111 mmol) was dissolved in 6.5 mL of DMSO. 3 mL of cooled (4° C.) 0.5 M sodium borate buffer (pH 8.5) and 27f (70 mg, 0.073 mmol) in 2.5 mL of DMSO were added and mixture was stirred for 5 min at RT. 400 µL AcOH were added and protected insulin conjugate was purified by RP HPLC.

Yield: 172 mg (0.025 mmol).

MS: m/z 1662.27=[M+4H]$^{4+}$ (calculated=1662.48).

Removal of protecting groups was affected by treatment of lyophilized product fractions with 6 mL of 90/10/2/2 (v/v/v/v) HFIP/TFA/TES/water for 1 h at RT. N$^{\varepsilon B29}$-conjugated insulin-linker conjugate 28 was purified by RP HPLC.

Yield: 143 mg (0.023 mmol).

MS: m/z 1531.46=[M+4H]$^{4+}$ (calculated=1531.71).

Example 39

Preparation of Insulin-Linker-Hydrogel 29

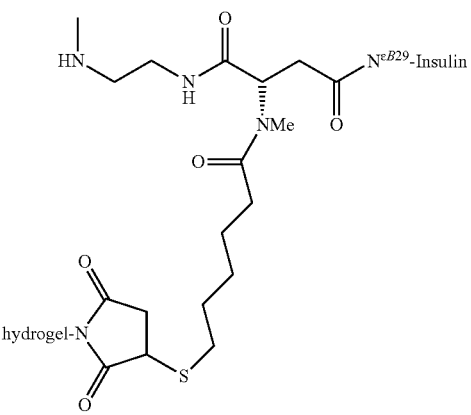

29 was prepared as follows: A suspension of maleimide functionalized hydrogel 4d in pH 2.5 HCl, 0.01% Tween-20 (58.3 mL, 958 µmol maleimido groups) was added to a solid phase synthesis reactor. A solution of insulin-linker-thiol 28 (117 mL, 460 µmol) in 2.5 HCl, 0.01% Tween-20 was added to 4d. The suspension was incubated at RT for 5 min. Succinate buffer (4.8 mL, pH 4.0, 150 mM; 1 mM EDTA, 0.01% Tween-20) was added to yield a pH of 3.6 and the suspension was incubated at RT for 90 min.

Consumption of thiol was monitored by Ellman test. Hydrogel was washed 10 times with succinate buffer (pH 3.0, 50 mM; 1 mM EDTA, 0.01% Tween-20) and 2 times with succinate buffer (pH 3.0, 50 mM; 1 mM EDTA, 0.01% Tween-20) containing 10 mM mercaptoethanol. Finally, the hydrogel was suspended in the mercaptoethanol containing buffer and incubated for 3 h at RT. Insulin-linker-hydrogel 29 was washed 10 times with succinate buffer (pH 3.0, 50 mM; 1 mM EDTA, 0.01% Tween-20) and 6 times with succinate/Tris buffer (pH 5.0, 10 mM; 85 g/L trehalose, 0.01% Tween-20).

Insulin loading of 29: 18.7 mg insulin/mL insulin-linker-hydrogel suspension

Example 40

Injectability of Insulin-Linker-Hydrogel Prodrug 29

5 mL insulin-linker-hydrogel prodrug 29 (bead size distribution from 32-75 µm, 18 mg insulin/ml insulin-linker-hydrogel prodrug suspension) was buffer exchanged into pH 5.0 succinic acid/tris (10 mM, 40 g/L mannitol; 10 g/L trehalose dihydrate; 0.05% TWEEN-20). The insulin-linker-hydrogel prodrug suspension was filled into a 1 mL syringe (length 57 mm) via a 20 G needle. The 20 G needle was replaced by a 30 G needle and placed into the syringe mounting (Aqua Computer GmbH&Co. KG) and the measurement was started with a piston velocity of 172 mm/min (equals 50 µL/s) (Force test stand: Multitest 1-d, Data recording software: EvaluatEmperor Lite, Version 1.16-015, Forge Gauge: BFG 200 N (all Mecmesin Ltd., UK). Experiments with increasing piston velocities shown in the table below were carried out with a new insulin-linker-hydrogel prodrug sample. The experiments with water and ethylene glycol were carried out accordingly. For all of the experiments the same 30 G needle was used. Force versus flow using a 30 G needle is shown in FIG. 16.

| Flow/ (sec/mL) | Flow/ (µL/sec) | Velocity of piston/ (mm/min) | Force/N (water) | Force/N (insulin-linker-hydrogel prodrug 29) | Force/N (ethylene glycol) |
|---|---|---|---|---|---|
| 6  | 167 | 573 | 13 | 36 | 83 |
| 8  | 125 | 430 | 10 | 29 | 62 |
| 10 | 100 | 344 | 7  | 24 | 51 |
| 15 | 67  | 229 | 4  | 22 | 35 |
| 20 | 50  | 172 | 3  | 17 | 27 |

Example 41

Preparation of Hydrogel Beads (30) and (30a) Containing Free Amino Groups

A solution of 275 mg 1g and 866 mg 2d in 14 mL DMSO was added to a solution of 100 mg Arlacel P135 (Croda International Plc) in 60 mL heptane. The mixture was stirred at 700 rpm with a custom metal stirrer for 10 min at 25° C. to form a suspension. 1.0 ml N,N,N',N'-tetramethyl-ethylene-diamine was added to effect polymerization. After 2 h, the stirrer speed was reduced to 400 rpm and the mixture was stirred for additional 16 h. 1.5 mL of acetic acid were added and then after 10 min 50 mL of water were added. After 5 min, the stirrer was stopped and the aqueous phase was drained.

For bead size fractionation, the water-hydrogel suspension was wet-sieved on 75, 50, 40, 32 and 20 µm mesh steel sieves. Bead fractions that were retained on the 32, 40, and 50 µm sieves were pooled and washed 3 times with water, 10 times with ethanol and dried for 16 h at 0.1 mbar to give 30 as a white powder.

30a was prepared as described for 30 except for the use of 1200 mg 1g, 3840 mg 2d, 28.6 ml DMSO, 425 mg Arlacel P135, 100 mL heptane and 4.3 ml TMEDA. For workup, 6.6 ml acetic acid were added and then after 10 min 50 mL of water and 50 mL of saturated aqueous sodium chloride solution were added.

Amino group content of hydrogel was determined by conjugation of a fmoc-amino acid to the free amino groups on the hydrogel and subsequent fmoc-determination as described by Gude, M., J. Ryf, et al. *Letters in Peptide Science* 9(4): 203-206 (2002).

The amino group content of 30 and 30a was determined to be between 0.11 and 0.16 mmol/g.

Abbreviations

ACN acetonitrile
AcOH acetic acid
Acp-OH 4-(2-aminoethyl)-1-carboxymethyl-piperazine
Ado 8-amino-3,6-dioxa-octanoic acid
Boc t-butyloxycarbonyl
DBU 1,3-diazabicyclo[5.4.0]undecene
DCC N,N'-dicyclohexyl carbodiimide
DCM dichloromethane
DIPEA diisopropylethylamine
DMAP dimethylamino-pyridine
DMF N,N-dimethylformamide
DMSO dimethylsulfoxide
EDC 1-Ethyl-3-(3-dimethylaminopropyl)carbodiimid
EDTA ethylenediaminetetraacetic acid
eq stoichiometric equivalent
Fmoc 9-fluorenylmethoxycarbonyl
HATU O-(7-Azabenzotriazol-1-yl)-N,N,N',N'-tetramethyl-uronium hexafluorophosphate
HFIP hexafluoroisopropanol
HOBt N-hydroxybenzotriazole
IS internal standard
LCMS mass spectrometry-coupled liquid chromatography
Lys lysine
Mal 3-maleimido propionyl
Mal-PEG6-NHS N-(3-maleimidopropyl)-21-amino-4,7,10,13,16,19-hexaoxa-heneicosanoic acid NHS ester
MHA 6-mercaptohexanoic acid
Mmt 4-methoxytrityl
MS mass spectrum
MW molecular mass
n.d. not determined
NHS N-hydroxy succinimide
PEG poly(ethylene glycol)
PyBOP benzotriazole-1-yl-oxy-tris-pyrrolidino-phosphonium hexafluorophosphate
rpm rounds per minute RP-HPLC reversed-phase high performance liquid chromatography
RT room temperature
SEC size exclusion chromatography
SRM selected reaction monitoring
TCP 2-chlorotrityl chloride resin
TES triethylsilane
TMEDA N,N,N',N'-tetramethyl ethylene diamine
Tmob 2,4,6-trimethoxybenzyl
TFA trifluoroacetic acid
THF tetrahydrofurane
TMEDA N,N,N',N'-tertramethylethylene diamine
UPLC ultra performance liquid chromatography
UV ultraviolet
VIS visual

The invention claimed is:

1. A biodegradable poly(ethylene glycol) based water-insoluble hydrogel consisting of:
   backbone moieties which are interconnected by hydrolytically degradable bonds;
   wherein the backbone moieties are linked together through crosslinker moieties, each crosslinker moiety being terminated by at least two of the hydrolytically degradable bonds; and
   wherein each backbone moiety has a molecular weight in the range of from 1 kDa to 20 kDa and has the structure:

$C^*(A-Hyp)_x$ wherein:
   $C^*$ is a branching core consisting of in bound form an oligoalcohol or polyalcohol;
   A is a poly(ethylene glycol) based polymeric chain;
   Hyp is a hyperbranched dendritic moiety consisting of:
     reactive functional groups;
     degradable interconnected functional groups, each degradable interconnected functional group being connected to one of the crosslinker moieties and consisting of one of the hydrolytically degradable bonds; and
     lysine in bound form; and
   x is an integer of from 3 to 16, so that each backbone moiety has at least 6 reactive functional groups and 6 degradable interconnected functional groups;
   wherein the hydrogel is in the form of microparticles; and
   wherein the hydrolytically degradable bonds include at least one bond selected from the group consisting of acetals, carboxylic anhydrides, esters, imines, hydrazones, maleamic acid amides, ortho esters, phosphamides, phosphoesters, phosphosilyl esters, silyl esters, sulfonic esters, aromatic carbamates, and combinations thereof.

2. The biodegradable hydrogel of claim 1;
   wherein each crosslinker moiety has a molecular weight in the range of from 0.5 kDa to 5 kDa; and
   wherein each crosslinker moiety is PEG based.

3. The biodegradable hydrogel of claim 1;
   wherein each backbone moiety comprises in sum at least 16 interconnected biodegradable and reactive functional groups.

4. A conjugate comprising:
   the hydrogel of claim 1;
   wherein the hydrogel additionally carries permanent linkages to spacer molecules or blocking groups or combinations thereof.

5. A conjugate comprising:
   the hydrogel of claim 1;
   wherein the hydrogel additionally carries permanent linkages to ligands or chelating groups.

6. A carrier-linked prodrug comprising:
   the biodegradable hydrogel of claim 1 as carrier;
   wherein a number of permanent linkages of the backbone moieties exist, each with a transient prodrug linker L to which a biologically active moiety D is covalently attached.

7. The carrier-linked prodrug of claim 6;
   wherein the transient linkage between D and L is a carbamate, carbonate, amide, or ester linkage.

8. The carrier-linked prodrug of claim 6;
   wherein the transient prodrug linker L comprises a moiety $L^1$, which is substituted with a moiety $L^2$; and
   wherein $L^2$ is bound to a carrier group Z, which is the hydrogel.

9. The carrier-linked prodrug of claim 8;
   wherein $L^2$ is attached to Z via a terminal group having the following structure:

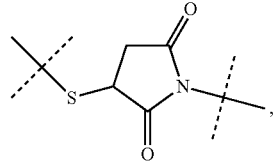

wherein the dashed lines indicate the attachment to $L^2$ and Z, respectively.

10. The hydrogel of claim 1;
    wherein the microparticles are obtained by comminution by a mechanical process.

* * * * *